(12) United States Patent
Yu et al.

(10) Patent No.: US 6,541,224 B2
(45) Date of Patent: Apr. 1, 2003

(54) TUMOR NECROSIS FACTOR DELTA POLYPEPTIDES

(75) Inventors: Guo-Liang Yu, Berkeley, CA (US); Jian Ni, Germantown, MD (US); Reiner L. Gentz, Rockville, MD (US); Patrick J. Dillon, Carlsbad, CA (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/879,919

(22) Filed: Jun. 14, 2001

(65) Prior Publication Data

US 2002/0064829 A1 May 30, 2002

Related U.S. Application Data

(63) Continuation-in-part of application No. 08/815,783, filed on Mar. 12, 1997.
(60) Provisional application No. 60/293,499, filed on May 25, 2001, provisional application No. 60/277,978, filed on Mar. 23, 2001, provisional application No. 60/276,248, filed on Mar. 16, 2001, provisional application No. 60/254,875, filed on Dec. 13, 2000, provisional application No. 60/241,952, filed on Oct. 23, 2000, provisional application No. 60/211,537, filed on Jun. 15, 2000, and provisional application No. 60/016,812, filed on Mar. 14, 1996.

(51) Int. Cl.$^7$ ........................ C12N 15/00; C12N 15/19; C07K 17/00; A61K 38/00
(52) U.S. Cl. .................... 435/69.5; 435/7.71; 435/69.1; 435/69.7; 435/70.1; 530/350; 530/351; 514/2; 514/12
(58) Field of Search ................................ 530/350, 351; 435/69.1, 69.5, 70.1, 69.7, 7.71; 514/2, 12

(56) References Cited

U.S. PATENT DOCUMENTS

| | | |
|---|---|---|
| 5,487,984 A | 1/1996 | Allet et al. |
| 5,925,548 A | 7/1999 | Beutler et al. |
| 6,171,787 B1 | 1/2001 | Wiley |
| 6,297,022 B1 | 10/2001 | McDonnell et al. |
| 6,297,367 B1 | 10/2001 | Tribouley |

FOREIGN PATENT DOCUMENTS

| | | |
|---|---|---|
| EP | 0 911 633 A1 | 4/1999 |
| EP | 0 919 620 A3 | 8/1999 |
| WO | WO93/16178 A2 | 8/1993 |
| WO | WO97/33902 A1 | 9/1997 |
| WO | WO99/00518 A1 | 1/1999 |
| WO | WO99/11791 A2 | 3/1999 |
| WO | WO99/12965 A3 | 3/1999 |
| WO | WO99/28462 A3 | 6/1999 |
| WO | WO99/33980 A2 | 7/1999 |
| WO | WO99/35170 A2 | 7/1999 |
| WO | WO99/50416 A1 | 10/1999 |
| WO | WO99/54460 A3 | 10/1999 |
| WO | WO99/55858 A3 | 11/1999 |
| WO | WO00/26244 A2 | 5/2000 |
| WO | WO00/32776 A3 | 6/2000 |
| WO | WO00/37640 A3 | 6/2000 |
| WO | WO00/50597 A2 | 8/2000 |
| WO | WO00/55320 A1 | 9/2000 |
| WO | WO00/68378 A1 | 11/2000 |
| WO | WO00/77256 A1 | 12/2000 |
| WO | WO01/24811 A1 | 4/2001 |
| WO | WO01/25256 A2 | 4/2001 |
| WO | WO01/58949 A3 | 8/2001 |
| WO | WO01/60397 A1 | 8/2001 |
| WO | WO01/77291 A2 | 10/2001 |
| WO | WO01/81417 A3 | 11/2001 |
| WO | WO01/87979 A3 | 11/2001 |

OTHER PUBLICATIONS

U.S. patent application Ser. No. 09/912,293, Rosen et al., filed not published.
Adams et al., GenBank Accession No. M78230, 1992.
Alignment of SEQ ID No.: 1 to Adams et al., GenBank Accession No. M78230 (May 26, 1992).
Cross et al., "Purification of CpG islands using a methylated DNA binding col.," Nature Genetics 6:236–44, 1994.
Gruss and Dower, "Tumor Necrosis Factor Ligand Superfamily: Involvement in the Pathology of Malignant Lymphomas," Blood 85(12):3378–3404, 1995.
Burns, The Science of Genetics: An Introduction to Heredity, 4th Edition, MacMillan Publishing Co., New York, p. 220, 1980.
George et al., "Current Methods in Sequence Comparison and Analysis," in Macromolecular Sequencing and Synthesis: Selected Methods and Applications, edited by D. Schlesinger, Alan R. Liss, Inc., New York, pp. 127–149, 1988.
Adams et al., "Initial assessment of human gene diversity and expression patterns based upon 83 million nucleotides of cDNA sequence," Nature 377 (6754 supplement), pp. 3–174, 1995.
MacDonald et al., GenBank Accession No. Z60980, 1995.
Adams et al., GenBank Accession No. AA337828, 1997.
Adams et al., GenBank Accession No. AA360555, 1997.
Adams et al., GenBank Accession No. AA361896, 1997.
Adams et al., GenBank Accession No. AA366583, 1997.
Adams et al., GenBank Accession No. AA357370, 1997.

(List continued on next page.)

*Primary Examiner*—Jeffrey Stucker
*Assistant Examiner*—Jegatheesan Seharaseyon
(74) *Attorney, Agent, or Firm*—Human Genome Sciences, Inc.

(57) ABSTRACT

The invention relates to human TNF delta and TNF epsilon polypeptides, polynucleotides encoding the polypeptides, methods for producing the polypeptides, in particular by expressing the polynucleotides, and agonists and antagonists of the polypeptides. The invention further relates to methods for utilizing such polynucleotides, polypeptides, agonists and antagonists for applications, which relate, in part, to research, diagnostic and clinical arts.

50 Claims, 11 Drawing Sheets

OTHER PUBLICATIONS

Hillier et al., GenBank Accession No. W20131, 1996.

Hahne et al., "APRIL, a New Ligand of the Tumor Necrosis Factor Family, Stimulates Tumor Cell Growth," Journal of Experimental Medicine 188(6):1185–1190, 1998.

Kelly et al., "APRIL/TRDL–1, a tumor necrosis factor–like ligand, stimulates cell death," Cancer Research 60(4):1021–1027, 2000.

Marsters et al., "Interaction of the TNF homologues BLyS and APRIL with the TNF receptor homologues BCMA and TACI," Current Biology 10(13):785–788, 2000.

Wu et al., "Tumor Necrosis Factor Receptor Superfamily Member TACI is a High Affinity Receptor for TNF Family Members APRIL and BLyS," Journal of Biological Chemistry in press Manuscript M005224200, published Journal of Biological Chemistry 275(45):35478–35485, 2000.

Rennert et al., "A Soluble Form of B Cell Maturation Antigen, a Receptor for the Tumor Necrosis Factor Family Member APRIL, Inhibits Tumor Cell Growth," Journal of Experimental Medicine 192(11):12677–12683, 2000.

Ware, "APRIL and BAFF Connect Autoimmunity and Cancer," Journal of Experimental Medicine 192(11):F35–F37, 2000.

Alignment of SEQ ID No.: 2 to Ito et al., PIR51 Accession No. A25451 (1986).

Yu et al., "APRIL and TALL–1 and receptors BCMA and TACI: system for regulating humoral immunity," Nature Immunology 1(3):252–256, 2000.

"Sequence Listing Comparison for Sequence database" cited by Examiner with Office Action of Dec. 9, 1998 in related 08/815,783 application.

Roth et al., "APRIL, a new member of the tumor necrosis factor family, modulates death ligand–induced apoptosis," Cell Death and Differentiation 8:403–410, 2001.

Von Bulow et al., "Regulation of the T–Independent Humoral Response by TACI," Immunity 14:573–582, 2001.

Xu and Lam, "B–Cell Maturation Protein, Which Binds the Tumor Necrosis Factor Family Members BAFF and APRIL, Is Dispensable for Humoral Immune Responses," Molecular and Cellular Biology 21(12):4067–4074, 2001.

Khare and Hsu, "The role of TALL–1 and APRIL in immune regulation," TRENDS In Immunology 22(2):61–63, 2001.

Laabi and Strasser, "Lymphocyte Survival—Ignorance is BLys," Science 289(5481):883, 2000.

Shu et al., "TALL–1 is a novel member of the TNF family that is down–regulated by mitogens," Journal of Leukocyte Biology 65:680–683, 1999.

```
  1  ACCTCTGTCCTTAGAGGGGACTGGAACCTAATTCTCCTGAGCCTGAGGGAGGGTGGAGGG   60

61  TCTCAAGACAACGCTGTCCCCACGACGGAGTGCCAGGAGCACTAACAGTACCCTTAGATT  120

121  GCTTTCCTCCTCCCTCCTTTTTTATTTTCAAGTTCCTTTTTATTTCTCCTTGCGTAACAA  180

181  CCTTCTTCCCTTCTGCACCACTGCCCGTACCCTTACCCGCGCCGCCACCTCCTTGCTACA  240

241  CCACTCTTGAAACCACAGCTGTTGGCAGGGTCCCCCAGCTCATGCCAGCCTCATCTCCTT  300

301  TCTTGCTAGCCCCCAAAGGGCCTCCAGGCAACATGGGGGGCCCAGTCAGAGAGCCGGCAC  360
  1                                  M  G  G  P  V  R  E  P  A  L   10

361  TCTCAGTTGCCCTCTGGTTGAGTTGGGGGGCAGCTCTGGGGGCCGTGGCTTGTGCCATGG  420
 11   S  V  A  L  W  L  S  W  G  A  A  L  G  A  V  A  C  A  M  A   30

421  CTCTGCTGACCCAACAAACAGAGCTGCAGAGCCTCAGGAGAGAGGTGAGCCGGCTGCAGA  480
 31   L  L  T  Q  Q  T  E  L  Q  S  L  R  R  E  V  S  R  L  Q  R   50
                                    CD-I
481  GGACAGGAGGCCCCTCCCAGAATGCGGAAGGGTATCCCTGGCAGAGTCTCCCGGAGCACA  540
 51   T  G  G  P  S  Q  N  G  E  Y  P  W  Q  S  L  P  E  Q  S      70

541  GTTCCGATGCCCTGGAAGCCTGGGAGAATGGGGAGAGATCCCGGAAAAGGAGAGCAGTGC  600
 71   S  D  A  L  E  A  W  E  N  G  E  R  S  R  K  R  R  A  V  L   90
                                    CD-II
601  TCACCCAAAAACAGAAGAAGCAGCACTCTGTCCTGCACCTGGTTCCCATTAACGCCACCT  660
 91   T  Q  K  Q  K  K  Q  H  S  V  L  H  L  V  P  I  N  A  T  S  110
                     CD-III                              CD-IV
661  CCAAGGATGACTCCGATGTGACAGAGGTCATGTGGCAACCAGCTCTTAGGCGTGGGAGAG  720
111   K  D  D  S  D  V  T  E  V  M  W  Q  P  A  L  R  R  G  R  G  130
          CD-IV                                         CD-V
721  GCCTACAGGCCCAAGGATATGGTGTCCGAATCCAGGATGCTGGAGTTTATCTGCTGTATA  780
131   L  Q  A  Q  G  Y  G  V  R  I  Q  D  A  G  V  Y  L  L  Y  S  150
```

FIG. 1A

```
              CD-V .           .           .           .       .   CD-VI  .
 781  GCCAGGTCCTGTTTCAAGACGTGACTTTCACCATGGGTCAGGTGGTGTCTCGAGAAGGCC  840
 151   Q   V   L   F   Q   D   V   T   F   T   M   G   Q   V   V   S   R   E   G   Q   170
                 CD-VI                    .   CD-VII .           .           .
 841  AAGGAAGGCAGGAGACTCTATTCCGATGTATAAGAAGTATGCCCTCCCACCCGGACCGGG  900
 171   G   R   Q   E   T   L   F   R   C   I   R   S   M   P   S   H   P   D   R   A   190
           CD-VIII   .           .           CD-IX  .           .
 901  CCTACAACAGCTGCTATAGCGCAGGTGTCTTCCATTTACACCAAGGGGATATTCTGAGTG  960
 191   Y   N   S   C   Y   S   A   G   V   F   H   L   H   Q   G   D   I   L   S   V   210
               .   CD-X  .           #           .           .   CD-XI
 961  TCATAATTCCCCGGGCAAGGGCGAAACTTAACCTCTCTCCACATGGAACCTTCCTGGGGT  1020
 211   I   I   P   R   A   R   A   K   L   N   L   S   P   H   G   T   F   L   G   F   230
      CD-XI .           .           .           .           .
1021  TTGTGAAACTGTGATTGTGTTATAAAAAGTGGCTCCCAGCTTGGAAGACCAGGGTGGGTA  1080
 231   V   K   L                                                           234

1081  CATACTGGAGACAGCCAAGAGCTGAGTATATAAAGGAGAGGGAATGTGCAGGAACAGAGG  1140

1141  CGTCTTCCTGGGTTTGGCTCCCCGTTCCTCACTTTTCCCTTTTCATTCCCACCCCCTAGA  1200

1201  CTTTGATTTTACGGATATCTTGCTTCTGTTCCCCATGGAGCTCCGAATTCTTGCGTGTGT  1260

1261  GTAGATGAGGGGCGGGGACGGGCGCCAGGCATTGTCCAGACCTGGTCGGGGCCCACTGG   1320

1321  AAGCATCCAGAACAGCACCACCATCTAGCGGCCGCTCTAGAGGATCCCTCGAGGGGCCCA  1380

1381  AGCTTACGCGTGCATGCGACGTCATAGCTCTCTCCCTATAGTGAGTCGTATTATAAGCTA  1440

1441  GCTTGGGATCTTTGTGAAGGAACCTTACTTCTGTGGTGTGACATAATTGGACAAACTACC  1500

1501  TACAGAGATTTAAAGCTCTAAGGTAAATATAAAATTTTTAAGTGTATAATGTGTTAAACT  1560

1561  AGCTGCATATGCTTGCTGCTTGAGAGTTTGGCTTACTGAGTATGATTATGAAAATATTAT  1620

1621  ACACAGGAGCTAGTGATCTATGTTGGTTTTAGATCAAGCCAAGGTCATTCAGGCCTCAGC  1680

1681  TCAAGCTGTCATGATCATATCAGCATACAATTGTGAG  1717
```

FIG. 1B

```
                                        CD-I
  1  GGGGACAGGAGGCCCCTCCCAGAATGGGGAAGGGTATCCCTGGCAGAGTCTCCCGGAGCA    60
  1  G  T  G  G  P  S  Q  N  G  E  G  Y  P  W  Q  S  L  P  E  Q     20
                                                     ‾  ‾  ‾  ‾  ‾  ‾  ‾  ‾  ‾  ‾  ‾  ‾

61  GAGTTCCGATGCCCTGGAAGCCTGGGAGAGTGGGGAGAGATCCCGGAAAAGGAGAGCAGT   120
 21  S  S  D  A  L  E  A  W  E  S  G  E  R  S  R  K  R  R  A  V    40

#           . CD-III .
121  GCTCACCCAAAAACAGAAGAATGACTCCGATGTGACAGAGGTGATGTGGCAACCAGCTCT   180
 41  L  T  Q  K  Q  K  N  D  S  D  V  T  E  V  M  W  Q  P  A  L    60
                       ‾  ‾  ‾  ‾  ‾  ‾  ‾  ‾  ‾  ‾  ‾

CD-IV                              CD-V.
181  TAGGCGTGGGAGAGGCCTACAGGCCCAAGGATATGGTGTCCGAATCCAGGATGCTGGAGT   240
 61  R  R  G  R  G  L  Q  A  Q  G  Y  G  V  R  I  Q  D  A  G  V    80
                                         ‾‾ ‾‾ ‾‾ ‾‾ ‾‾ ‾‾ ‾‾ ‾‾

. CD-V  .
241  TTATCTCCTGTATAGCCAGGTCCTGTTTCAAGACGTGACTTTCACCATGGGTCAGGTGGT   300
 81  Y  L  L  Y  S  Q  V  L  F  Q  D  V  T  F  T  M  G  Q  V  V   100
     ‾‾ ‾‾ ‾‾ ‾‾ ‾‾ ‾‾ ‾‾ ‾‾ ‾‾

. CD-VI .              .        CD-VII
301  GTCTCGAGAAGGCCAAGGAAGGCAGGAGACTCTATTCCGATGTATAAGAAGTATGCCCTC   360
101  S  R  E  G  Q  G  R  Q  E  T  L  F  R  C  I  R  S  M  P  S   120
     ‾  ‾  ‾  ‾  ‾  ‾  ‾  ‾  ‾  ‾              ‾  ‾  ‾  ‾  ‾

CD-VIII   .        .  CD-IX
361  CCACCCGGACCGGGCCTACAACAGCTGCTATAGCGCAGGTGTCTTCCATTTACACCAAGG   420
121  H  P  D  R  A  Y  N  S  C  Y  S  A  G  V  F  H  L  H  Q  G   140
                    ‾  ‾  ‾  ‾  ‾  ‾  ‾  ‾  ‾  ‾  ‾  ‾  ‾  ‾  ‾

CD-IX .              .     CD-X     .    #
421  GGATATTCTGAGTGTCATAATTCCCCGGGCAAGGGCGAAACTTAACCTCTCTCCACATGG   480
141  D  I  L  S  V  I  I  P  R  A  R  A  K  L  N  L  S  P  H  G   160
     ‾  ‾  ‾  ‾  ‾  ‾  ‾  ‾  ‾  ‾  ‾  ‾  ‾  ‾

CD-XI.
481  AACCTTCCTGGGGTTTGTGAAACTGTGATTGTGTTATAAAAAGTGGCTCCCAGCTTGGAA   540
161  T  F  L  G  F  V  K  L                                        168
           ‾  ‾  ‾  ‾  ‾  ‾

541  GACCAGGGTGGGTACATACTGGAGACAGCCAAGAGCTGAGTATATAAACGAGAGGGAATG   600
```

FIG. 2A

```
601  TGCAGGAACAGAGCCGTCTTCCTGGGTTTGGCTCCCCGTTCCTCACTTTTCCCTTTTCAT  660

661  TCCCACCCCCTAGACTTTGGATTTTACGGATATCTTGCTTCTGTTCCCCATGGAGCTCCG  720

721  AATTCTTGCGTGTGTGTAGATGAGCGGCGGGGACGGGCGCCAGGCATTGTTCAGACCTG   780

781  GTCGGGGCCCACTGGAAGCATCCAGAACAGCACCACCATCTAGCGGCGCTCGAGGGAAGC 840

841  ACCGCGGGTTGGCCGAAGTCCACGAAGCCGCCTCTGCTAGGGAAAACCCTGGTTCTCCAT 900

901  GCCACAACTCTCTCCAGGGTGGCCTCTGCCTCTTCAACCCCACAAAGAAGCCTTAACCTA 960

961  CGTCCTTCTCTCCATCTATCGGACCCCAGTTTCCATCACTATCTCCAGAGATGTAGCTAT 1020

1021 TATGCGCCCGTCTACAGGGGGTGCCCGACCATGACGGTGCCTTCGCAGTCAAATTACTCT 1080

1081 TCGGGTCCCAAGGTTTGGCTTTCACGCGCTCCATTGCCCCGGCGTGGCAGGCCATTCCAA 1140

1141 GCCCTTCCGGGCTGGAACTGGTGTCGGAGGAGCCTCGGGTGTATCGTACGCCCTGGTGTT 1200

1201 GGTGTTGCCTCACTCCTCTGAGCTCTTCTTTCTGATCAAGCCCTGCTTAAAGTTAAATAA 1260

1261 AATAGAATGAATGATAAAAAA 1281
```

Alignment Report of TNF-α, TNF-β, TNF-δ and TNF-ε
by Clustal Method with PAM250 Residue Weight Table

```
  1  MSTESMIRDVELAEEALPKTCGPQGSRRC----LFLSLFSFLIVAGATTLFCLLHFGVIGPQREESPRDLSL  TNFalpha
  1  MTPPERLF-------LPRVCGTT----------LHLTILGLIHV------LT-----EGAQGLP-GVGL    TNFbeta
  1  MGGPVREPALSV---AIWLSWCAALCAVACAMAI LTQQTELQSLRREVSRIQRICGPSQNGEGYPWQ-SL   TNFdelta
  1  G----------------------------------------------------ICGPSQNGEGYPWQ-SL  TNFepsilon 70  TSPLAQAV-------RSSSRI-----PSDK---PVAHVVA-------NPQAEGQLOWLN----RRANALLANGV  TNFalpha
 41  TPSAAQTA-------RQHPKMHLAISTTK----EAAL-LIG------LESKQNSILLWRA---NTDRAFLQLGF  TNFbeta
 67  PEQSSDALEAWENGERSRKRRAVLTQKQKKQHSVIHI VPINATSKDDSDVTEVMWQPAI RRGRGICAAGY    TNFdelta
 18  PEQSSDALEAWESGERSKRRAVLTQKQK------------NDSDVTEVMWQPAI RRGRGICAAGY         TNFepsilon 118  ELRDNQLVVPSEGLYLIYSQVLFKGQGC----PSTHVLLTHTISRIAVSYQTKVNLLSAIKSPCQRETPE     TNFalpha
 93  SLSNNSLLVPTSGIYFVYSQVVFSGKAYSPKAPSSPLYLAHEVQLFSSQYPFHVPLLSSQKMVYP----      TNFbeta
137  GVR--------IQDAGVYLLYSQVLFQDVTFT-----------MGQVVSREGQG---RQETLFR----CIRSMPS  TNFdelta
 72  GVR--------IQDAGVYLLYSQVLFQDVTFT-----------MGQVVSREGQG---RQETLFR----CIRSMPS  TNFepsilon 184  GAEAKPWYEPTYLGGVFQLEKGDRLSAETNRPDYLDFAESGQVYFGLTAT                         TNFalpha
158  -GLQEPWLHSMYHCAAFQITQGDQLSTHTDGI PHLVLS-PSTVFFGAFAL                        TNFbeta
186  HPDRA--YNSCYSAGVFHLHQGDI LSVIFRARAKLNLSPHGTFLGFVK-L                        TNFdelta
121  HPDRA--VNSCYSAGVFHLHQGDI LSVIFRARAKLNLSPHGTFLGFVKL.                        TNFepsilon
```

Decoration '': Shade (with solid black) residues that match TNFalpha exactly.

```
  1 ACCTCTGTCCTTAGAGGGGACTGGAACCTAATTCTCCTGAGCCTGAGGGAGGGTGGAGGG    60

61 TCTCAAGACAACGCTGTCCCCACGACGGAGTGCCAGGAGCACTAACAGTACCCTTAGATT   120

121 GCTTTCCTCCTCCCTCCTTTTTTATTTTCAAGTTCCTTTTTATTTCTCCTTGCGTAACAA   180

181 CCTTCTTCCCTTCTGCACCACTGCCCGTACCCTTACCCGCGCCGCCACCTCCTTGCTACA   240

241 CCACTCTTGAAACCACAGCTGTTGGCAGGGTCCCCCAGCTCATGCCAGCCTCATCTCCTT   300
  1                                               M  P  A  S  S  P  F    7

301 TCTTGCTAGCCCCCAAAGGGCCTCCAGGCAACATGGGGGCCCAGTCAGAGAGCCGGCAC   360
  8  L  L  A  P  K  G  P  P  G  N  M  G  G  P  V  R  E  P  A  L   27

361 TCTCAGTTGCCCTCTGGTTGAGTTGGGGGGCAGCTCTGGGGGCCGTGGCTTGTGCCATGG   420
 28  S  V  A  L  W  L  S  W  G  A  A  L  G  A  V  A  C  A  M  A   47

421 CTCTGCTGACCCAACAAACAGAGCTGCAGAGCCTCAGGAGAGAGGTGAGCCGGCTGCAGA   480
 48  L  L  T  Q  Q  T  E  L  Q  S  L  R  R  E  V  S  R  L  Q  R   67
                                        CD-I

481 GGACAGGAGGCCCCTCCCAGAATGGGGAAGGGTATCCCTGGCAGAGTCTCCCGGAGCAGA   540
 68  T  G  G  P  S  Q  N  G  E  G  Y  P  W  Q  S  L  P  E  Q  S   87

541 GTTCCGATGCCCTGGAAGCCTGGGAGAATGGGGAGAGATCCCGGAAAAGGAGAGCAGTGC   600
 88  S  D  A  L  E  A  W  E  N  G  E  R  S  R  K  R  R  A  V  L  107
                        CD-II

601 TCACCCAAAAACAGAAGAAGCAGCACTCTGTCCTGCACCTGGTTCCCATTAACGCCACCT   660
108  T  Q  K  Q  K  K  Q  H  S  V  L  H  L  V  P  I  N  A  T  S  127
              CD-III                               CD-IV

661 CCAAGGATGACTCCGATGTGACAGAGGTGATGTGGCAACCAGCTCTTAGGCGTGGGAGAG   720
128  K  D  D  S  D  V  T  E  V  M  W  Q  P  A  L  R  R  G  R  G  147
        CD-IV                                    CD-V

721 GCCTACAGGCCCAAGGATATGGTGTCCGAATCCAGGATGCTGGAGTTTATCTGCTGTATA   780
148  L  Q  A  Q  G  Y  G  V  R  I  Q  D  A  G  V  Y  L  L  Y  S  167
```

FIG. 6A

```
              CD-V .                                        .     CD-VI .
 781 GCCAGGTCCTGTTTCAAGACGTGACTTTCACCATGGGTCAGGTGGTGTCTCGAGAAGGCC  840
 168    Q   V   L   F   Q   D   V   T   F   T   M   G   Q   V   V   S   R   E   G   Q   187

CD-VI
 841 AAGGAAGGCAGGAGACTCTATTCCGATGTATAAGAAGTATGCCCTCCCACCCGGACCGGG  900
 188    G   R   Q   E   T   L   F   R   C   I   R   S   M   P   S   H   P   D   R   A   207
           CD-VIII                 .          CD-IX
 901 CCTACAACAGCTGCTATAGCGCACGTGTCTTCCATTTACACCAAGGGATATTCTGAGTG  960
 208    Y   N   S   C   Y   S   A   G   V   F   H   L   H   Q   G   D   I   L   S   V   227
              CD-X .              #                              CD-XI
 961 TCATAATTCCCCGGGCAAGGGCGAAACTTAACCTCTCTCCACATGGAACCTTCCTGGGGT 1020
 228    I   I   P   R   A   R   A   K   L   N   L   S   P   H   G   T   F   L   G   F   247
        CD-XI .
1021 TTGTGAAACTGTGATTGTGTTATAAAAAGTGGCTCCCAGCTTGGAAGACCAGGGTGGGTA 1080
 248    V   K   L                                                                         250

1081 CATACTGGAGACAGCCAAGAGCTGAGTATATAAAGGAGAGGGAATGTGCAGGAACAGAGG 1140

1141 CGTCTTCCTGGGTTTGGCTCCCCGTTCCTCACTTTTCCCTTTTCATTCCCACCCCCTAGA 1200

1201 CTTTGATTTTACGGATATCTTGCTTCTGTTCCCCATGGAGCTCCGAATTCTTGCGTGTGT 1260

1261 GTAGATGAGGGGCGGGGGACGGGCGCCAGGCATTGTCCAGACCTGGTCGGGGCCCACTGG 1320

1321 AAGCATCCAGAACAGCACCACCATCTAGCGGCCGCTCTAGAGGATCCCTCGAGGGGCCCA 1380

1381 AGCTTACGCGTGCATGCGACGTCATAGCTCTCTCCCTATAGTGAGTCGTATTATAAGCTA 1440

1441 GCTTGGGATCTTTGTGAAGGAACCTTACTTCTGTGGTGTGACATAATTGGACAAACTACC 1500

1501 TACAGAGATTTAAAGCTCTAAGGTAAATATAAAATTTTTAAGTGTATAATGTGTTAAACT 1560

1561 AGCTGCATATGCTTGCTGCTTGAGAGTTTGGCTTACTGAGTATGATTATGAAAATATTAT 1620

1621 ACACAGGAGCTAGTGATCTATGTTGGTTTTAGATCAAGCCAAGGTCATTCAGGCCTCAGC 1680

1681 TCAAGCTGTCATGATCATATCAGCATACAATTGTGAG 1717
```

FIG. 6B

```
  1 CCCACCCGTCCGCCCACGCGTCCGCCACTGCCCGTACCCTTACCCGCCCCGCCACCTACT  60

61 TGCTACCCCACTCTTGAAACCACAGCTGTTGGCAGGGTCCCCAGCTCATGCCAGCCTCAT 120
  1                                               M  P  A  S  S   5

121 CTCCTTTCTTGCTAGCCCCCAAAGGGCCTCCAGGCAACATGGGGGGCCCAGTCAGAGAGC 180
  6  P  F  L  L  A  P  K  G  P  P  G  N  M  G  G  P  V  R  E  P  25

181 CGGCACTCTCAGTTGCCCTCTGGTTGAGTTGGGGGGCAGCTCTGGGGGCCGTGGCTTGTG 240
 26  A  L  S  V  A  L  W  L  S  W  G  A  A  L  G  A  V  A  C  A  45

241 CCATGGCTCTGCTGACCCAACAAACAGAGCTGCAGAGCCTCAGGAGAGAGGTGAGCCGGC 300
 46  M  A  L  L  T  Q  Q  T  E  L  Q  S  L  R  R  E  V  S  R  L  65

. CD-I .
301 TGCAGAGGACAGGAGGCCCCTCCCAGAATGGGGAAGGGTATCCCTGGCAGAGTCTCCCGG 360
 66  Q  R  T  G  G  P  S  Q  N  G  E  G  Y  P  W  Q  S  L  P  E  85

361 AGCAGAGTTCCGATGCCCTGGAAGCCTGGGAGAGTGGGGAGAGATCCCGGAAAAGGAGAG 420
 86  Q  S  S  D  A  L  E  A  W  E  S  G  E  R  S  R  K  R  A  105

#       CD-III
421 CAGTGCTCACCCAAAAACAGAAGAATGACTCCGATGTGACAGAGGTGATGTGGCAACCAG 480
106  V  L  T  Q  K  Q  K  N  D  S  D  V  T  E  V  M  W  Q  P  A  125

. CD-IV .                         CD-V
481 CTCTTAGGCGTGGGAGAGGCCTACAGGCCCAAGGATATGGTGTCCGAATCCAGGATGCTG 540
126  L  R  R  G  R  G  L  Q  A  Q  G  Y  G  V  R  I  Q  D  A  G  145
```

FIG. 7A

```
               CD-V       .           .           .           .
541  GAGTTTATCTGCTGTATAGCCAGGTCCTGTTTCAAGACGTGACTTTCACCATGGGTCAGG  600
146    V  Y  L  L  Y  S  Q  V  L  F  Q  D  V  T  F  T  M  G  Q  V  165

CD-VI          .          .  CD-VII   .
601  TGGTGTCTCGAGAAGGCCAAGGAAGGCAGGAGACTCTATTCCGATGTATAAGAAGTATGC  660
166    V  S  R  E  G  Q  G  R  Q  E  T  L  F  R  C  I  R  S  M  P  185

.            .      CD-VIII      .       .CD-IX      .
661  CCTCCCACCCGGACCGGGCCTACAACAGCTGCTATAGCGCAGGTGTCTTCCATTTACACC  720
186    S  H  P  D  R  A  Y  N  S  C  Y  S  A  G  V  F  H  L  H  Q  205

CD-IX          .           .   CD-X     .       # .
721  AAGGGGATATTCTGAGTGTCATAATTCCCCGGGCAAGGGCGAAACTTAACCTCTCTCCAC  780
206    G  D  I  L  S  V  I  I  P  R  A  R  A  K  L  N  L  S  P  H  225

.       CD-XI        .           .           .
781  ATGGAACCTTCCTGGGGTTTGTGAAACTGTCATTGTGTTATAAAAAGTGGCTCCCAGCTT  840
226    G  T  F  L  G  F  V  K  L                                   235

841  GGAAGACCAGGGTGGGTACATACTGGAGACAGCCAAGAGCTGAGTATATAAAGGAGAGGG  900

901  AATGTGCAGGAACAGAGGCGTCTTCCTGGGTTTGGCTCCCCGTTCCTCACTTTTCCCTTT  960

961  TCATTCCCACCCCCTAGACTTTGATTTTACGGATATCTTGCTTCTGTTCCCCATGGAGCT  1020

1021 CCGAATTCTTGCGTGTGTGTAGATGAGGGGCGGGGGGACGGGCGCCAGGCATTGTTCAGA  1080

1081 CCTGGTCGGGGCCCACTGGAAGCATCCAGAACAGCACCACCATCTA  1126

FIG. 7B
```

TUMOR NECROSIS FACTOR DELTA POLYPEPTIDES

RELATED APPLICATIONS

This application claims benefit of priority under 35 U.S.C. § 119(e) based on the following U.S. Provisional Patent Application Ser. Nos.: 60/293,499, filed May 25, 2001; 60/277,978 filed Mar. 23, 2001; 60/276,248, filed Mar. 16, 2001; 60/254,875 filed Dec. 13, 2000; 60/241,952 filed Oct. 23, 2000; and 60/211,537 filed Jun. 15, 2000. This application is also a continuation-in-part of copending application Ser. No. 08/815,783, filed Mar. 12, 1997, which claims the benefit of priority under 35 U.S.C. § 119(e) based on the U.S. Provisional Patent Application Ser. No. 60/016,812 filed Mar. 14, 1996. Each of the foregoing provisional and non-provisional applications is hereby incorporated by refrence in its entirety.

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human tumor necrosis factor delta and epsilon, sometimes hereinafter referred to as "TNF delta" and "TNF epsilon".

BACKGROUND OF THE INVENTION

Human tumor necrosis factors alpha (TNF-alpha) and beta (TNF-beta or lymphotoxin) are related members of a broad class of polypeptide mediators, which includes the interferons, interleukins and growth factors, collectively called cytokines (Beutler, B. and Cerami, A., *Annu. Rev. Immunol.*, 7:625–655, 1989).

Tumor necrosis factor (TNF-alpha and TNF-beta) was originally discovered as a result of its anti-tumor activity, however, now it is recognized as a pleiotropic cytokine capable of numerous biological activities including apoptosis of some transformed cell lines, mediation of cell activation and proliferation and also as playing important roles in immune regulation and inflammation.

To date, there are nine known members of the TNF-ligand superfamily, TNF-alpha, TNF-beta (lymphatoxin-alpha), LT-beta, OX40L, FASL, CD30L, CD27L, CD40L and 4-1BBL. The ligands of the TNF ligand superfamily are acidic, TNF-like molecules with approximately 20% sequence homology in the extracellular domains (range, 12%-36%) and exist mainly as membrane-bound forms with the biologically active form being a trimeric/multimeric complex. Soluble forms of the TNF ligand superfamily have only been identified so far for TNF, LT-alpha, and FasL (for a general review, see Gruss, H. and Dower, S. K., *Blood,* 85 (12):3378–3404 (1995)), which is hereby incorporated by reference in its entirety.

These proteins are involved in regulation of cell proliferation, activation, and differentiation, including control of cell survival or death by apoptosis or cytotoxicity (Armitage, R. J., *Curr. Opin. Immunol.,* 6:407 (1994) and Smith, C. A., *Cell,* 75:959 1994).

TNF is produced by a number of cell types, including monocytes, fibroblasts, T cells, natural killer (NK) cells and predominately by activated machrophages. TNF-alpha has been reported to have a role in the rapid necrosis of tumors, immunostimulation, autoimmune disease, graft rejection, resistance to parasites, producing an anti-viral response, septic shock, growth regulation, vascular endothelium effects and metabolic effects. TNF-alpha also triggers endothelial cells to secrete various factors, including PAF-1, IL-1, GM-CSF and IL-6 to promote cell proliferation. In addition, TNF-alpha up-regulates various cell adhesion molecules such as E-Selectin, ICAM-1 and VCAM-1.

The first step in the induction of the various cellular responses mediated by the members of the TNF ligand superfamily is their binding to specific cell surface receptors. The TNF receptor superfamily contains at present ten known membrane proteins and several viral open reading frames encoding TNFR-related molecules. The p75 low-affinity Nerve Growth Factor (NGF) receptor was the first cloned receptor of this family (Johnson, D. et al. *Cell,* 47:545 (1986). Subsequently, cloning of two specific receptors for TNF show that they were related to the NGF receptor (Loetscher, H. et al., *Cell,* 61:351 (1990)). In recent years, a new type I-transmembrane TNF receptor superfamily has been established. This family includes the p75 nerve growth factor receptor, p60 TNFR-I, p80 TNFR-II, TNFR-RP/TNFR-II, CD27, CD30, CD40, 4-IBB, OX40 and FAS/APO-1. In addition, several viral open reading frames encoding soluble TNF receptors have been identified, such as SFV-T2 in Shope fibroma virus (Smith, C. A. et al., *Biochem. Biophys. Res. Commun.,* 176:335, 1991) and Va53 or SaIF19R in vaccinia virus (Howard, S. T., *Virology,* 180:633, 1991). These receptors are characterized by multiple cysteine-rich domains in the extracellular (aminoterminal) domain, which have been shown to be involved in ligand binding. The average homology in the cysteine-rich extracellular region between the human family members are in the range of 25 to 30%.

Inflammation, which is characterized by redness, swelling, heat, and pain, is an essential immune response which occurs following tissue injury or infection. The initial event triggers an elaborate signaling cascade which results in increased local blood flow, blood clotting, and vascular permeability. These acute changes facilitate the recruitment of phagocytic leukocytes to the site of injury or infection. Once at the affected site, the immune cells can begin to neutralize pathogens and contribute to tissue repair.

Among the many protein classes involved in the inflammatory response are blood clotting factors, vasodilating substances (such as histamine and bradykinin), cell adhesion molecules, cytokines (such as interleukins and chemokines), and immune system effector cells (such as neutrophils, macrophages, and lymphocytes).

Although the inflammatory response is an important defense mechanism against infection by foreign substances, inappropriate or excessive activation of inflammation can lead to tissue damage and even death. Medical conditions resulting from inflammation include, but are not limited to, inflammatory bowel disease, multiple sclerosis, arthritis, asthma, allergies, sarcoidosis, septic shock, gastrointestinal cancers, pancreatitis, dermatitis, gout, systemic lupus erythematosis, and Grave's disease. Inflammation is also a potentially life-threatening complication of cardiopulmonary bypass surgery, renal ischemia-reperfusion, and traumatic injury.

Several steroidal and nonsteroidal drugs have been used to control inflammation or to provide symptomatic relief. However, these therapies can be accompanied by numerous side effects which limit their usefulness. Therefore, there is a continuing need for more effective and less toxic alternatives for modulating the inflammatory response.

Clearly, there is also a need for factors that regulate activation, and differentiation of normal and abnormal cells. There is a need, therefore, for identification and characterization of such factors that modulate activation and differentiation of cells, both normally and in disease states. In particular, there is a need to isolate and characterize additional TNF ligands akin to members of the TNF ligand super-family that control apoptosis of transformed cell lines, mediate cell activation and proliferation and are functionally linked as primary mediators of immune regulation and inflammatory response, and, among other things, can play a role in preventing, ameliorating or correcting dysfunctions or diseases.

SUMMARY OF THE INVENTION

Toward these ends, and others, it is an object of the present invention to provide novel polypeptides, referred to as novel TNF delta and TNF epsilon which have been putatively identified as being tumor necrosis factor ligands by homology between the amino acid sequence set out in FIGS. 1A and 1B and 2A and 2B and known amino acid sequences of other proteins in the tumor necrosis factor family such as human TNF-alpha and TNF-beta.

The polypeptides of the present invention have been identified as a novel members of the TNF ligand super-family based on structural and biological similarities.

It is a further object of the invention, moreover, to provide polynucleotides that encode TNF delta and TNF epsilon, particularly polynucleotides that encode the polypeptide herein designated TNF delta and TNF epsilon.

In a particularly preferred embodiment of this aspect of the invention the polynucleotides comprise the region encoding human TNF delta and TNF epsilon in the sequences set out in FIGS. 1A and 1B, 2A and 2B, 6A and 6B and 7A and 7B.

In accordance with this aspect of the invention there are provided isolated nucleic acid molecules encoding human TNF delta, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human TNF delta and TNF epsilon.

In accordance with this aspect of the present invention there are provided isolated nucleic acid molecules encoding a mature human TNF delta polypeptide expressed by the human cDNA contained in ATCC Deposit No. 97377 deposited on Dec. 8, 1995 and a mature human TNF epsilon polypeptide expressed by the human cDNA contained in ATCC Deposit No. 97457 deposited on on Mar. 1, 1996, or a human TNF epsilon polypeptide expressed by the human cDNA corresponding to clone HADCA12 (SEQ ID NO:13) contained in the ATCC Deposit No. PTA-1543 of pooled plasmids deposited on Mar. 21, 2000. It is possible to retrieve a given cDNA clone from a pooled plasmid deposit by techniques known in the art and described elsewhere herein. The ATCC is located at 10801 University Boulevard, Manassas, Va. 20110-2209, USA. The ATCC deposits were made pursuant to the terms of the Budapest Treaty on the international recognition of the deposit of microorganisms for the purposes of patent procedure.

It also is an object of the invention to provide TNF delta polypeptides, particularly human TNF delta and TNF epsilon polypeptides, that destroy some transformed cell lines, mediate cell activation and proliferation and are functionally linked as primary mediators of immune regulation and inflammatory response.

In accordance with this aspect of the invention there are provided novel polypeptides of human origin referred to herein as TNF delta and TNF epsilon as well as biologically, diagnostically or therapeutically useful fragments, variants and derivatives thereof, variants and derivatives of the fragments, and analogs of the foregoing.

Among the particularly preferred embodiments of this aspect of the invention are variants of human TNF delta and TNF epsilon encoded by naturally occurring alleles of the human TNF delta and TNF epsilon gene.

It is another object of the invention to provide a process for producing the aforementioned polypeptides, polypeptide fragments, variants and derivatives, fragments of the variants and derivatives, and analogs of the foregoing.

In a preferred embodiment of this aspect of the invention there are provided methods for producing the aforementioned TNF delta and TNF epsilon polypeptides comprising culturing host cells having expressibly incorporated therein an exogenously-derived human TNF delta-encoding polynucleotide and TNF epsilon-encoding polynucleotide under conditions for expression of human TNF delta and TNF epsilon in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing TNF delta and TNF epsilon expression in cells by determining TNF delta and TNF epsilon polypeptides or TNF delta-encoding mRNA or TNF epsilon-encoding mRNA polypeptides; assaying genetic variation and aberrations, such as defects, in TNF delta and TNF epsilon genes; and administering a TNF delta or TNF epsilon polypeptide or polynucleotide to an organism to augment TNF delta or TNF epsilon function or remediate TNF delta or TNF epsilon dysfunction.

In accordance with certain preferred embodiments of this and other aspects of the invention there are provided polynucleotides and in particular probes that hybridize to human TNF delta or TNF epsilon sequences.

In certain additional preferred embodiments of this aspect of the invention there are provided antibodies against TNF delta or TNF epsilon polypeptides. In certain particularly preferred embodiments in this regard, the antibodies are highly selective for human TNF delta or TNF epsilon.

In accordance with another aspect of the present invention, there are provided TNF delta or TNF epsilon agonists. Among preferred agonists are molecules that mimic TNF delta or TNF epsilon, that bind to TNF delta-binding molecules or receptor molecules or to TNF epsilon-binding molecules or receptor molecules , and that elicit or augment TNF delta-induced or TNF epsilon-induced responses. Also among preferred agonists are molecules that interact with TNF delta and TNF epsilon or TNF delta and TNF epsilon polypeptides, or with other modulators of TNF delta activities, and thereby potentiate or augment an effect of TNF delta and TNF epsilon or more than one effect of TNF delta and TNF epsilon.

In accordance with yet another aspect of the present invention, there are provided TNF delta and TNF epsilon antagonists. Among preferred antagonists are those which mimic TNF delta and TNF epsilon so as to bind to TNF delta and TNF epsilon receptors or binding molecules but not elicit a TNF delta- and TNF epsilon-induced response or more than one TNF delta- and TNF epsilon-induced response. Also among preferred antagonists are molecules that bind to or interact with TNF delta and TNF epsilon so as to inhibit an effect of TNF delta and TNF epsilon or more than one effect of TNF delta and TNF epsilon or which prevent expression of TNF delta and TNF epsilon.

The agonists and antagonists may be used to mimic, augment or inhibit the action of TNF delta and TNF epsilon polypeptides. They may be used, for instance, to prevent septic shock, inflammation, cerebral malaria, activation of the HIV virus, graft-host rejection, bone resorption, rheumatoid arthritis and cachexia.

In a further aspect of the invention there are provided compositions comprising a TNF delta and TNF epsilon polynucleotide or a TNF delta and TNF epsilon polypeptide for administration to cells in vitro, to cells ex vivo and to cells in vivo, or to a multicellular organism. In certain particularly preferred embodiments of this aspect of the invention, the compositions comprise a TNF delta and TNF epsilon polynucleotide for expression of a TNF delta and TNF epsilon polypeptide in a host organism for treatment of disease. Particularly preferred in this regard is expression in a human patient for treatment of a dysfunction associated with aberrant endogenous activity of TNF delta and TNF epsilon.

Polynucleotides and/or polypeptides of the invention and/or agonists and/or antagonists thereof are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.))), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, wound healing (e.g., wounds, burns, and bone fractures).

Polynucleotides and/or polypeptides of the invention and/or agonists and/or antagonists thereof are also useful as an adjuvant to enhance immune responsiveness to specific antigen, anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1A and 1B show the nucleotide (SEQ ID NO:1) and deduced amino acid (SEQ ID NO:2) sequence of human TNF delta. A TNF family signature sequence is found at positions Val-138 through Phe-154 in the TNF-delta amino acid sequence shown in FIGS. 1A and 1B. See, Peitsch M. C., et al., *Int. Immunol.* 5:233–38 (1993); Farrah T., et al, *Nature* 358:26 (1992); Bazan J. F., *Curr. Biol.* 3:603–606 (1993). The sequence is marked in the Figures with a double underline under the corresponding amino acids.

A potential asparagine-linked glycosylation site is marked in FIGS. 1A and 1B with a bolded asparagine symbol (N) in the TNF-delta amino acid sequence and a bolded pound sign (#) above the first nucleotide encoding that asparagine residue in the TNF-delta nucleotide sequence. A potential N-linked glycosylation sequence is found at the following location in the TNF-delta amino acid sequence: N-220 through P-223 (N-220, L-221, S-222, and P-223).

Regions of high identity between TNF-delta, TNF-epsilon, TNF-alpha, and TNF-beta (an alignment of these sequences is presented in FIG. 3) are underlined in FIGS. 1A and 1B. These regions are not limiting and are labeled as Conserved Domain (CD)-I, CD-II, CD-III, CD-IV, CD-V, CD-VI, CD-VII, CD-VIII, CD-IX, CD-X, and CD-XI in FIGS. 1A and 1B.

FIGS. 2A and 2B show the nucleotide (SEQ ID NO:3) and deduced amino acid (SEQ ID NO:4) sequence of human TNF epsilon. A TNF family signature sequence is found at positions Val-73 through Phe-89 in the TNF-epsilon amino acid sequence shown in FIGS. 2A and 2B. See, Peitsch M. C., et al., *Int. Immunol.* 5:233–38 (1993); Farrah T., et al., *Nature* 358:26 (1992); Bazan J. F., *Curr. Biol.* 3:603–606 (1993). The sequence is marked in the Figures with a double underline under the corresponding amino acids.

Two potential asparagine-linked glycosylation sites are marked in FIGS. 2A and 2B with a bolded asparagine symbol (N) in the TNF-epsilon amino acid sequence and a bolded pound sign (#) above the first nucleotide encoding that asparagine residue in the TNF-epsilon nucleotide sequence. The potential N-linked glycosylation sequences are found at the following locations in the TNF-epsilon amino acid sequence: N-47 through D-50 (N-47, D-48, S-49, and D-50) and N-155 through P-158 (N-155, L-156, S-1 57, and P-158).

Regions of high identity between TNF-delta, TNF-epsilon, TNF-alpha, and TNF-beta (an alignment of these sequences is presented in FIG. 3) are underlined in FIGS. 2A and 2B. These regions are not limiting and are labeled as Conserved Domain (CD)-I, CD-III, CD-IV, CD-V, CD-VI, CD-VII, CD-VIII, CD-IX, CD-X, and CD-XI in FIGS. 2A and 2B.

FIG. 3 shows the regions of similarity (alignment report) between amino acid sequences of TNF alpha (SEQ ID NO:5; GenBank Accession No. Z15026), TNF beta (SEQ ID NO:6; GenBank Accession No. Z15026), TNF delta (SEQ ID NO:1), and TNF epsilon (SEQ ID NO:2), polypeptides.

Figure 4:
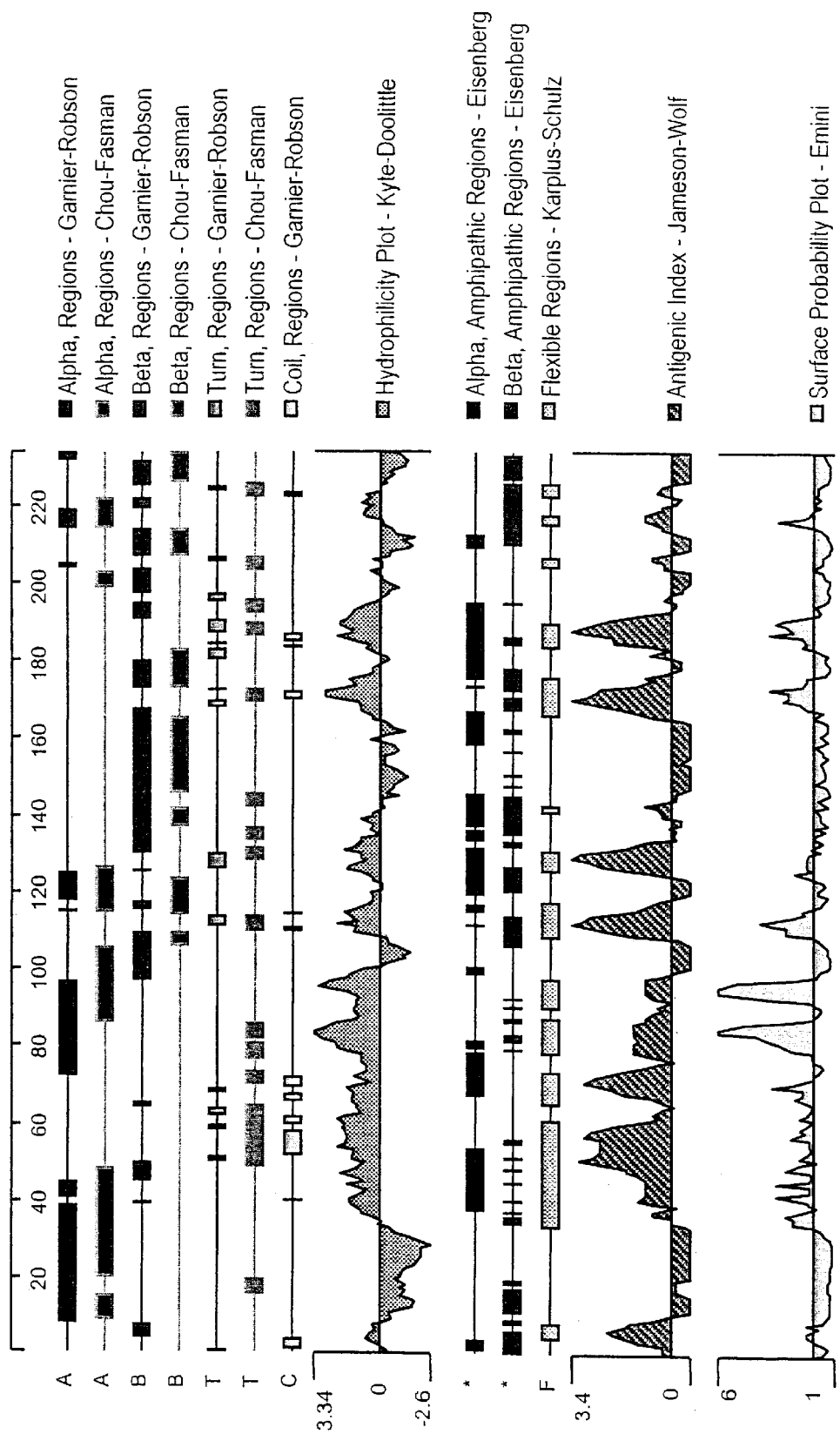

FIG. 4 shows structural and functional features of TNF delta deduced by the indicated techniques, as a function of amino acid sequence. Alpha, beta, turn and coil regions; hydrophilicity and hydrophobicity; amphipathic regions; flexible regions; antigenic index and surface probability are shown, as predicted for the amino acid sequence of SEQ ID NO:2 using the default parameters of the recited computer programs. In the "Antigenic Index—Jameson-Wolf" graph, the indicated location of the highly antigenic regions of the TNF-delta protein, i.e., regions from which epitope-bearing peptides of the invention may be obtained. The data shown in FIG. 4 can be easily represented in tabular format similar to the data shown in Table II. Such a tabular representation of the exact data disclosed in FIG. 4 can be generated using the MegAlign component of the DNA*STAR computer sequence analysis package set on default parameters.

Figure 5:
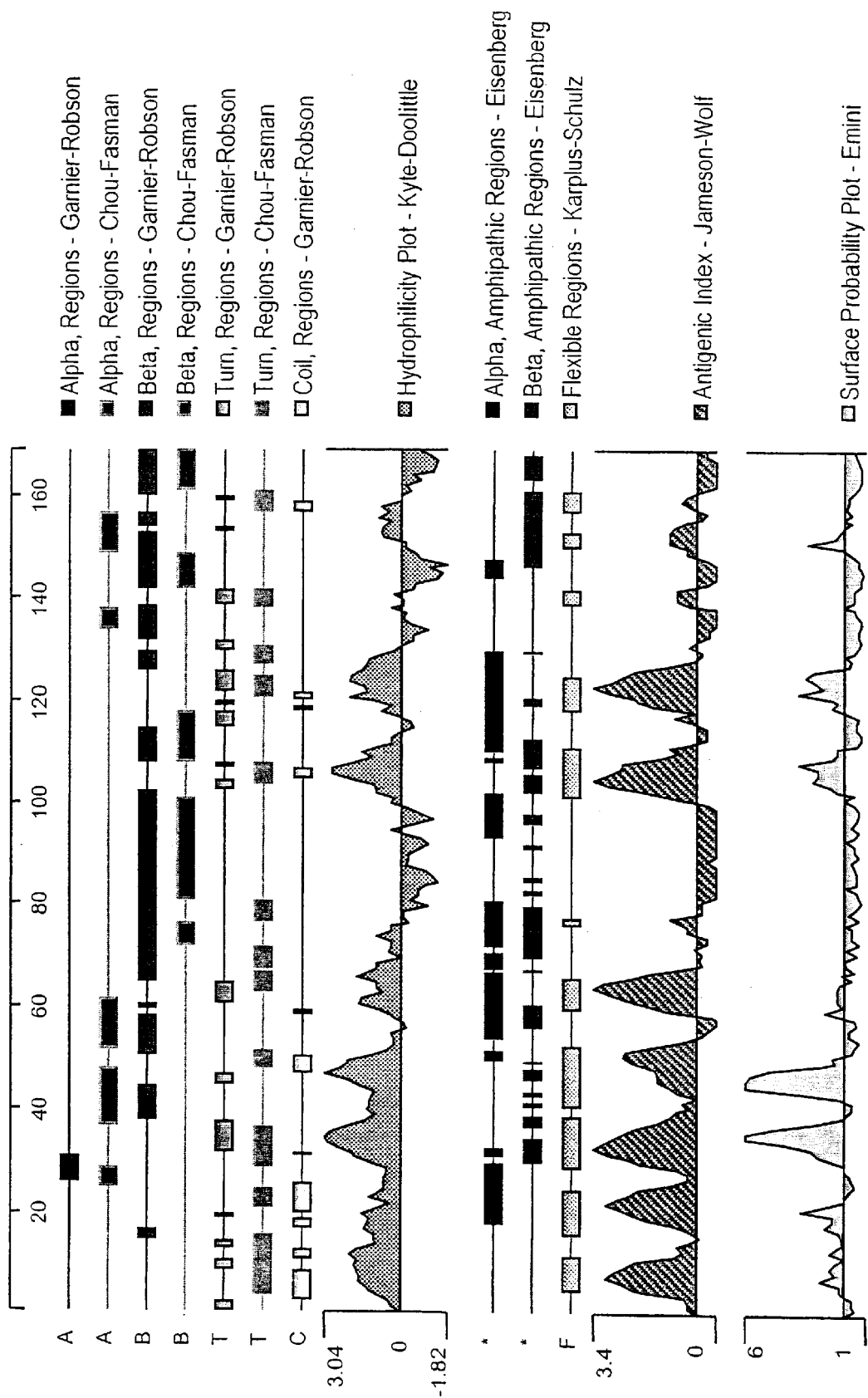

FIG. 5 shows structural and functional features of TNF epsilon deduced by the indicated techniques, as a function of amino acid sequence. Alpha, beta, turn and coil regions; hydrophilicity and hydrophobicity; amphipathic regions; flexible regions; antigenic index and surface probability are shown, as predicted for the amino acid sequence of SEQ ID NO:4 using the default parameters of the recited computer programs. In the "Antigenic Index—Jameson-Wolf" graph, the indicated location of the highly antigenic regions of the TNF-epsilon protein, i.e., regions from which epitope-bearing peptides of the invention may be obtained. The data shown in FIG. 5 can be easily represented in tabular format similar to the data shown in Table III. Such a tabular representation of the exact data disclosed in FIG. 5 can be generated using the MegAlign component of the DNA*STAR computer sequence analysis package set on default parameters.

FIGS. 6A and 6B show the nucleotide and deduced amino acid sequence of a longer open reading frame of human TNF delta obtained from the identical nucleotide sequence shown in FIGS. 1A and 1B (SEQ ID NOs: 1 and 2). The amino acid sequence shown in FIGS. 6A and 6B is also shown as SEQ ID NO: 11. A TNF family signature sequence is found at positions Val-155 through Phe-171 in the TNF-delta amino acid sequence shown in FIGS. 6A and 6B. See, Peitsch M. C., et al., *Int. Immunol.* 5:233–38 (1993); Farrah T., et al., *Nature* 358:26 (1992); Bazan J. F., *Curr. Biol.* 3:603–606 (1993). The sequence is marked in the Figures with a double underline under the corresponding amino acids.

A potential asparagine-linked glycosylation site is marked in FIGS. 6A and 6B with a bolded asparagine symbol (N) in the TNF-delta amino acid sequence and a bolded pound sign (#) above the first nucleotide encoding that asparagine residue in the TNF-delta nucleotide sequence. A potential N-linked glycosylation sequence is found at the following location in the TNF-delta amino acid sequence: N-237 through P-240 (N-237, L-238, S-239, and P-240).

Regions of high identity between TNF-delta, TNF-epsilon, TNF-alpha, and TNF-beta are underlined in FIGS. 6A and 6B. These regions are not limiting and are labeled as Conserved Domain (CD)-I, CD-II, CD-III, CD-IV, CD-V, CD-VI, CD-VII, CD-VIII, CD-IX, CD-X, and CD-XI in FIGS. 6A and 6B.

FIGS. 7A and 7B show the nucleotide and deduced amino acid sequence of a longer human TNF epsilon than that shown in FIGS. 2A and 2B (SEQ ID NOs:3 and 4). The nucleotide and amino acid sequences shown in FIGS. 7A and 7B are also shown as SEQ ID NO:12 and SEQ ID NO:13, respectively. A TNF family signature sequence is found at positions Val-139 through Phe-155 in the TNF-epsilon amino acid sequence shown in FIGS. 7A and 7B. See, Peitsch M. C., et al., *Int. Immunol.* 5:233–38 (1993); Farrah T., et al., *Nature* 358:26 (1992); Bazan J. F., *Curr. Biol.* 3:603–606(1993). The sequence is marked in the Figures with a double underline under the corresponding amino acids.

Two potential asparagine-linked glycosylation sites are marked in FIGS. 7A and 7B with a bolded asparagine symbol (N) in the TNF-epsilon amino acid sequence and a bolded pound sign (#) above the first nucleotide encoding that asparagine residue in the TNF-epsilon nucleotide sequence. The potential N-linked glycosylation sequences are found at the following locations in the TNF-epsilon amino acid sequence: N-1 13 through D-116 (N-113, D-114, S-115, and D-116) and N-221 through P-224 (N-221, L-222, S-223, and P-224).

Regions of high identity between TNF-delta, TNF-epsilon, TNF-alpha, and TNF-beta (an alignment of these sequences is presented in FIG. 3) are underlined in FIGS. 2A and 2B. These regions are not limiting and are labeled as Conserved Domain (CD)-I, CD-III, CD-IV, CD-V, CD-VI, CD-VII, CD-VIII, CD-IX, CD-X, and CD-XI in FIGS. 2A and 2B.

DETAILED DESCRIPTION OF THE INVENTION

The following illustrative explanations are provided to facilitate understanding of certain terms used frequently herein, particularly in the examples. The explanations are provided as a convenience and are not limitative of the invention.

The term "digestion" of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 microgram of plasmid or DNA fragment is digested with about 2 units of enzyme in about 20 microliters of reaction buffer. For the purpose of isolating DNA fragments for plasmid construction, typically 5 to 50 micrograms of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

The term "genetic element" generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. However, a nucleic acid molecule contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate (e.g., a "chromosome spread", as in a karyotype), is not "isolated" for the purposes of this invention. Moreover, a nucleic acid molecule contained in a preparation of mechanically or enzymatically cleaved genomic DNA is also not "isolated" for the purposes of this invention.

As part of or following isolation, such polynucleotides can be joined to other polynucleotides, for mutagenesis, to form fusion proteins, and for propagation or expression in a host, for instance. The isolated polynucleotides, alone or joined to other polynucleotides such as vectors, can be introduced into host cells, in culture or in whole organisms, after which such DNAs still would be isolated, as the term is used herein, because they would not be in their naturally occurring form or environment.

Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

The term "ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., Molecular Cloning, a Laboratory Manual, 2nd Ed.; Cold Spring Harbor Laboratory Press, Cold Spring Harbor, New York (1989) and Maniatis et al., pg. 146, as cited below.

The term "oligonucleotide(s)" refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

Plasmids generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "polynucleotide(s)" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

By a polynucleotide having a nucleotide sequence at least, for example, 95% "identical" to a reference nucleotide sequence encoding a TNF delta or TNF epsilon polypeptide is intended that the nucleotide sequence of the polynucleotide is identical to the reference sequence except that the polynucleotide sequence may include up to five mismatches per each 100 nucleotides of the reference nucleotide sequence encoding TNF delta or TNF epsilon. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire TNF delta-encoding nucleotide sequence shown in FIGS. 1A and 1B or FIGS. 6A and 6B or the entire TNF epsilon-encoding nucleotide sequence shown in FIGS. 2A and 2B or FIGS. 7A and 7B or any TNF delta or TNF epsilon polynucleotide fragment (e.g., a polynucleotide encoding the amino acid sequence of any of the TNF delta and TNF epsilon N- and/or C- terminal deletions described herein), variant, derivative or analog, as described herein.

As a practical matter, whether any particular nucleic acid molecule is at least 90%, 95%, 96%, 97%, 98% or 99% identical to, for instance, the encoding nucleotide sequence shown in FIGS. 1A and 1B, FIGS. 2A and 2B, FIGS. 6A and 6B or FIGS. 7A and 7B, or to the nucleotide sequence of the deposited cDNA clones, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty= 1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 90%, 95%, 96%, 97%, 98% or 99% identical to the nucleic acid sequences disclosed herein irrespective of whether they encode a polypeptide having TNF delta and/or TNF epsilon functional activity. This is because even where a particular nucleic acid molecule does not encode a polypeptide having TNF delta and/or TNF epsilon functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TNF delta and/or TNF epsilon functional activity include, inter alia, (1) isolating a TNF delta and/or TNF epsilon gene or allelic or splice variants thereof in a cDNA library; (2) in situ hybridization (e.g., "FISH") to metaphase chromosomal spreads to provide precise chromosomal location of the TNF delta and TNF epsilon genes, as described in Verma et al., Human Chromosomes: A Manual of Basic Techniques, Pergamon Press, New York (1988); and (3) Northern Blot analysis for detecting TNF delta and TNF epsilon mRNA expression in specific tissues.

Preferred, however, are nucleic acid molecules having sequences at least 90%, 95%, 96%, 97%, 98% or 99% identical to the nucleic acid sequences disclosed herein, which do, in fact, encode a polypeptide having TNF delta and/or TNF epsilon functional activity. By "a polypeptide having TNF delta and/or TNF epsilon functional activity" is intended polypeptides exhibiting activity similar, but not necessarily identical, to a functional activity of the TNF delta and/or TNF epsilon polypeptides of the present invention as measured, for example, in a particular immunoassay or biological assay. For example, TNF delta and/or TNF-epsilon polypeptide functional activity can be measured by the ability of a polypeptide sequence described herein to form multimers (e.g., homodimers and homotrimers) with the complete TNF delta and/or TNF-epsilon or extracellular domain of TNF delta and/or TNF-epsilon, and to bind a TNF delta and/or TNF-epsilon receptor. Additionally, TNF delta and/or TNF-epsilon polypeptide functional activity can be measured by the ability of a polypeptide sequence described herein to form heteromultimers with Neutrokine-alpha and/or Neutrokine-alphaSV fragments or variants (e.g., International Publication No. WO 98/18921; Science. 285:260 (1999); SEQ ID NOS: 23 and 24 respectively), especially the extracellular soluble domain of Neutrokine-alpha and/or Neutrokine-alphaSV (e.g., amino acids 134–285 of SEQ ID NO: 23). TNF delta and/or TNF-epsilon polypeptide functional activity can be also be measured by determining the ability of a polypeptide of the invention to induce lymphocyte (e.g., B cell) proliferation, differentiation or activation and/or to extend B cell survival. These functional assays can be routinely performed using techniques described herein (e.g., see Example 6) and otherwise known in the art. Additionally, TNF delta and/or TNF-epsilon polypeptides of the present invention modulate cell proliferation, cytotoxicity, cell survival and cell death. An in vitro cell proliferation, cytotoxicity, cell survival, and cell death assay for measuring the effect of a protein on certain cells can be performed by using reagents well known and commonly available in the art for detecting cell replication and/or death. For instance, numerous such assays for TNF-related protein activities are described in the various references in this disclosure. Briefly, an example of such an assay involves collecting human or animal (e.g., mouse) cells and mixing with (1) transfected host cell-supernatant containing TNF delta and/or TNF epsilon protein (or a candidate polypeptide) or (2) nontransfected host cell-supernatant control, and measuring the effect on cell numbers or viability after incubation of certain period of time. Such cell proliferation and/or survival modulation activities as can be measured in this type of assay are useful for treating tumor, tumor metastasis, infections, autoimmune diseases, inflammation and other immune-related diseases.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA, the nucleic acid sequences shown in FIGS. 1A and 1B and 6A and 6B (SEQ ID NO: 1), or fragments thereof, will encode polypeptides "having TNF-delta functional activity." One of ordinary skill in the art will also immediately recognize that a large number of the nucleic acid molecules having a sequence at least 90%, 95%, 96%, 97%, 98%, or 99% identical to the nucleic acid sequence of the deposited cDNA, the nucleic acid sequence shown in FIGS. 2A and 2B and 7A and 7B (SEQ ID NOs:3 and 12, respectively), or fragments thereof, will encode polypeptides "having TNF-epsilon functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having TNF-delta and/or TNF-epsilon functional activity or activities. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie, et al., "Deciphering the Message in Protein Sequences: Tolerance to Amino Acid Substitutions," *Science* 247:1306–10 (1990), wherein the authors indicate that proteins are surprisingly tolerant of amino acid substitutions.

The term "polypeptides," as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present invention are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance Proteins—Structure and Molecular Properties, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in Posttranslational Covalent Modification of Proteins, B. C. Johnson, Ed., Academic Press, New York (1983); Seifter et al., Analysis for protein modifications and nonprotein cofactors, *Meth. Enzymol.,* 182: 626–646 (1990) and Rattan et al., Protein Synthesis: Posttranslational Modifications and Aging, *Ann. N.Y. Acad. Sci.,* 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event, and events brought about by human manipulation which do not occur naturally. Circular, branched and branched circular polypeptides may be synthesized by non-translational natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli,* prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli.* Accordingly, when glycosylation is desired, a polypeptide should be expressed in a glycosylating host, generally a eukaryotic cell. Insect cells often carry out the same post-translational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized by expressing a polynucleotide in a host cell.

The term "variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

A polynucleotide variant is a polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

A polypeptide variant is a polypeptide that differs in amino acid sequence from another, reference polypeptide. Generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination.

By a polypeptide having an amino acid sequence at least, for example, 95% "identical" to a reference amino acid sequence of a TNF delta or a TNF epsilon polypeptide is intended that the amino acid sequence of the polypeptide is identical to the reference sequence except that the polypeptide sequence may include up to five amino acid alterations per each 100 amino acids of the reference amino acid of a respective TNF delta or TNF epsilon sequence. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A and 1B (SEQ ID NO:2), FIGS. 6A and 6B (SEQ ID NO: 11), FIGS. 2A and 2B (SEQ ID NO:4), and FIGS. 7A and 7B (SEQ ID NO: 13), the amino acid sequence encoded by the deposited cDNA clones, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The term "receptor molecule," as used herein, refers to molecules which bind or interact specifically with TNF delta or TNF epsilon polypeptides of the present invention, including not only classic receptors, which are preferred, but also other molecules that specifically bind to or interact with polypeptides of the invention (which also may be referred to as "binding molecules" and "interaction molecules," respectively and as "TNF delta binding molecules" and "TNF delta interaction molecules" or "TNF epsilon binding molecules" and "TNF epsilon interaction molecules." Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

The present invention relates to novel TNF delta and TNF epsilon polypeptides and polynucleotides, among other things, as described in greater detail below. In particular, the invention relates to polypeptides and polynucleotides which are related by amino acid sequence homology to the TNF ligand superfamily. The invention relates especially to TNF delta having the nucleotide and amino acid sequences set out in FIGS. 1A and 1B, FIGS. 6A and 6B, and to the TNF nucleotide and amino acid sequences of the human cDNA in ATCC Deposit No. 97377. The invention also relates especially to TNF epsilon having the nucleotide and amino acid sequences set out in FIGS. 2A and 2B, FIGS. 7A and 7B, and to the TNF epsilon nucleotide and amino acid sequences of the human cDNA in ATCC Deposit No. 97457 or ATCC Deposit No. PTA-1543. The deposits are hereinafter referred to as the deposited clones or as "the cDNA of the deposited clones." It will be appreciated that the nucleotide and amino acid sequences set out in FIGS. 1A and 1B, FIGS. 2A and 2B, FIGS. 6A and 6B and FIG. 7A and 7B were obtained by sequencing the human cDNA of the deposited clones. Hence, the sequence of the deposited clone is controlling as to any discrepancies between the two and any reference to the sequences of FIGS. 1A and 1B, FIGS. 2A and 2B, FIGS. 6A and 6B and/or FIGS. 7A and 7B include reference to the sequences of the human cDNA's of the deposited clones.

In accordance with one aspect of the present invention, there are provided isolated polynucleotides which encode the TNF delta polynucleotides having the deduced amino acid sequences of FIGS. 1A, 1B, 6A, and 6B and TNF epsilon polypeptides having the deduced amino acid sequences of FIGS. 2A, 2B, 7A and 7B.

Using the information provided herein, such as the polynucleotide sequence set out in FIGS. 1A and 1B, a polynucleotide of the present invention encoding human TNF delta polypeptide may be obtained using standard cloning and screening procedures, such as those for cloning cDNAs using mRNA from cells of human tissue as starting material. Illustrative of the invention, the polynucleotide set out in FIGS. 1A, 1B, 6A, and 6B was discovered in a cDNA library derived from cells of human heart tissue.

Human TNF delta of the invention is structurally related to other proteins of the TNF ligand superfamily, as shown by the results of sequencing the cDNA encoding human TNF delta in the deposited clone. The cDNA sequence thus obtained is set out in FIGS. 1A and 1B and 6A and 6B. In one embodiment, it contains an open reading frame encoding a protein of about 233 amino acid residues with a deduced molecular weight of about 25.871 kDa (FIGS. 1A and 1B, SEQ ID NO:2). In another embodiment, it contains an open reading frame encoding a protein of about 250 amino acid residues with a deduced molecular weight of about 27.531 kDa (FIGS. 6A and 6B, SEQ ID NO: 11). The protein exhibits greatest homology to TNF-alpha, among known proteins. The entire amino acid sequence of TNF delta of FIGS. 1A and 1B has about 38% identity to the amino acid sequence of TNF-alpha.

A polynucleotide of the present invention encoding human TNF epsilon polypeptide may be obtained using standard cloning and screening procedures, such as those for cloning cDNAs using mRNA from cells of human tissue as starting material. Illustrative of the invention, the polynucleotide set out in FIGS. 2A and 2B was discovered in a cDNA library derived from cells of human heart tissue.

Human TNF epsilon of the invention is structurally related to other proteins of the TNF ligand superfamily, as shown by the results of sequencing the cDNA encoding human TNF epsilon in the deposited clone. The cDNA sequence thus obtained is set out in FIGS. 2A and 2B. The TNF epsilon sequence is nearly identical to the sequence of TNF delta as set out in FIGS. 1A and 1B minus the initial 50 amino acids of SEQ ID NO:2, or initial 67 amino acids of SEQ ID NO: 11 and a region of TNF delta comprising amino acid 96–112 of SEQ ID NO:2 (or amino acids 113–129 of SEQ ID NO:11). Accordingly, TNF epsilon is a splicing variant of TNF delta. In one embodiment, TNF epsilon comprises 168 amino acid residues and the sequence of FIGS. 2A and 2B show a protein of TNF epsilon without any N-terminal hydrophobic region. In another embodiment, TNF epsilon comprises 234 amino acid residues and the sequence of FIGS. 7A and 7B show the full-length protein of TNF epsilon. The protein exhibits greatest homology to TNF-alpha. TNF epsilon of FIGS. 2A and 2B has about 20% identity to the amino acid sequence of TNF-alpha Another clone (HADCA12) containing cDNA sequence overlapping the coding region of SEQ ID NO:3 and which contains the complete amino terminus of TNF-epsilon has been identified. The polynucleotide sequence contained in HADCA12 is shown in FIGS. 7A and 7B and in SEQ ID NO:12 along with the deduced amino acid sequences of the TNF epsilon protein encoded by this polynucleotide (SEQ ID NO: 13).

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIGS. 1A and 1B, 2A and 2B, 6A and 6B, and 7A and 7B. It also may be a polynucleotide with a different sequence, which, as a result of the redundancy (degeneracy) of the genetic code, encodes the polypeptide of the DNA of FIGS. FIGS. 1A and 1B, 2A and 2B, 6A and 6B, and 7A and 7B.

Polynucleotides of the present invention which encode the polypeptide of Figures FIGS. 1A and 1B, 2A and 2B, 6A and 6B, and/or 7A and 7B may include, but are not limited to the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities.

Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.), among others, many of which are commercially available. As described in Gentz et al., *Proc. Natl. Acad. Sci., USA*, 86:821–824 (1989), for instance, hexa-histidine provides for convenient purification of the fusion protein. The HA tag corresponds to an epitope derived of influenza hemagglutinin protein, which has been described by Wilson et al., *Cell*, 37:767 (1984), for instance.

In further preferred embodiments, TNF-delta and/or TNF-epsilon polynucleotides of the invention are fused to a polynucleotide encoding a "FLAG" polypeptide. Thus, a TNF-delta-FLAG or a TNF-epsilon-FLAG fusion protein is encompassed by the present invention. The FLAG antigenic polypeptide may be fused to a TNF-delta or TNF-epsilon polypeptide of the invention at either or both the amino or the carboxy terminus. In preferred embodiments, a TNF-delta-FLAG or a TNF-epsilon-FLAG fusion protein is expressed from a pFLAG-CMV-5a or a pFLAG-CMV-1 expression vector (available from Sigma, St. Louis, Mo., USA). See, Andersson, S., et al., *J. Biol. Chem.* 264:8222–29 (1989); Thomsen, D. R., et al., *Proc. Natl. Acad. Sci. USA*, 81:659–63 (1984); and Kozak, M., *Nature* 308:241 (1984) (each of which is hereby incorporated by reference). In further preferred embodiments, a TNF-delta-FLAG or a TNF-epsilon-FLAG fusion protein is detectable by anti-FLAG monoclonal antibodies (also available from Sigma). See, e.g., Example 29.

The TNF delta and/or TNF epsilon polypeptides of the invention may be in monomers or multimers (i.e., dimers, trimers, tetramers, and higher multimers). In preferrred embodiments, the TNF delta and TNF epsilon polypeptides of the invention are trimers. Accordingly, the present invention relates to monomers and multimers of the TNF delta and/or TNF epsilon proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only TNF delta proteins of the invention (including TNF delta fragments, variants, and fusion proteins, as described herein). These homomers may contain TNF delta proteins having identical or different polypeptide sequences. As used herein, the term homomer, may alternatively refer to a multimer containing only TNF epsilon proteins of the invention (including TNF epsilon fragments, variants, and fusion proteins, as described herein). These homomers may contain TNF epsilon proteins having identical or different polypeptide sequences.

In a specific embodiment, a homomer of the invention is a multimer containing only TNF delta proteins having an identical polypeptide sequence. In another specific embodiment, a homomer of the invention is a multimer containing TNF delta proteins having different polypeptide sequences. Also in a specific embodiment, a homomer of the invention is a multimer containing only TNF epsilon proteins having an identical polypeptide sequence. In another specific embodiment, a homomer of the invention is a multimer containing TNF epsilon proteins having different polypeptide sequences.

In specific embodiments, the multimer of the invention is a homodimer (e.g., containing TNF delta proteins having identical or different polypeptide sequences or also e.g., containing TNF epsilon proteins having identical or different polypeptide sequences) or a homotrimer (e.g., containing TNF delta proteins having identical or also e.g., different polypeptide sequences or a homotrimer containing TNF epsilon proteins having identical or different polypeptide sequences). In additional embodiments, the homomeric multimer of the invention is at least a homodimer, at least a homotrimer, or at least a homotetramer.

As used herein, the term heteromer refers to a multimer containing TNF delta proteins of the invention and heterologous proteins (i.e., proteins containing only polypeptide sequences that do not correspond to a polypeptide sequence encoded by the TNF delta gene or TNF-epsilon gene). Alternatively, the term heteromer, as used herein, refers to a multimer containing TNF epsilon proteins of the invention and heterologous proteins (i.e., proteins containing only polypeptide sequences that do not correspond to a polypeptide sequence encoded by the TNF delta gene or TNF-epsilon gene). In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer. In highly preferred embodiments, the heteromeric multimer of the invention is a heterotrimer comprising both TNF-delta polypeptides and Neutrokine-alpha and/or Neutokine-alphaSV polypeptides (e.g., International Publication No. WO 98/18921; Science. 285:260 (1999); SEQ ID NOS:23 and 24 respectively). In other highly preferred embodiments, the heteromeric multimer of the invention is a heterotrimer consisting of one TNF-delta polypeptide and two Neutrokine-alpha and/or Neutrokine-alphaSV polypeptides. In other highly preferred embodiments, the heteromeric multimer of the invention is a heterotrimer consisting of two TNF-delta polypeptides and one Neutrokine-alpha and/or Neutrokine-alphaSV polypeptide. In other highly preferred embodiments, the heteromeric multimer of the invention is a heterotrimer comprising TNF-delta and/or TNF-epsilon polypeptides and Neutrokine-alpha and/or Neutrokine-alphaSV polypeptides (e.g., International Publication No. WO 98/18921; Science. 285:260 (1999); SEQ ID NOS:23 and 24 respectively).

In other highly preferred embodiments, the heteromeric multimer of the invention is a heterotrimer consisting of one TNF-epsilon polypeptide and two Neutrokine-alpha and/or Neutrokine-alphaSV polypeptides. In other highly preferred embodiments, the heteromeric multimer of the invention is a heterotrimer consisting of two TNF-epsilon polypeptides and one Neutrokine-alpha and/or Neutokine-alphaSV polypeptide. In still other highly preferred embodiments, the heteromeric multimer of the invention is a heterotrimer comprising TNF-delta and/or TNF epsilon polypeptides and Neutrokine-alpha and/or Neutrokine-alphaSV polypeptides (e.g., International Publication No. WO 98/18921; Science. 285:260 (1999); SEQ ID NOS:23 and 24, respectively).

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the TNF delta and/or TNF epsilon proteins of the invention. Such covalent associations may involve one or more amino acid residues contained in the polypeptide sequence of the protein (e.g., the polypeptide sequence recited in SEQ ID NO:2, SEQ ID NO:4, SEQ ID NO:11, and/or SEQ ID NO: 13 or the polypeptides encoded by the deposited cDNA clones). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TNF delta and/or TNF epsilon fusion protein. In one example, covalent associations are between the heterologous sequence contained in a fusion protein of the invention (see, e.g., U.S. Pat. No. 5,478,925). In specific examples, the covalent associations are between the heterologous sequences contained in a TNF delta-Fc fusion protein of the invention (as described herein) or between the heterologous sequences contained in a TNF epsilon-Fc fusion protein of the invention (as described herein). In a specific example, covalent associations of fusion proteins of the invention are between the heterologous sequences contained in a TNF delta-Fc fusion protein of the invention and the heterologous sequences contained in a TNF epsilon-Fc fusion protein of the invention. In another specific example, covalent associations of fusion proteins of the invention are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety).

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C- or N-termini of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In accordance with the foregoing, the term "polynucleotide encoding a polypeptide" as used herein encompasses polynucleotides which include a sequence encoding a polypeptide of the present invention, particularly the human TNF delta having the amino acid sequence set out in FIGS. 1A and 1B and/or FIGS. 6A and 6B and TNF epsilon having the amino acid sequences set out in FIGS. 2A and 2B, and/or FIGS. 7A and 7B. The term encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIGS. 1A and 1B, 2A and 2B, 6A and 6B, and/or 7A and 7B. In preferred embodiments, the present invention encompasses polynucleotides encoding the extracellular soluble form of the TNF delta and TNF epsilon proteins, (e.g., a polynucleotide encoding amino acid residues 88–233 of SEQ ID NO:2, a polynucleotide encoding amino acid residues 105–250 of SEQ ID NO:11, a polynucleotide encoding amino acid residues 39–168 of SEQ ID NO:4, and or a polynucleotide encoding amino acid residues 105–234 of SEQ ID NO: 13. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence TNF delta having the amino acid sequence set out in FIGS. 1A and 1B and/or FIGS. 6A and 6B and TNF epsilon having the amino acid sequences set out in FIGS. 2A and 2B, and/or FIGS. 7A and 7B; variants, analogs, derivatives and fragments thereof, and fragments of the variants, analogs and derivatives.

Further particularly preferred in this regard are polynucleotides encoding TNF delta and TNF epsilon which have the amino acid sequence of the TNF delta having the amino acid sequence set out in FIGS. 1A and 1B and/or FIGS. 6A and 6B and TNF epsilon having the amino acid sequences set out in FIGS. 2A and 2B, and/or FIGS. 7A and 7B in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the TNF delta and TNF epsilon. Also especially preferred in this regard are conservative substitutions. Most highly preferred are polynucleotides encoding polypeptides having the amino acid sequence of FIGS. 1A and 1B, 2A and 2B, 6A and 6B, and/or 7A and 7B without substitutions. Further preferred embodiments of the invention are polynucleotides that are at least 70% identical to a polynucleotide encoding the TNF delta polypeptide having the amino acid sequence set out in FIGS. 1A and 1B and/or FIGS. 6A and 6B and the TNF epsilon polypeptide having the amino acid sequences set out in FIGS. 2A and 2B, and/or FIGS. 7A and 7B, and polynucleotides which are complementary to such polynucleotides. Alternatively, most highly preferred are polynucleotides that comprise a region that is at least 80% identical to a polynucleotide encoding the TNF delta and TNF epsilon polypeptide and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the cDNA of FIGS. 1A and 1B, 2A and 2B, and/or 7A and 7B.

The present invention further relates to polynucleotides that hybridize to the herein above-described sequences. In this regard, the present invention especially relates to polynucleotides that hybridize under stringent conditions to the herein above-described polynucleotides. As herein used, the term "stringent conditions" means hybridization will occur when at least 95% and preferably at least 97% of the bases between sequences are complementary (e.g., G:C; A:T). Also as used herein, the term "stringent conditions" means hybridization according to any stringent conditions recited herein. For example, 7% SDS, 0.5 M NaPO$_4$, pH 7.4 at 65° C., overnight, followed by two washes at room temperature and two additional washes at 60° C. with 0.5×SSC, 0.1% SDS.

As discussed additionally herein regarding polynucleotide assays of the invention, for instance, polynucleotides of the invention as discussed above, may be used as a hybridization probe for cDNA and genomic DNA to isolate full-length cDNAs and genomic clones encoding TNF delta and TNF epsilon and to isolate cDNA and genomic clones of other genes that have a high sequence similarity to the human TNF delta and TNF epsilon gene. Such probes generally will comprise at least 15 bases. Preferably, such probes will have at least 30 bases and may have at least 50 bases.

For example, the coding region of the TNF delta and TNF epsilon gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposits containing human TNF delta and human TNF epsilon cDNA have been deposited with the American Type Culture Collection, as noted above. Also as noted above, the cDNA deposit is referred to herein as "the deposited clone" or as "the cDNA of the deposited clone." The clones were deposited with the American Type Culture Collection, 10801 University Boulevard, Manassas, Va., USA, on Dec. 8, 1995, Mar. 1, 1996, and March 21, 2000 and assigned ATCC Deposit No. 97377 97457, and PTA-1543, respectively. The deposited materials in Deposit Nos. 97377 ans 97457 are pBluescript SK (−) plasmids (Stratagene, La Jolla, Calif.) that contain TNF epsilon human cDNA and the full length TNF delta cDNA, as described above.

The deposits have been made under the terms of the Budapest Treaty on the international recognition of the deposit of micro-organisms for purposes of patent procedure. The strains will be irrevocably and without restriction or condition released to the public upon the issuance of a patent. The deposits are provided merely as convenience to those of skill in the art and are not an admission that a deposit is required for enablement, such as that required under 35 U.S.C. § 112. The sequence of the polynucleotides contained in the deposited material, as well as the amino acid sequence of the polypeptide encoded thereby, are controlling in the event of any conflict with any description of sequences herein. A license may be required to make, use or sell the deposited materials, and no such license is hereby granted.

The present invention further relates to human TNF delta and TNF epsilon polypeptides having the deduced amino acid sequences of FIGS. 1A and 1B, 2A and 2B, 6A and 6B, and/or 7A and 7B. The polypeptide of the present invention may be a recombinant polypeptide, a natural polypeptide or a synthetic polypeptide. In certain preferred embodiments, it is a recombinant polypeptide.

The invention also relates to fragments, analogs and derivatives of these polypeptides. The terms "fragment," "derivative" and "analog" when referring to the polypeptide of FIGS. 1A and 1B, 2A and 2B, 6A and 6B, and/or 7A and 7B means a polypeptide which retains essentially the same biological function or activity as such polypeptide. Thus, an analog includes a proprotein that can be activated by cleavage of the proprotein portion to produce an active mature polypeptide.

It will be recognized by one of ordinary skill in the art that some amino acid sequences of the TNF-delta and TNF-epsilon polypeptides can be varied without significant effect of the structure or function of the polypeptide. If such differences in sequence are contemplated, it should be remembered that there will be critical areas on the polypeptide which determine activity.

Thus, the invention further includes variations of the TNF-delta polypeptide which show substantial TNF-delta polypeptide functional activity (e.g., biological activity) or which include regions of TNF-delta polypeptide such as the protein portions discussed below. The invention also includes variations of the TNF-epsilon polypeptide which show substantial TNF-epsilon polypeptide functional activity (e.g., biological activity) or which include regions of TNF-epsilon polypeptide such as the polypeptide portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

The fragment, derivative or analog of the polypeptide FIGS. 1A and 1B, 2A and 2B, 6A and 6B, and/or 7A and 7B may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or a leader, human serum albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), a secretory sequence, or a sequence which is employed for purification of the mature polypeptide or a proprotein sequence. Such fragments, derivatives and analogs are deemed to be within the scope of those skilled in the art from the teachings herein.

Thus, the TNF-delta and/or TNF-epsilon polypeptides of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table I).

TABLE I

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Among the particularly preferred embodiments of the invention in this regard are polypeptides having the amino acid sequence of TNF delta and TNF epsilon set out in FIGS. FIGS. 1A and 1B, 2A and 2B, 6A and 6B, and/or 7A and 7B, variants, analogs, derivatives and fragments thereof, and variants, analogs and derivatives of the fragments. Alternatively, particularly preferred embodiments of the invention in this regard are polypeptides having the amino acid sequence of the TNF delta and TNF epsilon of the human cDNA in the deposited clone, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the TNF delta as set out in FIGS. 1A and 1B and/or FIGS. 6A and 6B, and/or TNF epsilon as set out in FIGS. 2A and 2B, and/or FIGS. 7A and 7B, or of the cDNA in the deposited clones, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the TNF delta and TNF epsilon. Also especially preferred in this regard are conservative substitutions. Most highly preferred are polypeptides having the amino acid sequence of FIGS. 1A and 1B, 2A and 2B, 6A and 6B, and/or 7A and 7B without substitutions.

The polypeptides and polynucleotides of the present invention are preferably provided in an isolated form, and preferably are purified to homogeneity.

The TNF delta polypeptides of the present invention include the polypeptide of SEQ ID NO:2 (in particular the mature polypeptide, e.g., amino acid residues 88–233 of SEQ ID NO:2) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

The TNF delta polypeptides of the present invention include the polypeptide of SEQ ID NO:11 (in particular the mature polypeptide, e.g., amino acid residues 105–250 of SEQ ID NO:11) as well as polypeptides which have at least 70% similarity (preferably at least 70% identity) to the polypeptide of SEQ ID NO: 11 and more preferably at least 90% similarity (more preferably at least 90% identity) to the polypeptide of SEQ ID NO: 11 and still more preferably at least 95% similarity (still more preferably at least 95% identity) to the polypeptide of SEQ ID NO: 11 and also include portions of such polypeptides with such portion of the polypeptide generally containing at least 30 amino acids and more preferably at least 50 amino acids.

The TNF epsilon polypeptides of the present invention include the polypeptide of SEQ ID NO:4 (in particular the mature polypeptide, e.g., amino acid residues 39–168 of SEQ ID NO:4) as well as polypeptides which have at least 70% similarity (preferably at least 70% identity) to the polypeptide of SEQ ID NO:4 and more preferably at least 90% similarity (more preferably at least 90% identity) to the polypeptide of SEQ ID NO:4 and still more preferably at least 95% similarity (still more preferably at least 95% identity) to the polypeptide of SEQ ID NO:4 and also include portions of such polypeptides with such portion of the polypeptide generally containing at least 30 amino acids and more preferably at least 50 amino acids.

The TNF epsilon polypeptides of the present invention include the polypeptide of SEQ ID NO: 13 (in particular the mature polypeptide, e.g., amino acid residues 105–234 of SEQ ID NO:13) as well as polypeptides which have at least 70% similarity (preferably at least 70% identity) to the polypeptide of SEQ ID NO: 13 and more preferably at least 90% similarity (more preferably at least 90% identity) to the polypeptide of SEQ ID NO: 13 and still more preferably at least 95% similarity (still more preferably at least 95% identity) to the polypeptide of SEQ ID NO: 13 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

A fragment is a polypeptide having an amino acid sequence that entirely is the same as part but not all of the amino acid sequence of the aforementioned TNF delta and TNF epsilon polypeptides and variants or derivatives thereof. Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a TNF delta and TNF epsilon polypeptide of the present comprised within a precursor polypeptide designed for expression in a host and having heterologous pre and pro-polypeptide regions fused to the amino terminus of the TNF delta and TNF epsilon fragment and an additional region fused to the carboxyl terminus of the fragment. Therefore, fragments in one aspect of the meaning intended herein, refers to the portion or portions of a fusion polypeptide or fusion protein derived from TNF delta and TNF epsilon.

As representative examples of polypeptide fragments of the invention, there may be mentioned those which have from about 30 to about 233 amino acids. In this context, "about" includes the particularly recited range and ranges larger or smaller by several, a few, 5, 4, 3, 2 or 1 amino acid at either extreme or at both extremes. For instance, about 100 to 233 amino acids in this context means a polypeptide fragment of 100 plus or minus several, a few, 5, 4, 3, 2 or 1 amino acids to 233 plus or minus several a few, 5, 4, 3, 2 or 1 amino acid residues, i.e., ranges as broad as 100 minus several amino acids to 233 plus several amino acids to as narrow as 100 plus several amino acids to 233 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 15 to about 233 amino acids.

The present invention is further directed to fragments of the isolated nucleic acid molecules described herein. By a fragment of an isolated nucleic acid molecule having, for example, the nucleotide sequence of the deposited cDNA (clone HLTBT71), a nucleotide sequence encoding the polypeptide sequence encoded by the deposited cDNA, a nucleotide sequence encoding the polypeptide sequence depicted in FIGS. 1A and 1B (SEQ ID NO:2) and/or FIGS. 6A and 6B (SEQ ID NO: 11), the nucleotide sequence shown in FIGS. 1A and 1B (SEQ ID NO: 1), or the complementary strand thereto, is intended fragments at least 15 nt, and more preferably at least about 20 nt, still more preferably at least 30 nt, and even more preferably, at least about 40, 50, 100, 150, 200, 250, 300, 325, 350, 375, 400, 450, 500, 550, or 600 nt in length.

By a fragment of an isolated nucleic acid molecule having, for example, the nucleotide sequence of the deposited cDNA (clone HPDDO12 or clone HADCA12), a nucleotide sequence encoding the polypeptide sequence encoded by the either or both deposited cDNAs, a nucleotide sequence encoding the polypeptide sequence depicted in FIGS. 2A and 2B (SEQ ID NO:4), a nucleotide sequence encoding the polypeptide sequence depicted in FIGS. 7A and 7B (SEQ ID NO:13), the nucleotide sequence shown in FIGS. 2A and 2B (SEQ ID NO:3), or the complementary strand thereto, the nucleotide sequence shown in FIGS. 7A and 7B (SEQ ID NO:12), or the complementary strand thereto, is intended fragments at least 15 nt, and more preferably at least about 20 nt, still more preferably at least 30 nt, and even more preferably, at least about 40, 50, 100, 150, 200, 250, 300, 325, 350, 375, 400, 450, 500, 550, or 600 nt in length.

These fragments have numerous uses that include, but are not limited to, diagnostic probes and primers as discussed herein. Of course, larger fragments, such as those of 501–1500 nt in length are also useful according to the present invention as are fragments corresponding to most, if not all, of the nucleotide sequences of the deposited cDNAs (clones HLTBT71, HPDDO12, and/or HADCA12) or as shown in FIGS. 1A and 1B (SEQ ID NO:1), 2A and 2B (SEQ ID NO:3) 7A and 7B (SEQ ID NO:12), respectively. By a fragment at least 20 nt in length, for example, is intended fragments which include 20 or more contiguous bases from, for example, the nucleotide sequence of the deposited cDNAs, or the nucleotide sequences as shown in FIGS. 1A and 1B (SEQ ID NO:1), 2A and 2B (SEQ ID NO:3), or 7A and 7B (SEQ ID NO:12), respectively.

By a fragment at least about 20 nt in length, for example, is intended fragments which include 20 or more contiguous bases from the nucleotide sequence. In this context "about" includes the particularly recited size, larger or smaller by several (5, 4, 3, 2, or 1) nucleotides, at either terminus or at both termini.

Representative examples of TNF-delta polynucleotide fragments of the invention include, for example, fragments that comprise, or alternatively, consist of, a sequence from about nucleotide 282 to 315, 316 to 348, 349 to 380, 381 to 410, 411 to 440, 441 to 470, 471 to 500, 501 to 530, 531 to 560, 561 to 590, 591 to 620, 621 to 650, 651 to 680, 681 to 710, 711 to 740, 741 to 770, 771 to 800, 801 to 830, 831 to 860, 861 to 890, 891 to 920, 921 to 950, 951 to 980, 981 to 1010, 1011 to 1040 of SEQ ID NO:1, or the complementary strand thereto, or the cDNA contained in the deposited clone. In this context "about" includes the particularly recited ranges, larger or smaller by several (5, 4, 3, 2, or 1) nucleotides, at either terminus or at both termini.

Representative examples of TNF-epsilon polynucleotide fragments of the invention include, for example, fragments that comprise, or alternatively, consist of, a sequence from about nucleotide 2 to 31, 32 to 61, 62 to 91, 92 to 121, 122 to 151, 152 to 181, 182 to 211, 212 to 241, 242 to 271, 272 to 301, 302 to 331, 332 to 361, 362 to 391, 392 to 421, 422 to 451, 452 to 481, 482 to 511, 512 to 541, 542 to 571 of SEQ ID NO:3, or the complementary strand thereto, or the cDNA contained in the deposited clone. In this context "about" includes the particularly recited ranges, larger or smaller by several (5, 4, 3, 2, or 1) nucleotides, at either terminus or at both termini.

Additional examples of TNF-epsilon polynucleotide fragments of the invention include, for example, fragments that comprise, or alternatively, consist of, a sequence from about nucleotide 108 to 139, 140 to 170, 171 to 201, 202 to 232, 233 to 263, 264 to 294, 295 to 325, 326 to 356, 357 to 381, 382 to 419, 420 to 452, 453 to 485, 486 to 517, 518 to 550, 551 to 582, 583 to 615, 616 to 648, 649 to 680, 681 to 713, 714 to 746, 747 to 778, 779 to 809 of SEQ ID NO: 12, or the complementary strand thereto, or the cDNA contained in the deposited clone. In this context "about" includes the particularly recited ranges, larger or smaller by several (5, 4, 3, 2, or 1) nucleotides, at either terminus or at both termini.

Preferably, the polynucleotide fragments of the invention encode a polypeptide which demonstrates a TNF-delta and/or TNF-epsilon functional activity. By a polypeptide demonstrating a TNF-delta and/or TNF-epsilon "functional activity" is meant, a polypeptide capable of displaying one or more known functional activities associated with a full-length (complete) TNF-delta and/or TNF-epsilon protein. Such functional activities include, but are not limited to, biological activity (e.g., cell proliferation, differentiation, and/or growth), antigenicity, ability to bind (or compete with a TNF-delta and/or TNF-epsilon polypeptide for binding) to an anti-TNF-delta and/or TNF-epsilon antibody, immunogenicity (ability to generate/induce antibody which binds to a TNF-delta and/or TNF-epsilon polypeptide), ability to form multimers with TNF-delta and/or TNF-epsilon polypeptides of the invention, ability to form heteromultimers with Neutrokine alpha-and/or Neutrokine-alphaSV polypeptides (e.g., International Publication No. WO 98/18921; Science. 285:260 (1999); SEQ ID NOS 23 and 24, respectively); and ability to bind to a receptor or ligand for a TNF-delta and/or TNF-epsilon polypeptide (e.g., TACI (See, von Bulow, G. U. and Bram, R. J., Science 278:138–41 (1997) and GenBank accesion number AAC51790, and/or BCMA (GenBank accession number NP_001183)), and/or TR11, and/or TR11SV1, and/or TR11SV2 (See, International Publication No. WO99/22085).

The functional activity of TNF-delta and/or TNF-epsilon polypeptides, and fragments, variants derivatives, and analogs thereof, can be assayed by various methods.

For example, in one embodiment where one is assaying for the ability to bind or compete with full-length TNF-delta and/or TNF-epsilon polypeptide for binding to anti-TNF-delta and/or anti-TNF-epsilon antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Among especially preferred fragments of the invention are truncation mutants of TNF delta and TNF epsilon. Truncation mutants include TNF delta and TNF epsilon polypeptides having the amino acid sequence of FIGS. 1A and 1B and 2A and 2B, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of TNF delta and TNF epsilon. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TNF delta and TNF epsilon.

Certain preferred regions in these regards are set out in FIG. 4 for TNF delta and FIG. 5 for TNF epsilon, and include, but are not limited to, regions of the aforementioned types identified by analysis of the amino acid sequence set out in FIGS. 1A and 1B and 2A and 2B. As set out in FIGS. 4 and 5, such preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions.

Among highly preferred fragments in this regard are those that comprise regions of TNF delta and TNF epsilon that combine several structural features, such as several of the features set out above. In this regard, the regions defined by the residues following the signal peptide region of FIGS. 1A, 1B, 2A, 2B, 4 and 5, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

In additional embodiments, the polynucleotides of the invention encode functional attributes of TNF delta and/or TNF epsilon. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TNF delta and/or TNF epsilon.

The data representing the structural or functional attributes of TNF delta and/or TNF epsilon set forth in FIGS. 1A and 1B, 4 and/or Table II, and/or as set forth in FIGS. 2A and 2B, 5 and/or Table III, as described above, was generated using the various modules and algorithms of the DNA*STAR set on default parameters. In a preferred embodiment, the data presented in columns VIII, IX, XIII, and XIV of Tables II and III can be used to determine regions of TNF delta and TNF epsilon, respectively, which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIGS. 4 and 5, but may, as shown in Tables II and III, respectively, be represented or identified by using tabular representations of the data presented in FIGS. 4 and 5. The DNA*STAR computer algorithm used to generate FIGS. 4 and 5 (set on the original default parameters) was used to present the data in FIGS. 4 and 5 in a tabular format (See Tables II and III, respectively). The tabular format of the data in FIGS. 4 and 5 may be used to easily determine specific boundaries of a preferred region.

The above-mentioned preferred regions set out in FIGS. 4 and 5 and in Tables II and III, respectively, include, but are not limited to, regions of the aforementioned types identified by analysis of the amino acid sequence set out in FIGS. 4 and 5. As set out in FIGS. 4 and 5, and in Tables II and III, respectively, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE II

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | . | . | . | T | . | . | −0.41 | 0.19 | . | * | . | 0.30 | 0.56 |
| Gly | 2 | . | . | . | . | . | . | . | C | 0.09 | 0.40 | * | * | . | 0.32 | 0.33 |
| Gly | 3 | . | . | . | . | . | . | . | C | 0.48 | −0.03 | * | * | . | 1.14 | 0.50 |
| Pro | 4 | . | . | . | . | . | . | . | C | 0.66 | −0.46 | * | * | . | 1.36 | 0.87 |
| Val | 5 | . | . | . | B | . | . | . | . | 0.46 | −0.64 | . | * | F | 1.98 | 1.37 |
| Arg | 6 | . | . | . | B | . | . | . | . | 0.24 | −0.57 | . | * | F | 2.20 | 1.39 |
| Glu | 7 | . | . | . | B | . | . | . | . | 0.29 | −0.31 | . | . | F | 1.53 | 0.74 |
| Pro | 8 | A | . | . | . | . | . | . | . | −0.22 | −0.36 | . | * | F | 1.46 | 1.34 |
| Ala | 9 | A | A | . | . | . | . | . | . | −0.60 | −0.36 | . | * | . | 0.74 | 0.51 |
| Leu | 10 | A | A | . | . | . | . | . | . | −0.56 | 0.14 | . | . | . | −0.08 | 0.30 |
| Ser | 11 | A | A | . | . | . | . | . | . | −0.96 | 0.83 | . | * | . | −0.60 | 0.16 |
| Val | 12 | A | A | . | . | . | . | . | . | −1.77 | 1.31 | . | * | . | −0.60 | 0.16 |
| Ala | 13 | A | A | . | . | . | . | . | . | −1.86 | 1.50 | . | * | . | −0.60 | 0.16 |
| Leu | 14 | A | A | . | . | . | . | . | . | −1.56 | 1.20 | . | * | . | −0.60 | 0.16 |
| Trp | 15 | A | A | . | . | . | . | . | . | −1.09 | 1.73 | . | * | . | −0.60 | 0.23 |
| Leu | 16 | A | . | . | . | . | . | T | . | −1.38 | 1.51 | . | * | . | −0.20 | 0.23 |
| Ser | 17 | A | . | . | . | . | . | T | . | −1.11 | 1.51 | . | * | . | −0.20 | 0.28 |
| Trp | 18 | A | . | . | . | . | . | T | . | −1.33 | 1.33 | . | . | . | −0.20 | 0.27 |
| Gly | 19 | A | . | . | . | . | . | T | . | −0.87 | 1.10 | . | * | . | −0.20 | 0.27 |
| Ala | 20 | A | A | . | . | . | . | . | . | −1.17 | 0.84 | . | . | . | −0.60 | 0.20 |
| Ala | 21 | A | A | . | . | . | . | . | . | −1.21 | 0.96 | . | . | . | −0.60 | 0.19 |
| Leu | 22 | A | A | . | . | . | . | . | . | −1.50 | 0.69 | . | . | . | −0.60 | 0.14 |
| Gly | 23 | A | A | . | . | . | . | . | . | −1.88 | 0.76 | . | . | . | −0.60 | 0.14 |
| Ala | 24 | A | A | . | . | . | . | . | . | −2.12 | 0.83 | . | . | . | −0.60 | 0.08 |
| Val | 25 | A | A | . | . | . | . | . | . | −2.13 | 0.83 | . | . | . | −0.60 | 0.09 |
| Ala | 26 | A | A | . | . | . | . | . | . | −2.13 | 0.76 | . | . | . | −0.60 | 0.09 |
| Cys | 27 | A | A | . | . | . | . | . | . | −2.13 | 0.83 | . | . | . | −0.60 | 0.09 |
| Ala | 28 | A | A | . | . | . | . | . | . | −2.60 | 1.01 | . | . | . | −0.60 | 0.10 |
| Met | 29 | A | A | . | . | . | . | . | . | −2.32 | 1.06 | . | . | . | −0.60 | 0.08 |
| Ala | 30 | A | A | . | . | . | . | . | . | −1.47 | 1.04 | . | . | . | −0.60 | 0.23 |
| Leu | 31 | A | A | . | . | . | . | . | . | −0.88 | 0.87 | . | . | . | −0.60 | 0.39 |
| Leu | 32 | A | A | . | . | . | . | . | . | −0.52 | 0.77 | . | . | . | −0.60 | 0.68 |
| Thr | 33 | A | A | . | . | . | . | . | . | 0.07 | 0.64 | . | . | F | −0.45 | 0.97 |
| Gln | 34 | A | A | . | . | . | . | . | . | −0.14 | 0.14 | . | * | F | 0.00 | 2.05 |
| Gln | 35 | A | A | . | . | . | . | . | . | 0.44 | 0.14 | . | * | F | 0.00 | 2.05 |
| Thr | 36 | A | A | . | . | . | . | . | . | 0.96 | −0.14 | . | . | F | 0.60 | 2.45 |
| Glu | 37 | A | A | . | . | . | . | . | . | 0.96 | −0.24 | . | * | F | 0.60 | 1.90 |
| Leu | 38 | A | A | . | . | . | . | . | . | 1.38 | 0.04 | * | . | F | −0.15 | 0.90 |
| Gln | 39 | . | A | B | . | . | . | . | . | 1.49 | −0.36 | * | . | F | 0.60 | 1.23 |
| Ser | 40 | . | A | . | . | . | . | . | C | 1.49 | −0.84 | * | * | F | 1.10 | 1.39 |
| Leu | 41 | A | A | . | . | . | . | . | . | 0.94 | −0.84 | * | . | F | 0.90 | 2.91 |
| Arg | 42 | A | A | . | . | . | . | . | . | 0.64 | −0.89 | * | . | F | 0.90 | 1.25 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 43 | A | A | . | . | . | . | . | 1.57 | −0.90 | * | . | F | 0.90 | 1.25 |
| Glu | 44 | A | A | . | . | . | . | . | 0.76 | −1.29 | * | * | F | 0.90 | 2.97 |
| Val | 45 | . | A | B | . | . | . | . | 1.06 | −1.29 | * | . | F | 0.90 | 1.25 |
| Ser | 46 | . | A | B | . | . | . | . | 1.98 | −0.89 | * | . | F | 1.21 | 1.10 |
| Arg | 47 | . | A | B | . | . | . | . | 1.56 | −0.89 | * | . | F | 1.52 | 1.25 |
| Leu | 48 | . | A | B | . | . | . | . | 1.10 | −0.40 | * | * | F | 1.53 | 2.43 |
| Gln | 49 | . | . | B | . | . | T | . | 0.76 | −0.61 | * | . | F | 2.54 | 1.79 |
| Arg | 50 | . | . | . | . | T | T | . | 1.40 | −0.57 | * | . | F | 3.10 | 0.91 |
| Thr | 51 | . | . | . | . | T | T | . | 1.40 | −0.14 | * | * | F | 2.64 | 1.70 |
| Gly | 52 | . | . | . | . | . | T | C | 1.29 | −0.44 | * | . | F | 2.43 | 1.32 |
| Gly | 53 | . | . | . | . | . | T | C | 2.10 | −0.44 | * | . | F | 2.42 | 1.16 |
| Pro | 54 | . | . | . | . | . | T | C | 1.76 | −0.04 | . | . | F | 2.41 | 1.30 |
| Ser | 55 | . | . | . | . | . | T | C | 1.64 | −0.10 | * | . | F | 2.40 | 1.30 |
| Gln | 56 | . | . | . | . | . | T | C | 1.61 | −0.53 | . | . | F | 3.00 | 2.27 |
| Asn | 57 | . | . | . | . | . | T | C | 1.71 | −0.53 | . | . | F | 2.70 | 1.45 |
| Gly | 58 | . | . | . | . | T | T | . | 1.84 | −0.20 | . | . | F | 2.30 | 1.70 |
| Glu | 59 | . | . | . | . | T | T | . | 1.77 | −0.16 | . | . | F | 2.00 | 1.51 |
| Gly | 60 | . | . | . | . | . | T | C | 2.07 | 0.36 | . | . | F | 0.75 | 0.99 |
| Tyr | 61 | . | . | . | . | . | T | C | 1.77 | 0.36 | . | . | . | 0.45 | 1.73 |
| Pro | 62 | . | . | . | . | T | T | . | 0.96 | 0.31 | . | . | . | 0.65 | 1.34 |
| Trp | 63 | . | . | . | . | T | T | . | 1.09 | 1.00 | . | . | . | 0.35 | 1.12 |
| Gln | 64 | . | . | B | . | . | T | . | 1.09 | 1.00 | . | . | . | −0.05 | 1.10 |
| Ser | 65 | . | . | B | . | . | . | . | 1.43 | 0.24 | . | . | F | 0.20 | 1.24 |
| Leu | 66 | . | . | . | . | . | . | C | 1.38 | 0.21 | . | . | F | 0.70 | 2.03 |
| Pro | 67 | . | . | . | . | . | . | C | 1.29 | −0.31 | * | . | F | 1.60 | 1.57 |
| Glu | 68 | . | . | . | . | T | . | . | 1.58 | −0.33 | * | . | F | 2.10 | 1.57 |
| Gln | 69 | . | . | . | . | . | . | C | 0.99 | −0.71 | * | . | F | 2.50 | 3.19 |
| Ser | 70 | . | . | . | . | . | T | C | 0.48 | −0.90 | * | . | F | 3.00 | 2.08 |
| Ser | 71 | . | . | . | . | . | T | C | 1.29 | −0.64 | * | . | F | 2.55 | 0.99 |
| Asp | 72 | A | . | . | . | . | T | . | 0.91 | −0.64 | * | . | F | 2.05 | 0.99 |
| Ala | 73 | A | . | . | . | . | T | . | 0.62 | −0.54 | * | . | F | 1.75 | 0.75 |
| Leu | 74 | A | . | . | . | . | . | . | 0.62 | −0.01 | * | . | . | 0.80 | 0.59 |
| Glu | 75 | A | . | . | . | . | . | . | 0.92 | −0.40 | * | . | . | 0.50 | 0.61 |
| Ala | 76 | A | . | . | . | . | . | . | 0.88 | 0.00 | * | . | . | −0.10 | 0.97 |
| Trp | 77 | A | . | . | . | . | T | . | 0.88 | −0.07 | * | . | . | 0.85 | 1.16 |
| Glu | 78 | A | . | . | . | . | T | . | 1.58 | −0.76 | * | . | F | 1.30 | 1.16 |
| Asn | 79 | A | . | . | . | . | T | . | 2.09 | −0.76 | . | * | F | 1.30 | 2.25 |
| Gly | 80 | A | . | . | . | . | T | . | 2.20 | −0.87 | * | . | F | 1.30 | 2.87 |
| Glu | 81 | A | . | . | . | . | . | . | 2.83 | −1.79 | * | * | F | 1.10 | 3.25 |
| Arg | 82 | A | . | . | . | . | T | . | 3.23 | −1.79 | . | * | F | 1.30 | 4.04 |
| Ser | 83 | A | . | . | . | . | T | . | 3.34 | −2.19 | . | . | F | 1.30 | 7.99 |
| Arg | 84 | A | . | . | . | . | T | . | 2.76 | −2.61 | . | . | F | 1.30 | 9.04 |
| Lys | 85 | A | . | . | . | . | T | . | 2.24 | −2.11 | . | . | F | 1.30 | 4.66 |
| Arg | 86 | A | A | . | . | . | . | . | 1.43 | −1.47 | . | * | F | 0.90 | 2.58 |
| Arg | 87 | A | A | . | . | . | . | . | 1.01 | −1.17 | . | * | F | 0.90 | 1.09 |
| Ala | 88 | A | A | . | . | . | . | . | 1.31 | −0.69 | . | . | . | 0.60 | 0.78 |
| Val | 89 | A | A | . | . | . | . | . | 1.24 | −0.29 | . | . | . | 0.30 | 0.69 |
| Leu | 90 | A | A | . | . | . | . | . | 1.20 | −0.29 | . | * | F | 0.45 | 0.71 |
| Thr | 91 | A | A | . | . | . | . | . | 1.13 | 0.11 | . | . | F | 0.00 | 1.21 |
| Gln | 92 | A | A | . | . | . | . | . | 1.07 | −0.39 | . | * | F | 0.60 | 3.27 |
| Lys | 93 | A | A | . | . | . | . | . | 1.66 | −1.03 | . | . | F | 0.90 | 7.94 |
| Gln | 94 | A | A | . | . | . | . | . | 2.48 | −1.31 | . | . | F | 0.90 | 9.52 |
| Lys | 95 | A | A | . | . | . | . | . | 2.99 | −1.30 | . | . | F | 0.90 | 7.48 |
| Lys | 96 | A | A | . | . | . | . | . | 2.44 | −1.31 | . | . | F | 0.90 | 5.01 |
| Gln | 97 | . | A | B | . | . | . | . | 1.63 | −0.67 | . | . | F | 0.90 | 2.15 |
| His | 98 | . | A | B | . | . | . | . | 1.56 | −0.39 | . | . | . | 0.30 | 0.89 |
| Ser | 99 | . | A | B | . | . | . | . | 0.74 | 0.11 | * | . | . | −0.30 | 0.60 |
| Val | 100 | . | A | B | . | . | . | . | −0.16 | 0.80 | * | . | . | −0.60 | 0.29 |
| Leu | 101 | . | A | B | . | . | . | . | −0.41 | 1.04 | . | . | . | −0.60 | 0.16 |
| His | 102 | . | A | B | . | . | . | . | −1.30 | 0.97 | . | . | . | −0.60 | 0.18 |
| Leu | 103 | . | A | B | . | . | . | . | −1.27 | 1.27 | . | . | . | −0.60 | 0.17 |
| Val | 104 | . | A | B | . | . | . | . | −1.56 | 1.03 | . | . | . | −0.60 | 0.33 |
| Pro | 105 | . | A | B | . | . | . | . | −1.01 | 0.84 | . | . | . | −0.60 | 0.25 |
| Ile | 106 | . | . | B | B | . | . | . | −0.50 | 0.83 | . | * | . | −0.60 | 0.43 |
| Asn | 107 | . | . | B | B | . | . | . | −0.42 | 0.53 | . | * | . | −0.26 | 0.78 |
| Ala | 108 | . | . | B | B | . | . | . | 0.39 | −0.11 | . | * | F | 1.28 | 1.01 |
| Thr | 109 | . | . | B | B | . | . | . | 1.24 | −0.54 | . | * | F | 1.92 | 2.41 |
| Ser | 110 | . | . | . | . | . | T | C | 1.16 | −1.23 | . | * | F | 2.86 | 2.50 |
| Lys | 111 | . | . | . | . | T | T | . | 2.04 | −1.24 | * | * | F | 3.40 | 3.31 |
| Asp | 112 | . | . | . | . | T | T | . | 1.19 | −1.74 | . | * | F | 3.06 | 3.83 |
| Asp | 113 | . | . | . | . | T | T | . | 1.47 | −1.59 | . | * | F | 2.72 | 2.12 |
| Ser | 114 | . | . | . | B | . | . | C | 1.78 | −1.49 | . | . | F | 1.78 | 1.53 |
| Asp | 115 | A | A | . | B | . | . | . | 1.22 | −1.49 | * | . | F | 1.24 | 1.59 |
| Val | 116 | . | A | B | B | . | . | . | 0.58 | −0.84 | * | . | F | 0.75 | 0.71 |
| Thr | 117 | . | A | B | B | . | . | . | 0.29 | −0.23 | . | . | F | 0.45 | 0.52 |
| Glu | 118 | A | A | . | B | . | . | . | 0.29 | 0.30 | . | . | . | −0.30 | 0.33 |
| Val | 119 | A | A | . | B | . | . | . | 0.38 | 0.70 | * | . | . | −0.60 | 0.77 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Met | 120 | A | A | . | B | . | . | . | −0.21 | 0.49 | * | * | . | −0.60 | 0.82 |
| Trp | 121 | A | A | . | B | . | . | . | −0.17 | 0.50 | * | * | . | −0.60 | 0.48 |
| Gln | 122 | A | A | . | B | . | . | . | 0.26 | 1.19 | * | * | . | −0.60 | 0.53 |
| Pro | 123 | A | A | . | B | . | . | . | 0.37 | 0.54 | * | * | . | −0.45 | 1.05 |
| Ala | 124 | A | A | . | . | . | . | . | 0.88 | −0.07 | * | * | . | 0.79 | 1.96 |
| Leu | 125 | . | A | B | . | . | . | . | 1.59 | −0.56 | * | * | F | 1.58 | 1.12 |
| Arg | 126 | . | A | . | . | T | . | . | 1.53 | −0.96 | * | * | F | 2.32 | 1.42 |
| Arg | 127 | . | . | . | . | T | . | . | 0.72 | −0.96 | * | . | F | 2.86 | 1.39 |
| Gly | 128 | . | . | . | . | T | T | . | 0.93 | −0.77 | * | . | F | 3.40 | 1.39 |
| Arg | 129 | . | . | . | . | T | T | . | 0.93 | −1.06 | * | . | F | 3.06 | 1.23 |
| Gly | 130 | . | . | B | . | . | T | . | 1.74 | −0.56 | * | . | F | 2.17 | 0.63 |
| Leu | 131 | . | . | B | . | . | T | . | 1.29 | −0.16 | * | . | . | 1.53 | 1.11 |
| Gln | 132 | . | . | B | . | . | . | . | 0.93 | −0.16 | . | * | . | 0.84 | 0.56 |
| Ala | 133 | . | . | B | . | . | T | . | 0.93 | 0.60 | * | . | . | −0.20 | 0.89 |
| Gln | 134 | . | . | B | . | . | T | . | −0.03 | 0.60 | * | . | . | −0.05 | 1.07 |
| Gly | 135 | . | . | B | . | . | T | . | 0.42 | 0.56 | * | * | . | −0.20 | 0.46 |
| Tyr | 136 | . | . | B | . | . | T | . | 0.34 | 0.16 | . | * | . | 0.10 | 0.89 |
| Gly | 137 | . | . | B | B | . | . | . | 0.34 | 0.34 | * | * | . | −0.30 | 0.36 |
| Val | 138 | . | . | B | B | . | . | . | 0.93 | 0.34 | * | * | . | −0.30 | 0.63 |
| Arg | 139 | . | . | B | B | . | . | . | 0.34 | −0.09 | * | * | . | 0.30 | 0.67 |
| Ile | 140 | . | . | B | B | . | . | . | 0.34 | −0.34 | * | * | . | 0.30 | 0.68 |
| Gln | 141 | . | . | B | B | . | . | . | −0.27 | −0.34 | * | * | F | 0.45 | 0.91 |
| Asp | 142 | . | . | B | . | . | T | . | −0.17 | −0.34 | * | * | F | 0.85 | 0.34 |
| Ala | 143 | . | . | B | . | . | T | . | −0.12 | 0.41 | * | * | . | −0.20 | 0.77 |
| Gly | 144 | . | . | B | . | . | T | . | −1.04 | 0.41 | * | * | . | −0.20 | 0.37 |
| Val | 145 | . | . | B | . | . | T | . | −0.40 | 0.70 | * | . | . | −0.20 | 0.18 |
| Tyr | 146 | . | . | B | B | . | . | . | −0.70 | 1.46 | . | . | . | −0.60 | 0.28 |
| Leu | 147 | . | . | B | B | . | . | . | −0.70 | 1.34 | . | * | . | −0.60 | 0.38 |
| Leu | 148 | . | . | B | B | . | . | . | −0.97 | 1.31 | . | . | . | −0.60 | 0.89 |
| Tyr | 149 | . | . | B | B | . | . | . | −1.43 | 1.31 | . | . | . | −0.60 | 0.42 |
| Ser | 150 | . | . | B | B | . | . | . | −1.28 | 1.24 | . | * | . | −0.60 | 0.42 |
| Gln | 151 | . | . | B | B | . | . | . | −1.03 | 1.34 | . | . | . | −0.60 | 0.44 |
| Val | 152 | . | . | B | B | . | . | . | −0.22 | 1.06 | . | . | . | −0.60 | 0.49 |
| Leu | 153 | . | . | B | B | . | . | . | −0.27 | 0.30 | . | . | . | −0.30 | 0.61 |
| Phe | 154 | . | . | B | B | . | . | . | −0.33 | 0.56 | . | . | . | −0.60 | 0.26 |
| Gln | 155 | . | . | B | B | . | . | . | −0.73 | 0.64 | . | . | . | −0.60 | 0.51 |
| Asp | 156 | . | . | B | B | . | . | . | −1.04 | 0.79 | . | * | . | −0.60 | 0.53 |
| Val | 157 | . | . | B | B | . | . | . | −0.79 | 0.59 | . | . | . | −0.60 | 0.89 |
| Thr | 158 | . | . | B | B | . | . | . | −0.32 | 0.41 | * | . | . | −0.60 | 0.51 |
| Phe | 159 | . | . | B | B | . | . | . | 0.38 | 0.44 | * | . | . | −0.60 | 0.30 |
| Thr | 160 | . | . | B | B | . | . | . | −0.48 | 0.84 | * | . | . | −0.60 | 0.70 |
| Met | 161 | . | . | B | B | . | . | . | −1.33 | 0.84 | * | * | . | −0.60 | 0.36 |
| Gly | 162 | . | . | B | B | . | . | . | −0.78 | 1.00 | * | * | . | −0.60 | 0.31 |
| Gln | 163 | . | . | B | B | . | . | . | −0.36 | 0.60 | * | . | . | −0.60 | 0.29 |
| Val | 164 | . | . | B | B | . | . | . | 0.34 | 0.11 | * | . | . | −0.30 | 0.57 |
| Val | 165 | . | . | B | B | . | . | . | 0.31 | −0.50 | * | . | . | 0.64 | 0.99 |
| Ser | 166 | . | . | B | . | . | . | . | 0.91 | −0.50 | * | . | F | 1.33 | 0.57 |
| Arg | 167 | . | . | B | . | . | . | . | 0.91 | −0.50 | . | * | F | 1.82 | 1.33 |
| Glu | 168 | . | . | . | . | T | . | . | 1.02 | −0.71 | . | * | F | 2.86 | 1.77 |
| Gly | 169 | . | . | . | . | T | T | . | 1.88 | −1.36 | . | * | F | 3.40 | 2.58 |
| Gln | 170 | . | . | . | . | . | T | C | 2.73 | −1.34 | . | * | F | 2.86 | 2.28 |
| Gly | 171 | . | . | . | . | . | T | C | 2.72 | −1.34 | . | * | F | 2.52 | 2.28 |
| Arg | 172 | . | . | . | . | T | T | . | 1.80 | −0.86 | . | * | F | 2.38 | 3.33 |
| Gln | 173 | . | . | B | B | . | . | . | 1.10 | −0.60 | * | * | F | 1.24 | 1.59 |
| Glu | 174 | . | . | B | B | . | . | . | 1.56 | −0.21 | * | * | F | 1.60 | 1.39 |
| Thr | 175 | . | . | B | B | . | . | . | 0.89 | −0.64 | * | * | F | 0.90 | 1.39 |
| Leu | 176 | . | . | B | B | . | . | . | 0.34 | −0.07 | * | * | . | 0.30 | 0.43 |
| Phe | 177 | . | . | B | B | . | . | . | 0.34 | 0.21 | * | * | . | −0.30 | 0.17 |
| Arg | 178 | . | . | B | B | . | . | . | 0.04 | 0.21 | * | . | . | −0.30 | 0.24 |
| Cys | 179 | . | . | B | B | . | . | . | −0.56 | 0.11 | * | . | . | −0.30 | 0.38 |
| Ile | 180 | . | . | . | B | T | . | . | −0.46 | 0.04 | * | . | . | 0.10 | 0.44 |
| Arg | 181 | . | . | . | B | T | . | . | 0.06 | −0.31 | * | . | . | 0.70 | 0.35 |
| Ser | 182 | . | . | . | B | T | . | . | 0.72 | 0.07 | * | . | . | 0.10 | 0.86 |
| Met | 183 | . | . | . | . | . | . | C | 0.40 | 0.00 | * | . | F | 0.74 | 1.68 |
| Pro | 184 | . | . | . | . | T | . | . | 1.07 | −0.26 | * | * | F | 1.88 | 1.33 |
| Ser | 185 | . | . | . | . | . | . | C | 2.07 | −0.26 | * | * | F | 2.02 | 1.65 |
| His | 186 | . | . | . | . | T | . | C | 1.37 | −0.64 | * | . | F | 2.86 | 3.27 |
| Pro | 187 | . | . | . | . | T | T | . | 1.42 | −0.76 | * | . | F | 3.40 | 2.14 |
| Asp | 188 | . | . | . | . | T | T | . | 2.02 | −0.43 | * | . | F | 2.76 | 2.50 |
| Arg | 189 | . | . | . | . | T | T | . | 1.93 | −0.41 | * | . | F | 2.42 | 2.95 |
| Ala | 190 | . | . | . | . | T | . | . | 1.57 | −0.53 | * | . | . | 2.03 | 2.56 |
| Tyr | 191 | . | . | B | . | . | . | . | 1.36 | −0.39 | * | . | . | 0.84 | 0.82 |
| Asn | 192 | . | . | B | . | . | . | T | 1.27 | 0.37 | * | . | . | 0.10 | 0.66 |
| Ser | 193 | . | . | B | . | . | . | T | 0.68 | 0.76 | * | . | . | −0.20 | 0.87 |
| Cys | 194 | . | . | B | . | . | . | T | 0.22 | 0.76 | * | * | . | −0.20 | 0.56 |
| Tyr | 195 | . | . | . | . | T | T | . | −0.04 | 0.43 | . | . | . | 0.20 | 0.35 |
| Ser | 196 | . | . | . | . | T | . | . | −0.50 | 0.67 | . | . | . | 0.00 | 0.19 |

TABLE II-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 197 | . | . | B | . | . | . | . | −0.53 | 1.07 | . | . | . | −0.40 | 0.31 |
| Gly | 198 | . | . | B | . | . | . | . | −1.04 | 1.00 | . | . | . | −0.40 | 0.27 |
| Val | 199 | . | A | B | . | . | . | . | −0.41 | 0.93 | . | . | . | −0.60 | 0.17 |
| Phe | 200 | . | A | B | . | . | . | . | −0.17 | 1.04 | . | . | . | −0.60 | 0.22 |
| His | 201 | . | A | B | . | . | . | . | −0.21 | 0.94 | . | . | . | −0.60 | 0.39 |
| Leu | 202 | . | A | B | . | . | . | . | 0.38 | 0.94 | . | . | . | −0.60 | 0.52 |
| His | 203 | . | . | B | . | . | T | . | −0.17 | 0.30 | . | . | . | 0.25 | 1.00 |
| Gln | 204 | A | . | . | . | . | T | . | −0.12 | 0.20 | . | . | F | 0.25 | 0.52 |
| Gly | 205 | . | . | . | . | T | T | . | 0.28 | 0.39 | . | . | F | 0.65 | 0.52 |
| Asp | 206 | . | . | . | . | T | T | . | −0.54 | 0.09 | . | . | F | 0.65 | 0.51 |
| Ile | 207 | . | . | B | B | . | . | . | −0.62 | 0.23 | . | . | . | −0.30 | 0.22 |
| Leu | 208 | . | . | B | B | . | . | . | −1.48 | 0.51 | . | . | . | −0.60 | 0.15 |
| Ser | 209 | . | . | B | B | . | . | . | −1.69 | 0.77 | * | . | . | −0.60 | 0.06 |
| Val | 210 | . | . | B | B | . | . | . | −1.23 | 1.20 | * | . | . | −0.60 | 0.14 |
| Ile | 211 | . | . | B | B | . | . | . | −1.82 | 0.51 | * | * | . | −0.60 | 0.34 |
| Ile | 212 | . | . | B | B | . | . | . | −0.82 | 0.33 | * | * | . | −0.30 | 0.26 |
| Pro | 213 | . | . | B | B | . | . | . | −0.60 | −0.06 | . | * | . | 0.30 | 0.68 |
| Arg | 214 | A | A | . | . | . | . | . | −0.26 | −0.20 | . | * | . | 0.30 | 0.97 |
| Ala | 215 | A | A | . | . | . | . | . | −0.21 | −0.89 | . | * | F | 0.90 | 2.78 |
| Arg | 216 | A | A | . | . | . | . | . | 0.68 | −0.89 | . | * | F | 0.90 | 1.48 |
| Ala | 217 | A | A | . | . | . | . | . | 0.76 | −0.91 | . | * | F | 0.90 | 1.22 |
| Lys | 218 | A | A | . | . | . | . | . | 0.67 | −0.23 | . | * | . | 0.30 | 0.99 |
| Leu | 219 | . | A | B | . | . | . | . | 0.34 | −0.34 | . | * | . | 0.30 | 0.68 |
| Asn | 220 | . | A | B | . | . | . | . | 0.90 | 0.09 | . | * | . | −0.15 | 1.04 |
| Leu | 221 | . | A | B | . | . | . | . | 0.44 | 0.09 | . | * | . | −0.30 | 0.71 |
| Ser | 222 | . | . | . | . | . | T | C | 0.72 | 0.51 | . | * | F | 0.15 | 0.85 |
| Pro | 223 | . | . | . | . | . | T | C | −0.02 | 0.31 | . | * | F | 0.45 | 0.76 |
| His | 224 | . | . | . | . | T | T | . | −0.02 | 0.70 | . | * | F | 0.35 | 0.80 |
| Gly | 225 | . | . | B | . | . | T | . | −0.37 | 0.70 | . | * | F | −0.05 | 0.49 |
| Thr | 226 | . | . | B | B | . | . | . | −0.26 | 0.74 | . | . | . | −0.60 | 0.31 |
| Phe | 227 | . | . | B | B | . | . | . | −0.81 | 1.10 | . | * | . | −0.60 | 0.20 |
| Leu | 228 | . | . | B | B | . | . | . | −0.56 | 1.24 | . | * | . | −0.60 | 0.15 |
| Gly | 229 | . | . | B | B | . | . | . | −1.33 | 0.81 | . | * | . | −0.60 | 0.21 |
| Phe | 230 | . | . | B | B | . | . | . | −1.38 | 1.01 | . | * | . | −0.60 | 0.20 |
| Val | 231 | . | . | B | B | . | . | . | −1.46 | 0.66 | . | * | . | −0.60 | 0.31 |
| Lys | 232 | A | . | . | B | . | . | . | −1.14 | 0.40 | . | * | . | −0.60 | 0.40 |
| Leu | 233 | A | . | . | B | . | . | . | −0.72 | 0.40 | . | * | . | −0.60 | 0.59 |
| Ter | 234 | A | . | . | B | . | . | . | −0.77 | 0.04 | . | * | . | −0.15 | 1.01 |

TABLE III

| Res | Position | I | II | III | IV | V | VI | VII | VIII | IX | X | XI | XII | XIII | XIV |
|---|---|---|---|---|---|---|---|---|---|---|---|---|---|---|---|
| Gly | 1 | . | . | . | . | . | T | . | . | 0.39 | 0.06 | . | . | . | 0.30 | 0.52 |
| Thr | 2 | . | . | . | . | . | T | . | . | 0.48 | 0.06 | . | . | . | 0.30 | 0.63 |
| Gly | 3 | . | . | . | . | . | . | C | 0.87 | 0.01 | . | . | . | 0.40 | 0.66 |
| Gly | 4 | . | . | . | . | . | T | C | 1.26 | −0.01 | . | . | . | 1.65 | 1.16 |
| Pro | 5 | . | . | . | . | . | T | C | 1.30 | −0.04 | . | . | F | 2.10 | 1.30 |
| Ser | 6 | . | . | . | . | . | T | C | 1.64 | −0.10 | . | . | F | 2.40 | 1.30 |
| Gln | 7 | . | . | . | . | . | T | C | 1.61 | −0.53 | . | . | F | 3.00 | 2.27 |
| Asn | 8 | . | . | . | . | . | T | C | 1.71 | −0.53 | . | . | F | 2.70 | 1.45 |
| Gly | 9 | . | . | . | . | T | T | . | 1.84 | −0.20 | . | . | F | 2.30 | 1.70 |
| Glu | 10 | . | . | . | . | T | T | . | 1.77 | −0.16 | . | . | F | 2.00 | 1.51 |
| Gly | 11 | . | . | . | . | . | T | C | 2.07 | 0.36 | . | . | F | 0.75 | 0.99 |
| Tyr | 12 | . | . | . | . | . | T | C | 1.77 | 0.36 | . | . | . | 0.45 | 1.73 |
| Pro | 13 | . | . | . | . | T | T | . | 0.96 | 0.31 | . | . | . | 0.65 | 1.34 |
| Trp | 14 | . | . | . | . | T | T | . | 1.09 | 1.00 | . | . | . | 0.35 | 1.12 |
| Gln | 15 | . | . | B | . | . | T | . | 1.09 | 1.00 | . | . | . | −0.05 | 1.10 |
| Ser | 16 | . | . | B | . | . | . | . | 1.43 | 0.24 | . | . | F | 0.20 | 1.24 |
| Leu | 17 | . | . | . | . | . | . | C | 1.38 | 0.21 | . | . | . | 0.70 | 2.03 |
| Pro | 18 | . | . | . | . | . | . | C | 1.29 | −0.31 | * | . | F | 1.60 | 1.57 |
| Glu | 19 | . | . | . | . | T | . | . | 1.58 | −0.33 | * | . | F | 2.10 | 1.57 |
| Gln | 20 | . | . | . | . | . | . | C | 0.99 | −0.71 | * | . | F | 2.50 | 3.19 |
| Ser | 21 | . | . | . | . | . | T | C | 0.48 | −0.90 | * | . | F | 3.00 | 2.08 |
| Ser | 22 | . | . | . | . | . | T | C | 1.29 | −0.64 | * | . | F | 2.55 | 0.99 |
| Asp | 23 | . | . | . | . | . | T | C | 0.91 | −0.64 | * | . | F | 2.25 | 0.99 |
| Ala | 24 | . | . | . | . | . | T | C | 0.62 | −0.54 | * | . | F | 1.95 | 0.75 |
| Leu | 25 | . | A | . | . | . | . | C | 0.62 | −0.01 | * | . | . | 0.80 | 0.59 |
| Glu | 26 | A | A | . | . | . | . | . | 0.62 | −0.40 | * | . | . | 0.30 | 0.61 |
| Ala | 27 | A | A | . | . | . | . | . | 0.58 | −0.01 | * | . | . | 0.30 | 0.81 |
| Trp | 28 | A | A | . | . | . | . | . | 0.58 | −0.09 | * | . | . | 0.64 | 0.97 |
| Glu | 29 | A | . | . | . | . | T | . | 1.28 | −0.77 | * | . | F | 1.83 | 0.97 |
| Ser | 30 | A | . | . | . | . | T | . | 1.79 | −0.77 | * | * | F | 2.32 | 1.88 |
| Gly | 31 | . | . | . | . | . | T | C | 1.90 | −0.89 | * | * | F | 2.86 | 2.39 |

TABLE III-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 32 | . | . | . | . | T | T | . | 2.53 | −1.80 | * | * | F | 3.40 | 2.71 |
| Arg | 33 | . | . | . | . | T | T | . | 2.93 | −1.80 | . | * | F | 3.06 | 4.04 |
| Ser | 34 | . | . | . | . | T | T | . | 3.04 | −2.19 | . | * | F | 2.72 | 7.99 |
| Arg | 35 | . | . | . | . | T | T | . | 2.76 | −2.61 | . | . | F | 2.38 | 9.04 |
| Lys | 36 | . | . | . | . | T | T | . | 2.24 | −2.11 | . | . | F | 2.04 | 4.66 |
| Arg | 37 | . | A | . | . | T | . | . | 1.43 | −1.47 | . | * | F | 1.30 | 2.58 |
| Arg | 38 | . | A | B | . | . | . | . | 1.01 | −1.17 | . | * | F | 0.90 | 1.09 |
| Ala | 39 | . | A | B | . | . | . | . | 1.31 | −0.69 | . | . | . | 0.60 | 0.78 |
| Val | 40 | . | A | B | . | . | . | . | 1.24 | −0.29 | . | . | . | 0.30 | 0.69 |
| Leu | 41 | . | A | B | . | . | . | . | 1.20 | −0.29 | . | * | F | 0.45 | 0.71 |
| Thr | 42 | . | A | B | . | . | . | . | 1.13 | 0.11 | . | . | F | 0.00 | 1.21 |
| Gln | 43 | . | A | B | . | . | . | . | 1.02 | −0.39 | . | * | F | 0.60 | 3.27 |
| Lys | 44 | . | A | B | . | . | . | . | 1.61 | −0.63 | . | . | F | 0.90 | 6.38 |
| Gln | 45 | . | A | . | . | T | . | . | 2.17 | −1.31 | . | . | F | 1.30 | 7.38 |
| Lys | 46 | . | A | . | . | T | . | . | 2.98 | −1.41 | . | * | F | 1.30 | 5.71 |
| Asn | 47 | . | A | . | . | . | . | C | 2.43 | −1.81 | . | * | F | 1.33 | 4.77 |
| Asp | 48 | . | . | . | . | . | T | C | 2.12 | −1.17 | . | . | F | 1.96 | 2.05 |
| Ser | 49 | . | . | . | . | . | T | C | 2.08 | −1.09 | . | * | F | 2.19 | 1.48 |
| Asp | 50 | . | . | . | . | . | T | C | 1.22 | −1.09 | * | . | F | 2.42 | 1.59 |
| Val | 51 | . | . | B | . | . | T | . | 0.58 | −0.84 | * | . | F | 2.30 | 0.71 |
| Thr | 52 | . | A | B | . | . | . | . | 0.29 | −0.23 | . | . | F | 1.37 | 0.52 |
| Glu | 53 | . | A | B | . | . | . | . | 0.29 | 0.30 | . | . | . | 0.39 | 0.33 |
| Val | 54 | . | A | B | . | . | . | . | 0.38 | 0.70 | * | . | . | −0.14 | 0.77 |
| Met | 55 | . | A | B | . | . | . | . | −0.21 | 0.49 | * | . | . | −0.37 | 0.82 |
| Trp | 56 | . | A | B | . | . | . | . | −0.17 | 0.50 | * | * | . | −0.60 | 0.48 |
| Gln | 57 | . | A | B | . | . | . | . | 0.26 | 1.19 | * | * | . | −0.60 | 0.53 |
| Pro | 58 | . | A | B | . | . | . | . | 0.37 | 0.54 | * | * | . | −0.45 | 1.05 |
| Ala | 59 | . | A | . | . | . | . | C | 0.88 | −0.07 | * | * | . | 0.99 | 1.96 |
| Leu | 60 | . | A | B | . | . | . | . | 1.59 | −0.56 | * | * | F | 1.58 | 1.12 |
| Arg | 61 | . | A | . | . | . | T | . | 1.53 | −0.96 | * | . | F | 2.32 | 1.42 |
| Arg | 62 | . | . | . | . | . | T | . | 0.72 | −0.96 | * | . | F | 2.86 | 1.39 |
| Gly | 63 | . | . | . | . | T | T | . | 0.93 | −0.77 | * | . | F | 3.40 | 1.39 |
| Arg | 64 | . | . | . | . | T | T | . | 0.93 | −1.06 | * | . | F | 3.06 | 1.23 |
| Gly | 65 | . | . | B | . | . | T | . | 1.74 | −0.56 | * | . | F | 2.17 | 0.63 |
| Leu | 66 | . | . | B | . | . | T | . | 1.29 | −0.16 | * | . | . | 1.53 | 1.11 |
| Gln | 67 | . | . | B | . | . | . | . | 0.93 | −0.16 | . | * | . | 0.84 | 0.56 |
| Ala | 68 | . | . | B | . | . | T | . | 0.93 | 0.60 | * | . | . | −0.20 | 0.89 |
| Gln | 69 | . | . | B | . | . | T | . | −0.03 | 0.60 | * | . | . | −0.05 | 1.07 |
| Gly | 70 | . | . | B | . | . | T | . | 0.42 | 0.56 | * | * | . | −0.20 | 0.46 |
| Tyr | 71 | . | . | B | . | . | T | . | 0.34 | 0.16 | . | * | . | 0.10 | 0.89 |
| Gly | 72 | . | . | B | B | . | . | . | 0.34 | 0.34 | * | * | . | −0.30 | 0.36 |
| Val | 73 | . | . | B | B | . | . | . | 0.93 | 0.34 | * | * | . | −0.30 | 0.63 |
| Arg | 74 | . | . | B | B | . | . | . | 0.34 | −0.09 | * | * | . | 0.30 | 0.67 |
| Ile | 75 | . | . | B | B | . | . | . | 0.34 | −0.34 | * | * | . | 0.30 | 0.68 |
| Gln | 76 | . | . | B | B | . | . | . | −0.27 | −0.34 | * | * | F | 0.45 | 0.91 |
| Asp | 77 | . | . | B | . | . | T | . | −0.17 | −0.34 | * | * | F | 0.85 | 0.34 |
| Ala | 78 | . | . | B | . | . | T | . | −0.12 | 0.41 | * | * | . | −0.20 | 0.77 |
| Gly | 79 | . | . | B | . | . | T | . | −1.04 | 0.41 | * | * | . | −0.20 | 0.37 |
| Val | 80 | . | . | B | . | . | T | . | −0.40 | 0.70 | * | . | . | −0.20 | 0.18 |
| Tyr | 81 | . | . | B | B | . | . | . | −0.70 | 1.46 | . | . | . | −0.60 | 0.28 |
| Leu | 82 | . | . | B | B | . | . | . | −0.70 | 1.34 | . | * | . | −0.60 | 0.38 |
| Leu | 83 | . | . | B | B | . | . | . | −0.97 | 1.31 | . | . | . | −0.60 | 0.89 |
| Tyr | 84 | . | . | B | B | . | . | . | −1.43 | 1.31 | . | . | . | −0.60 | 0.42 |
| Ser | 85 | . | . | B | B | . | . | . | −1.28 | 1.24 | . | * | . | −0.60 | 0.42 |
| Gln | 86 | . | . | B | B | . | . | . | −1.03 | 1.34 | . | . | . | −0.60 | 0.44 |
| Val | 87 | . | . | B | B | . | . | . | −0.22 | 1.06 | . | . | . | −0.60 | 0.49 |
| Leu | 88 | . | . | B | B | . | . | . | −0.27 | 0.30 | . | . | . | −0.30 | 0.61 |
| Phe | 89 | . | . | B | B | . | . | . | −0.33 | 0.56 | . | . | . | −0.60 | 0.26 |
| Gln | 90 | . | . | B | B | . | . | . | −0.73 | 0.64 | . | . | . | −0.60 | 0.51 |
| Asp | 91 | . | . | B | B | . | . | . | −1.04 | 0.79 | . | * | . | −0.60 | 0.53 |
| Val | 92 | . | . | B | B | . | . | . | −0.79 | 0.59 | . | . | . | −0.60 | 0.89 |
| Thr | 93 | . | . | B | B | . | . | . | −0.32 | 0.41 | * | . | . | −0.60 | 0.51 |
| Phe | 94 | . | . | B | B | . | . | . | 0.38 | 0.44 | * | . | . | −0.60 | 0.30 |
| Thr | 95 | . | . | B | B | . | . | . | −0.48 | 0.84 | * | . | . | −0.60 | 0.70 |
| Met | 96 | . | . | B | B | . | . | . | −1.33 | 0.84 | * | * | . | −0.60 | 0.36 |
| Gly | 97 | . | . | B | B | . | . | . | −0.78 | 1.00 | * | * | . | −0.60 | 0.31 |
| Gln | 98 | . | . | B | B | . | . | . | −0.36 | 0.60 | * | . | . | −0.60 | 0.29 |
| Val | 99 | . | . | B | B | . | . | . | 0.34 | 0.11 | * | . | . | −0.30 | 0.57 |
| Val | 100 | . | . | B | B | . | . | . | 0.31 | −0.50 | * | . | . | 0.64 | 0.99 |
| Ser | 101 | . | . | B | . | . | . | . | 0.91 | −0.50 | * | . | F | 1.33 | 0.57 |
| Arg | 102 | . | . | B | . | . | . | . | 0.91 | −0.50 | . | * | F | 1.82 | 1.33 |
| Glu | 103 | . | . | . | . | . | T | . | 1.02 | −0.71 | . | * | F | 2.86 | 1.77 |
| Gly | 104 | . | . | . | . | T | T | . | 1.88 | −1.36 | . | * | F | 3.40 | 2.58 |
| Gln | 105 | . | . | . | . | . | T | C | 2.73 | −1.34 | . | * | F | 2.86 | 2.28 |
| Gly | 106 | . | . | . | . | . | T | C | 2.72 | −1.34 | . | . | F | 2.52 | 2.28 |
| Arg | 107 | . | . | . | . | T | T | . | 1.80 | −0.86 | * | * | F | 2.38 | 3.33 |
| Gln | 108 | . | . | . | B | B | . | . | 1.10 | −0.60 | * | * | F | 1.24 | 1.59 |

TABLE III-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 109 | . | . | B | B | . | . | . | 1.56 | −0.21 | . | * | F | 0.60 | 1.39 |
| Thr | 110 | . | . | B | B | . | . | . | 0.89 | −0.64 | * | * | F | 0.90 | 1.39 |
| Leu | 111 | . | . | B | B | . | . | . | 0.34 | −0.07 | * | * | . | 0.30 | 0.43 |
| Phe | 112 | . | . | B | B | . | . | . | 0.34 | 0.21 | * | * | . | −0.30 | 0.17 |
| Arg | 113 | . | . | B | B | . | . | . | 0.04 | 0.21 | * | . | . | −0.30 | 0.24 |
| Cys | 114 | . | . | B | B | . | . | . | −0.56 | 0.11 | * | . | . | −0.30 | 0.38 |
| Ile | 115 | . | . | . | B | T | . | . | −0.46 | 0.04 | * | . | . | 0.10 | 0.44 |
| Arg | 116 | . | . | . | B | T | . | . | 0.06 | −0.31 | * | . | . | 0.70 | 0.35 |
| Ser | 117 | . | . | . | B | T | . | . | 0.72 | 0.07 | * | . | . | 0.10 | 0.86 |
| Met | 118 | . | . | . | . | . | . | C | 0.40 | −0.00 | * | . | F | 1.34 | 1.68 |
| Pro | 119 | . | . | . | . | T | . | . | 1.07 | −0.26 | * | * | F | 1.88 | 1.33 |
| Ser | 120 | . | . | . | . | . | . | C | 2.07 | −0.26 | * | * | F | 2.02 | 1.65 |
| His | 121 | . | . | . | . | T | . | C | 1.37 | −0.64 | * | . | F | 2.86 | 3.27 |
| Pro | 122 | . | . | . | . | T | T | . | 1.42 | −0.76 | * | . | F | 3.40 | 2.14 |
| Asp | 123 | . | . | . | . | T | T | . | 2.02 | −0.43 | * | . | F | 2.76 | 2.50 |
| Arg | 124 | . | . | . | . | T | T | . | 1.93 | −0.41 | * | . | F | 2.42 | 2.95 |
| Ala | 125 | . | . | . | . | T | . | . | 1.57 | −0.53 | * | . | . | 2.03 | 2.56 |
| Tyr | 126 | . | . | B | . | . | . | . | 1.36 | −0.39 | * | . | . | 0.84 | 0.82 |
| Asn | 127 | . | . | B | . | . | T | . | 1.27 | 0.37 | * | . | . | 0.10 | 0.66 |
| Ser | 128 | . | . | B | . | . | T | . | 0.68 | 0.76 | * | . | . | −0.20 | 0.87 |
| Cys | 129 | . | . | B | . | . | T | . | 0.22 | 0.76 | * | * | . | −0.20 | 0.56 |
| Tyr | 130 | . | . | . | . | T | T | . | −0.04 | 0.43 | . | . | . | 0.20 | 0.35 |
| Ser | 131 | . | . | . | . | T | . | . | −0.50 | 0.67 | . | . | . | 0.00 | 0.19 |
| Ala | 132 | . | . | B | . | . | . | . | −0.53 | 1.07 | . | . | . | −0.40 | 0.31 |
| Gly | 133 | . | . | B | . | . | . | . | −1.04 | 1.00 | . | . | . | −0.40 | 0.27 |
| Val | 134 | . | A | B | . | . | . | . | −0.41 | 0.93 | . | . | . | −0.60 | 0.17 |
| Phe | 135 | . | A | B | . | . | . | . | −0.17 | 1.04 | . | . | . | −0.60 | 0.22 |
| His | 136 | . | A | B | . | . | . | . | −0.21 | 0.94 | . | . | . | −0.60 | 0.39 |
| Leu | 137 | . | A | B | . | . | . | . | 0.38 | 0.94 | . | . | . | −0.60 | 0.52 |
| His | 138 | . | . | B | . | . | T | . | −0.17 | 0.30 | . | . | . | 0.25 | 1.00 |
| Gln | 139 | . | . | . | . | T | T | . | −0.12 | 0.20 | . | . | F | 0.65 | 0.52 |
| Gly | 140 | . | . | . | . | T | T | . | 0.28 | 0.39 | . | . | F | 0.65 | 0.52 |
| Asp | 141 | . | . | . | . | T | T | . | −0.54 | 0.09 | . | . | F | 0.65 | 0.51 |
| Ile | 142 | . | . | B | B | . | . | . | −0.62 | 0.23 | . | . | . | −0.30 | 0.22 |
| Leu | 143 | . | . | B | B | . | . | . | −1.48 | 0.51 | . | . | . | −0.60 | 0.15 |
| Ser | 144 | . | . | B | B | . | . | . | −1.69 | 0.77 | * | . | . | −0.60 | 0.06 |
| Val | 145 | . | . | B | B | . | . | . | −1.23 | 1.20 | * | . | . | −0.60 | 0.14 |
| Ile | 146 | . | . | B | B | . | . | . | −1.82 | 0.51 | * | * | . | −0.60 | 0.34 |
| Ile | 147 | . | . | B | B | . | . | . | −0.82 | 0.33 | * | * | . | −0.30 | 0.26 |
| Pro | 148 | . | . | B | B | . | . | . | −0.60 | −0.06 | . | * | . | 0.30 | 0.68 |
| Arg | 149 | . | A | B | . | . | . | . | −0.26 | −0.20 | . | * | . | 0.30 | 0.97 |
| Ala | 150 | . | A | B | . | . | . | . | −0.21 | −0.89 | . | * | F | 0.90 | 2.78 |
| Arg | 151 | . | A | B | . | . | . | . | 0.68 | −0.89 | . | * | F | 0.90 | 1.48 |
| Ala | 152 | . | A | B | . | . | . | . | 0.76 | −0.91 | . | * | F | 0.90 | 1.22 |
| Lys | 153 | . | A | . | . | T | . | . | 0.67 | −0.23 | . | * | . | 0.70 | 0.99 |
| Leu | 154 | . | A | B | . | . | . | . | 0.34 | −0.34 | . | * | . | 0.30 | 0.68 |
| Asn | 155 | . | A | B | . | . | . | . | 0.90 | 0.09 | . | * | . | −0.15 | 1.04 |
| Leu | 156 | . | A | B | . | . | . | . | 0.44 | 0.09 | . | * | . | −0.30 | 0.71 |
| Ser | 157 | . | . | . | . | . | T | C | 0.72 | 0.51 | . | * | F | 0.15 | 0.85 |
| Pro | 158 | . | . | . | . | . | T | C | −0.02 | 0.31 | . | * | F | 0.45 | 0.76 |
| His | 159 | . | . | . | . | T | T | . | −0.02 | 0.70 | . | * | F | 0.35 | 0.80 |
| Gly | 160 | . | . | B | . | . | . | T | −0.37 | 0.70 | . | * | F | −0.05 | 0.49 |
| Thr | 161 | . | . | B | B | . | . | . | −0.26 | 0.74 | . | . | . | −0.60 | 0.31 |
| Phe | 162 | . | . | B | B | . | . | . | −0.81 | 1.10 | . | . | . | −0.60 | 0.20 |
| Leu | 163 | . | . | B | B | . | . | . | −0.56 | 1.24 | . | * | . | −0.60 | 0.15 |
| Gly | 164 | . | . | B | B | . | . | . | −1.33 | 0.81 | . | * | . | −0.60 | 0.21 |
| Phe | 165 | . | . | B | B | . | . | . | −1.38 | 1.01 | . | * | . | −0.60 | 0.20 |
| Val | 166 | . | . | B | B | . | . | . | −1.46 | 0.66 | . | * | . | −0.60 | 0.31 |
| Lys | 167 | . | . | B | B | . | . | . | −1.14 | 0.40 | . | * | . | −0.30 | 0.40 |
| Leu | 168 | . | . | B | B | . | . | . | −0.72 | 0.40 | . | . | . | −0.30 | 0.59 |
| Ter | 169 | . | . | B | B | . | . | . | −0.77 | 0.04 | . | * | . | −0.15 | 1.01 |

Among the especially preferred fragments of the invention are fragments characterized by structural or functional attributes of TNF delta and/or TNF epsilon. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) TNF delta (SEQ ID NO:2) and/or TNF epsilon (SEQ ID NO:4). Certain preferred regions are those set out in FIGS. 4 and 5 and include, but are not limited to, regions of the aforementioned types identified by analysis of the amino acid sequence depicted in FIGS. 1A and 1B (SEQ ID NO:2), 2A and 2B (SEQ ID NO:4), 6A and 6B (SEQ ID NO: 11) and 7A and 7B (SEQ ID NO: 13), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

Among highly preferred fragments in this regard are those that comprise regions of TNF delta and/or TNF epsilon that combine several structural features, such as several of the features set out above.

In specific embodiments, the polynucleotides of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of TNF delta or TNF epsilon coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide set forth in FIGS. 1A and 1B (SEQ ID NO:1), FIGS. 2A and 2B (SEQ ID NO:4), 6A and 6B (SEQ ID NO:11), and/or 7A and 7B (SEQ ID NO: 13), respectively. In further embodiments, polynucleotides of the invention comprise at least 15, at least 30, at least 50, at least 100, or at least 250, at least 500, or at least 1000 contiguous nucleotides of TNF delta or TNF epsilon coding sequence, but do not comprise all or a portion of any TNF delta or TNF epsilon intron. In another embodiment, the nucleic acid comprising TNF delta or TNF epsilon coding sequence does not contain coding sequences of a genomic flanking gene (i.e., 5' or 3' to the TNF delta or TNF epsilon gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

Further preferred regions are those that mediate activities of TNF delta and TNF epsilon. Most highly preferred in this regard are fragments that have a chemical, biological or other activity of TNF delta and TNF epsilon, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides set out in FIG. 3, including human TNF-alpha and beta. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention. Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques. In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli,* Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TNF-delta and/or TNF-epsilon coding sequence), and/or to include genetic material (e.g., heterologous polynucleotide sequences) that is operably associated with TNF-delta and/or TNF-epsilon polynucleotides of the invention, and which activates, alters, and/or amplifies endogenous TNF-delta and/or TNF-epsilon polynucleotides. For example, techniques known in the art may be used to operably associate heterologous control regions (e.g., promoter and/or enhancer) and endogenous TNF-delta and/or TNF-epsilon polynucleotide sequences via homologous recombination (see, e.g., U.S. Pat. No. 5,641,670, issued Jun. 24, 1997; International Publication Number WO 96/29411, published Sep. 26, 1996; International Publication Number WO 94/12650, published Aug. 4, 1994; Koller, et al., *Proc. Natl. Acad. Sci. USA* 86:8932–35 (1989); and Zijlstra, et al., *Nature* 342:435–38 (1989), the disclosures of each of which are incorporated by reference in their entireties).

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the E. coli lacI and lacZ and promoters, the T3 and T7 promoters, the gpt promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter. Selection of appropriate vectors and promoters for expression in a host cell is a well known procedure and the requisite techniques for expression vector construction, introduction of the vector into the host and expression in the host are routine skills in the art.

In one embodiment, polynucleotides encoding TNF-delta and/or TNF-epsilon polypeptides of the invention may be fused to signal sequences which will direct the localization of a protein of the invention to particular compartments of a prokaryotic or eukaryotic cell and/or direct the secretion of a protein of the invention from a prokaryotic or eukaryotic cell. For example, in E. coli, one may wish to direct the expression of the protein to the periplasmic space. Examples of signal sequences or proteins (or fragments thereof) to which the polypeptides of the invention may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic E. coli heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment,, polynucleotides encoding TNF delta or TNF epsilon polypeptides of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that may be fused to a polypeptide of the invention in order to direct its secretion in mammalian cells include, but are not limited to, the MPIF-1 signal sequence (amino acids 1–21 of GenBank Accession number AAB51134), the stanniocalcin signal sequence (MLQNSAVLLLLVISASA, SEQ ID NO:23), and a consensus signal sequence (MPTWAWWLFLVLLLALWAPARG, SEQ ID NO:24). A suitable signal sequence that may be used in conjunction with baculoviral expression systems is the gp67 signal sequence, (amino acids 1–19 of GenBank Accession Number AAA72759).

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. Basic Methods in Molecular Biology, (1986). Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trp1 gene of S. cerevisiae.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium*. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., *Cell,* 23:175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

As mentioned above, even if deletion of one or more amino acids from the N-terminus of a protein results in modification of loss of one or more biological functions of the protein, other functional activities (e.g., biological activities, ability to multimerize, ability to bind TNF delta ligand (e.g., TACI and/or BCMA and/or TR11, and/or TR11SV1, and/or TR11 SV2)) may still be retained. For example, the ability of shortened TNF delta muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TNF delta mutein with a large number of deleted N-terminal amino acid residues may retain some biological or immunogenic activities. In fact, peptides composed of as few as six TNF delta amino acid residues may often evoke an immune response.

Accordingly, the present invention further provides polypeptides having one or more residues deleted from the amino terminus of the TNF delta amino acid sequence shown in FIGS. 1A and 1B (i.e., SEQ ID NO:2), up to the Leucine residue at position number 228 and polynucleotides encoding such polypeptides. In particular, the present invention provides polypeptides comprising the amino acid sequence of residues $n^1$-233 of FIGS. 1A and 1B (SEQ ID NO:2), where $n^1$ is an integer from 2 to 228 corresponding to the position of the amino acid residue in FIGS. 1A and 1B (SEQ ID NO:2).

More in particular, the invention provides polynucleotides encoding polypeptides comprising, or alternatively consisting of, an amino acid sequence selected from the following amino acid sequences: G-2 to L-233; G-3 to L-233; P-4 to L-233; V-5 to L-233; R-6 to L-233; E-7 to L-233; P-8 to L-233; A-9 to L-233; L-10 to L-233; S-11 to L-233; V-12 to L-233; A-13 to L-233; L-14 to L-233; W-15 to L-233; L-16 to L-233; S-17 to L-233; W-18 to L-233; G-19 to L-233; A-20 to L-233; A-21 to L-233; L-22 to L-233; G-23 to L-233; A-24 to L-233; V-25 to L-233; A-26 to L-233; C-27 to L-233; A-28 to L-233; M-29 to L-233; A-30 to L-233; L-31 to L-233; L-32 to L-233; T-33 to L-233; Q-34 to L-233;

Q-35 to L-233; T-36 to L-233; E-37 to L-233; L-38 to L-233; Q-39 to L-233; S-40 to L-233; L-41 to L-233; R-42 to L-233; R-43 to L-233; E-44 to L-233; V-45 to L-233; S-46 to L-233; R-47 to L-233; L-48 to L-233; Q-49 to L-233; R-50 to L-233; T-51 to L-233; G-52 to L-233; G-53 to L-233; P-54 to L-233; S-55 to L-233; Q-56 to L-233; N-57 to L-233; G-58 to L-233; E-59 to L-233; G-60 to L-233; Y-61 to L-233; P-62 to L-233; W-63 to L-233; Q-64 to L-233; S-65 to L-233; L-66 to L-233; P-67 to L-233; E-68 to L-233; Q-69 to L-233; S-70 to L-233; S-71 to L-233; D-72 to L-233; A-73 to L-233; L-74 to L-233; E-75 to L-233; A-76 to L-233; W-77 to L-233; E-78 to L-233; N-79 to L-233; G-80 to L-233; E-81 to L-233; R-82 to L-233; S-83 to L-233; R-84 to L-233; K-85 to L-233; R-86 to L-233; R-87 to L-233; A-88 to L-233; V-89 to L-233; L-90 to L-233; T-91 to L-233; Q-92 to L-233; K-93 to L-233; Q-94 to L-233; K-95 to L-233; K-96 to L-233; Q-97 to L-233; H-98 to L-233; S-99 to L-233; V-100 to L-233; L-101 to L-233; H-102 to L-233; L-103 to L-233; V-104 to L-233; P-105 to L-233; I-106 to L-233; N-107 to L-233; A-108 to L-233; T-109 to L-233; S-110 to L-233; K-111 to L-233; D-112 to L-233; D-113 to L-233; S-114 to L-233; D-115 to L-233; V-116 to L-233; T-117 to L-233; E-118 to L-233; V-119 to L-233; M-120 to L-233; W-121 to L-233; Q-122 to L-233; P-123 to L-233; A-124 to L-233; L-125 to L-233; R-126 to L-233; R-127 to L-233; G-128 to L-233; R-129 to L-233; G-130 to L-233; L-131 to L-233; Q-132 to L-233; A-133 to L-233; Q-134 to L-233; G-135 to L-233; Y-136 to L-233; G-137 to L-233; V-138 to L-233; R-139 to L-233; I-140 to L-233; Q-141 to L-233; D-142 to L-233; A-143 to L-233; G-144 to L-233; V-145 to L-233; Y-146 to L-233; L-147 to L-233; L-148 to L-233; Y-149 to L-233; S-150 to L-233; Q-151 to L-233; V-152 to L-233; L-153 to L-233; F-154 to L-233; Q-155 to L-233; D-156 to L-233; V-157 to L-233; T-158 to L-233; F-159 to L-233; T-160 to L-233; M-161 to L-233; G-162 to L-233; Q-163 to L-233; V-164 to L-233; V-165 to L-233; S-166 to L-233; R-167 to L-233; E-168 to L-233; G-169 to L-233; Q-170 to L-233; G-171 to L-233; R-172 to L-233; Q-173 to L-233; E-174 to L-233; T-175 to L-233; L-176 to L-233; F-177 to L-233; R-178 to L-233; C-179 to L-233; I-180 to L-233; R-181 to L-233; S-182 to L-233; M-183 to L-233; P-184 to L-233; S-185 to L-233; H-186 to L-233; P-187 to L-233; D-188 to L-233; R-189 to L-233; A-190 to L-233; Y-191 to L-233; N-192 to L-233; S-193 to L-233; C-194 to L-233; Y-195 to L-233; S-196 to L-233; A-197 to L-233; G-198 to L-233; V-199 to L-233; F-200 to L-233; H-201 to L-233; L-202 to L-233; H-203 to L-233; Q-204 to L-233; G-205 to L-233; D-206 to L-233; I-207 to L-233; L-208 to L-233; S-209 to L-233; V-210 to L-233; I-211 to L-233; I-212 to L-233; P-213 to L-233; R-214 to L-233; A-215 to L-233; R-216 to L-233; A-217 to L-233; K-218 to L-233; L-219 to L-233; N-220 to L-233; L-221 to L-233; S-222 to L-233; P-223 to L-233; H-224 to L-233; G-225 to L-233; T-226 to L-233; F-227 to L-233; and L-228 to L-233 of the TNF delta sequence shown in FIGS. 1A and 1B (SEQ ID NO:2). Polypeptides encoded by these polynucleotides are also encompassed by the invention. The present application is also directed to nucleic acid molecules comprising, or alternatively, consisting of, a polynucleotide sequence at least 90%, 92%, 95%, 96%, 97%, 98% or 99% identical to the polynucleotide sequence encoding the TNF-delta polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

In another embodiment, the mature form of TNF delta comprises, or alternatively consists of Ala-88 to Leu-233 of the TNF delta sequence shown in FIGS. 1A and 1B (SEQ ID NO:2). Polynucleotides encoding these polypeptides are also encompassed by the invention. The present application is also directed to nucleic acid molecules comprising, or alternatively, consisting of, a polynucleotide sequence at least 90%, 92%, 95%, 96%, 97%, 98% or 99% identical to the polynucleotide sequence encoding the mature TNF-delta polypeptides described above. The present invention also encompasses polynucleotides encoding the above polypeptide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

In another embodiment, the mature form of TNF delta comprises, or alternatively consists of Ala-105 to Leu-250 of the TNF delta sequence shown in FIGS. 6A and 6B (SEQ ID NO:11). Polynucleotides encoding these polypeptides are also encompassed by the invention. The present application is also directed to nucleic acid molecules comprising, or alternatively, consisting of, a polynucleotide sequence at least 90%, 92%, 95%, 96%, 97%, 98% or 99% identical to the polynucleotide sequence encoding the mature TNF-delta polypeptides described above. The present invention also encompasses polynucleotides encoding the above polypeptide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

Also as mentioned above, even if deletion of one or more amino acids from the C-terminus of a protein results in modification of loss of one or more biological functions of the protein, other functional activities (e.g., biological activities, ability to multimerize, ability to bind TNF delta ligand (e.g., TACI and/or BCMA and/or TR11, and/or TR11SV1, and/or TR11SV2)) may still be retained. For example the ability of the shortened TNF delta mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TNF delta mutein with a large number of deleted C-terminal amino acid residues may retain some biological or immunogenic activities. In fact, peptides composed of as few as six TNF delta amino acid residues may often evoke an immune response.

Accordingly, the present invention further provides polypeptides having one or more residues deleted from the carboxy terminus of the amino acid sequence of the TNF delta polypeptide shown in FIGS. 1A and 1B (SEQ ID NO:2), up to the arginine residue at position number 6, and polynucleotides encoding such polypeptides. In particular, the present invention provides polypeptides comprising the amino acid sequence of residues 1-m¹ of FIGS. 1A and 1B (i.e., SEQ ID NO:2), where m¹ is an integer from 6 to 232 corresponding to the position of the amino acid residue in FIGS. 1A and 1B (SEQ ID NO:2).

More in particular, the invention provides polynucleotides encoding polypeptides comprising, or alternatively consisting of, an amino acid sequence selected from the following amino acid sequences: M-1 to K-232; M-1 to V-231; M-1 to F-230; M-1 to G-229; M-1 to L-228; M-1 to F-227; M-1 to T-226; M-1 to G-225; M-1 to H-224; M-1 to P-223; M-1 to S-222; M-1 to L-221; M-1 to N-220; M-1 to L-219; M-1 to K-218; M-1 to A-2 17; M-1 to R-216; M-1 to A-215; M-1 to R-214; M-1 to P-213; M-1 to I-212; M-1 to I-211; M-1 to V-210; M-1 to S-209; M-1 to L-208; M-1 to I-207; M-1 to D-206; M-1 to G-205; M-1 to Q-204; M-1 to H-203; M-1 to L-202; M-1 to H-201; M-1 to F-200; M-1 to V-199; M-1 to G-198; M-1 to A-197; M-1 to S-196; M-1 to Y-195; M-1 to C-194; M-1 to S-193; M-1 to N-192; M-1 to Y-191; M-1 to A-190; M-1 to R-189; M-1 to D-188; M-1 to P-187; M-1 to H-186; M-1 to S-185; M-1 to P-184; M-1 to M-183; M-1 to S-182; M-1 to R-181; M-1 to I-180; M-1 to C-179; M-1 to R-178; M-1 to F-177; M-1 to L-176; M-1 to T-175; M-1 to E-174; M-1 to Q-173; M-1 to R-172; M-1 to G-171; M-1 to Q-170; M-1 to G-169; M-1 to E-168; M-1 to R-167; M-1 to S-166; M-1 to V-165; M-1 to V-164; M-1 to Q-163; M-1 to G-162; M-1 to M-161; M-1 to T-160; M-1 to F-159; M-1 to T-158; M-1 to V-157; M-1 to D-156; M-1 to Q-155; M-1 to F-154; M-1 to L-153; M-1 to V-152; M-1 to Q-151; M-1 to S-150; M-1 to Y-149; M-1 to L-148; M-1 to L-147; M-1 to Y-146; M-1 to V-145; M-1 to G-144; M-1 to A-143; M-1 to D-142; M-1 to Q-141; M-1 to I-140; M-1 to R-139; M-1 to V-138; M-1 to G-137; M-1 to Y-136; M-1 to G-135; M-1 to Q-134; M-1 to A-133; M-1 to Q-132; M-1 to L-131; M-1 to G-130; M-1 to R-129; M-1 to G-128; M-1 to R-127; M-1 to R-126; M-1 to L-125; M-1 to A-124; M-1 to P-123; M-1 to Q-122; M-1 to W-121; M-1 to M-120; M-1 to V-119; M-1 to E-118; M-1 to T-117; M-1 to V-116; M-1 to D-115; M-1 to S-114; M-1 to D-113; M-1 to D-112; M-1 to K-111; M-1 to S-110; M-1 to T-109; M-1 to A-108; M-1 to N-107; M-1 to I-106; M-1 to P-105; M-1 to V-104; M-1 to L-103; M-1 to H-102; M-1 to L-101; M-1 to V-100; M-1 to S-99; M-1 to H-98; M-1 to Q-97; M-1 to K-96; M-1 to K-95; M-1 to Q-94; M-1 to K-93; M-1 to Q-92; M-1 to T-91; M-1 to L-90; M-1 to V-89; M-1 to A-88; M-1 to R-87; M-1 to R-86; M-1 to K-85; M-1 to R-84; M-1 to S-83; M-1 to R-82; M -1 to E-81; M -1 to G-80; M-1 to N-79; M-1 to E-78; M-1 to W-77; M-1 to A-76; M-1 to E-75; M-1 to L-74; M-1 to A-73; M-1 to D-72; M-1 to S-71; M-1 to S-70; M-1 to Q-69; M-1 to E-68; M-1 to P-67; M-1 to L-66; M-1 to S-65; M-1 to Q-64; M-1 to W-63; M-1 to P-62; M-1 to Y-61; M-1 to G-60; M-1 E-59; M-1 to G-58; M-1 to N-57; M-1 to Q-56; M-1 to S-55; M-1 to P-54; M-1 to G-53; M-1 to G-52; M-1 to T-51; M-1 to R-50; M-1 to Q-49; M-1 to L-48; M-1 to R-47; M-1 S-46; M-1 to V-45; M-1 to E-44; M-1 to R-43; M-1 to R-42; M-1 to L-41; M-1 to S-40; M-1 to Q-39; M-1 to L-38; M-1 to E-37; M-1 to T-36; M-1 to Q-35; M-1 Q-34; M-1 to T-33; M-1 to L-32; M-1 to L-31; M-1 to A-30; M-1 to M-29; M-1 to A-28; M-1 to C-27; M-1 to A-26; M-1 to V-25; M-1 to A-24; M-1 to G-23; M-1 to L-22; M-1 to A-21; M-1 to A-20; M-1 to G-19; M-1 to W-18; M-1 to S-17; M-1 to L-16; M-1 to W-15; M-1 to L-14; M-1 to A-13; M-1 to V-12; M-1 to S-11; M-1 to L-10; M-1 to A-9; M -1 to P-8; M-1 to E-7; M-I to R-6 of the sequence of the TNF delta sequence shown in FIGS. 1A and 1B (SEQ ID NO:2). Polypeptides encoded by these polynucleotides are also encompassed by the invention. The present application is also directed to nucleic acid molecules comprising, or alternatively, consisting of, a polynucleotide sequence at least 90%, 92%, 95%, 96%, 97%, 98% or 99% identical to the polynucleotide sequence encoding the TNF-delta polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

The invention also provides polypeptides having one or more amino acids deleted from both the amino and the carboxyl termini of a TNF delta polypeptide, which may be described generally as having residues n-$m^1$ of FIGS. 1A and 1B (i.e., SEQ ID NO:2), where $n^1$ and $m^1$ are integers as described above.

Also as mentioned above, even if deletion of one or more amino acids from the N-terminus of a protein results in modification of loss of one or more biological functions of the protein, other functional activities (e.g., biological activities, ability to multimerize, ability to bind TNF epsilon ligand) may still be retained. For example, the ability of shortened TNF epsilon muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a TNF epsilon mutein with a large number of deleted N-terminal amino acid residues may retain some biological or immunogenic activities. In fact, peptides composed of as few as six TNF epsilon amino acid residues may often evoke an immune response.

Accordingly, the present invention further provides polypeptides having one or more residues deleted from the amino terminus of the TNF epsilon amino acid sequence shown in FIGS. 2A and 2B (i.e., SEQ ID NO:4), up to the leucine residue at position number 163 and polynucleotides encoding such polypeptides. In particular, the present invention provides polypeptides comprising the amino acid sequence of residues $n^2$- 168 of FIGS. 2A and 2B (SEQ ID NO:4), where $n^2$ is an integer from 2 to 163 corresponding to the position of the amino acid residue in FIGS. 2A and 2B (SEQ ID NO:4).

More in particular, the invention provides polynucleotides encoding polypeptides comprising, or alternatively consisting of, an amino acid sequence selected from the following amino acid sequences: T-2 to L-168; G-3 to L-168; G-4 to L-168; P-5 to L-168; S-6 to L-168; Q-7 to L-168; N-8 to L-168; G-9 to L-168; E-10 to L-168; G-11 to L-168; Y-12 to L-168; P-13 to L-168; W-14 to L-168; Q-15 to L-168; S-16 to L-168; L-17 to L-168; P-18 to L-168; E-19 to L-168; Q-20 to L-168; S-21 to L-168; S-22 to L-168; D-23 to L-168; A-24 to L-168; L-25 to L-168; E-26 to L-168; A-27 to L-168; W-28 to L-168; E-29 to L-168; S-30 to L-168; G-31 to L-168; E-32 to L-168; R-33 to L-168; S-34 to L-168; R-35 to L-168; K-36 to L-168; R-37 to L-168; R-38 to L-168; A-39 to L-168; V-40 to L-168; L-41 to L-168; T-42 to L-168; Q-43 to L-168; K-44 to L-168; Q-45 to L-168; K-46 to L-168; N-47 to L-168; D-48 to L-168; S-49 to L-168; D-50 to L-168; V-51 to L-168; T-52 to L-168; E-53 to L-168; V-54 to L-168; M-55 to L-168; W-56 to L-168; Q-57 to L-168; P-58 to L-168; A-59 to L-168; L-60 to L-168; R-61 to L-168; R-62 to L-168; G-63 to L-168; R-64 to L-168; G-65 to L-168; L-66 to L-168; Q-67 to L-168; A-68 to L-168; Q-69 to L-168; G-70 to L-168; Y-71 to L-168; G-72 to L-168; V-73 to L-168; R-74 to L-168; I-75 to L-168; Q- 76 to L-168; D-77 to L-168; A-78 to L-168; G-79 to L-168; V-80 to L-168; Y-81 to L-168; L-82 to L-168; L-83 to L-168; Y-84 to L-168; S-85 to L-168; Q-86 to L-168; V-87 to L-168; L-88 to L-168; F-89 to L-168; Q-90 to L-168; D-91 to L-168; V-92 to L-168; T-93 to L-168; F-94 to L-168; T-95 to L-168; M-96 to L-168; G-97 to L-168; Q-98 to L-168; V-99 to L-168; V-100 to L-168; S-101 to L-168; R-102 to L-168; E-103 to L-168; G-104 to L-168; Q-105 to L-168; G-106 to L-168; R-107 to L-168; Q-108 to L-168; E-109 to L-168; T-110 to L-168; L-111 to L-168; F-112 to L-168; R-113 to L-168; C-114 to L-168; I-115 to L-168; R-116 to L-168; S-117 to L-168; M-118 to L-168; P-119 to L-168; S-120 to L-168; H-121 to L-168; P-122 to L-168; D-123 to L-168; R-124 to L-168; A-125 to L-168; Y-126 to L-168; N-127 to L-168; S-128 to L-168; C-129 to L-168; Y-130 to L-168; S-131 to L-168; A-132 to L-168; G-133 to L-168; V-134 to L-168; F-135 to L-168; H-136 to L-168; L-137 to L-168; H-138 to L-168; Q-139 to L-168; G-140 to L-168; D-141 to L-168; I-142 to L-168; L-143 to L-168; S-144 to L-168; V-145 to L-168; I-146 to L-168; I-147 to L-168; P-148 to L-168; R-149 to L-168; A-150 to L-168; R-151 to L-168; A-152 to L-168; K-153 to L-168; L-154 to L-168; N-155 to L-168; L-156 to L-168; S-157 to L-168; P-158 to L-168; H-159 to L-168; G-160 to L-168; T-161 to L-168; F-162 to L-168; and L-163 to L-168 of the TNF epsilon sequence shown in FIGS. 2A and 2B (SEQ ID NO:4). Polypeptides encoded by these polynucleotides are also encompassed by the invention. The present application is also directed to nucleic acid molecules comprising, or alternatively, consisting of, a polynucleotide sequence at least 90%, 92%, 95%, 96%, 97%, 98% or 99% identical to the polynucleotide sequence encoding the TNF-epsilon polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

In one embodiment, the mature form of TNF epsilon comprises, or alternatively consists of, amino acid residues Ala-39 to Leu- 168 of the TNF epsilon sequence shown in FIGS. 2A and 2B (SEQ ID NO:4). Polynucleotides encoding these polypeptides are also encompassed by the invention. The present application is also directed to nucleic acid molecules comprising, or alternatively, consisting of, a polynucleotide sequence at least 90%, 92%, 95%, 96%, 97%, 98% or 99% identical to the polynucleotide sequence encoding the mature TNF-epsilon polypeptides described above. The present invention also encompasses polynucleotides encoding the above polypeptide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

In another embodiment, the mature form of TNF epsilon comprises, or alternatively consists of Ala-105 to Leu-234 of the TNF epsilon sequence shown in FIGS. 7A and 7B (SEQ ID NO:13). Polynucleotides encoding these polypeptides are also encompassed by the invention. The present application is also directed to nucleic acid molecules comprising, or alternatively, consisting of, a polynucleotide sequence at least 90%, 92%, 95%, 96%, 97%, 98% or 99% identical to the polynucleotide sequence encoding the mature TNF-epsilon polypeptides described above. The present invention also encompasses polynucleotides encoding the above polypeptide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

Also as mentioned above, even if deletion of one or more amino acids from the C-terminus of a protein results in modification of loss of one or more biological functions of the protein, other functional activities (e.g., biological activities, ability to multimerize, ability to bind TNF epsilon ligand) may still be retained. For example the ability of the shortened TNF epsilon mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a TNF epsilon mutein with a large number of deleted C-terminal amino acid residues may retain some biological or immunogenic activities. In fact, peptides composed of as few as six TNF epsilon amino acid residues may often evoke an immune response.

Accordingly, the present invention further provides polypeptides having one or more residues deleted from the carboxy terminus of the amino acid sequence of the TNF epsilon polypeptide shown in FIGS. 2A and 2B (SEQ ID NO:4), up to the serine residue at position number 6, and polynucleotides encoding such polypeptides. In particular, the present invention provides polypeptides comprising the amino acid sequence of residues 1-m² of FIGS. 2A and 2B (i.e., SEQ ID NO:4), where m² is an integer from 6 to 167 corresponding to the position of the amino acid residue in FIGS. 2A and 2B (SEQ ID NO:4).

More in particular, the invention provides polynucleotides encoding polypeptides comprising, or alternatively consisting of, an amino acid sequence selected from the following amino acid sequences: G-1 to K-167; G-1 to V-166; G-1 to F-165; G-1 to G-164; G-1 to L-163; G-1 to F-162; G-1 to T-161; G-1 to G-160; G-1 to H-159; G-1 to P-158; G-1 to S-157; G-1 to L-156; G-1 to N-155; G-1 to L-154; G-1 to K-153; G-1 to A-152; G-1 to R-151; G-1 to A-150; G-1 to R-149; G-1 to P-148; G-1 to I-147; G-1 to I-146; G-1 to V-145; G-1 to S-144; G-1 to L-143; G-1 to I-142; G-1 to D-141; G-1 to G-140; G-1 to Q-139; G-1 to H-138; G-1 to L-137; G-1 to H-136; G-1 to F-135; G-1 to V-134; G-1 to G-133; G-1 to A-132; G-1 to S-131; G-1 to Y-130; G-1 to C-129; G-1 to S-128; G-1 to N-127; G-1 to Y-126; G-1 to A-125; G-1 to R-124; G-1 to D-123; G-1 to P-122; G-1 to H-121; G-1 to S-120; G-1 to P-119; G-1 to M-118; G-1 to S-1 17; G-1 to R-116; G-1 to I-115; G-1 to C-114; G-1 to R-113; G-1 to F-112; G-1 to L-111; G-1 to T-110; G-1 to E-109; G-1 to Q-108; G-1 to R-107; G-1 to G-106; G-1 to Q-105; G-1 to G-104; G-1 to E-103; G-1 to R-102; G-1 to S-101; G-1 to V-100; G-1 to V-99; G-1 to Q-98; G-1 to G-97; G-1 to M-96; G-1 to T-95; G-1 to F-94; G-1 to T-93; G-1 to V-92; G-1 to D-91; G-1 to Q-90; G-1 to F-89; G-1 to L-88; G-1 to V-87; G-1 to Q-86; G-1 to S-85; G-1 to Y-84; G-1 to L-83; G-1 to L-82; G-1 to Y-81; G-1 to V-80; G-1 to G-79; G-1 to A-78; G-1 to D-77; G-1 to Q-76; G-1 to I-75; G-1 to R-74; G-1 to V-73; G-1 to G-72; G-1 to Y-71; G-1 to G-70; G-1 to Q-69; G-1 to A-68; G-1 to Q-67; G-1 to L-66; G-1 to G-65; G-1 to R-64; G-1 to G-63; G-1 to R-62; G-1 to R-61; G-1 to L-60; G-1 to A-59; G-1 to P-58; G-1 to Q-57; G-1 to W-56; G-1 to M-55; G-1 to V-54; G-1 to E-53; G-1 to T-52; G-1 to V-51; G-1 to D-50; G-1 to S-49; G-1 to D-48; G-1 to N-47; G-1 to K-46; G-1 to Q-45; G-1 to K-44; G-1 to Q-43; G-1 to T-42; G-1 to L-41; G-1 to V-40; G-1 to A-39; G-1 to R-38; G-1 to R-37; G-1 to K-36; G-1 to R-35; G-1 to S-34; G-1 to R-33; G-1 to E-32; G-1 to G-31; G-1 to S-30; G-1 to E-29; G-1 to W-28; G-1 to A-27; G-1 to E-26; G-1 to L-25; G-1 to A-24; G-1 to D-23; G-1 to S-22; G-1 to S-21; G-1 to Q-20; G-1 to E-19; G-1 to P-18; G-1 to L-17; G-1 to S-16; G-1 to Q-15; G-1 to W-14; G-1 to P-13; G-1 to Y-12; G-1 to G-11; G-1 to E-10; G-1 to G-9; G-1 to N-8; G-1 to Q-7; and G-1 to S-6 of the sequence of the TNF epsilon sequence shown in FIGS. 2A and 2B (SEQ ID NO:4). Polypeptides encoded by these polynucleotides are also encompassed by the invention. The present application is also directed to nucleic acid molecules comprising, or alternatively, consisting of, a polynucleotide sequence at least 90%, 92%, 95%, 96%, 97%, 98% or 99% identical to the polynucleotide sequence encoding the TNF-delta polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

The invention also provides polypeptides having one or more amino acids deleted from both the amino and the carboxyl termini of a TNF epsilon polypeptide, which may be described generally as having residues $n^2$-$m^2$ of FIGS. 2A and 2B (i.e., SEQ ID NO:2), where $n^2$ and $m^2$ are integers as described above.

The present application is also directed to proteins cotaining polypeptides at least 90%, 95%, 96%, 97%, 98% or 99% identical to the TNF-delta and/or TNF-epsilon polypeptide sequence set forth herein as $n^1$-$m^1$ and/or $n^2$-$m^2$. In preferred embodiments, the application is directed to proteins containing polypeptides at least 90%, 95%, 96%, 97%, 98% or 99% identical to polypeptides having the amino acid sequence of the specific TNF-delta and/or TNF-epsilon N- and C-terminal deletions recited herein. Polynucleotides encoding these polypeptides are also encompassed by the invention.

In certain preferred embodiments, TNF-delta and/or TNF-epsilon proteins of the invention comprise fusion proteins as described above wherein the TNF-delta and/or TNF-epsilon polypeptides are those described as $n^1$-$m^1$ and/or $n^2$-$m^2$, herein. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

TNF-delta polypeptide fragments of the present invention include polypeptides comprising or alternatively, consisting of, an amino acid sequence contained in SEQ ID NO:2, encoded by the cDNA contained in the deposited clone, or encoded by nucleic acids which hybridize (e.g., under stringent hybridization conditions) to the nucleotide sequence contained in the deposited clone, or shown in FIGS. 1A and 1B (SEQ ID NO:1) or the complementary strand thereto. TNF-epsilon polypeptide fragments of the present invention include polypeptides comprising or alternatively, consisting of, an amino acid sequence contained in SEQ ID NO:4, encoded by the cDNA contained in the deposited clone, or encoded by nucleic acids which hybridize (e.g., under stringent hybridization conditions) to the nucleotide sequence contained in the deposited clone, or shown in FIGS. 2A and 2B (SEQ ID NO:3) or the complementary strand thereto. Protein fragments may be "free-standing," or comprised within a larger polypeptide of which the fragment forms a part or region, most preferably as a single continuous region.

The present invention also encompasses polypeptides comprising, or alternatively consisting of, an epitope of the polypeptide having an amino acid sequence of SEQ ID NO:2, or an epitope of the polypeptide sequence encoded by a polynucleotide sequence contained in deposited clone, or encoded by a polynucleotide that hybridizes to the complement of the sequence of SEQ ID NO:1 or contained in the deposited clone under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO: 1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The present invention also encompasses polypeptides comprising, or alternatively consisting of, an epitope of the polypeptide having an amino acid sequence of SEQ ID NO:4, or an epitope of the polypeptide sequence encoded by a polynucleotide sequence contained in deposited clone, or encoded by a polynucleotide that hybridizes to the complement of the sequence of SEQ ID NO:3 or contained in the deposited clone under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:3), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments that function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, for instance, Wilson et al., Cell 37:767–778 (1984); Sutcliffe et al., *Science* 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). A preferred immunogenic epitope includes the secreted protein (e.g., amino acid residues 88–233 of SEQ ID NO:2, amino acid residues 105–250 of SEQ ID NO:11, amino acid residues 39–168 of SEQ ID NO:4, and/or amino acid residues 105–234 of SEQ ID NO: 13). The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2): 76–82 (1998); Hansson, et al., J. Mol. Biol. 287:265–76 (1999); and Lorenzo and Blasco, Biotechniques 24(2): 308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

Proteins of the invention can be chemically synthesized using techniques known in the art (e.g., see Creighton, Proteins: Structures and Molecular Principles, W.H. Freeman & Co., N.Y. (1983), and Hunkapiller, et al., Nature 310:105–111 (1984)). For example, a peptide corresponding to a fragment of the TNF delta and/or TNF epsilon polypeptides of the invention can be synthesized by use of a peptide synthesizer. Furthermore, if desired, nonclassical amino acids or chemical amino acid analogs can be introduced as a substitution or addition into the TNF delta and/or TNF epsilon polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses TNF delta and/or TNF epsilon polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, $^{213}Bi$, or other radioisotopes such as, for example, iodine ($^{131}I$, $^{125}I$, $^{123}I$, $^{121}I$), carbon ($^{14}C$), sulfur ($^{35}S$), tritium ($^{3}H$), indium ($^{115m}In$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Tin$.

In specific embodiments, TNF delta and/or TNF epsilon-mpolypetides of the invention are attached to macrocyclic chelators useful for conjugating radiometal ions, including but not limited to, $^{111}In$, $^{177}Lu$, $^{90}Y$, $^{166}Ho$, and $^{153}Sm$, to polypeptides. In a preferred embodiment, the radiometal ion associated with the macrocyclic chelators attached to TNF delta and/or TNF epsilon polypeptides of the invention is $^{111}In$. In another preferred embodiment, the radiometal ion associated with the macrocyclic chelator attached to TNF delta and/or TNF epsilon polypeptides of the invention is $^{90}Y$. In specific embodiments, the macrocyclic chelator is 1,4,7,10-tetraazacyclododecane-N,N',N'',N'''-tetraacetic acid (DOTA). In other specific embodiments, the DOTA is attached to the TNF delta and/or TNF epsilon polypeptide of the invention via a linker molecule. Examples of linker molecules useful for conjugating DOTA to a polypeptide are commonly known in the art - see, for example, DeNardo et al., Clin Cancer Res. 4(10):2483–90, 1998; Peterson et al., Bioconjug. Chem. 10(4):553–7,1999; and Zimmerman et al, Nucl. Med. Biol. 26(8):943–50,1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties. Though U.S. Pat. Nos. 5,652,361 and 5,756,065 focus on conjugating chelating agents to antibodies, one skilled in the art could readily adapt the method disclosed therein in order to conjugate chelating agents to other polypeptides.

In one embodiment, TNF delta and/or TNF epsilon polypeptides of the invention may be labeled with biotin. In other related embodiments, biotinylated TNF delta and/or TNF epsilon polypeptides of the invention may be used, for example, as an imaging agent or as a means of identifying one or more TNF delta and/or TNF epsilon receptor(s) or other coreceptor or coligand molecules.

In another embodiment, the TNF delta and/or TNF epsilon polypeptides of the invention can be used as an agent to target and kill cells expressing a TNF delta and/or TNF epsilon receptor (e.g., TACI and/or BCMA). In this embodiment the polypeptides of the invention are associated, e.g., by covalent association or through protein-protein interactions, to a cytotoxin or cytotoxic agent. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine), improsulfan, piposulfan, benzodopa, carboquone, meturedopa, uredopa, altretamine, triethylenemelamine, trietylenephosphoramide, triethylenethiophosphaoramide trimethylolomelamine, chlomaphazine, cholophosphamide, estramustine, ifosfamide, novembichin, phenesterine, prednimustine, trofosfamide, uracil mustard, chlorozotocin, fotemustine, nimustine, ranimustine, aclacinomysins, azaserine, cactinomycin, calicheamicin, carabicin, carminomycin, carzinophilin, chromomycins, detorubicin, 6-diazo-5-oxo-L-norleucine, epirubicin, esorubicin, idarubicin, marcellomycin, mycophenolic acid, nogalamycin, olivomycins, peplomycin, potfiromycin, quelamycin, rodorubicin, streptonigrin, tubercidin, ubenimex, zinostatin, zorubicin, denopterin, pteropterin, trimetrexate, fludarabine, thiamiprine, ancitabine, azacitidine, 6-azauridine, carmofur, dideoxyuridine, doxifluridine, enocitabine, floxuridine, 5-FU, calusterone, dromostanolone propionate, epitiostanol, mepitiostane, testolactone, aminoglutethimide, mitotane, trilostane, frolinic acid, aceglatone, aldophosphamide glycoside, aminolevulinic acid, amsacrine, bestrabucil, bisantrene, edatraxate, defofamine, demecolcine, diaziquone, elfornithine, elliptinium acetate, etoglucid, gallium nitrate, hydroxyurea, lentinan, lonidamine, mitoguazone, mopidamol, nitracrine, pentostatin, phenamet, pirarubicin, podophyllinic acid, 2-ethylhydrazide, procarbazine, PSKO, razoxane, sizofiran, spirogermanium, tenuazonic acid, triaziquone, 2, 2',2"-trichlorotriethylamine, urethan, vindesine, dacarbazine, mannomustine, mitobronitol, mitolactol, pipobroman, gacytosine, arabinoside ("Ara-C"), taxoids, e.g. paclitaxel (TAXOL", Bristol-Myers Squibb Oncology, Princeton, N.J.) doxetaxel (TAXOTERE", Rh6ne-Poulenc Rorer, Antony, France), gemcitabine, ifosfamide, vinorelbine, navelbine, novantrone, teniposide, aminopterin, xeloda, ibandronate, CPT-I 1, topoisomerase inhibitor RFS 2000, difluoromethylornithine (DMFO), retinoic acid, esperamicins, capecitabine, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4 hydroxytamoxifen, trioxifene, keoxifene, LY 117018, onapristone, toremifene (Fareston), and anti-androgens such as flutamide, nilutamide, bicalutamide, leuprolide, and goserelin, and pharmaceutically acceptable salts, acids or derivatives of any of the above.

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), CD40 Ligand, a thrombotic agent or an anti- angiogenic agent, e.g., angiostatin or endostatin; or, biological response modifiers such as, for example, lymphokines, interleukin-1 ("IL- 1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Also provided by the invention are chemically modified derivatives of TNF delta and/or TNF epsilon which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59–72 (1996); Vorobjev et al., Nucleosides Nucleotides 18:2745–2750 (1999); and Caliceti et al, Bioconjug. Chem. 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1,2,3,4,5,6,7,8,9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

As mentioned, the TNF delta and/or TNF epsilon proteins of the invention may be modified by either natural processes, such as posttranslational processing, or by chemical modification techniques which are well known in the art. It will be appreciated that the same type of modification may be present in the same or varying degrees at several sites in a given TNF delta and/or TNF epsilon polypeptide. TNF delta and/or TNF epsilon polypeptides may be branched, for example, as a result of ubiquitination, and they may be cyclic, with or without branching. Cyclic, branched, and branched cyclic TNF delta and/or TNF epsilon polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., *Meth Enzymol* 182:626–646 (1990); Rattan et al., *Ann NY Acad Sci* 663:48–62 (1992)).

The polynucleotides and polypeptides of the present invention may be used in accordance with the present invention for a variety of applications, particularly those that make use of the chemical and biological properties TNF delta and TNF epsilon. Among these are applications in apoptosis of transformed cell lines, mediation of cell activation and proliferation and primary mediators of immune regulation antimicrobial, antiviral and inflammatory response susceptibility to pathogens. Additional applications relate to diagnosis and to treatment of disorders of cells, tissues and organisms. These aspects of the invention are illustrated further by the following discussion.

The proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., *Appl. Microbiol. Biotechnol.* 40:691–698 (1994); Carver et al., *Biotechnology (NY)* 11:1263–1270 (1993); Wright et al., *Biotechnology (NY)* 9:830–834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," *Intl. Rev. Cytol.* 115:171–229 (1989), which is incorporated by reference herein in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (*Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (*Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of TNF delta and/or TNF epsilon polypeptides, studying conditions and/or disorders associated with aberrant TNF delta and/or TNF epsilon expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

This invention is also related to the use of the polynucleotides of the present invention to detect complementary polynucleotides such as, for example, as a diagnostic reagent. Detection of a mutated form of a polypeptide of the present invention associated with a dysfunction will provide a diagnostic tool that can add or define a diagnosis of a disease or susceptibility to a disease which results from under-expression over-expression or altered expression of polypeptide of the present invention, such as, for example, neoplasia such as tumors.

Individuals carrying mutations in a gene of the present invention may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., Nature, 324: 163–166 1986). RNA or cDNA may also be used in the same ways. As an example, PCR primers complementary to the nucleic acid encoding TNF delta or TNF epsilon can be used to identify and analyze TNF delta or TNF epsilon expression and mutations. For example, deletions and insertions can be detected by a change in size of the amplified product in comparison to the normal genotype. Point mutations can be identified by hybridizing amplified DNA to radiolabeled TNF delta or TNF epsilon RNA or alternatively, radiolabeled TNF delta or TNF epsilon antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 1985).

Sequence changes at specific locations also may be revealed by nuclease protection assays, such as RNase and S 1 protection or the chemical cleavage method (e.g., Cotton et al., Proc. Natl. Acad. Sci., USA, 85:4397–4401, 1985). Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA. In addition to more conventional gel-electrophoresis and DNA sequencing, mutations also can be detected by in situ analysis.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a gene of the present invention. This can be accomplished using a variety of well known techniques and libraries, which generally are available commercially. The genomic DNA the is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 50 or 60. For a review of this technique, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The present invention also relates to a diagnostic assays such as quantitative and diagnostic assays for detecting levels of a protein in the present invention in cells and tissues, including determination of normal and abnormal levels. Thus, for instance, a diagnostic assay in accordance with the invention for detecting over-expression of TNF protein of the present invention compared to normal control tissue samples may be used to detect the presence of neoplasia, for example. Assay techniques that can be used to determine levels of a protein, such as a protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to a protein of the present invention, preferably a monoclonal antibody. In addition a reporter antibody generally is prepared which binds to the monoclonal antibody. The reporter antibody is attached to a detectable reagent such as radioactive, fluorescent or enzymatic, which in this example is horseradish peroxidase enzyme.

To carry out an ELISA assay a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any protein of the present invention attached to the polystyrene dish. Unbound monoclonal antibody is washed out with buffer. The reporter antibody linked to horseradish peroxidase is placed in the dish resulting in binding of the reporter antibody to any monoclonal antibody bound to a protein of the present invention. Unattached reporter antibody is then washed out. Reagents for peroxidase activity, including a colorimetric substrate are then added to the dish. Immobilized peroxidase, linked to protein of the present invention through the primary and secondary antibodies, produces a colored reaction product. The amount of color developed in a given time period indicates the amount of protein of the present invention present in the sample. Quantitative results typically are obtained by reference to a standard curve.

A competition assay may be employed wherein antibodies specific to protein of the present invention attached to a solid support and labeled protein of the present invention and a sample derived from the host are passed over the solid support and the amount of label detected attached to the solid support can be correlated to a quantity of protein of the present invention in the sample.

Antibodies

Further polypeptides of the invention include antibodies and T-cell antigen receptors (TCR) which immunospecifically bind a polypeptide (e.g. TNF delta and/or TNF epsilon), preferably an epitope, of the present invention (as determined by immunoassays well known in the art for assaying specific antibody-antigen binding). In specific embodiments, antibodies of the invention bind homomeric, especially homotrimeric, TNF delta and/or TNF epsilon polypeptides. In other specific embodiments, antibodies of the invention bind heteromeric, especially heterotrimeric, TNF delta and/or TNF epsilon polypeptides such as a heterotrimer containing two TNF delta and/or TNF epsilon polypeptides and one Neutrokine-alpha and/or Neutokine-alphaSV polypeptides (e.g., International Publication No. WO 98/18921; Science. 285:260 (1999); SEQ ID NOS:23 and 24 respectively) or a heterotrimer containing one TNF delta and/or TNF epsilon polypeptide and two Neutrokine-alpha and/or Neutokine-alphaSV polypeptides.

In particularly preferred embodiments, the antibodies of the invention bind homomeric, especially homotrimeric, TNF delta polypeptides, wherein the individual protein components of the multimers consist of the mature form of TNF delta (e.g., amino acids residues 88–233 of SEQ ID NO:2, or amino acids residues 105–250 of SEQ ID NO:11.) In particularly preferred embodiments, the antibodies of the invention bind homomeric, especially homotrimeric, TNF epsilon polypeptides, wherein the individual protein components of the multimers consist of the mature form of TNF epsilon (e.g., amino acids residues 39–168 of SEQ ID NO:4, or amino acids residues 105–234 of SEQ ID NO:13.)

In other specific embodiments, antibodies of the invention bind heteromeric, especially heterotrimeric, TNF delta and/or TNF epsilon polypeptides such as a heterotrimer containing two TNF delta and/or TNF epsilon polypeptides and one Neutrokine-alpha polypeptide or a heterotrimer containing one TNF delta and/or TNF epsilon polypeptide and two Neutrokine-alpha polypeptides, and wherein the individulal protein components of the TNF delta and/or TNF epsilon heteromer consist of the mature extracellular soluble portion of either TNF delta and/or TNF epsilon or (e.g., amino acids residues 88–233 of SEQ ID NO:2, amino acids residues 105–250 of SEQ ID NO:1 1, amino acids residues 39–168 of SEQ ID NO:4, or amino acids residues 105–234 of SEQ ID NO: 13.) or the mature extracellular soluble portion Neutrokine-alpha (e.g., amino acid residues 134–285 of SEQ ID NO:23, or amino acid residues 134–266 of SEQ ID NO:24).

In specific embodiments, the antibodies of the invention bind conformational epitopes of a TNF delta and/or TNF monomeric protein. In specific embodiments, the antibodies of the invention bind conformational epitopes of a TNF delta and/or TNF epsilon multimeric, especially trimeric, protein. In other embodiments, antibodies of the invention bind conformational epitopes that arise from the juxtaposition of TNF delta and/or TNF epsilon with a heterologous polypeptide, such as might be present when TNF delta and/or TNF epsilon forms heterotrimers (e.g., with Neutrokine-alpha and/or Neutrokine-alpha SV polypetides polypeptides (see, e.g, (International Publication No. WO 98/18921; Science. 285:260 (1999); SEQ ID NOS, 23 and 24), or in fusion proteins between TNF delta and/or TNF epsilon and a heterologous polypeptide.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

In specific embodiments, immunoglobulin molecules of the invention are IgG1.

In other specific embodiments, immunoglobulin molecules of the invention are IgG4.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In a specific embodiment, antibodies of the present invention cross react with Neutrokine-alpha (also known as B lymphocyte stimulator (BLyS)) and/or Neutrokine alpha splice variant (International Publication No. WO 98/18921; Science. 285:260 (1999); SEQ ID NOS:23 and 24, respectively). In specific embodiments, antibodies of the present invention cross-react with murine, rat and/or rabbit homologs of human proteins and the corresponding epitopes thereof.

Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, antibodies of the present invention do not cross react with Neutrokine-alpha (also known as B lymphocyte stimulator (BLyS)) and/or Neutrokine alpha splice variant (Science. 285:260 (1999)). In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$M, $10^{-2}$M, $5 \times 10^{-3}$M, $10^{-3}$M, $5 \times 10^{-4}$M, $10^{-4}$M, $5 \times 10^{-5}$M, $10^{-5}$M. Even more preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. For example, the present invention includes antibodies which disrupt binding of polypeptides of the invention with TACI and/or BCMA and/or TR11, and/or TR11SV1, and/or TR11SV2. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting stimulation of the transcription factor NF-AT by measuring the expression of an NF-AT regulatory element linked to a SEAP, beta-gal, CAT, or other reporter element. Alternatively, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 95%, at least 90%, at least 85%, at least 80%, at least 75% at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen, et al., Cancer Res. 58(16):3668–3678 (1998); Harrop et al., J. Immunol. 161(4):1786–1794 (1998); Zhu et al., Cancer Res. 58(15):3209–3214 (1998); Yoon, et al., J. Immunol. 160(7):3170–3179 (1998); Prat et al., J. Cell. Sci. 111 (Pt2):237–247 (1998); Pitard et al., J. Immunol. Methods 205(2):177–190 (1997); Liautard et al., Cytokine 9(4): 233–241 (1997); Carlson et al., J. Biol. Chem. 272(17): 11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, radionuclides, metal ion chelating agents, drugs, or toxins, or any combination thereof. A preferred radionuclide is $^{90}$Y. Another preferred radionuclide is $^{111}$In. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of- interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. A "monoclonal antibody" may comprise, or alternatively consist of, two proteins, i.e., a heavy and a light chain.

Methods for producing and screening for specific antibodies using hybridoma technology are routine and well-known in the art and are discussed in detail in Example 9. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Another well known method for producing both polyclonal and monoclonal human B cell lines is transformation using Epstein Barr Virus (EBV). Protocols for generating EBV-transformed B cell lines are commonly known in the art, such as, for example, the protocol outlined in Chapter 7.22 of Current Protocols in Immunology, Coligan et al., Eds., 1994, John Wiley & Sons, NY, which is hereby incorporated in its entirety by reference herein. The source of B cells for transformation is commonly human peripheral blood, but B cells for transformation may also be derived from other sources including, but not limited to, lymph nodes, tonsil, spleen, tumor tissue, and infected tissues. Tissues are generally made into single cell suspensions prior to EBV transformation. Additionally, steps may be taken to either physically remove or inactivate T cells (e.g., by treatment with cyclosporin A) in B cell-containing samples, because T cells from individuals seropositive for anti-EBV antibodies can suppress B cell immortalization by EBV.

In general, the sample containing human B cells is innoculated with EBV, and cultured for 3–4 weeks. A typical source of EBV is the culture supernatant of the B95-8 cell line (ATCC #VR-1492). Physical signs of EBV transformation can generally be seen towards the end of the 3–4 week culture period. By phase-contrast microscopy, transformed cells may appear large, clear, hairy and tend to aggregate in tight clusters of cells. Initially, EBV lines are generally polyclonal. However, over prolonged periods of cell cultures, EBV lines may become monoclonal or polyclonal as a result of the selective outgrowth of particular B cell clones. Alternatively, polyclonal EBV transformed lines may be subcloned (e.g., by limiting dilution culture) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human x mouse; e.g, SPAM-8, SBC-H20, and CB-F7), and human cell lines (e.g., GM 1500, SKO-007, RPMI 8226, and KR-4). Thus, the present invention also provides a method of generating polyclonal or monoclonal human antibodies against polypeptides of the invention or fragments thereof, comprising EBV-transformation of human B cells.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene II or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089;

Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65–93 (1995)). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Intrabodies of the invention can be produced using methods known in the art, such as those disclosed and reviewed in Chen et al., Hum. Gene Ther. 5:595–601 (1994); Marasco, W. A., Gene Ther. 4:11–15 (1997); Rondon and Marasco, Annu. Rev. Microbiol. 51:257–283 (1997); Proba et al., J. Mol. Biol. 275:245–253 (1998); Cohen et al., Oncogene 17:2445–2456 (1998); Ohage and Steipe, J. Mol. Biol. 291:1119–1128 (1999); Ohage et al., J. Mol. Biol. 291:1129–1134 (1999); Wirtz and Steipe, Protein Sci. 8:2245–2250 (1999); Zhu et al., J. Immunol. Methods 231:207–222 (1999); and references cited therein. In particular, a CCR5 intrabody has been produced by Steinberger et al., Proc. Natl. Acad. Sci. USA 97:805–810 (2000).

Polynucleotides Encoding Antibodies.

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, Proc. Natl. Acad. Sci. 81:851–855; Neuberger et al., 1984, Nature 312:604–608; Takeda et al., 1985, Nature 314:452–454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, 1988, Science 242:423–42; Huston et al., 1988, Proc. Natl. Acad. Sci. USA 85:5879–5883; and Ward et al., 1989, Nature 334:544–54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, Science 242:1038–1041).

Methods of Producing Antibodies

The antibodies of the invention can be produced by any method known in the art for the synthesis of antibodies, in particular, by chemical synthesis or preferably, by recombinant expression techniques.

Methods of producing antibodies include, but are not limited to, hybridoma technology, EBV transformation, and other methods discussed herein as well as through the use recombinant DNA technology, as discussed below.

Recombinant expression of an antibody of the invention, or fragment, derivative or analog thereof, (e.g., a heavy or light chain of an antibody or single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli,* and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 24:5503–5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non- essential region of the viral genome (e.g., region E1 or E3) will result in a recombinant virus that is viable and capable of expressing the antibody molecule in infected hosts. (e.g., see Logan & Shenk, 1984, Proc. Natl. Acad. Sci. USA 81:355–359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, NSO, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes can be employed in tk-, hgprt- or aprt- cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488–505; Wu and Wu, 1991, Biotherapy 3:87–95; Tolstoshev, 1993, Ann. Rev.

Pharmacol. Toxicol. 32:573–596; Mulligan, 1993, Science 260:926–932; and Morgan and Anderson, 1993, Ann. Rev. Biochem. 62:191–217; May, 1993, TIB TECH 11(5):155–215); and hygro, which confers resistance to hygromycin (Santerre et al., 1984, Gene 30:147). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

Vectors which use glutamine synthase (GS) or DHFR as the selectable marker can be amplified in the presence of the drugs methionine sulphoximine or methotrexate, respectively. An advantage of glutamine synthase based vectors are the availabilty of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from supliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995) which are incorporated in their entirities by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once an antibody molecule of the invention has been produced by an animal, chemically synthesized or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Antibody conjugates

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995)0.

Moreover, the antibodies or fragments thereof of the present invention can be fused to marker sequences, such as a peptide to facilitates their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{131}$I, $^{125}$I, $^{123}$I, $^{121}$I), carbon ($^{14}$C), sulfur ($^{35}$S), tritium ($^3$H), indium ($^{115m}$In, $^{113m}$In, 112In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

In specific embodiments, antibodies of the invention are attached to macrocyclic chelators useful for conjugating radiometal ions, including but not limited to, $^{177}$Lu, $^{90}$Y, $^{166}$Ho, and $^{153}$Sm, to polypeptides. In a preferred embodiment, the radiometal ion associated with the macrocyclic chelator attached to antibodies of the invention is $^{111}$In. In another preferred embodiments, the radiometal ion associated with the macrocyclic chelator attached to antibodies of the invention is $^{90}$Y. In specific embodiments, the macrocyclic chelator is 1,4,7,10-tetraazacyclododecane-N, N',N'',N'''-tetraacetic acid (DOTA). In other specific embodiments, the DOTA is attached to the TNF delta and/or TNF epsilon polypeptide of the invention via a linker molecule. Examples of linker molecules useful for conjugating DOTA to a polypeptide are commonly known in the art—see, for example, DeNardo et al., Clin Cancer Res. 4(10):2483–90, 1998; Peterson et al., Bioconjug. Chem. 10(4):553–7, 1999; and Zimmerman et al, Nucl. Med. Biol. 26(8):943–50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), CD40 Ligand, a thrombotic agent or an anti- angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C, washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the described disorders. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein). The antibodies of the invention can be used to treat, inhibit or prevent diseases and disorders associated with aberrant expression and/or activity of a polypeptide of the invention and/or a receptor for the polypeptide of the invention (e.g., transmembrane activator and CAML interactor (TACI, GenBank accesion number AAC51790), and B-cell maturation antigen (BCMA, GenBank accession number NP_001183)), including, but not limited to, any one or more of the diseases, disorders, or conditions described herein (e.g., autoimmune diseases, disorders, or conditions associated with such diseases or disorders, including, but not limited to, autoimmune hemolytic anemia (including but not limited to cryoglobinemia or Coombs positive anemia), autoimmune neonatal thrombocytopenia, idiopathic thrombocytopenia purpura, autoimmunocytopenia, autoimmune neutropenia, hemolytic anemia, antiphospholipid syndrome, dermatitis (e.g., atopic dermatitis), allergic encephalomyelitis, myocarditis, relapsing polychondritis, rheumatic heart disease, Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, diabetes mellitus (e.g., Type I diabetes mellitus or insulin dependent diabetes mellitus, juvenile onset diabetes, and autoimmune inflammatory eye, autoimmune thyroiditis, hypothyroidism (i.e., Hashimoto's thyroiditis, systemic lupus erythematosus, discoid lupus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia (Addison's disease), idiopathic Addison's disease, infertility, glomerulonephritis such as primary glomerulonephritis, IgA glomerulonephritis, and IgA nephropathy, bullous pemphigoid, Sjögren's syndrome, diabetes millitus, and adrenergic drug resistance (including adrenergic drug resistance with asthma or cystic fibrosis), gluten sensitive enteropathy, dense deposit disease, chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders) and other disorders such as inflammatory skin diseases including psoriasis and sclerosis, responses associated with inflammatory bowel disease (such as Crohn's disease and ulcerative colitis), respiratory distress syndrome (including adult respiratory distress syndrome, ARDS), meningitis, encephalitis, colitis, allergic conditions such as eczema and other conditions involving infiltration of T cells and chronic inflammatory responses, atherosclerosis, leukocyte adhesion deficiency, Reynaud's syndrome, and immune responses associated with acute and delayed hypersensitivity mediated by cytokines and T-lymphocytes typically found in tuberculosis, sarcoidosis, granulomatosis and diseases involving leukocyte diapedesis, central nervous system (CNS) inflammatory disorder, multiple organ injury syndrome, antigen-antibody complex mediated diseases, anti-glomerular basement membrane disease, Lambert-Eaton myasthenic syndrome, Beheet disease, giant cell arteritis, immune complex nephritis, IgA nephropathy, IgM polyneuropathies or autoimmune thrombocytopenia etc.

In a specific embodiment, antibodies of the invention are be used to treat, inhibit, prognose, diagnose or prevent rheumatoid arthritis. In a another embodiment, antibodies of the invention are used to treat, inhibit, prognose, diagnose or prevent advanced rheumatoid arthritis.

In another specific embodiment, antibodies of the invention are used to treat, inhibit, prognose, diagnose or prevent systemic lupus erythematosus.

For example, an antibody, or antibodies, of the present invention are used to treat patients with clinical diagnosis of rheumatoid arthritis (RA). The patient treated will not have a B cell malignancy. Moreover, the patient is optionally further treated with any one or more agents employed for treating RA such as salicylate; nonsteroidal anti-inflammatory drugs such as indomethacin, phenylbutazone, phenylacetic acid derivatives (e.g. ibuprofen and fenoprofen), naphthalene acetic acids (naproxen), pyrroleal-kanoic acid (tometin), indoleacetic acids (sulindac), halogenated anthranilic acid (meclofenamate sodium), piroxicam, zomepirac and diflunisal; antimalarials such as chloroquine; gold salts; penicillamine; or immunosuppressive agents such as methotrexate or corticosteroids in dosages known for such drugs or reduced dosages. Preferably however, the patient is only treated with an antibody, or antibodies, of the present invention. Antibodies of the present invention are administered to the RA patient according to a dosing schedule as described infra, which may be readily determined by one of ordinary skill in the art. The primary response is determined by the Paulus index (Paulus et al. Athritis Rheum. 33:477–484 (1990)), i.e. improvement in morning stiffness, number of painful and inflamed joints, erythrocyte sedimentation (ESR), and at least a 2-point improvement on a 5-point scale of disease severity assessed by patient and by physician. Administration of an antibody, or antibodies, of the present invention will alleviate one or more of the symptoms of RA in the patient treated as described above.

In a further specific embodiment, antibodies of the invention are used to treat, inhibit, prognose, diagnose or prevent hemolytic anemia. For example, patients diagnosed with autoimmune hemolytic anemia (AIHA), e.g., cryoglobinemia or Coombs positive anemia, are treated with an antibody, or antibodies, of the present invention. AIHA is an acquired hemolytic anemia due to auto-antibodies that react with the patient's red blood cells. The patient treated will not have a B cell malignancy. Further adjunct therapies (such as glucocorticoids, prednisone, azathioprine, cyclophosphamide, vinca-laden platelets or Danazol) may be combined with the antibody therapy, but preferably the patient is treated with an antibody, or antibodies, of the present invention as a single-agent throughout the course of therapy. Antibodies of the present invention are administered to the hemolytic anemia patient according to a dosing schedule as described infra, which may be readily determined by one of ordinary skill in the art. Overall response rate is determined based upon an improvement in blood counts, decreased requirement for transfusions, improved hemoglobin levels and/or a decrease in the evidence of hemolysis as determined by standard chemical parameters. Administration of an antibody, or antibodies of the present invention will improve any one or more of the symptoms of hemolytic anemia in the patient treated as described above. For example, the patient treated as described above will show an increase in hemoglobin and an improvement in chemical parameters of hemolysis or return to normal as measured by serum lactic dehydrogenase and/or bilirubin.

In another specific embodiment, antibodies of the invention are used to treat, inhibit, prognose, diagnose or prevent adult immune thrombocytopenic purpura. Adult immune thrombocytopenic purpura (ITP) is a relatively rare hematologic disorder that constitutes the most common of the immune-mediated cytopenias. The disease typically presents with severe thrombocytopenia that may be associated with acute hemorrhage in the presence of normal to increased megakaryocytes in the bone marrow. Most patients with ITP have an IgG antibody directed against target antigens on the outer surface of the platelet membrane, resulting in platelet sequestration in the spleen and accelerated reticuloendothelial destruction of platelets (Bussell, J. B. Hematol. Oncol. Clin. North Am. (4):179 (1990)). A number of therapeutic interventions have been shown to be effective in the treatment of ITP. Steroids are generally considered first-line therapy, after which most patients are candidates for intravenous immunoglobulin (IVIG), splenectomy, or other medical therapies including vincristine or immunosuppressive/cytotoxic agents. Up to 80% of patients with ITP initially respond to a course of steroids, but far fewer have complete and lasting remissions. Splenectomy has been recommended as standard second-line therapy for steroid failures, and leads to prolonged remission in nearly 60% of cases yet may result in reduced immunity to infection. Splenectomy is a major surgical procedure that may be associated with substantial morbidity (15%) and mortality (2%). IVIG has also been used as second line medical therapy, although only a small proportion of adult patients with ITP achieve remission. Therapeutic options that would interfere with the production of autoantibodies by activated B cells without the associated morbidities that occur with corticosteroids and/or splenectomy would provide an important treatment approach for a proportion of patients with ITP. Patients with clinical diagnosis of ITP are treated with an antibody, or antibodies of the present invention, optionally in combination with steroid therapy. The patient treated will not have a B cell malignancy. Antibodies of the present invention are administered to the RA patient according to a dosing schedule as described infra, which may be readily determined by one of ordinary skill in the art. Overall patient response rate is determined based upon a platelet count determined on two consecutive occasions two weeks apart following treatments as described above. See, George et al. "Idiopathic Thrombocytopenic Purpura: A Practice Guideline Developed by Explicit Methods for The American Society of Hematology", Blood 88:3–40 (1996), expressly incorporated herein by reference.

In other embodiments, antibody agonists of the invention are be used to treat, inhibit or prevent immunodeficiencies, and/or disorders, or conditions associated with immunodeficiencies. Such immunodeficiencies include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

In another specific embodiment, antibodies of the invention are used to treat, inhibit, prognose, diagnose or prevent CVID, or a subgroup of individuals having CVID.

In another specific embodiment, antibody agonists of the invention are used as an adjuvant to stimulate B cell proliferation, immunoglobulin production, and/or to enhance B cell survival.

The treatment and/or prevention of diseases, disorders, or conditions associated with aberrant expression and/or activity of a polypeptide of the invention and/or a receptor for the polypeptide of the invention (e.g., TACI, BCMA) includes, but is not limited to, alleviating symptoms associated with those diseases, disorders or conditions. The antibodies of the invention may also be used to target and kill cells expressing TNF delta and/or TNF epsilon on their surface and/or cells having TNF delta and/or TNF epsilon bound to their surface. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy, anti-tumor agents, antibiotics, and immunoglobulin therapy). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than 5×10−6 M, 10−6 M, 5×10−7 M, 10−7 M, 5×10−8 M, 10−8 M, 5×10−9 M, 10−9 M, 5×10−10 M, 10−10 M, 5×10−11 M, 10−11 M, 5×10−12 M, 10−12 M, 5×10−13 M, 10−13 M, 5×10−14 M, 10−14 M, 5×10−15 M, and 10−15 M.

In a specific embodiment, antibodies may act as antagonists to the TNF-delta and/or TNF-epsilon polypeptides of the invention. Such an antagonist is useful in reducing, preventing, and/or eliminating specific T cell activity mediated and/or induced by TNF-delta and/or TNF-epsilon polypeptides of the invention. Examples of such activities include autoimmune diseases, graft-versus-host disorders, allergic diseases, T cell regulated immune responses, and diseases and/or disorders related to T cell stimulation. Additional examples of T cell and general immune diseases and/or disorders that may be reduced, prevented, and/or treated by using antagonistic antibodies directed against TNF-delta and/or TNF-epsilon polypeptides of the invention as recited herein.

In another specific embodiment, anti-TNF-delta and/or anti-TNF-epsilon antibodies of the present invention may be used to treat, diagnose, prevent, and/or prognose acute myelogenous leukemia. In a preferred embodiment, anti-TNF-delta and/or anti-TNF-epsilon antibodies of the present invention conjugated to a toxin or a radioactive isotope, as described herein, may be used to treat, diagnose, prevent, and/or prognose acute myelogeneous leukemia. In a further preferred embodiment, anti-TNF-delta and/or anti-TNF-epsilon antibodies of the present invention conjugated to a toxin or a radioactive isotope, as described herein, may be used to treat, diagnose, prevent, and/or prognose chronic myelogeneous leukemia, multiple myeloma, non-Hodgkins lymphoma, and/or Hodgkins disease.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11 (5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred embodiment, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue- specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932–8935; Zijlstra et al., 1989, Nature 342:435–438). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid- carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429–4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, viral vectors that contains nucleic acid sequences encoding an antibody of the invention are used. For example, a retroviral vector can be used (see Miller et al., 1993, Meth. Enzymol. 217:581–599). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., 1994, Biotherapy 6:291–302, which describes the use of a retroviral vector to deliver the mdrl gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; Mastrangeli et al., 1993, J. Clin. Invest. 91:225–234; PCT Publication WO94/12649; and Wang, et al., 1995, Gene Therapy 2:775–783. In a preferred embodiment, adenovirus vectors are used.

Adeno-associated virus (AAV) has also been proposed for use in gene therapy (Walsh et al., 1993, Proc. Soc. Exp. Biol. Med. 204:289–300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Lymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, 1992, Cell 71:973–985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J.Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (1990, Science 249:1527–1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, M., et al., J. Cell. Biol. 101:976–985 (1985); Jalkanen, M., et al., J. Cell . Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention comprise two or more antibodies (monoclonal and/or polyclonal) that recognize the same and/or different sequences or regions of the polypeptide of the invention. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface- bound recombinant antigens, and a reporter-labeled anti-human antibody for detecting surface-bound anti-antigen antibody.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., *Nature*, 256:495–497 (1975), the trioma technique, the human B-cell hybridoma technique (Kozbor et al., *Immunology Today*, 4:72 (1983) and the EBV-hybridoma technique to produce human monoclonal antibodies (Cole et al., pg. 77–96 in Monoclonal Antibodies and Cancer Therapy, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Antisense and Ribozymes (Antagonists)

In specific embodiments, antagonists according to the present invention are nucleic acids corresponding to the sequences contained in TNF-delta and/or TNF-epsilon, or the complementary strand thereof, and/or to nucleotide sequences contained in the deposited clones. In one embodiment, antisense sequence is generated internally by the organism, in another embodiment, the antisense sequence is separately administered (see, for example, Okano H. et al., *J. Neurochem.* 56:560 (1991), and Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the TNF-delta and/or TNF-epsilon antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TNF-delta and/or TNF-epsilon antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding TNF-delta and/or TNF-epsilon, or fragments thereof, can be by any promoter known in the art to act in vertebrate, preferably human cells. Such promoters can be inducible or constitutive. Such promoters include, but are not limited to, the SV40 early promoter region (Bernoist and Chambon, *Nature* 29:304–310 (1981), the promoter contained in the 3' long terminal repeat of Rous sarcoma virus (Yamamoto et al., *Cell* 22:787–797 (1980), the herpes thymidine promoter (Wagner et al., *Proc. Natl. Acad. Sci. U.S.A.* 78:1441–1445 (1981), the regulatory sequences of the metallothionein gene (Brinster, et al., *Nature* 296:39–42 (1982)), etc.

The antisense nucleic acids of the invention comprise a sequence complementary to at least a portion of an RNA transcript of a TNF-delta and/or TNF-epsilon gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TNF-delta and/or TNF-epsilon antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TNF-delta and/or TNF-epsilon RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333–335 (1994). Thus, oligonucleotides complementary to either the 5'- or 3'-non-translated, non-coding regions of the TNF-delta and TNF-epsilon shown in FIGS. 1A and 1B, and 2A and 2B, respectively, could be used in an antisense approach to inhibit translation of endogenous TNF-delta and TNF-epsilon mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of TNF-delta and/or TNF-epsilon mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553–6556 (1989); Lemaitre et al., *Proc. Natl. Acad. Sci.* 84:648–652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958–976 (1988)) or intercalating agents. (See, e.g., Zon, *Pharm. Res.* 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an alpha-anomeric oligonucleotide. An alpha-anomeric oligonucleotide forms specific double-stranded hybrids with complementary RNA in which, contrary to the usual alpha-units, the strands run parallel to each other (Gautier et al., *Nucl. Acids Res.* 15:6625–6641 (1987)). The oligonucleotide is a 2 alpha-0-methylribonucleotide or a 2 beta-0-methylribonucleotide (Inoue et al., *Nucl. Acids Res.* 15:6131–6148 (1987)), or a chimeric RNA-DNA analogue (Inoue et al., *FEBS Lett.* 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448–7451 (1988)), etc.

While antisense nucleotides complementary to the TNF-delta and/or TNF-epsilon coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, *Science* 247:1222–1225 (1990). While ribozymes that cleave mRNA at site specific recognition sequences can be used to destroy TNF-delta and/or TNF-epsilon mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of TNF-delta (FIGS. 1A and 1B (SEQ ID NO:1)) and TNF-epsilon (FIGS. 2A and 2B (SEQ ID NO:3) and FIGS. 7A and 7B (SEQ ID NO:12)). Preferably, the ribozyme is engineered so that the cleavage recognition site is located near the 5' end of the TNF-delta and TNF-epsilon mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells which express TNF-delta and/or TNF-epsilon in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TNF-delta and/or TNF-epsilon messages and inhibit translation. Since ribozymes unlike antisense molecules, are catalytic, a lower intracellular concentration is required for efficiency.

Endogenous gene expression can also be reduced by inactivating or "knocking out" the TNF-delta and/or TNF-epsilon gene and/or its promoter using targeted homologous recombination. (e.g., see Smithies et al., *Nature* 317:230–234 (1985); Thomas & Capecchi, *Cell* 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In other embodiments, antagonists according to the present invention include soluble forms of TNF-delta (e.g., fragments of the TNF-delta shown in FIGS. 1A and 1B (SEQ ID NO:2) and FIGS. 6A and 6B and/or TNF-epsilon (e.g., fragments of the TNF-epsilon shown in FIGS. 2A and 2B (SEQ ID NO:4) and and FIGS. 7A and 7B (SEQ ID NO: 13) that include the receptor binding domain from the extracellular region of the full length ligand). Such soluble forms of TNF-delta and/or TNF-epsilon, which may be naturally occurring or synthetic, antagonize TNF-delta and/or TNF-epsilon mediated signaling by competing with the ligand for binding to TNF-family receptors. Antagonists of the present invention also include antibodies specific for TNF-family ligands and TNF-delta- and/or TNF-epsilon-Fc fusion proteins.

In certain other embodiments, anti-TNF delta antibodies, and/or anti-TNF epsilon antibodies, and/or Neutrokine-alpha, and/or Neutrokine-alphaSV, and/or TACI soluble domain fused to Fc, and/or BCMA soluble domain fused to Fc function as TNF delta and/or TNF epsilon antagonists.

In specific embodiments, the expression of IL-2 receptor messenger RNA is highly increased when cells are cultured in the presence of a TNF delta and/or TNF epsilon antagonist.

In specific embodiments, the expression of IL-2 receptor messenger RNA is highly decreased when cells are cultured in the presence of a TNF delta and/or TNF epsilon agonist.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-alpha, lymphotoxin-alpha (LT-alpha, also known as TNF-beta), LT-beta (found in complex heterotrimer LT-alpha2-beta), FasL, TNF-gamma (International Publication No. WO 96/14328), AIM-I (International Publication No. WO 97/33899), AIM-II (International Publication No. WO 97/34911), Neutrokine-alpha and/or Neutrokine-alphaSV (International Publication No. WO98/18921), endokine-alpha (International Publication No. WO 98/07880), CD40L, CD27L, CD30L, 4-1BBL, OX40L and nerve growth factor (NGF).

TNF-alpha has been shown to protect mice from infection with herpes simplex virus type 1 (HSV-1). Rossol-Voth et al., J .Gen. Virol. 72:143–147 (1991). The mechanism of the protective effect of TNF-alpha is unknown but appears to involve neither interferons nor NK cell killing. One member of the family has been shown to mediate HSV-1 entry into cells. Montgomery et al., Eur. Cytokine Newt. 7:159 (1996). Further, antibodies specific for the extracellular domain of this block HSV-1 entry into cells. Thus, TNF-delta and/or TNF-epsilon antagonists of the present invention include both TNF-delta and/or TNF-epsilon amino acid sequences and antibodies capable of preventing mediated viral entry into cells. Such sequences and antibodies can function by either competing with cell surface localized for binding to virus or by directly blocking binding of virus to cell surface receptors.

Antibodies according to the present invention may be prepared by any of a variety of standard methods using TNF-delta and/or TNF-epsilon receptor immunogens of the present invention. Such TNF-delta and/or TNF-epsilon receptor immunogens include the TNF-delta and TNF-epsilon proteins shown in FIGS. 1A and 1B (SEQ ID NO:2) and FIGS. 2A and 2B (SEQ ID NO:4), respectively, (which may or may not include a leader sequence) and polypeptide fragments of the receptor comprising the ligand binding, extracellular, transmembrane, the intracellular domains of TNF-delta and/or TNF-epsilon, or any combination thereof.

Polyclonal and monoclonal antibody agonists or antagonists according to the present invention can be raised according to the methods disclosed herein and and/or known in the art, such as, for example, those methods described in Tartaglia and Goeddel, J. Biol. Chem. 267(7):4304–4307(1992)); Tartaglia et al., Cell 73:213–216 (1993)), and PCT Application WO 94/09137 (the contents of each of these three applications are herein incorporated by reference in their entireties), and are preferably specific to polypeptides of the invention having the amino acid sequence of SEQ ID NO:2 and/or SEQ ID NO:4.

Exon Shuffling

The techniques of gene-shuffling, motif-shuffling, exon-shuffling, and/or codon-shuffling (collectively referred to as "DNA shuffling") may be employed to modulate the activities of TNF-delta and/or TNF-epsilon thereby effectively generating agonists and antagonists of TNF-delta and/or TNF-epsilon. See generally, U.S. Pat. Nos. 5,605,793, 5,811, 238, 5,830,721, 5,834,252, and 5,837,458, and Patten et al., *Curr. Opinion Biotechnol.* 8:724–33 (1997); Harayama, *Trends Biotechnol.* 16(2):76–82 (1998); Hansson et al., *J. Mol. Biol.* 287:265–76 (1999); and Lorenzo and Blasco, *Biotechniques* 24(2):308–13 (1998) (each of these patents and publications are hereby incorporated by reference). In one embodiment, alteration of TNF-delta and/or TNF-epsilon polynucleotides and corresponding polypeptides may be achieved by DNA shuffling. DNA shuffling involves the assembly of two or more DNA segments into a desired TNF-delta and/or TNF-epsilon molecule by homologous, or site-specific, recombination. In another embodiment, TNF-delta and/or TNF-epsilon polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of TNF-delta and/or TNF-epsilon may be recombined with one or more components, motifs, sections, parts, domains, fragments, etc. of one or more heterologous molecules. In preferred embodiments, the heterologous molecules are TNF-alpha, TNF-beta, lymphotoxin-alpha, lymphotoxin-beta, FAS ligand, Neutrokine-alpha, and/or Neutrokine-alphaSV. In further preferred embodiments, the heterologous molecules are any member of the TNF family.

Non-naturally occurring variants also may be produced using art-known mutagenesis techniques, which include, but are not limited to, oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), and restriction selection mutagenesis (see e.g., Wells et al., *Philos. Trans. R. Soc. London SerA* 317:415 (1986)).

In another embodiment, the present invention is directed to a method for inhibiting apoptosis induced by a TNF-family ligand, which involves administering to a cell which expresses the TNF-delta and/or TNF-epsilon polypeptide an effective amount of an antagonist capable of decreasing TNF-delta and/or TNF-epsilon mediated signaling. Preferably, TNF-delta- and/or TNF-epsilon-mediated signaling is decreased to treat a disease wherein increased apoptosis, NF-kappaB expression and/or JNK expression is exhibited. Antagonists include, but are not limited to, soluble forms of TNF-delta and/or TNF-epsilon polypeptide and antibodies (preferably monoclonal) directed against the TNF-delta and/or TNF-epsilon polypeptide.

Thus, the polypeptides of the present invention (including antibodies of the present invention) may be employed to inhibit neoplasia, such as tumor cell growth. The polypeptides of the present invention may be responsible for tumor destruction through apoptosis and cytotoxicity to certain cells. The polypeptides of the present invention also induce up-regulation of adhesion cells, for example, LFA-1, therefore, may be employed for wound-healing. The polypeptides of the present invention may also be employed to treat diseases which require growth promotion activity, for example, restenosis, since the polypeptides of the present invention have proliferation effects on cells of endothelial origin. The polypeptides of the present invention may, therefore, also be employed to regulate hematopoiesis in endothelial cell development.

The polypeptides of the present invention also stimulate the activation of T-cells, and may, therefore, be employed to stimulate an immune response against a variety of parasitic, bacterial and viral infections. The polypeptides of the present invention may also be employed in this respect to eliminate autoreactive T-cells to treat and/or prevent autoimmune diseases. An example of an autoimmune disease is Type I diabetes.

This invention also provides a method for identification of molecules, such as receptor molecules, that bind the proteins of the present invention. Genes encoding proteins that bind the proteins of the present invention, such as receptor proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell responsive to the proteins of the present invention, a cDNA library is created from this RNA, the library is divided into pools and the pools are transfected individually into cells that are not responsive to the proteins of the present invention. The transfected cells then are exposed to labeled the proteins of the present invention. The proteins of the present invention can be labeled by a variety of well-known techniques including standard methods of radio-iodination or inclusion of a recognition site for a site-specific protein kinase. Following exposure, the cells are fixed and binding of cytostatin is determined. These procedures conveniently are carried out on glass slides.

Pools are identified of cDNA that produced TNF delta or TNF epsilon binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess TNF delta or TNF epsilon binding capacity of TNF delta or TNF epsilon binding molecules, such as receptor molecules, in cells or in cell-free preparations.

The polypeptides of the present invention have uses which include, but are not limited to, as sources for generating antibodies that bind the polypeptides of the invention, and as molecular weight markers on SDS-PAGE gels or on molecular sieve gel filtration columns using methods well known to those of skill in the art.

In one embodiment, TNF-delta and/or TNF-epsilon polynucleotides or polypeptides or TNF-delta and/or TNF-epsilon antagonists (e.g., anti-TNF-delta and/or TNF-epsilon antibodies) of the invention are used to treat, diagnose, or prognose an individual having an immunodeficiency. According to this embodiment, an individual having an immunodeficiency expresses aberrantly low levels of TNF-delta and/or TNF-epsilon when compared to an individual not having an immunodeficiency. Any means described herein or otherwise known in the art may be applied to detect TNF-delta and/or TNF-epsilon polynucleotides or polypeptides of the invention (e.g., FACS analysis or ELISA detection of TNF-delta and/or TNF-epsilon polypeptides of the invention and hybridization or PCR detection of TNF-delta and/or TNF-epsilon polynucleotides of the invention) and to determine the expression profile of TNF-delta and/or TNF-epsilon, polynucleotides and/or polypeptides of the invention in a biological sample.

A biological sample of a person afflicted with an immunodeficiency is characterized by low levels of expression of TNF-delta and/or TNF-epsilon when compared to that observed in individuals not having an immunodeficiency. Thus, TNF-delta and/or TNF-epsilon polynucleotides and/or polypeptides of the invention, and/or agonists or antagonists thereof, may be used according to the methods of the invention in the diagnosis and/or prognosis of an immunodeficiency. For example, a biological sample obtained from a person suspected of being afflicted with an immunodeficiency ("the subject") may be analyzed for the relative expression level(s) of TNF-delta and/or TNF-epsilon polynucleotides and/or polypeptides of the invention. The expression level(s) of one or more of these molecules of the invention is (are) then compared to the expression level(s) of the same molecules of the invention as expressed in a person known not to be afflicted with an immunodeficiency. A significant difference in expression level(s) of TNF-delta and/or TNF-epsilon polynucleotides and/or polypeptides of the invention, and/or agonists and/or antagonists thereof, between samples obtained from the subject and the control suggests that the subject is afflicted with an immunodeficiency.

In another embodiment, TNF-delta and/or TNF-epsilon polynucleotides or polypeptides or TNF-delta and/or TNF-epsilon antagonists (e.g., anti-TNF-delta and/or TNF-epsilon antibodies) of the invention are used to treat, diagnose and/or prognose an individual having common variable immunodeficiency disease ("CVID"; also known as "acquired agammaglobulinemia" and "acquired hypogammaglobulinemia") or a subset of this disease. According to this embodiment, an individual having CVID or a subset of individuals having CVID expresses aberrant levels of TNF-delta and/or TNF-epsilon receptor on their T cells, when compared to individuals not having CVID. Any means described herein or otherwise known in the art may be applied to detect TNF-delta and/or TNF-epsilon receptor polynucleotides or polypeptides of the invention (e.g., FACS analysis or ELISA detection of TNF-delta and/or TNF-epsilon polypeptides of the invention and hybridization or PCR detection of TNF-delta and/or TNF-epsilon polynucleotides of the invention) and to determine differentially the expression profile of TNF-delta and/or TNF-epsilon polynucleotides or polypeptides of the invention in a sample containing at least T cells or some component thereof (e.g., RNA) as compared to a sample containing at least B cells or a component thereof (e.g., RNA). In the instance where a sample containing at least T cells or some component thereof (e.g., RNA) is determined to reflect TNF-delta and/or TNF-epsilon polynucleotide or polypeptide expression and a sample containing at least B cells or a component thereof (e.g., RNA) is determined to reflect less than normal levels of TNF-delta and/or TNF-epsilon receptor polynucleotide or polypeptide expression, the samples may be correlated with the occurrence of CVID (i.e., "acquired agammaglobulinemia" or "acquired hypogammaglobulinemia").

A subject of persons afflicted with CVID are characterized by high levels of expression of both TNF-delta and/or TNF-epsilon in peripheral or circulating T cells when compared to that observed in individuals not having CVID. In contrast, persons who are not afflicted with CVID are typically characterized by low levels of TNF-delta and/or TNF-epsilon expression. Thus, TNF-delta and/or TNF-epsilon polynucleotides and/or polypeptides of the invention, and/or agonists or antagonists thereof, may be used according to the methods of the invention in the differential diagnosis of this subset of CVID. For example, a sample of peripherial T cells obtained from a person suspected of being afflicted with CVID ("the subject") may be analyzed for the relative expression level(s) of TNF-delta and/or TNF-epsilon polynucleotides and/or polypeptides of the invention. The expression level(s) of one or more of these molecules of the invention is (are) then compared to the expression level(s) of the same molecules of the invention as expressed in a person known not to be afflicted with CVID ("the control"). A significant difference in expression level(s) of TNF-delta and/or TNF-epsilon polynucleotides and/or polypeptides of the invention, and/or agonists and/or antagonists thereof, between samples obtained from the subject and the control suggests that the subject is afflicted with this subset of CVID.

Cunningham-Rundles and Bodian followed 248 CVID patients over a period of 1–25 years and discovered that a number of associated diseases or conditions appear with increased frequency in CVID patients (Cunningham-Rundles and Bodian, *J. Clin. Immunol.*, 92:34–48 (1999) which is herein incorporated by reference in its entirety.) The most important clinical events include infections, autoimmunity, inflammatory disorders, marked by gastrointestinal and granulomatous disease, cancer and hepatitis. Most CVID patients are at increased risk of recurrent infections particularly of the respiratory tract. The types of acute and recurring bacterial infections exhibited in most patients include pneumonia, bronchitis and sinusitis. Children with CVID have a marked increased risk of otitis media. Additionally, blood borne infections including sepsis, meningitis, septic arthritis, and osteomyelitis are seen with increased frequency in these patients.

In another specific embodiment TNF-delta and/or TNF-epsilon polynucleotides or polypeptides, or agonists or antagonists thereof (e.g., anti- TNF-delta and/or anti-TNF-epsilon antibodies) are used to diagnose, prognose, treat, or prevent conditions associated with CVID, including, but not limited to, conditions associated with acute and recurring infections (e.g., pneumonia, bronchitis, sinusitis, otitis media, sepsis, meningitis, septic arthritis, and osteomyelitis), chronic lung disease, autoimmunity, granulomatous disease, lymphoma, cancers (e.g., cancers of the breast, stomach, colon, mouth, prostate, lung, vagina, ovary, skin, and melanin forming cells (i.e. melanoma), inflammatory bowel disease (e.g., Crohn's disease, ulcerative colitis, and ulcerative proctitis), malabsoption, Hodgkin's disease, and Waldenstrom's macroglobulinemia.

In a specific embodiment, TNF-delta and/or TNF-epsilon polynucleotides or polypeptides, or agonists thereof (e.g., anti-TNF-delta and/or anti-TNF-epsilon antibodies) are used to treat or prevent a disorder characterized by deficient serum immunoglobulin production, recurrent infections, and/or immune system dysfunction. Moreover, TNF-delta and/or TNF-epsilon polynucleotides or polypeptides, or agonists thereof (e.g., anti-TNF-delta and/or anti-TNF-epsilon antibodies) may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, multiple myeloma, recurrent bronchitis, sinusitis, otitis media, conjunctivitis, pneumonia, hepatitis, meningitis, herpes zoster (e.g., severe herpes zoster), and/or pneumocystis carmii.

In another embodiment, TNF-delta and/or TNF-epsilon polynucleotides or polypeptides or TNF-delta and/or TNF-epsilon antagonists (e.g., anti-TNF-delta and/or anti-TNF-epsilon antibodies) of the invention are used to treat, diagnose, or prognose an individual having an autoimmune disease or disorder. According to this embodiment, an individual having an autoimmune disease or disorder expresses aberrantly high levels of TNF-delta and/or TNF-epsilon when compared to an individual not having an autoimmune disease or disorder. Any means described herein or otherwise known in the art may be applied to detect TNF-delta and/or TNF-epsilon polynucleotides or polypeptides of the invention (e.g., FACS analysis or ELISA detection of TNF-delta and/or TNF-epsilon polypeptides of the invention and hybridization or PCR detection of TNF-delta and/or TNF-epsilon polynucleotides of the invention) and to determine the expression profile of TNF-delta and/or TNF-epsilon polynucleotides and/or polypeptides of the invention in a biological sample.

TNF-delta and/or TNF-epsilon polynucleotides or polypeptides, or agonists or antagonists of TNF-delta and/or TNF-epsilon, can be used in assays to test for one or more biological activities. If TNF-delta and/or TNF-epsilon polynucleotides or polypeptides, or agonists or antagonists of TNF-delta and/or TNF-epsilon, do exhibit activity in a particular assay, it is likely that TNF-delta and/or TNF-epsilon may be involved in the diseases associated with the biological activity. Therefore, TNF-delta and/or TNF-epsilon could be used to treat the associated disease.

In a specific embodiment, TNF-delta and/or TNF-epsilon polynucleotides or polypeptides, or agonists or antagonists of TNF-delta and/or TNF-epsilon may be used to treat, diagnose, prevent, and/or prognose acute myelogenous leukemia. In a preferred embodiment, TNF-delta and/or TNF-epsilon polynucleotides or polypeptides, or agonists or antagonists of TNF-delta and/or TNF-epsilon conjugated to a toxin or a radioactive isotope, as described herein, may be used to treat, diagnose, prevent, and/or prognose acute myelogeneous leukemia. In a further preferred embodiment, TNF-delta and/or TNF-epsilon polynucleotides or polypeptides, or agonists or antagonists of TNF-delta and/or TNF-epsilon conjugated to a toxin or a radioactive isotope, as described herein, may be used to treat, diagnose, prevent, and/or prognose chronic myelogeneous leukemia, multiple myeloma, non-Hodgkins lymphoma, and/or Hodgkins disease.

In another specific embodiment, TNF-delta and/or TNF-epsilon polynucleotides or polypeptides, or agonists or antagonists of TNF-delta and/or TNF-epsilon may be used to treat, diagnose, prognose, and/or prevent T cell deficiencies. T cell deficiencies include, but are not limited to, for example, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity.

In another specific embodiment, TNF-delta and/or TNF-epsilon polynucleotides or polypeptides, or agonists or antagonists of TNF-delta and/or TNF-epsilon may be used to treat, diagnose, prognose, and/or prevent selective IgA deficiency, myeloperoxidase deficiency, C2 deficiency, ataxia-telangiectasia, DiGeorge anomaly, common variable immunodeficiency (CVI), X-linked agammaglobulinemia, severe combined immunodeficiency (SCID), chronic granulomatous disease (CGD), and Wiskott-Aldrich syndrome.

TNF-delta and/or TNF-epsilon polynucleotides or polypeptides, or agonists or antagonists of TNF-delta and/or TNF-epsilon, may be useful in treating deficiencies or disorders of the immune system, by activating or inhibiting the proliferation, differentiation, or mobilization (chemotaxis) of immune cells, or through involvement in the regulation of cell-mediated immune responses. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, TNF-delta and/or TNF-epsilon polynucleotides or polypeptides, or agonists or antagonists of TNF-delta and/or TNF-epsilon, can be used as a marker or detector of a particular immune system disease or disorder.

TNF-delta and/or TNF-epsilon polynucleotides or polypeptides, or agonists or antagonists of TNF-delta and/or TNF-epsilon, may be useful in treating or detecting deficiencies or disorders of hematopoietic cells. TNF-delta and/or TNF-epsilon polynucleotides or polypeptides, or agonists or antagonists of TNF-delta and/or TNF-epsilon, could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, TNF-delta and/or TNF-epsilon polynucleotides or polypeptides, or agonists or antagonists of TNF-delta and/or TNF-epsilon, can also be used to modulate hemostatic (the stopping of bleeding) or thrombolytic activity (clot formation). For example, by increasing hemostatic or thrombolytic activity, TNF-delta and/or TNF-epsilon polynucleotides or polypeptides, or agonists or antagonists of TNF-delta and/or TNF-epsilon, could be used to treat blood coagulation disorders (e.g., afibrinogenemia, factor deficiencies), blood platelet disorders (e.g. thrombocytopenia), or wounds resulting from trauma, surgery, or other causes. Alternatively, TNF-delta and/or TNF-epsilon polynucleotides or polypeptides, or agonists or antagonists of TNF-delta and/or TNF-epsilon, that can decrease hemostatic or thrombolytic activity could be used to inhibit or dissolve clotting, important in the treatment of heart attacks (infarction), strokes, or scanning.

TNF-delta and/or TNF-epsilon polynucleotides or polypeptides, or agonists or antagonists of TNF-delta and/or TNF-epsilon, may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of TNF-delta and/or TNF-epsilon polynucleotides or polypeptides, or agonists or antagonists of TNF-delta and/or TNF-epsilon, that can inhibit an immune response, particularly the proliferation, differentiation, or chemotaxis of T-cells, may be an effective therapy in preventing autoimmune disorders.

Examples of autoimmune disorders that can be treated or detected include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Additional autoimmune disorders (that are highly probable) that may be treated, prevented, and/or diagnosed with the compositions of the invention include, but are not limited to, autoimmune thyroiditis (i.e., Hashimoto's thyroiditis) (often characterized, e.g., by cell-mediated and humoral thyroid cytotoxicity), systemic lupus erhthematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders (that are probable) that may be treated, prevented, and/or diagnosed with the compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity), infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjögren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using TNF-delta and/or TNF-epsilon antibodies and/or anti-TNF-delta and/or anti-TNF-epsilon antibodies and/or soluble TNF-delta and/or TNF-epsilon polypeptides of the invention.

Similarly, allergic reactions and conditions, such as asthma (particularly allergic asthma) or other respiratory problems, may also be treated by TNF-delta and/or TNF-epsilon polynucleotides or polypeptides, or agonists or antagonists of TNF-delta and/or TNF-epsilon. Moreover, these molecules can be used to treat anaphylaxis, hypersensitivity to an antigenic molecule, or blood group incompatibility.

In specific embodiments, TNF-delta and/or TNF-epsilon antibodies and/or anti-TNF-delta and/or anti-TNF-epsilon antibodies and/or soluble TNF-delta and/or TNF-epsilon polypeptides of the invention are useful to treat, diagnose, prevent, and/or prognose autoimmune and inflammatory diseases, transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE).

Moreover, inflammatory conditions may also be treated, diagnosed, prevented and/or prognosed with TNF-delta and/or TNF-epsilon polynucleotides or polypeptides, or agonists or antagonists of TNF-delta and/or TNF-epsilon (e.g., anti-TNF-delta and/or anti-TNF-epsilon antibodies) of the invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease), AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosis, diabetes mellitus (i.e., type 1 diabetes), and allogenic transplant rejection).

TNF-delta and/or TNF-epsilon polynucleotides or polypeptides, or agonists or antagonists of TNF-delta and/or TNF-epsilon, may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of TNF-delta and/or TNF-epsilon polynucleotides or polypeptides, or agonists or antagonists of TNF-delta and/or TNF-epsilon, that inhibits an immune response, particularly the proliferation, differentiation, or chemotaxis of T-cells, may be an effective therapy in preventing organ rejection or GVHD.

Similarly, TNF-delta and/or TNF-epsilon polynucleotides or polypeptides, or agonists or antagonists of TNF-delta and/or TNF-epsilon, may also be used to modulate inflammation. For example, TNF-delta and/or TNF-epsilon polynucleotides or polypeptides, or agonists or antagonists of TNF-delta and/or TNF-epsilon, may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)."

A biological sample of persons afflicted with an autoimmune disease or disorder is characterized by high levels of expression of TNF-delta and/or TNF-epsilon when compared to that observed in individuals not having an autoimmune disease or disorder. Thus, TNF-delta and/or TNF-epsilon polynucleotides and/or polypeptides of the invention, and/or agonists or antagonists thereof, may be used according to the methods of the invention in the diagnosis and/or prognosis of an autoimmune disease or disorder. For example, a biological sample obtained from a person suspected of being afflicted with an autoimmune disease or disorder ("the subject") may be analyzed for the relative expression level(s) of TNF-delta and/or TNF-epsilon polynucleotides and/or polypeptides of the invention. The expression level(s) of one or more of these molecules of the invention is (are) then compared to the expression level(s) of the same molecules of the invention as expressed in a person known not to be afflicted with an autoimmune disease or disorder. A significant difference in expression level(s) of TNF-delta and/or TNF-epsilon polynucleotides and/or polypeptides of the invention, and/or agonists and/or antagonists thereof, between samples obtained from the subject and the control suggests that the subject is afflicted with an autoimmune disease or disorder.

In another embodiment, TNF-delta and/or TNF-epsilon polynucleotides or polypeptides or TNF-delta and/or TNF-epsilon antagonists (e.g., anti-TNF-delta and/or anti-TNF-epsilon antibodies) of the invention are used to treat, diagnose, or prognose an individual having systemic lupus erythramatosus or a subset of this disease. According to this embodiment, an individual having systemic lupus erythramatosus or a subset of individuals having systemic lupus erythramatosus expresses aberrantly high levels of TNF-delta and/or TNF-epsilon when compared to an individual not having systemic lupus erythramatosus or this subset of systemic lupus erythramatosus. Any means described herein or otherwise known in the art may be applied to detect TNF-delta and/or TNF-epsilon polynucleotides or polypeptides of the invention (e.g., FACS analysis or ELISA detection of TNF-delta and/or TNF-epsilon polypeptides of the invention and hybridization or PCR detection of TNF-delta and/or TNF-epsilon polynucleotides of the invention) and to determine the expression profile of TNF-delta and/or TNF-epsilon polynucleotides and/or polypeptides of the invention in a biological sample.

A biological sample of persons afflicted with systemic lupus erythramatosus is characterized by high levels of expression of TNF-delta and/or TNF-epsilon when compared to that observed in individuals not having systemic lupus erythramatosus. Thus, TNF-delta and/or TNF-epsilon polynucleotides and/or polypeptides of the invention, and/or agonists or antagonists thereof, may be used according to the methods of the invention in the diagnosis and/or prognosis of systemic lupus erythramatosus or a subset of systemic lupus erythramatosus. For example, a biological sample obtained from a person suspected of being afflicted with systemic lupus erythramatosus ("the subject") may be analyzed for the relative expression level(s) of TNF-delta and/or TNF-epsilon polynucleotides and/or polypeptides of the invention. The expression level(s) of one or more of these molecules of the invention is (are) then compared to the expression level(s) of the same molecules of the invention as expressed in a person known not to be afflicted with systemic lupus erythramatosus. A significant difference in expression level(s) of TNF-delta and/or TNF-epsilon polynucleotides and/or polypeptides of the invention, and/or agonists and/or antagonists thereof, between samples obtained from the subject and the control suggests that the subject is afflicted with systemic lupus erythramatosus or a subset thereof.

Furthermore, there is a direct correlation between the severity of systemic lupus erythramatosus, or a subset of this disease, and the concentration of TNF-delta and/or TNF-epsilon polynucleotides (RNA) and/or polypeptides of the invention. Thus, TNF-delta and/or TNF-epsilon polynucleotides, (RNA), polypeptides and/or agonists or antagonists of the invention, may be used according to the methods of the invention in prognosis of the severity of ystemic lupus erythramatosus or a subset of systemic lupus erythramatosus. For example, a biological sample obtained from a person suspected of being afflicted with systemic lupus erythramatosus ("the subject") may be analyzed for the relative expression level(s) of TNF-delta and/or TNF-epsilon polynucleotides and/or polypeptides of the invention. The expression level(s) of one or more of these molecules of the invention is (are) then compared to the expression level(s) of the same molecules of the invention as expressed in a panel of persons known to represent a range in severities of this disease.

In another embodiment, TNF-delta and/or TNF-epsilon polynucleotides or polypeptides or TNF-delta and/or TNF-epsilon antagonists (e.g., anti-TNF-delta and/or anti-TNF-epsilon antibodies) of the invention are used to treat, diagnose, or prognose an individual having rheumatoid arthritis or a subset of this disease. According to this embodiment, an individual having rheumatoid arthritis or a subset of individuals having rheumatoid arthritis expresses aberrantly high levels of TNF-delta and/or TNF-epsilon when compared to an individual not having rheumatoid arthritis or this subset of rheumatoid arthritis. Any means described herein or otherwise known in the art may be applied to detect TNF-delta and/or TNF-epsilon polynucleotides or polypeptides of the invention (e.g., FACS analysis or ELISA detection of TNF-delta and/or TNF-epsilon polypeptides of the invention and hybridization or PCR detection of TNF-delta and/or TNF-epsilon polynucleotides of the invention) and to determine the expression profile of TNF-delta and/or TNF-epsilon polynucleotides and/or polypeptides of the invention in a biological sample.

A biological sample of persons afflicted with rheumatoid arthritis is characterized by high levels of expression of TNF-delta and/or TNF-epsilon when compared to that observed in individuals not having rheumatoid arthritis. Thus, TNF-delta and/or TNF-epsilon polynucleotides and/or polypeptides of the invention, and/or agonists or antagonists thereof, may be used according to the methods of the invention in the diagnosis and/or prognosis of rheumatoid arthritis or a subset of rheumatoid arthritis. For example, a biological sample obtained from a person suspected of being afflicted with rheumatoid arthritis ("the subject") may be analyzed for the relative expression level(s) of TNF-delta and/or TNF-epsilon polynucleotides and/or polypeptides of the invention. The expression level(s) of one or more of these molecules of the invention is (are) then compared to the expression level(s) of the same molecules of the invention as expressed in a person known not to be afflicted with rheumatoid arthritis. A significant difference in expression level(s) of TNF-delta and/or TNF-epsilon polynucleotides and/or polypeptides of the invention, and/or agonists and/or antagonists thereof, between samples obtained from the subject and the control suggests that the subject is afflicted with rheumatoid arthritis or a subset thereof.

In other specific embodiments, antibodies of the invention which specifically bind to TNF delta and/or TNF epsilon can be used for diagnostic purposes to detect, diagnose, prognose, or monitor Sjögren's Syndrome or conditions associated therewith. The invention provides for the detection of aberrant expression of TNF delta and/or TNF epsilon comprising: (a) assaying the expression of TNF delta and/or TNF epsilon in a biological sample of an individual using one or more antibodies of the invention that immunospecifically binds to TNF delta and/or TNF epsilon; and (b) comparing the level of TNF delta and/or TNF epsilon with a standard level TNF delta and/or TNF epsilon, e.g., in normal biological samples, whereby an increase in the assayed level of TNF delta and/or TNF epsilon compared to the standard level of TNF delta and/or TNF epsilon is indicative of Sjögren's Syndrome.

In other specific embodiments, antibodies of the invention which specifically bind to TNF delta and/or TNF epsilon can be used for diagnostic purposes to detect, diagnose, prognose, or monitor HIV infection or conditions associated therewith (e.g., AIDS). The invention provides for the detection of aberrant expression of TNF delta and/or TNF epsilon comprising: (a) assaying the expression of TNF delta and/or TNF epsilon in a biological sample of an individual using one or more antibodies of the invention that immunospecifically binds to Neutrokine-alpha and/or Neutrokine-alphaSV; and (b) comparing the level of TNF delta and/or TNF epsilon with a standard level of TNF delta and/or TNF epsilon, e.g., in normal biological samples, whereby an increase in the assayed level of TNF delta and/or TNF epsilon compared to the standard level of TNF delta and/or TNF epsilon is indicative of HIV infection.

Thus, the invention provides a diagnostic method useful during diagnosis of a immune system disorder, including cancers of this system, which involves measuring the expression level of the gene encoding the TNF-delta and/or TNF-epsilon polypeptide in immune system tissue or other cells or body fluid from an individual and comparing the measured gene expression level with a standard TNF-delta and/or TNF-epsilon gene expression level, whereby an increase or decrease in the gene expression level compared to the standard is indicative of an immune system disorder.

Where a diagnosis of a disorder in the immune system, including diagnosis of a tumor, has already been made according to conventional methods, the present invention is useful as a prognostic indicator, whereby patients exhibiting enhanced or depressed TNF-delta and/or TNF-epsilon gene expression will experience a worse clinical outcome relative to patients expressing the gene at a level nearer the standard level.

By "assaying the expression level of the gene encoding the TNF-delta and/or TNF-epsilon polypeptide" is intended qualitatively or quantitatively measuring or estimating the level of the TNF-delta and/or TNF-epsilon polypeptide or the level of the mRNA encoding the TNF-delta and/or TNF-epsilon polypeptide in a first biological sample either directly (e.g., by determining or estimating absolute protein level or mRNA level) or relatively (e.g., by comparing to the TNF-delta and/or TNF-epsilon polypeptide level or mRNA level in a second biological sample). Preferably, the TNF-delta and/or TNF-epsilon polypeptide level or mRNA level in the first biological sample is measured or estimated and compared to a standard TNF-delta and/or TNF-epsilon polypeptide level or mRNA level, the standard being taken from a second biological sample obtained from an individual not having the disorder or being determined by averaging levels from a population of individuals not having a disorder of the immune system. As will be appreciated in the art, once a standard TNF-delta and/or TNF-epsilon polypeptide level or mRNA level is known, it can be used repeatedly as a standard for comparison.

By "biological sample" is intended any biological sample obtained from an individual, body fluid, cell line, tissue culture, or other source which contains TNF-delta and/or TNF-epsilon polypeptide or mRNA. As indicated, biological samples include body fluids (such as sera, plasma, urine, synovial fluid and spinal fluid) which contain free extracellular domains of the TNF-delta and/or TNF-epsilon polypeptide, immune system tissue, and other tissue sources found to express complete or free extracellular domain of the TNF-delta and/or TNF-epsilon or a TNF-delta and/or TNF-epsilon receptor. Methods for obtaining tissue biopsies and body fluids from mammals are well known in the art. Where the biological sample is to include mRNA, a tissue biopsy is the preferred source.

The compounds of the present invention are useful for diagnosis or treatment of various immune system-related disorders in mammals, preferably humans. Such disorders include but are not limited to tumors (e.g., T cell and monocytic cell leukemias and lymphomas) and tumor metastasis, infections by bacteria, viruses and other parasites, immunodeficiencies, inflammatory diseases, lymphadenopathy, autoimmune diseases, and graft versus host disease.

Total cellular RNA can be isolated from a biological sample using any suitable technique such as the single-step guanidinium-thiocyanate-phenol-chloroform method described in Chomczynski and Sacchi, *Anal Biochem.* 162:156–159 (1987). Levels of mRNA encoding the TNF-delta and/or TNF-epsilon polypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying TNF-delta and/or TNF-epsilon polypeptide levels in a biological sample can occur using antibody-based techniques. For example, TNF-delta and/or TNF-epsilon polypeptide expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting TNF-delta and/or TNF-epsilon polypeptide gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112m}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

The tissue or cell type to be analyzed will generally include those which are known, or suspected, to express the TNF-delta and/or TNF-epsilon gene (such as, for example, cells of T lineage) or cells or tissue which are known, or suspected, to express the TNF-delta and/or TNF-epsilon receptor gene (such as, for example, cells of B cell lineage and the spleen). The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the TNF-delta and/or TNF-epsilon receptor gene.

For example, antibodies, or fragments of antibodies, such as those described herein, may be used to quantitatively or qualitatively detect the presence of TNF-delta and/or TNF-epsilon gene products or conserved variants or peptide fragments thereof. This can be accomplished, for example, by immunofluorescence techniques employing a fluorescently labeled antibody coupled with light microscopic, flow cytometric, or fluorimetric detection.

The antibodies (or fragments thereof) or TNF-delta and/or TNF-epsilon polypeptides or polypeptides of the present invention may, additionally, be employed histologically, as in immunofluorescence, immunoelectron microscopy or non-immunological assays, for in situ detection of TNF-delta and/or TNF-epsilon gene products or conserved variants or peptide fragments thereof, or for TNF-delta and/or TNF-epsilon binding to TNF-delta and/or TNF-epsilon receptor. In situ detection may be accomplished by removing a histological specimen from a patient, and applying thereto a labeled antibody or TNF-delta and/or TNF-epsilon polypeptide of the present invention. The antibody (or fragment) or TNF-delta and/or TNF-epsilon polypeptide is preferably applied by overlaying the labeled antibody (or fragment) onto a biological sample. Through the use of such a procedure, it is possible to determine not only the presence of the TNF-delta and/or TNF-epsilon gene product, or conserved variants or peptide fragments, or TNF-delta and/or TNF-epsilon polypeptide binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for TNF-delta and/or TNF-epsilon gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying TNF-delta and/or TNF-epsilon gene products or conserved variants or peptide fragments thereof, and detecting the bound antibody by any of a number of techniques well-known in the art.

Immunoassays and non-immunoassays for TNF-delta and/or TNF-epsilon receptor gene products or conserved variants or peptide fragments thereof will typically comprise incubating a sample, such as a biological fluid, a tissue extract, freshly harvested cells, or lysates of cells which have been incubated in cell culture, in the presence of a detectable or labeled TNF-delta and/or TNF-epsilon polypeptide capable of identifying TNF-delta and/or TNF-epsilon receptor gene products or conserved variants or peptide fragments thereof, and detecting the bound TNF-delta and/or TNF-epsilon polypeptide by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-TNF-delta and/or anti-TNF-epsilon antibody or detectable TNF-delta and/or TNF-epsilon polypeptide. The solid phase support may then be washed with the buffer a second time to remove unbound antibody or polypeptide. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-TNF-delta and/or anti-TNF-epsilon antibody or TNF-delta and/or TNF-epsilon polypeptide may be determined according to well-known methods. Those skilled in the art will be able to determine operative and optimal assay conditions for each determination by employing routine experimentation.

In addition to assaying TNF-delta and/or TNF-epsilon polypeptide levels or polynucleotide levels in a biological sample obtained from an obtained from an individual, TNF-delta and/or TNF-epsilon polypeptide or polynucleotide can also be detected in vivo by imaging. For example, in one embodiment of the invention, TNF-delta and/or TNF-epsilon polypeptide is used to image T cell lymphomas. In another embodiment, TNF-delta and/or TNF-epsilon polynucleotides o the invention (e.g., polynucleotides complementary to all or a portion of TNF-delta and/or TNF-epsilon mRNA) is used to image T cell lymphomas.

Antibody labels or markers for in vivo imaging of TNF-delta and/or TNF-epsilon polypeptide include those detectable by X-radiography, NMR, MRI, CAT-scans or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. Where in vivo imaging is used to detect enhanced levels of TNF-delta and/or TNF-epsilon polypeptide for diagnosis in humans, it may be preferable to use human antibodies or "humanized" chimeric monoclonal antibodies. Such antibodies can be produced using techniques described herein or otherwise known in the art. For example methods for producing chimeric antibodies are known in the art. See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

Additionally, any TNF-delta and/or TNF-epsilon polypeptide whose presence can be detected, can be administered. For example, TNF-delta and/or TNF-epsilon polypeptides labeled with a radio-opaque or other appropriate compound can be administered and visualized in vivo, as discussed, above for labeled antibodies. Further such TNF-delta and/or TNF-epsilon polypeptides can be utilized for in vitro diagnostic procedures.

A TNF-delta and/or TNF-epsilon polypeptide-specific antibody or antibody fragment which has been labeled with an appropriate detectable imaging moiety, such as a radioisotope (for example, $^{131}$I, $^{112}$In, $^{99m}$Tc, ($^{131}$I, $^{125}$I, $^{123}$I, $^{121}$I), carbon ($^{14}$C), Sulfr ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum (99Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, 105Rh, $^{97}$Ru), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TNF delta and/or TNF epsilon protein. In vivo tumor imaging is described in S. W. Burchiel et al., "Immunopharmacokinetics of Radiolabeled Antibodies and Their Fragments" (Chapter 13 in Tumor Imaging: The Radiochemical Detection of Cancer, S. W. Burchiel and B. A. Rhodes, eds., Masson Publishing Inc. (1982)).

With respect to antibodies, one of the ways in which the anti-TNF delta and/or anti-TNF epsilon antibody can be detectably labeled is by linking the same to an enzyme and using the linked product in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller et al., J. Clin. Pathol. 31:507–520 (1978); Butler, J. E., Meth. Enzymol 73:482–523 (1981); Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means.

Enzymes which can be used to detectably label the antibody include, but are not limited to, malate dehydrogenase, staphylococcal nuclease, delta-S-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect TNF-delta and/or TNF-epsilon through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by means including, but not limited to, a gamma counter, a scintillation counter, or autoradiography.

It is also possible to label the antibody with a fluorescent compound. When the fluorescently labeled antibody is exposed to light of the proper wave-length, its presence can then be detected due to fluorescence. Among the most commonly used fluorescent labeling compounds are fluorescein isothiocyanate, rhodamine, phycoerythrin, phycocyanin, allophycocyanin, ophthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors: Gene Structure and Biological Activities," Symp. Quant. Biol. 51:597–609 (1986), Cold Spring Harbor; Beutler, B., and Cerami, A., Annu. Rev. Biochem. 57:505–518 (1988); Old, L. J., Sci. Am. 258:59–75 (1988); Fiers, W., FEBS Lett. 285:199–224 (1991)). The TNF-family ligands induce such various cellular responses by binding to TNF-family receptors.

TNF delta and/or TNF epsilon polynucleotides, polypeptides, agonists and/or antagonists of the invention may be administered to a patient (e.g., mammal, preferably human) afflicted with any disease or disorder mediated (directly or indirectly) by defective, or deficient levels of, TNF delta and/or TNF epsilon. Alternatively, a gene therapy approach may be applied to treat such diseases or disorders. In one embodiment of the invention, TNF delta and/or TNF epsilon polynucleotide sequences are used to detect mutein TNF delta and/or TNF epsilon genes, including defective genes. Mutein genes may be identified in in vitro diagnostic assays, and by comparison of the TNF delta and/or TNF epsilon nucleotide sequence disclosed herein with that of a TNF delta and/or TNF epsilon gene obtained from a patient suspected of harboring a defect in this gene. Defective genes may be replaced with normal TNF delta and/or TNF epsilon-encoding genes using techniques known to one skilled in the art.

In another embodiment, the TNF delta and/or TNF epsilon polypeptides, polynucleotides, agonists and/or antagonists of the present invention are used as research tools for studying the phenotypic effects that result from inhibiting TRAIL/TNF delta and/or TRAIL/TNF epsilon interactions on various cell types. TNF delta and/or TNF epsilon polypeptides and antagonists (e.g. monoclonal antibodies to TNF delta and/or TNF epsilon) also may be used in in vitro assays for detecting TRAIL or TNF delta and/or TNF epsilon or the interactions thereof.

It has been reported that certain ligands of the TNF family (of which TRAIL is a member) bind to more than one distinct cell surface receptor protein. For example, a receptor protein designated DR4 reportedly binds TRAIL, but is distinct from the TNF delta and/or TNF epsilon of the present invention (Pan et al., Science 276:111–113, (1997); hereby incorporated by reference). In another embodiment, a purified TNF delta and/or TNF epsilon polypeptide, agonist and/or antagonist is used to inhibit binding of TRAIL to endogenous cell surface TRAIL. By competing for TRAIL binding, soluble TNF delta and/or TNF epsilon polypeptides of the present invention may be employed to inhibit the interaction of TRAIL not only with cell surface TNF delta and/or TNF epsilon, but also with TRAIL receptor proteins distinct from TNF delta and/or TNF epsilon. Thus, in a further embodiment, TNF delta and/or TNF epsilon polynucleotides, polypeptides, agonists and/or antagonists of the invention are used to inhibit a functional activity of TRAIL, in in vitro or in vivo procedures. By inhibiting binding of TRAIL to cell surface receptors, TNF delta and/or TNF epsilon also inhibits biological effects that result from the binding of TRAIL to endogenous receptors. Various forms of TNF delta and/or TNF epsilon may be employed, including, for example, the above-described TNF delta and/or TNF epsilon fragments, derivatives, and variants that are capable of binding TRAIL. In a preferred embodiment, a soluble TNF delta and/or TNF epsilon, is employed to inhibit a functional activity of TRAIL, e.g., to inhibit TRAIL-mediated apoptosis of cells susceptible to such apoptosis. Thus, in an additional embodiment, TNF delta and/or TNF epsilon is administered to a mammal (e.g., a human) to treat a TRAIL-mediated disorder. Such TRAIL-mediated disorders include conditions caused (directly or indirectly) or exacerbated by TRAIL.

Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjögren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, TNF delta and/or TNF epsilon polynucleotides, polypeptides, and/or antagonists of the invention are used to inhibit growth, progression, and/or metastasis of cancers, in particular those listed above.

Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjögren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (such as hepatitis related liver injury, ischemia/reperfusion injury, cholestosis (bile duct injury) and liver cancer); toxin-induced liver disease (such as that caused by alcohol), septic shock, cachexia and anorexia. In preferred embodiments, TNF delta and/or TNF epsilon polynucleotides, polypeptides and/or agonists are used to treat the diseases and disorders listed above.

Many of the pathologies associated with HIV are mediated by apoptosis, including HIV-induced nephropathy and HIV encephalitis. Thus, in additional preferred embodiments, DR4 polynucleotides, polypeptides, and/or DR4 agonists of the invention are used to treat AIDS and pathologies associated with AIDS. Another embodiment of the present invention is directed to the use of DR4 to reduce TRAIL-mediated death of T cells in HIV-infected patients.

Another embodiment of the present invention is directed to the use of TRID to reduce TRAIL-mediated death of T cells in HIV-infected patients. The role of T cell apoptosis in the development of AIDS has been the subject of a number of studies (see, for example, Meyaard et al., Science 257:217–219, 1992; Groux et al., J. Exp. Med., 175:331, 1992; and Oyaizu et al., in Cell Activation and Apoptosis in HIV Infection, Andrieu and Lu, Eds., Plenum Press, New York, 1995, pp. 101–114). Fas-mediated apoptosis has been implicated in the loss of T cells in HIV individuals (Katsikis et al., J. Exp. Med. 181:2029–2036, 1995).

The state of immunodeficiency that defines AIDS is secondary to a decrease in the number and function of $CD4^+$ T-lymphocytes. Recent reports estimate the daily loss of $CD4^+$ T cells to be between $3.5 \times 10^7$ and $2 \times 10^9$ cells (Wei X. et al., Nature 373:117–122 (1995)). One cause of $CD4^+$ T cell depletion in the setting of HIV infection is believed to be HIV-induced apoptosis (see, for example, Meyaard et al., Science 257:217–219, 1992; Groux et al., J. Exp. Med., 175:331, 1992; and Oyaizu et al., in Cell Activation and Apoptosis in HIV Infection, Andrieu and Lu, Eds., Plenum Press, New York, 1995, pp. 101–114). Indeed, HIV-induced apoptotic cell death has been demonstrated not only in vitro but also, more importantly, in infected individuals (Ameisen, J. C., AIDS 8:1197–1213 (1994); Finkel, T. H., and Banda, N. K., Curr. Opin. Immunol. 6:605–615(1995); Muro-Cacho, C. A. et al., J. Immunol. 154:5555–5566 (1995)). Furthermore, apoptosis and $CD4^+$ T-lymphocyte depletion is tightly correlated in different animal models of AIDS (Brunner, T., et al., Nature 373:441–444 (1995); Gougeon, M. L., et al., AIDS Res. Hum. Retroviruses 9:553–563 (1993)) and, apoptosis is not observed in those animal models in which viral replication does not result in AIDS (Gougeon, M. L. et al., AIDS Res. Hum. Retroviruses 9:553–563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al, J. Virol. 70:199–206 (1996)). Further the TNF-family ligand was detectable in uninfected macrophages and its expression was upregulated following HIV infection resulting in selective killing of uninfected CD4 T-lymphocytes (Badley, A. D et al., J. Virol. 70:199–206 (1996)). Further, additional studies have implicated Fas-mediated apoptosis in the loss of T cells in HIV individuals (Katsikis et al., J. Exp. Med. 181:2029–2036 (1995)). It is also possible that T cell apoptosis occurs through multiple mechanisms. Further, at least some of the T cell death seen in HIV patients may be mediated by TRAIL.

Thus, by the invention, a method for treating HIV+ individuals is provided which involves administering TNF delta and/or TNF epsilon agonists of the present invention to reduce selective killing of $CD4^+$ T-lymphocytes.

While not wanting to be bound by theory, activated human T cells are believed to be induced to undergo programmed cell death (apoptosis) upon triggering through the CD3/T cell receptor complex, a process termed activated-induced cell death (AICD). AICD of $CD4^+$ T cells isolated from HIV-Infected asymptomatic individuals has been reported (Groux et al., supra). Thus, AICD may play a role in the depletion of $CD4^+$ T cells and the progression to AIDS in HIV-infected individuals. Thus, the present invention provides a method of inhibiting TRAIL-mediated T cell death in HIV patients, comprising administering a DR4 polypeptide of the invention (preferably, a soluble DR4 polypeptide) and/or DR4 antagonist of the invention to the patients. Modes of administration and dosages are discussed in detail below. In one embodiment, the patient is asymptomatic when treatment with DR4 commences. If desired, prior to treatment, peripheral blood T cells may be extracted from an HIV patient, and tested for susceptibility to TRAIL-mediated cell death by procedures known in the art. In one embodiment, a patient's blood or plasma is contacted with DR4 polypeptides of the invention ex vivo. The DR4 polypeptides of the invention may be bound to a suitable chromatography matrix by procedures known in the art. The patient's blood or plasma flows through a chromatography column containing DR4 bound to the matrix, before being returned to the patient. The immobilized DR4 polypeptide binds TRAIL, thus removing TRAIL protein from the patient's blood.

In additional embodiments a DR4 polypeptide and/or antagonist of the invention is administered in combination with other inhibitors of T cell apoptosis. For example, as discussed above, Fas-mediated apoptosis also has been implicated in loss of T cells in HIV individuals (Katsikis et al., J. Exp. Med. 181:2029–2036, 1995). Thus, a patient susceptible to both Fas ligand mediated and TRAIL mediated T cell death may be treated with both an agent that blocks TRAIL/TRAIL receptor interactions and an agent that blocks Fas-ligand/Fas interactions. Suitable agents for blocking binding of Fas-ligand to Fas include, but are not limited to, soluble Fas polypeptides; mulitmeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in International application publication number WO 95/10540, hereby incorporated by reference.

Suitable agents, which also block binding of TRAIL to a TRAIL receptor that may be administered with the polynucleotides and/or polypeptides of the present invention include, but are not limited to, soluble TRAIL receptor polypeptides (e.g., a soluble form of OPG, TR5 (International application publication number WO 98/30693); DR5 (International application publication number WO 98/41629); and TR10 (International application publication number WO 98/54202)); multimeric forms of soluble TRAIL receptor polypeptides; and TRAIL receptor antibodies that bind the TRAIL receptor without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis. Preferably, the antibodies employed according to this method are monoclonal antibodies.

Because TNF-delta and TNF-epsilon belong to the TNF superfamily, the polypeptides should also modulate angiogenesis. In addition, since TNF-delta and/or TNF-epsilon inhibit immune cell functions, the polypeptides will have a wide range of anti-inflammatory activities. TNF-delta and/or TNF-epsilon may be employed as an anti-neovascularizing agent to treat, prevent, and/or diagnose solid tumors by stimulating the invasion and activation of host defense cells, e.g., cytotoxic T cells and macrophages and by inhibiting the angiogenesis of tumors. Those of skill in the art will recognize other non-cancer indications where blood vessel proliferation is not wanted. They may also be employed to enhance host defenses against resistant chronic and acute infections, for example, myobacterial infections via the attraction and activation of microbicidal leukocytes. TNF-delta and/or TNF-epsilon may also be employed to inhibit T-cell proliferation by the inhibition of IL-2 biosynthesis for the treatment of T-cell mediated auto-immune diseases and lymphocytic leukemias (including, for example, chronic lymphocytic leukemia (CLL)). TNF-delta and/or TNF-epsilon may also be employed to stimulate wound healing, both via the recruitment of debris clearing and connective tissue promoting inflammatory cells. In this same manner, TNF-delta and/or TNF-epsilon may also be employed to treat, prevent, and/or diagnose other fibrotic disorders, including liver cirrhosis, osteoarthritis and pulmonary fibrosis. TNF-delta and/or TNF-epsilon also increases the presence of eosinophils that have the distinctive function of killing the larvae of parasites that invade tissues, as in schistosomiasis, trichinosis and ascariasis. It may also be employed to regulate hematopoiesis, by regulating the activation and differentiation of various hematopoietic progenitor cells, for example, to release mature leukocytes from the bone marrow following chemotherapy, i.e., in stem cell mobilization. TNF-delta and/or TNF-epsilon may also be employed to treat, prevent, and/or diagnose sepsis.

The invention also provides methods for blocking or inhibiting activated B cells using compositions of the invention for the treatment of asthma and other chronic airway diseases such as bronchitis and emphysema.

TNF-delta and/or TNF-epsilon polynucleotides or polypeptides, or agonists of TNF-delta and/or TNF-epsilon, can be used in the treatment of infectious agents. For example, by increasing the immune response, particularly increasing the proliferation and differentiation of B cells, infectious diseases may be treated. The immune response may be increased by either enhancing an existing immune response, or by initiating a new immune response. Alternatively, TNF-delta and/or TNF-epsilon polynucleotides or polypeptides, or agonists or antagonists of TNF-delta and/or TNF-epsilon, may also directly inhibit the infectious agent, without necessarily eliciting an immune response.

Viruses are one example of an infectious agent that can cause disease or symptoms that can be treated by TNF-delta and/or TNF-epsilon polynucleotides or polypeptides, or agonists of TNF-delta and/or TNF-epsilon. Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections ( e . g ., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. TNF-delta and/or TNF-epsilon polynucleotides or polypeptides, or agonists or antagonists of TNF-delta and/or TNF-epsilon, can be used to treat, prevent, diagnose, and/or detect any of these symptoms or diseases. In specific embodiments, TNF-delta and/or TNF-epsilon polynucleotides, polypeptides, or agonists are used to treat, prevent, and/or diagnose: meningitis, Dengue, EBV, and/or hepatitis (e.g., hepatitis B). In an additional specific embodiment TNF-delta and/or TNF-epsilon polynucleotides, polypeptides, or agonists are used to treat patients nonresponsive to one or more other commercially available hepatitis vaccines. In a further specific embodiment, TNF-delta and/or TNF-epsilon polynucleotides, polypeptides, or agonists are used to treat, prevent, and/or diagnose AIDS. In an additional specific embodiment TNF-delta and/or TNF-epsilon polynucleotides, polypeptides, agonists, and/or antagonists are used to treat, prevent, and/or diagnose patients with cryptosporidiosis.

Similarly, bacterial or fungal agents that can cause disease or symptoms and that can be treated by TNF-delta and/or TNF-epsilon polynucleotides or polypeptides, or agonists or antagonists of TNF-delta and/or TNF-epsilon, include, but not limited to, the following Gram-Negative and Gram-positive bacteria and bacterial families and fungi: Actinomycetales (e.g., Corynebacterium, Mycobacterium, Norcardia), Cryptococcus neoformans, Aspergillosis, Bacillaceae (e.g., Anthrax, Clostridium), Bacteroidaceae, Blastomycosis, Bordetella, Borrelia (e.g., *Borrelia burgdorferi,* Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Klebsiella, Salmonella (e.g., *Salmonella typhi,* and *Salmonella paratyphi*), Serratia, Yersinia), Erysipelothrix, Helicobacter, Legionellosis, Leptospirosis, Listeria (e.g, Listeria monocytogenes), Mycoplasmatales, *Mycobacterium leprae, Vibrio cholerae,* Neisseriaceae (e.g., Acinetobacter, Gonorrhea, Menigococcal), *Meisseria meningitidis,* Pasteurellacea Infections (e.g., Actinobacillus, Heamophilus (e.g., *Heamophilus influenza* type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. TNF delta and/or TNF epsilon polynucleotides or polypeptides, or agonists or antagonists of TNF-delta and/or TNF-epsilon, can be used to treat, prevent, diagnose, and/or detect any of these symptoms or diseases. In specific embodiments, TNF-delta and/or TNF-epsilon polynucleotides, polypeptides, or agonists thereof are used to treat, prevent, and/or diagnose: tetanus, Diptheria, botulism, and/or meningitis type B.

Moreover, parasitic agents causing disease or symptoms that can be treated by TNF-delta and/or TNF-epsilon polynucleotides or polypeptides, or agonists of TNF-delta and/or TNF-epsilon, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. TNF-delta and/or TNF-epsilon polynucleotides or polypeptides, or agonists or antagonists of TNF-delta and/or TNF-epsilon, can be used to treat, prevent, diagnose, and/or detect any of these symptoms or diseases. In specific embodiments, TNF-delta and/or TNF-epsilon polynucleotides, polypeptides, or agonists thereof are used to treat, prevent, and/or diagnose malaria.

In another embodiment, the invention provides a method of delivering compositions containing the polypeptides of the invention (e.g., compositions containing TNF-delta and/or TNF-epsilon polypeptides or anti-TNF-delta and/or anti-TNF-epsilon antibodies associated with heterologous polypeptides, heterologous nucleic acids, toxins, or prodrugs) to targeted cells, such as, for example, B cells expressing TNF-delta and/or TNF-epsilon receptor, or T cells expressing a cell surface bound form of TNF-delta and/or TNF-epsilon. TNF-delta and/or TNF-epsilon polypeptides or anti-TNF-delta and/or anti-TNF-epsilon antibodies of the invention may be associated with heterologous polypeptides, heterologous nucleic acids, toxins, radioisotopes, or prodrugs via hydrophobic, hydrophilic, ionic and/or covalent interactions.

In one embodiment, the invention provides a method for the specific delivery of compositions of the invention to cells by administering polypeptides of the invention (e.g., TNF-delta and/or TNF-epsilon polypeptides or anti-TNF-delta and/or anti-TNF-epsilon antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., TNF-delta and/or TNF-epsilon polypeptides or anti-TNF-delta and/or anti-TNF-epsilon antibodies) in association with toxins, radioisotopes, or cytotoxic prodrugs.

In a specific embodiment, the invention provides a method for the specific destruction of cells of B cell lineage (e.g., B cell related leukemias or lymphomas) by administering TNF-delta and/or TNF-epsilon polypeptides in association with toxins, radioisotopes, or cytotoxic prodrugs.

In another specific embodiment, the invention provides a method for the specific destruction of cells of T cell lineage (e.g., T cell leukemias or lymphomas) by administering anti-TNF-delta and/or anti-TNF-epsilon antibodies and/or soluble receptor that binds TNF-delta and/or TNF-epsilon in association with toxins, radioisotopes, or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thyrnidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

In specific embodiments, TNF-delta and/or TNF-epsilon polynucleotides or polypeptides, or anti-TNF-delta and/or anti-TNF-epsilon polynucleotides or polypeptides in association with radioisotopes, toxins or cytotoxic prodrugs are used to treat or ameliorate the symptoms of autoimmune diseases. In preferred emodiments, TNF-delta and/or TNF-epsilon polynucleotides or polypeptides, or anti-TNF-delta and/or anti-TNF-epsilon polynucleotides or polypeptides in association with radioisotopes, toxins or cytotoxic prodrugs are used to treat or ameliorate the symptoms of systemic lupus erythematosus In preferred emodiments, TNF-delta and/or TNF-epsilon polynucleotides or polypeptides, or anti-TNF-delta and/or anti-TNF-epsilon polynucleotides or polypeptides in association with radioisotopes, toxins or cytotoxic prodrugs are used to treat or ameliorate the symptoms of rheumatoid arthritis including advanced rheumatoid arthritis. In preferred emodiments, TNF-delta and/or TNF-epsilon polynucleotides or polypeptides, or anti-TNF-delta and/or anti-TNF-epsilon polynucleotides or polypeptides in association with radioisotopes, toxins or cytotoxic prodrugs are used to treat or ameliorate the symptoms of idiopathic thrombocytopenic purpura (ITP).

In other preferred embodiments TNF-delta and/or TNF-epsilon polynucleotides or polypeptides, or anti-TNF-delta and/or anti-TNF-epsilon polynucleotides or polypeptides in association with radioisotopes, toxins or cytotoxic prodrugs are used to treat or ameliorate the symptoms of Sjögren's syndrome. In other preferred embodiments, TNF-delta and/or TNF-epsilon polynucleotides or polypeptides, or anti-TNF-delta and/or anti-TNF-epsilon polynucleotides or polypeptides in association with radioisotopes, toxins or cytotoxic prodrugs are used to treat or ameliorate the symptoms of IgA nephropathy. In other preferred embodiments, TNF-delta and/or TNF-epsilon polynucleotides or polypeptides, or anti-TNF-delta and/or anti-TNF-epsilon polynucleotides or polypeptides in association with radioisotopes, toxins or cytotoxic prodrugs are used to treat or ameliorate the symptoms of *Myasthenia gravis*. In preferred emodiments, TNF-delta and/or TNF-epsilon polynucleotides or polypeptides, or anti-TNF-delta and/or anti-TNF-epsilon polynucleotides or polypeptides in association with radioisotopes, toxins or cytotoxic prodrugs are used to treat or ameliorate the symptoms of multiple sclerosis. In still other preferred embodiments, TNF delta, TNF epsilon, anti-TNF delta, and/or anti-TNF epsilon polypeptides in association with radioisotopes, toxins or cytotoxic prodrugs are used to treat or ameliorate the symptoms of vasculitis.

An additional condition, disease or symptom that can be treated, prevented, and/or diagnosed by TNF-delta and/or TNF-epsilon polynucleotides or polypeptides, or agonists of TNF-delta and/or TNF-epsilon, is osteomyelitis.

An additional condition, disease or symptom that can be treated, prevented, and/or diagnosed by TNF-delta and/or TNF-epsilon polynucleotides or polypeptides, or agonists of TNF-delta and/or TNF-epsilon, is endocarditis.

Preferably, treatment using TNF-delta and/or TNF-epsilon polynucleotides or polypeptides, or agonists of TNF-delta and/or TNF-epsilon, could either be by administering an effective amount of TNF-delta and/or TNF-epsilon polypeptide to the patient, or by removing cells from the patient, supplying the cells with TNF-delta and/or TNF-epsilon polynucleotide, and returning the engineered cells to the patient (ex vivo therapy). Moreover, as further discussed herein, the TNF-delta and/or TNF-epsilon polypeptide or polynucleotide can be used as an adjuvant in a vaccine to raise an immune response against infectious disease.

TNF delta and/or TNF epsilon polypeptides or polynucleotides encoding TNF delta and/or TNF epsilon of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, thrombotic microangiopathies (e.g., thrombotic thrombocytopenic purpura (TTP)) and hemolytic-uremic syndrome (HUS)), ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyammoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

The naturally occurring balance between endogenous stimulators and inhibitors of angiogenesis is one in which inhibitory influences predominate. Rastinej ad et al., Cell 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al, *Biotech.* 9:630–634 (1991); Folkman et al., *N. Engl. J Med.,* 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J Opthalmol.* 94:715–743 (1982); and Folkman et al., *Science* 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases or disorders associated with neovascularization by administration of the TNF delta and/or TNF epsilon polynucleotides and/or polypeptides of the invention (including TNF delta and/or TNF epsilon agonists and/or antagonists). Malignant and metastatic conditions which can be treated with the polynucleotides and polypeptides of the invention include, but are not limited to those malignancies, solid tumors, and cancers described herein and otherwise known in the art (for a review of such disorders, see Fishman et al., Medicine, 2d Ed., J. B. Lippincott Co., Philadelphia (1985)).

Additionally, ocular disorders associated with neovascularization which can be treated with the TNF delta and/or TNF epsilon polynucleotides and polypeptides of the present invention (including TNF delta and/or TNF epsilon agonists and TNF delta and/or TNF epsilon antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Additionally, disorders which can be treated with the TNF delta and/or TNF epsilon polynucleotides and polypeptides of the present invention (including TNF delta and/or TNF epsilon agonists and TNF delta and/or TNF epsilon antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Additional preferred embodiments of the invention include, but are not limited to, the use of TNF delta and/or TNF epsilon polypeptides, TNF delta and/or TNF epsilon polynucleotides, and functional agonists thereof, in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

A vaccine adjuvant that enhances immune responsiveness to specific antigen. In a specific embodiment, the vaccine adjuvant is a TNF delta and/or TNF epsilon polypeptide described herein. In another specific embodiment, the vaccine adjuvant is a TNF delta and/or TNF epsilon polynucleotide described herein (i.e., the TNF delta and/or TNF epsilon polynucleotide is a genetic vaccine adjuvant). As discussed herein, TNF delta and/or TNF epsilon polynucleotides may be administered using techniques known in the art, including but not limited to, liposomal delivery, recombinant vector delivery, injection of naked DNA, and gene gun delivery.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae,* Group B streptococcus, Shigella spp., Enterotoxigenic *Escherichia coli,* Enterohemorrhagic *E. coli, Borrelia burgdorferi,* and Plasmodium (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell immunodeficient individuals, such as, for example, an individual who has undergone a partial or complete splenectomy. B cell immunodeficiencies that may be ameliorated or treated by administering the TNF delta and/or TNF epsilon polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVI) (acquired), chronic granulomatous disease, Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymophoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

As an agent to boost immunoresponsiveness among individuals having an acquired loss of B cell function. Conditions resulting in an acquired loss of B cell function that may be ameliorated or treated by administering the TNF delta and/or TNF epsilon polypeptides or polynucleotides of the invention, or agonists thereof, include, but are not limited to, HIV Infection, AIDS, bone marrow transplant, multiple myeloma and B cell chronic lymphocytic leukemia (CLL).

Patients with CLL and myeloma are at risk for increased infections. Thus, one aspect of the present invention provides for the use TNF-delta and/or TNF-epsilon polynucleotides or polypeptides, or anti-TNF-delta and/or anti-TNF-epsilon polynucleotides or polypeptides as an agent to boost immunoresponsiveness in CLL and myeloma patients.

As an agent to boost immunoresponsiveness among individuals having a temporary immune deficiency or compromised immune system. Conditions resulting in a temporary immune deficiency/compromised immune system that may be ameliorated or treated by administering the TNF delta and/or TNF epsilon polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery, and recovery from burns.

As a regulator of antigen presentation by monocytes, dendritic cells, and/or B-cells. In one embodiment, TNF delta and/or TNF epsilon polypeptides (in soluble, membrane-bound or transmembrane forms) or polynucleotides enhance antigen presentation or antagonize antigen presentation in vitro or in vivo. Moreover, in related embodiments, said enhancement or antagonization of antigen presentation may be useful as an anti-tumor treatment or to modulate the immune system.

As an agent to direct an individual's immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a B cell specific binding protein to which specific activators or inhibitors of cell growth may be attached. The result would be to focus the activity of such activators or inhibitors onto normal, diseased, or neoplastic B cell populations.

As a means of detecting B-lineage cells by virtue of its specificity. This application may require labeling the protein with biotin or other agents to afford a means of detection.

As a stimulator of B cell production in pathologies such as AIDS, chronic lymphocyte disorder and/or Common Variable Immunodificiency.

As part of a B cell selection device the function of which is to isolate B cells from a heterogenous mixture of cell types. TNF delta and/or TNF epsilon could be coupled to a solid support to which B cells would then specifically bind. Unbound cells would be washed out and the bound cells subsequently eluted. This technique would allow purging of tumor cells from, for example, bone marrow or peripheral blood prior to transplant.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance TNF delta- and/or TNF epsilon-mediated responses.

As a means of activating monocytes/macrophages to defend against parasitic diseases that effect monocytes such as Leshmania.

As pretreatment of bone marrow samples prior to transplant. Such treatment would increase B cell representation and thus accelerate recover.

As a means of regulating secreted cytokines that are elicited by TNF delta and/or TNF epsilon.

TNF delta and/or TNF epsilon polypeptides or polynucleotides of the invention, or agonists may be used to modulate IgE concentrations in vitro or in vivo.

Additionally, TNF delta and/or TNF epsilon polypeptides or polynucleotides of the invention, or agonists thereof, may be used to treat, prevent, and/or diagnose IgE-mediated allergic reactions. Such allergic reactions include, but are not limited to, asthma, rhinitis, and eczema.

In a specific embodiment, TNF delta and/or TNF epsilon polypeptides or polynucleotides of the invention, or agonists thereof, is administered to treat, prevent, diagnose, and/or ameliorate selective IgA deficiency.

In another specific embodiment, TNF delta and/or TNF epsilon polypeptides or polynucleotides of the invention, or agonists thereof, is administered to treat, prevent, diagnose, and/or ameliorate ataxia-telangiectasia.

In another specific embodiment, TNF delta and/or TNF epsilon polypeptides or polynucleotides of the invention, or agonists thereof, is administered to treat, prevent, diagnose, and/or ameliorate common variable immunodeficiency.

In another specific embodiment, TNF delta and/or TNF epsilon polypeptides or polynucleotides of the invention, or agonists thereof, is administered to treat, prevent, diagnose, and/or ameliorate X-linked agammaglobulinemia.

In another specific embodiment, TNF delta and/or TNF epsilon polypeptides or polynucleotides of the invention, or agonists thereof, is administered to treat, prevent, diagnose, and/or ameliorate severe combined immunodeficiency (SCID).

In another specific embodiment, TNF delta and/or TNF epsilon polypeptides or polynucleotides of the invention, or agonists thereof, is administered to treat, prevent, diagnose, and/or ameliorate Wiskott-Aldrich syndrome.

In another specific embodiment, TNF delta and/or TNF epsilon polypeptides or polynucleotides of the invention, or agonists thereof, is administered to treat, prevent, diagnose, and/or ameliorate X-linked Ig deficiency with hyper IgM.

In another specific embodiment, TNF delta and/or TNF epsilon polypeptides or polynucleotides of the invention, or agonists or antagonists (e.g., anti-TNF delta and/or anti-TNF epsilon antibodies) thereof, is administered to treat, prevent, and/or diagnose chronic myelogenous leukemia, acute myelogenous leukemia, leukemia, hysticocytic leukemia, monocytic leukemia (e.g., acute monocytic leukemia), leukemic reticulosis, Shilling Type monocytic leukemia, and/or other leukemias derived from monocytes and/or monocytic cells and/or tissues.

In another specific embodiment, TNF delta and/or TNF epsilon polypeptides or polynucleotides of the invention, or agonists thereof, is administered to treat, prevent, diagnose, and/or ameliorate monocytic leukemoid reaction, as seen, for example, with tuberculosis.

In another specific embodiment, TNF delta and/or TNF epsilon polypeptides or polynucleotides of the invention, or agonists thereof, is administered to treat, prevent, diagnose, and/or ameliorate monocytic leukocytosis, monocytic leukopenia, monocytopenia, and/or monocytosis.

In a specific embodiment, TNF delta and/or TNF epsilon polynucleotides or polypeptides of the invention, and/or anti-TNF delta and/or anti-TNF epsilon antibodies and/or agonists or antagonists thereof, are used to treat, prevent, detect, and/or diagnose primary B lymphocyte disorders and/or diseases, and/or conditions associated therewith. In one embodiment, such primary B lymphocyte disorders, diseases, and/or conditions are characterized by a complete or partial loss of humoral immunity. Primary B lymphocyte disorders, diseases, and/or conditions associated therewith that are characterized by a complete or partial loss of humoral immunity and that may be prevented, treated, detected and/or diagnosed with compositions of the invention include, but are not limited to, X-Linked Agammaglobulinemia (XLA), severe combined immunodeficiency disease (SCID), and selective IgA deficiency.

In a preferred embodiment, TNF delta and/or TNF epsilon polynucleotides, polypeptides, and/or agonists and/or antagonists thereof are used to treat, prevent, and/or diagnose diseases or disorders affecting or conditions associated with any one or more of the various mucous membranes of the body. Such diseases or disorders include, but are not limited to, for example, mucositis, mucoclasis, mucocolitis, mucocutaneous leishmaniasis (such as, for example, American leishmaniasis, leishmaniasis americana, nasopharyngeal leishmaniasis, and New World leishmaniasis), mucocutaneous lymph node syndrome (for example, Kawasaki disease), mucoenteritis, mucoepidermoid carcinoma, mucoepidermoid tumor, mucoepithelial dysplasia, mucoid adenocarcinoma, mucoid degeneration, myxoid degeneration; myxomatous degeneration; myxomatosis, mucoid medial degeneration (for example, cystic medial necrosis), mucolipidosis (including, for example, mucolipidosis I, mucolipidosis II, mucolipidosis III, and mucolipidosis IV), mucolysis disorders, mucomembranous enteritis, mucoenteritis, mucopolysaccharidosis (such as, for example, type I mucopolysaccharidosis (i.e., Hurler's syndrome), type IS mucopolysaccharidosis (i.e., Scheie's syndrome or type V mucopolysaccharidosis), type II mucopolysaccharidosis (i.e., Hunter's syndrome), type III mucopolysaccharidosis (i.e., Sanfilippo's syndrome), type IV mucopolysaccharidosis (i.e., Morquio's syndrome), type VI mucopolysaccharidosis (i.e., Maroteaux-Lamy syndrome), type VII mucopolysaccharidosis (i.e., mucopolysaccharidosis due to beta-glucuronidase deficiency), and mucosulfatidosis), mucopolysacchariduria, mucopurulent conjunctivitis, mucopus, mucormycosis (i.e., zygomycosis), mucosal disease (i.e., bovine virus diarrhea), mucous colitis (such as, for example, mucocolitis and myxomembranous colitis), and mucoviscidosis (such as, for example, cystic fibrosis, cystic fibrosis of the pancreas, Clarke-Hadfield syndrome, fibrocystic disease of the pancreas, mucoviscidosis, and viscidosis). In a highly preferred embodiment, TNF delta and/or TNF epsilon polynucleotides, polypeptides, and/or agonists and/or antagonists thereof are used to treat, prevent, and/or diagnose mucositis, especially as associated with chemotherapy.

In a preferred embodiment, TNF delta and/or TNF epsilon polynucleotides, polypeptides, and/or agonists and/or antagonists thereof are used to treat, prevent, and/or diagnose diseases or disorders affecting or conditions associated with sinusitis.

All of the above described applications as they may apply to veterinary medicine.

Antagonists of TNF delta and/or TNF epsilon include binding and/or inhibitory antibodies, antisense nucleic acids, ribozymes or soluble forms of the TNF delta and/or TNF epsilon receptor(s). These would be expected to reverse many of the activities of the ligand described above as well as find clinical or practical application as:

A means of blocking various aspects of immune responses to foreign agents or self. Examples include autoimmune disorders such as lupus, and arthritis, as well as immuno-responsiveness to skin allergies, inflammation, bowel disease, injury and pathogens. Although our current data speaks directly to the potential role of TNF delta and/or TNF epsilon in B cell and monocyte related pathologies, it remains possible that other cell types may gain expression or responsiveness to TNF delta and/or TNF epsilon. Thus, TNF delta and/or TNF epsilon may, like CD40 and its ligand, be regulated by the status of the immune system and the microenvironment in which the cell is located.

A therapy for preventing the B cell proliferation and Ig secretion associated with autoimmune diseases such as idiopathic thrombocytopenic purpura, systemic lupus erythramatosus and MS.

An inhibitor of graft versus host disease or transplant rejection.

A therapy for B cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

TNF delta and/or TNF epsilon polypeptides or polynucleotides of the invention, or antagonists may be used to modulate IgE concentrations in vitro or in vivo.

In another embodiment, administration of TNF delta and/or TNF epsilon polypeptides or polynucleotides of the invention, or antagonists thereof, may be used to treat, prevent, and/or diagnose IgE-mediated allergic reactions including, but not limited to, asthma, rhinitis, and eczema.

An inhibitor of signaling pathways involving ERK1, COX2 and Cyclin D2 which have been associated with TNF delta and/or TNF epsilon induced B cell activation.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The agonists and antagonists may be employed in a composition with a pharmaceutically acceptable carrier, e.g., as described above.

The antagonists may be employed for instance to inhibit TNF delta- and/or TNF epsilon-mediated chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat, prevent, and/or diagnose infectious diseases including silicosis, sarcoidosis, idiopathic pulmonary fibrosis by preventing the recruitment and activation of mononuclear phagocytes. They may also be employed to treat, prevent, and/or diagnose idiopathic hyper-eosinophilic syndrome by preventing eosinophil production and migration. Endotoxic shock may also be treated by the antagonists by preventing the migration of macrophages and their production of the TNF delta and/or TNF epsilon polypeptides of the present invention. The antagonists may also be employed for treating atherosclerosis, by preventing monocyte infiltration in the artery wall. The antagonists may also be employed to treat, prevent, and/or diagnose histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat, prevent, and/or diagnose chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat, prevent, and/or diagnose rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-I and TNF, which prevents the biosynthesis of other inflammatory cytokines. In this way, the antagonists may be employed to prevent inflammation. The antagonists may also be employed to inhibit prostaglandin-independent fever induced by TNF delta and/or TNF epsilon. The antagonists may also be employed to treat, prevent, and/or diagnose cases of bone marrow failure, for example, aplastic anemia and myelodysplastic syndrome. The antagonists may also be employed to treat, prevent, and/or diagnose asthma and allergy by preventing eosinophil accumulation in the lung. The antagonists may also be employed to treat, prevent, and/or diagnose subepithelial basement membrane fibrosis which is a prominent feature of the asthmatic lung. The antagonists may also be employed to treat, prevent, and/or diagnose lymphomas (e.g., one or more of the extensive, but not limiting, list of lymphomas provided herein).

All of the above described applications as they may apply to veterinary medicine. Moreover, all applications described herein may also apply to veterinary medicine.

Antibodies against TNF delta and/or TNF epsilon may be employed to bind to and inhibit TNF delta and/or TNF epsilon activity to treat, prevent, and/or diagnose ARDS, by preventing infiltration of neutrophils into the lung after injury. The antagonists and antagonists of the instant may be employed in a composition with a pharmaceutically acceptable carrier, e.g., as described hereinafter.

TNF delta and/or TNF epsilon polynucleotides or polypeptides of the invention and/or agonists and/or antagonists thereof, are used to treat, prevent, and/or diagnose diseases and disorders of the pulmonary system (e.g., bronchi such as, for example, sinopulmonary and bronchial infections and conditions associated with such diseases and disorders and other respiratory diseases and disorders. In specific embodiments, such diseases and disorders include, but are not limited to, bronchial adenoma, bronchial asthma, pneumonia (such as, e.g., bronchial pneumonia, bronchopneumonia, and tuberculous bronchopneumonia), chronic obstructive pulmonary disease (COPD), bronchial polyps, bronchiectasia (such as, e.g., bronchiectasia sicca, cylindrical bronchiectasis, and saccular bronchiectasis), bronchiolar adenocarcinoma, bronchiolar carcinoma, bronchiolitis (such as, e.g., exudative bronchiolitis, bronchiolitis fibrosa obliterans, and proliferative bronchiolitis), bronchiolo-alveolar carcinoma, bronchitic asthma, bronchitis (such as, e.g., asthmatic bronchitis, Castellani's bronchitis, chronic bronchitis, croupous bronchitis, fibrinous bronchitis, hemorrhagic bronchitis, infectious avian bronchitis, obliterative bronchitis, plastic bronchitis, pseudomembranous bronchitis, putrid bronchitis, and verminous bronchitis), bronchocentric granulomatosis, bronchoedema, bronchoesophageal fistula, bronchogenic carcinoma, bronchogenic cyst, broncholithiasis, bronchomalacia, bronchomycosis (such as, e.g., bronchopulmonary aspergillosis), bronchopulmonary spirochetosis, hemorrhagic bronchitis, bronchorrhea, bronchospasm, bronchostaxis, bronchostenosis, Biot's respiration, bronchial respiration, Kussmaul respiration, Kussmaul-Kien respiration, respiratory acidosis, respiratory alkalosis, respiratory distress syndrome of the newborn, respiratory insufficiency, respiratory scleroma, respiratory syncytial virus, and the like.

In a specific embodiment, TNF delta and/or TNF epsilon polynucleotides or polypeptides of the invention and/or agonists and/or antagonists thereof, are used to treat, prevent, and/or diagnose chronic obstructive pulmonary disease (COPD).

In another embodiment, TNF delta and/or TNF epsilon polynucleotides or polypeptides of the invention and/or agonists and/or antagonists thereof, are used to treat, prevent, and/or diagnose fibroses and conditions associated with fibroses, such as, for example, but not limited to, cystic fibrosis (including such fibroses as cystic fibrosis of the pancreas, Clarke-Hadfield syndrome, fibrocystic disease of the pancreas, mucoviscidosis, and viscidosis), endomyocardial fibrosis, idiopathic retroperitoneal fibrosis, leptomeningeal fibrosis, mediastinal fibrosis, nodular subepidermal fibrosis, pericentral fibrosis, perimuscular fibrosis, pipestem fibrosis, replacement fibrosis, subadventitial fibrosis, and Symmers' clay pipestem fibrosis.

In another embodiment, TNF delta and/or TNF epsilon polynucleotides or polypeptides of the invention and/or agonists and/or antagonists thereof, are used to treat, prevent, and/or diagnose inner ear infection (such as, for example, otitis media), as well as other infections characterized by infection with *Streptococcus pneumoniae* and other pathogenic organisms.

TNF delta and/or TNF epsilon polynucleotides or polypeptides of the invention and/or agonists and/or antagonists thereof, are used to treat, prevent, and/or diagnose various immune system-related disorders and/or conditions associated with these disorders, in mammals, preferably humans. Many autoimmune disorders result from inappropriate recognition of self as foreign material by immune cells. This inappropriate recognition results in an immune response leading to the destruction of the host tissue. Therefore, the administration of TNF delta and/or TNF epsilon polynucleotides or polypeptides of the invention and/or agonists and/or antagonists thereof that can inhibit an immune response, particularly the proliferation, differentiation, or chemotaxis of T cells, may be an effective therapy in treating and/or preventing autoimmune disorders. Thus, in preferred embodiments, TNF delta and/or TNF epsilon antagonists of the invention (e.g., polypeptide fragments of TNF delta and/or TNF epsilon and anti-TNF delta and/or anti-TNF epsilon antibodies) are used to treat, prevent, and/or diagnose an autoimmune disorder.

Such autoimmune disorders include, but are not limited to, autoimmune diseases such as, for example, autoimmune hemolytic anemia, autoimmune neonatal thrombocytopenia, autoimmunocytopenia, hemolytic anemia, antiphospholipid syndrome, dermatitis, allergic encephalomyelitis, glomerulonephritis, Multiple Sclerosis, Neuritis, Ophthalmia, Polyendocrinopathies, Purpura, Reiter's Disease, Stiff-Man Syndrome, Autoimmune Pulmonary Inflammation, Guillain-Barre Syndrome, insulin dependent diabetes mellitis, and autoimmune inflammatory eye disease.

Additional autoimmune disorders (that are highly probable) that may be treated, prevented, and/or diagnosed with the compositions of the invention include, but are not limited to, autoimmune thyroiditis (i.e., Hashimoto's thyroiditis) (often characterized, e.g., by cell-mediated and humoral thyroid cytotoxicity), systemic lupus erhthematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders (that are probable) that may be treated, prevented, and/or diagnosed with the compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjögren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using anti-TNF-delta antibodies and/or anti-TNF-epsilon antibodies and/or a soluble TNF delta and/or TNF epsilon receptor polypeptide of the invention.

In a specific preferred embodiment, rheumatoid arthritis is treated, prevented, and/or diagnosed using anti-TNF delta antibodies and/or anti-TNF epsilon antibodies and/or a soluble TNF delta and/or TNF epsilon receptor polypeptide and/or other antagonist of the invention.

In a specific preferred embodiment, lupus is treated, prevented, and/or diagnosed using anti-TNF delta antibodies and/or anti-TNF epsilon antibodies and/or a soluble TNF delta and/or TNF epsilon receptor polypeptide and/or other antagonist of the invention.

In a specific preferred embodiment, nephritis associated with lupus is treated, prevented, and/or diagnosed using anti-TNF delta antibodies and/or anti-TNF epsilon antibodies and/or a soluble TNF delta and/or TNF epsilon receptor polypeptide and/or other antagonist of the invention.

In a specific preferred embodiment, Sjögren's Syndrome is treated, prevented, and/or diagnosed using anti-TNF delta antibodies and/or anti-TNF epsilon antibodies and/or other antagonist of the invention.

In a specific preferred embodiment, AIDS is treated, prevented, and/or diagnosed using anti-TNF delta antibodies and/or anti-TNF epsilon antibodies and/or other antagonist of the invention.

In a specific preferred embodiment, HIV infection is treated, prevented, and/or diagnosed using anti-TNF delta antibodies and/or anti-TNF epsilon antibodies and/or other antagonist of the invention.

In another specific preferred embodiment, therapeutic and pharmaceutical compositions of the invention, are used to treat, prevent, ameliorate, diagnose or prognose, Myasthenia gravis and/or medical conditions associated therewith.

In another specific preferred embodiment, therapeutic and pharmaceutical compositions of the invention, are used to treat, prevent, ameliorate, diagnose or prognose, IgA nephropathy and/or medical conditions associated therewith.

In another specific preferred embodiment, therapeutic and pharmaceutical compositions of the invention, are used to treat, prevent, ameliorate, diagnose or prognose, hemolytic anemia and/or medical conditions associated therewith.

In another specific preferred embodiment, therapeutic and pharmaceutical compositions of the invention, are used to treat, prevent, ameliorate, diagnose or prognose, thyroiditis and/or medical conditions associated therewith.

In another specific preferred embodiment, therapeutic and pharmaceutical compositions of the invention, are used to treat, prevent, ameliorate, diagnose or prognose, Goodpasture's Syndrome and/or medical conditions associated therewith.

In another specific preferred embodiment, therapeutic and pharmaceutical compositions of the invention, are used to treat, prevent, ameliorate, diagnose or prognose, multiple sclerosis and/or medical conditions associated therewith.

In another specific preferred embodiment, therapeutic and pharmaceutical compositions of the invention, are used to treat, prevent, ameliorate, diagnose or prognose, chronic lymphocytic leukemia (CLL) and/or medical conditions associated therewith.

In another specific preferred embodiment, therapeutic and pharmaceutical compositions of the invention, are used to treat, prevent, ameliorate, diagnose or prognose, multiple myeloma and/or medical conditions associated therewith.

In another specific preferred embodiment, therapeutic and pharmaceutical compositions of the invention, are used to treat, prevent, ameliorate, diagnose or prognose, Non-Hodgkin's lymphoma and/or medical conditions associated therewith.

In another specific preferred embodiment, therapeutic and pharmaceutical compositions of the invention, are used to treat, prevent, ameliorate, diagnose or prognose, Hodgkin's disease and/or medical conditions associated therewith.

In a specific embodiment, TNF delta and/or TNF epsilon polynucleotides or polypeptides, or antagonists thereof (e.g., anti-TNF delta and/or anti-TNF epsilon antibodies) are used to treat or prevent systemic lupus erythramatosus and/or diseases, disorders or conditions associated therewith. Lupus-associated diseases, disorders, or conditions that may be treated or prevented with TNF delta and/or TNF epsilon polynucleotides or polypeptides, or antagonists of the invention, include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleuricy)), renal disorders (e.g., nephritis), neurological disorders (e.g., seizures, peripheral neuropathy, CNS related disorders), gastroinstestinal disorders, Raynaud phenomenon, and pericarditis. In a preferred embodiment, the TNF delta and/or TNF epsilon polynucleotides or polypeptides, or antagonists thereof (e.g., anti-TNF delta and/or anti-TNF epsilon antibodies) are used to treat or prevent renal disorders associated with systemic lupus erythramatosus. In a most preferred embodiment, TNF delta and/or TNF epsilon polynucleotides or polypeptides, or antagonists thereof (e.g., anti-TNF delta and/or anti-TNF epsilon antibodies) are used to treat or prevent nephritis associated with systemic lupus erythramatosus.

In one embodiment, the invention provides methods and compositions for inhibiting or reducing immunoglobulin production (e.g. IgM, IgG, and/or IgA production), comprising, or alternatively consisting of, contacting an effective amount of TNF delta and/or TNF epsilon polypeptide or agonist or antagonist thereof with cells of hematopoietic origin, wherein the effective amount of TNF delta and/or TNF epsilon polypeptide inhibits or reduces TNF delta and/or TNF epsilon mediated immunoglobulin production. In specific embodiments, the invention provides methods and compositions for inhibiting or reducing immunoglobulin production (e.g. IgM, IgG, and/or IgA production) in response to T cell dependent antigens, comprising, or alternatively consisting of, contacting an effective amount of TNF delta and/or TNF epsilon polypeptide or agonist or antagonist thereof with cells of hematopoietic origin, wherein the effective amount of TNF delta and/or TNF epsilon polypeptide or agonist or antagonist thereof inhibits or reduces TNF delta and/or TNF epsilon mediated immunoglobulin production in response to T cell dependent antigens. In specific embodiments, the invention provides methods and compositions for inhibiting or reducing immunoglobulin production (e.g. IgM, IgG, and/or IgA production) in response to T cell independent antigens, comprising, or alternatively consisting of, contacting an effective amount of TNF delta and/or TNF epsilon polypeptide or agonist or antagonist thereof with cells of hematopoietic origin, wherein the effective amount of TNF delta and/or TNF epsilon polypeptide inhibits or reduces TNF delta and/or TNF epsilon mediated immunoglobulin production in response to T cell independent antigens.

In another embodiment, the invention provides methods and compositions for inhibiting or reducing immunoglobulin production (e.g. IgM, IgG, and/or IgA production), comprising, or alternatively consisting of, administering to an animal in which such inhibition or reduction is desired, a TNF delta and/or TNF epsilon polypeptide or agonist or antagonist thereof in an amount effective to inhibit or reduce immunoglobulin production. In another embodiment, the invention provides methods and compositions for inhibiting or reducing immunoglobulin production (e.g. IgM, IgG, and/or IgA production) in response to T cell dependent antigens, comprising, or alternatively consisting of, administering to an animal in which such inhibition or reduction is desired, a TNF delta and/or TNF epsilon polypeptide or agonist or antagonist thereof in an amount effective to inhibit or reduce immunoglobulin production in response to T cell dependent antigens. In another embodiment, the invention provides methods and compositions for inhibiting or reducing immunoglobulin production (e.g. IgM, IgG, and/or IgA production) in response to T cell independent antigens, comprising, or alternatively consisting of, administering to an animal in which such inhibition or reduction is desired, a TNF delta and/or TNF epsilon polypeptide or agonist or antagonist thereof in an amount effective to inhibit or reduce immunoglobulin production in response to T cell independent antigens.

In another embodiment, the invention provides methods and compositions for stimulating immunoglobulin production (e.g. IgM, IgG, IgG, and/or IgA production) in response to T cell dependent antigens comprising, or alternatively consisting of, contacting an effective amount of TNF delta and/or TNF epsilon polypeptide with cells of hematopoietic origin, wherein the effective amount of the TNF delta and/or TNF epsilon polypeptide stimulates TNF delta and/or TNF epsilon mediated immunoglobulin production in response to T cell dependent antigens. In another embodiment, the invention provides methods and compositions for stimulating immunoglobulin production (e.g. IgM, IgG, and/or IgA production) in response to T cell independent antigens comprising, or alternatively consisting of, contacting an effective amount of TNF delta and/or TNF epsilon polypeptide with cells of hematopoietic origin, wherein the effective amount of the TNF delta and/or TNF epsilon polypeptide stimulates TNF delta and/or TNF epsilon mediated immunoglobulin production in response to T cell independent antigens.

In another embodiment, the invention provides methods and compositions for stimulating immunoglobulin production (e.g. IgM, and/or IgA production), comprising, or alternatively consisting of, contacting an effective amount of TNF delta and/or TNF epsilon polypeptide or agonist thereof with cells of hematopoietic origin, wherein the effective amount of the TNF delta and/or TNF epsilon polypeptide or agonist thereof stimulates TNF delta and/or TNF epsilon mediated immunoglobulin production. In another embodiment, the invention provides methods and compositions for stimulating immunoglobulin production (e.g. IgM, IgG, and/or IgA production) comprising, or alternatively consisting of, administering to an animal in which such stimulation is desired, a TNF delta and/or TNF epsilon polypeptide or agonist thereof in an amount effective to stimulate immunoglobulin production. In another embodiment, the invention provides methods and compositions for stimulating immunoglobulin production (e.g. IgM, IgG, and/or IgA production) in response to T cell dependent antigens comprising, or alternatively consisting of, administering to an animal in which such stimulation is desired, a TNF delta and/or TNF epsilon polypeptide or agonist thereof in an amount effective to stimulate immunoglobulin production in response to T cell dependent antigens.

In another embodiment, the invention provides methods and compositions for stimulating immunoglobulin production (e.g. IgM, IgG, and/or IgA production) in response to T cell independent antigens comprising, or alternatively consisting of, administering to an animal in which such stimulation is desired, a TNF delta and/or TNF epsilon polypeptide or agonist thereof in an amount effective to stimulate immunoglobulin production in response to T cell independent antigens.

Determination of immunoglobulin levels are most often performed by comparing the level of immunoglobulin in a sample to a standard containing a known amount of immunoglobulin using ELISA assays. Determination of immunoglobulin levels in a given sample, can readily be determined using ELISA or other method known in the art.

In one embodiment, the invention provides methods and compositions for inhibiting or reducing proliferation of cells of hematopoietic origin, comprising, or alternatively consisting of, contacting an effective amount of TNF delta and/or TNF epsilon polypeptide or agonist or antagonist thereof with cells of hematopoietic origin, wherein the effective amount of TNF delta and/or TNF epsilon polypeptide or agonist or antagonist thereof inhibits or reduces TNF delta and/or TNF epsilon mediated proliferation of cells of hemtopoietic origin. In another embodiment, the invention provides methods and compositions for inhibiting or reducing proliferation of cells of hematopoietic origin comprising, or alternatively consisting of, administering to an animal in which such inhibition or reduction is desired, a TNF delta and/or TNF epsilon polypeptide or agonist or antagonist thereof in an amount effective to inhibit or reduce B cell proliferation. In preferred embodiments, the cells of hematopoietic origin are B cells.

In one embodiment, the invention provides methods and compositions for stimulating proliferation of cells of hematopoietic origin, comprising, or alternatively consisting of, contacting an effective amount of TNF delta and/or TNF epsilon polypeptide or agonist thereof with cells of hematopoietic origin, wherein the effective amount of TNF delta and/or TNF epsilon polypeptide or agonist thereof stimulates TNF delta and/or TNF epsilon mediated proliferation of cells of hemtopoietic origin. In another embodiment, the invention provides methods and compositions for stimulating proliferation of cells of hematopoietic origin comprising, or alternatively consisting of, administering to an animal in which such stimulation is desired, a TNF delta and/or TNF epsilon polypeptide or agonist thereof in an amount effective to stimulate B cell proliferation. In preferred embodiments, the cells of hematopoietic origin are B cells. B cell proliferation is most commonly assayed in the art by measuring tritiated thymidine incorporation (see Examples 6 & 7). This and other assays are commonly known in the art and could be routinely adapted for the use of determining the effect of TNF delta and/or TNF epsilon polypeptides on B cell proliferation.

In one embodiment, the invention provides methods and compositions for inhibiting or reducing activation of cells of hematopoietic origin, comprising, or alternatively consisting of, contacting an effective amount of TNF delta and/or TNF epsilon polypeptide or agonist or antagonist thereof with cells of hematopoietic origin, wherein the effective amount of TNF delta and/or TNF epsilon polypeptide or agonist or antagonist thereof inhibits or reduces TNF delta and/or TNF epsilon mediated activation of cells of hematopoietic origin. In one embodiment, the invention provides methods and compositions for inhibiting or reducing activation of cells of hematopoietic origin, comprising, or alternatively consisting of, administering to an animal in which such inhibition or reduction is desired, a TNF delta and/or TNF epsilon polypeptide or agonist or antagonist thereof in an amount effective to inhibit or reduce activation of cells of hematopoietic origin. In preferred embodiments, the cells of hematopoietic origin are B cells.

In one embodiment, the invention provides methods and compositions for increasing activation of cells of hematopoietic origin, comprising, or alternatively consisting of, contacting an effective amount of TNF delta and/or TNF epsilon polypeptide or agonist thereof with cells of hematopoietic origin, wherein the effective amount of TNF delta and/or TNF epsilon polypeptide or agonist thereof increases TNF delta and/or TNF epsilon mediated activation of cells of hematopoietic origin. In one embodiment, the invention provides methods and compositions for increasing activation of cells of hematopoietic origin, comprising, or alternatively consisting of, administering to an animal in which such increase is desired, a TNF delta and/or TNF epsilon polypeptide or agonist thereof in an amount effective to increase activation of cells of hematopoietic origin. In preferred embodiments, the cells of hematopoietic origin are B cells.

B cell activation can measured in a variety of ways, such as FACS analysis of activation markers expressed on B cells. B cells activation markers include, but are not limited to, CD26, CD 28, CD 30, CD 38, CD 39, CD 69, CD70 CD71, CD 77, CD 83, CD126, CDw130, and B220. Additionally, B cell activation maybe measured by analysis of the activation of signaling molecules involved in B cell activation. By way of non-limiting example, such analysis may take the form of analyzing mRNA levels of signaling molecules by Northern analysis or real time PCR (See Example 11). One can also measure, for example, the phosphorylation of signaling molecules using anti-phosphotyrosine antibodies in a Western blot. B cell activation may also be measured by measuring the calcium levels in B cells. These and other methods of determining B cell activation are commonly known in the art and could be routinely adapted for the use of determining the effect of TNF delta and/or TNF epsilon polypeptides on B cell activation.

In one embodiment, the invention provides methods and compositions for decreasing lifespan of cells of hematopoietic origin, comprising, or alternatively consisting of, contacting an effective amount of TNF delta and/or TNF epsilon polypeptide or agonist or antagonist thereof with cells of hematopoietic origin, wherein the effective amount of TNF delta and/or TNF epsilon polypeptide or agonist or antagonist thereof inhibits or reduces TNF delta and/or TNF epsilon regulated lifespan of cells of hematopoietic origin. In one embodiment, the invention provides methods and compositions for decreasing lifespan of cells of hematopoietic origin, comprising, or alternatively consisting of, administering to an animal in which such decrease is desired, a TNF delta and/or TNF epsilon polypeptide or agonist or antagonist thereof in an amount effective to decrease lifespan of cells of hematopoietic origin. In preferred embodiments, the cells of hematopoietic origin are B cells.

In one embodiment, the invention provides methods and compositions for increasing lifespan of cells of hematopoietic origin, comprising, or alternatively consisting of, contacting an effective amount of TNF delta and/or TNF epsilon polypeptide or agonist thereof with cells of hematopoietic origin, wherein the effective amount of TNF delta and/or TNF epsilon polypeptide or agonist thereof increases TNF delta and/or TNF epsilon regulated lifespan of cells of hematopoietic origin. In one embodiment, the invention provides methods and compositions for increasing lifespan of cells of hematopoietic origin, comprising, or alternatively consisting of, administering to an animal in which such increase is desired, a TNF delta and/or TNF epsilon polypeptide or agonist thereof in an amount effective to increase lifespan of cells of hematopoietic origin. In preferred embodiments, the cells of hematopoietic origin are B cells.

B cell life span in vivo may be measured by 5-bromo-2'-deoxyuridine (BrdU) labeling experiments which are well known to one skilled in the art. BrdU is a thymidine analogue that gets incorporated into the DNA of dividing cells. Cells containing BrdU in their DNA can be detected using, for example fluorescently labeled anti-BrdU antibody and flow cytometry. Briefly, an animal is injected with BrdU in an amount sufficient to label developing B cells. Then, a sample of B cells is withdrawn from the animal, for example, from peripheral blood, and analyzed for the percentage of cells that contain BrdU. Such an analysis performed at several time points can be used to calculate the half life of B cells. Alternatively, B cell survival may be measured in vitro. For example B cells may be cultured under conditions where proliferation does not occur, (for example the media should contain no reagents that crosslink the immunoglobulin receptor, such as anti-IgM antibodies) for a period of time (usually 2–4 days). At the end of this time, the percent of surviving cells is determined, using for instance, the vital dye Trypan Blue, or by staining cells with propidium iodide or any other agent designed to specifically stain apoptotic cells and analyzing the percentage of cells stained using flow cytometry. One could perform this experiment under several conditions, such as B cells treated with TNF delta, B cells treated with TNF delta and/or TNF epsilon polypeptide complexes, and untreated B cells in order to determine the effects of TNF delta and/or TNF epsilon polypeptides on B cells survival. These and other methods for determining B cell lifespan are commonly known in the art and could routinely be adapted to determining the effect of TNF delta and/or TNF epsilon polypeptides on TNF delta and/or TNF epsilon regulated B cell lifespan.

It will be appreciated that conditions caused by a decrease in the standard or normal level of TNF delta and/or TNF epsilon activity in an individual, particularly disorders of the immune system, can be treated by administration of TNF delta and/or TNF epsilon polypeptide (in the form of soluble extracellular domain or cells expressing the complete protein) or agonist. Thus, the invention also provides a method of treatment of an individual in need of an increased level of TNF delta and/or TNF epsilon activity comprising administering to such an individual a pharmaceutical composition comprising an amount of an isolated TNF delta and/or TNF epsilon polypeptide of the invention, or agonist thereof, effective to increase the TNF delta and/or TNF epsilon activity level in such an individual.

It will also be appreciated that conditions caused by a increase in the standard or normal level of TNF delta and/or TNF epsilon activity in an individual, particularly disorders of the immune system, can be treated by administration of TNF delta and/or TNF epsilon polypeptides (in the form of soluble extracellular domain or cells expressing the complete protein) or antagonist (e.g, an anti-TNF delta and /or anti-TNF epsilon antibody). Thus, the invention also provides a method of treatment of an individual in need of an decreased level of TNF delta and/or TNF epsilon activity comprising administering to such an individual a pharmaceutical composition comprising an amount of an isolated TNF delta and/or TNF epsilon polypeptide of the invention, or antagonist thereof, effective to decrease the TNF delta and/or TNF epsilon activity level in such an individual. A non-limiting example of a TNF delta and/or TNF epsilon polypeptide of the invention that can be administered to an individual in need of a decreased level of TNF delta and/or TNF epsilon activity, is a dominant negative mutant of a TNF delta and/or TNF epsilon, which binds to a TNF delta and/or TNF epsilon receptor but that does not induce signal transduction.

Autoantibody production is common to several autoimmune diseases and contributes to tissue destruction and exacerbation of disease. Autoantibodies can also lead to the occurrence of immune complex deposition complications and lead to many symptoms of systemic lupus erythomatosis, including kidney failure, neuralgic symptoms and death. Modulating antibody production independent of cellular response would also be beneficial in many disease states. B cells have also been shown to play a role in the secretion of arthritogenic immunoglobulins in rheumatoid arthritis, (Korganow et al., *Immunity* 10:451–61, 1999). As such, inhibition of TNF delta and/or TNF epsilon mediated antibody production would be beneficial in treatment of autoimmune diseases such as myasthenia gravis and rheumatoid arthritis. Compounds of the invention that selectively block or neutralize the action of B-lymphocytes would be useful for such purposes. To verify these capabilities in compositions of the present invention, such compositions are evaluated using assays known in the art and described herein.

The invention provides methods employing compositions of the invention (e.g., TNF delta and/or TNF epsilon polynucleotides or polypeptides of the invention and/or agonists and/or antagonists thereof) for selectively blocking or neutralizing the actions of B-cells in association with end stage renal diseases, which may or may not be associated with autoimmune diseases. Such methods would also be useful for treating immunologic renal diseases. Such methods would be would be useful for treating glomerulonephritis associated with diseases such as membranous nephropathy, IgA nephropathy or Berger's Disease, IgM nephropathy, Goodpasture's Disease, post-infectious glomerulonephritis, mesangioproliferative disease, minimal-change nephrotic syndrome. Such methods would also serve as therapeutic applications for treating secondary glomerulonephritis or vasculitis associated with such diseases as lupus, polyarteritis, Henoch-Schonlein, Scleroderma, HIV-related diseases, amyloidosis or hemolytic uremic syndrome. The methods of the present invention would also be useful as part of a therapeutic application for treating interstitial nephritis or pyelonephritis associated with chronic pyelonephritis, analgesic abuse, nephrocalcinosis, nephropathy caused by other agents, nephrolithiasis, or chronic or acute interstitial nephritis.

The methods of the present invention also include use of compositions of the invention in the treatment of hypertensive or large vessel diseases, including renal artery stenosis or occlusion and cholesterol emboli or renal emboli.

The present invention also provides methods for diagnosis and treatment of renal or urological neoplasms, multiple myelomas, lymphomas, light chain neuropathy or amyloidosis.

Similarly, allergic reactions and conditions, such as asthma (particularly allergic asthma) or other respiratory problems, may also be treated by TNF delta and/or TNF epsilon polynucleotides or polypeptides of the invention and/or agonists and/or antagonists thereof. Moreover, these molecules can be used to treat, prevent, and/or diagnose anaphylaxis, hypersensitivity to an antigenic molecule, or blood group incompatibility.

TNF delta and/or TNF epsilon polynucleotides or polypeptides of the invention and/or agonists and/or antagonists thereof, may also be used to treat, prevent, and/or diagnose organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. The administration of TNF delta and/or TNF epsilon polynucleotides or polypeptides of the invention and/or agonists and/or antagonists thereof, that inhibits an immune response, particularly the proliferation, differentiation, or chemotaxis of T-cells, may be an effective therapy in preventing organ rejection or GVHD.

Similarly, TNF delta and/or TNF epsilon polynucleotides or polypeptides of the invention and/or agonists and/or antagonists thereof, may also be used to modulate inflammation. For example, TNF delta and/or TNF epsilon polynucleotides or polypeptides of the invention and/or agonists and/or antagonists thereof, may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

In a specific embodiment, anti-TNF delta and/or anti-TNF epsilon antibodies of the invention are used to treat, prevent, modulate, detect, and/or diagnose inflammation.

In a specific embodiment, anti-TNF delta and/or anti-TNF epsilon antibodies of the invention are used to treat, prevent, modulate, detect, and/or diagnose inflamatory disorders.

In another specific embodiment, anti-TNF delta and/or anti-TNF epsilon antibodies of the invention are used to treat, prevent, modulate, detect, and/or diagnose allergy and/or hypersensitivity.

The TNF family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," *Symp. Quant. Biol.* 51:597–609 (1986), Cold Spring Harbor; B. Beutler and A. Cerami, *Annu. Rev. Biochem.* 57:505–518 (1988); L. J. Old, *Sci. Am.* 258:59–75 (1988); W. Fiers, *FEBS Lett.* 285:199–224 (1991)). The TNF-family ligands, including TNF delta and/or TNF epsilon of the present invention, induce such various cellular responses by binding to TNF-family receptors. TNF delta and/or TNF epsilon polypeptides are believed to elicit a potent cellular response including any genotypic, phenotypic, and/or morphologic change to the cell, cell line, tissue, tissue culture or patient. As indicated, such cellular responses include not only normal physiological responses to TNF-family ligands, but also diseases associated with increased apoptosis or the inhibition of apoptosis. Apoptosis-programmed cell death-is a physiological mechanism involved in the deletion of peripheral B and/or T lymphocytes of the immune system, and its disregulation can lead to a number of different pathogenic processes (J. C. Ameisen, *AIDS* 8:1197–1213 (1994); P. H. Krammer et al, *Curr. Opin. Immunol.* 6:279–289 (1994)).

Diseases associated with increased cell survival, or the inhibition of apoptosis, include cancers (such as follicular lymphomas, carcinomas with p53 mutations, and hormone-dependent tumors, including, but not limited to, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. Thus, in preferred embodiments TNF delta and/or TNF epsilon polynucleotides or polypeptides of the invention are used to treat, prevent, and/or diagnose autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment TNF delta and/or TNF epsilon polynucleotides or polypeptides of the invention are used to activate, differentiate or proliferate cancerous cells or tissue (e.g., B cell lineage related cancers (e.g., CLL and MLL), lymphocytic leukemia, or lymphoma) and thereby render the cells more vulnerable to cancer therapy (e.g., chemotherapy or radiation therapy).

Moreover, in other embodiments, TNF delta and/or TNF epsilon polynucleotides or polypeptides of the invention are used to inhibit the growth, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. Thus, in preferred embodiments TNF delta and/or TNF epsilon polynucleotides or polypeptides of the invention are used to treat, prevent, and/or diagnose the diseases and disorders listed above.

Thus, in additional preferred embodiments, the present invention is directed to a method for enhancing apoptosis induced by a TNF-family ligand, which involves administering to a cell which expresses a TNF delta and/or TNF epsilon receptor an effective amount of TNF delta and/or TNF epsilon, analog or an agonist capable of increasing TNF delta- and/or TNF epsilon-mediated signaling. Preferably, TNF delta and/or TNF epsilon mediated signaling is increased to treat, prevent, and/or diagnose a disease wherein decreased apoptosis or decreased cytokine and adhesion molecule expression is exhibited. An agonist can include soluble forms of TNF delta and/or TNF epsilon and monoclonal antibodies directed against the TNF delta and/or TNF epsilon polypeptide.

In a further aspect, the present invention is directed to a method for inhibiting apoptosis induced by a TNF-family ligand, which involves administering to a cell which expresses the TNF delta and/or TNF epsilon receptor an effective amount of an antagonist capable of decreasing TNF delta- and/or TNF epsilon-mediated signaling. Preferably, TNF delta- and/or TNF epsilon-mediated signaling is decreased to treat, prevent, and/or diagnose a disease wherein increased apoptosis or NF-kappaB expression is exhibited. An antagonist can include soluble forms of TNF delta and/or TNF epsilon and monoclonal antibodies directed against the TNF delta and/or TNF epsilon polypeptides.

Polynucleotides and/or polypeptides of the invention and/or agonists and/or antagonists thereof are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), Helicobacter pylori infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

In a preferrred embodiments, TNF delta and/or TNF epsilon antagonists (e.g., anti-TNF delta and/or anti-TNF epsilon antibodies) used to prevent, detect, diagnose, and/or treat immune-based rheumatologic diseases, including but not limited to, SLE, rheumatoid arthritis, CREST syndrome (a variant of scleroderma characterized by calcinosis, Raynaud's phenomenon, esophageal motility disorders, sclerodactyly, and telangiectasia.), seronegative spondyloarthropathy (SpA), polymyositis/dermatomyositis, microscopic polyangiitis, hepatitis C-asociated arthritis, Takayasu's arteritis, and undifferentiated connective tissue disorder.

Polynucleotides and/or polypeptides of the invention and/or agonists and/or antagonists thereof are useful in promoting angiogenesis, wound healing (e.g., wounds, burns, and bone fractures). Polynucleotides and/or polypeptides of the invention and/or agonists and/or antagonists thereof are also useful as an adjuvant to enhance immune responsiveness to specific antigen, anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

Combinatorial formulations:

The TNF delta and/or TNF epsilon polypeptide composition (preferably containing a polypeptide which is a soluble form of the TNF delta and/or TNF epsilon extracellular domains) will be formulated and dosed in a fashion consistent with good medical practice, taking into account the clinical condition of the individual patient (especially the side effects of treatment with TNF delta and/or TNF epsilon polypeptide alone), the site of delivery of the TNF delta and/or TNF epsilon polypeptide composition, the method of administration, the scheduling of administration, and other factors known to practitioners. The "effective amount" of TNF delta and/or TNF epsilon polypeptide for purposes herein is thus determined by such considerations.

As a general proposition, the total pharmaceutically effective amount of TNF delta and/or TNF epsilon polypeptide administered parenterally per dose will be in the range of about 1 microgram/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day.

In another embodiment, the TNF delta and/or TNF epsilon polypeptide of the invention is administered to a human at a dose betweeen 0.0001 and 0.045 mg/kg/day, preferably, at a dose between 0.0045 and 0.045 mg/kg/day, and more preferably, at a dose of about 45 microgram/kg/day in humans; and at a dose of about 3 mg/kg/day in mice.

If given continuously, the TNF delta and/or TNF epsilon polypeptide is typically administered at a dose rate of about 1 microgram/kg/hour to about 50 micrograms/kg/hour, either by 1–4 injections per day or by continuous subcutaneous infusions, for example, using a mini-pump. An intravenous bag solution may also be employed.

The length of treatment needed to observe changes and the interval following treatment for responses to occur appears to vary depending on the desired effect.

In a specific embodiment, the total pharmaceutically effective amount of TNF delta and/or TNF epsilon polypeptide administered parenterally per dose will be in the range of about 0.1 microgram/kg/day to 45 micrograms/kg/day of patient body weight, although, as noted above, this will be subject to therapeutic discretion. More preferably, this dose is at least 0.1 microgram/kg/day, and most preferably for humans between about 0.01 and 50 micrograms/kg/day for the protein. TNF delta and/or TNF epsilon may be administered as a continuous infusion, multiple dicreet injections per day (e.g., three or more times daily, or twice daily), single injection per day, or as discreet injections given intermitently (e.g., twice daily, once daily, every other day, twice weekly, weekly, biweekly, monthly, bimonthly, and quarterly). If given continuously, the TNF delta and/or TNF epsilon polypeptide is typically administered at a dose rate of about 0.001 to 10 microgram/kg/hour to about 50 micrograms/kg/hour, either by 1–4 injections per day or by continuous subcutaneous infusions, for example, using a mini-pump.

Effective dosages of the compositions of the present invention to be administered may be determined through procedures well known to those in the art which address such parameters as biological half-life, bioavailability, and toxicity. Such determination is well within the capability of those skilled in the art, especially in light of the detailed disclosure provided herein.

Bioexposure of an organism to TNF delta and/or TNF epsilon polypeptide during therapy may also play an important role in determining a therapeutically and/or pharmacologically effective dosing regime. Variations of dosing such as repeated administrations of a relatively low dose of TNF delta and/or TNF epsilon polypeptide for a relatively long period of time may have an effect which is therapeutically and/or pharmacologically distinguishable from that achieved with repeated administrations of a relatively high dose of TNF delta and/or TNF epsilon for a relatively short period of time. See, for instance, the serum immunoglobulin level experiments presented in Example 6.

Using the equivalent surface area dosage conversion factors supplied by Freireich, E. J., et al. (*Cancer Chemotherapy Reports* 50(4):219–44 (1966)), one of ordinary skill in the art is able to conveniently convert data obtained from the use of TNF delta and/or TNF epsilon in a given experimental system into an accurate estimation of a pharmaceutically effective amount of TNF delta and/or TNF epsilon polypeptide to be administered per dose in another experimental system. Experimental data obtained through the administration of Neutrokine-alpha in mice (see, for instance, Example 6) may converted through the conversion factors supplied by Freireich, et al., to accurate estimates of pharmaceutically effective doses of Neutrokine-alpha in rat, monkey, dog, and human. The following conversion table (Table III) is a summary of the data provided by Freireich, et al. Table III gives approximate factors for converting doses expressed in terms of mg/kg from one species to an equivalent surface area dose expressed as mg/kg in another species tabulated.

TABLE III

Equivalent Surface Area Dosage Conversion Factors.

| | TO | | | | |
|---|---|---|---|---|---|
| FROM | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

Thus, for example, using the conversion factors provided in Table III, a dose of 50 mg/kg in the mouse converts to an appropriate dose of 12.5 mg/kg in the monkey because (50 mg/kg)×(¼)=12.5 mg/kg. As an additional example, doses of 0.02, 0.08, 0.8, 2, and 8 mg/kg in the mouse equate to effect doses of 1.667 micrograms/kg, 6.67 micrograms/kg, 66.7 micrograms/kg, 166.7 micrograms/kg, and 0.667 mg/kg, respectively, in the human.

Pharmaceutical compositions containing TNF delta and/or TNF epsilon polypeptides of the invention may be administered orally, rectally, parenterally, subcutaneously, intracistemally, intravaginally, intraperitoneally, topically (as by powders, ointments, drops or transdermal patch), bucally, or as an oral or nasal spray (e.g., via inhalation of a vapor or powder). In one embodiment, "pharmaceutically acceptable carrier" means a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can be employed as liquid carriers, particularly for injectable solutions. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The term "parenteral" as used herein refers to modes of administration which include intravenous, intramuscular, intraperitoneal, intrastemal, subcutaneous and intraarticular injection and infusion.

In a preferred embodiment, TNF delta and/or TNF epsilon compositions of the invention (including polypeptides, polynucleotides, and antibodies, and agonists and/or antagonists thereof) are administered subcutaneously.

In another preferred embodiment, TNF delta and/or TNF epsilon compositions of the invention (including polypeptides, polynucleotides, and antibodies, and agonists and/or antagonists of TNF delta or TNF epsilon) are administered intravenously.

TNF delta and/or TNF epsilon compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D- (-)-3-hydroxybutyric acid (EP 133,988).

Sustained-release compositions also include liposomally entrapped compositions of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing TNF delta and/or TNF epsilon polypeptide my be prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TNF delta and/or TNF epsilon polypeptide therapy.

In another embodiment sustained release compositions of the invention include crystal formulations known in the art.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, the TNF delta and/or TNF epsilon polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the TNF delta and/or TNF epsilon polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, sucrose, or dextrins; chelating agents such as EDTA; sugar alcohols such as mannitol or sorbitol; counterions such as sodium; preservatives, such as cresol, phenol, chlorobutanol, benzyl alcohol and parabens, and/or nonionic surfactants such as polysorbates, poloxamers, or PEG.

The TNF delta and/or TNF epsilon polypeptide is typically formulated in such vehicles at a concentration of about 0.001 mg/ml to 100 mg/ml, or 0.1 mg/ml to 100 mg/ml, preferably 1–10 mg/ml or 1–10 mg/ml, at a pH of about 3 to 10, or 3 to 8, more preferably 5–8, most preferably 6–7. It will be understood that the use of certain of the foregoing excipients, carriers, or stabilizers will result in the formation of TNF delta and/or TNF epsilon polypeptide salts.

TNF delta and/or TNF epsilon polypeptide to be used for therapeutic administration must be sterile. Sterility is readily accomplished by filtration through sterile filtration membranes (e.g., 0.2 micron membranes). Therapeutic TNF delta and/or TNF epsilon polypeptide compositions generally are placed into a container having a sterile access port, for example, an intravenous solution bag or vial having a stopper pierceable by a hypodermic injection needle.

TNF delta and/or TNF epsilon polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous TNF delta and/or TNF epsilon polypeptide solution, and the resulting mixture is lyophilized. The infusion solution is prepared by reconstituting the lyophilized TNF delta and/or TNF epsilon polypeptide using bacteriostatic Water-for-Injection.

Alternatively, TNF delta and/or TNF epsilon polypeptide is stored in single dose containers in lyophilized form. The infusion selection is reconstituted using a sterile carrier for injection.

The invention also provides a pharmaceutical pack or kit comprising one or more containers filled with one or more of the ingredients of the pharmaceutical compositions of the invention. Optionally, associated with such container(s) is a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In a specific embodiment, compositions of the invention (e.g., TNF delta and/or TNF epsilon polypeptides of the invention, TNF delta and/or TNF epsilon fragments and variants, and anti-Neutokine-alpha and/or anti-Netrokine-alphaSV antibodies) may be administered to patients as vaccine adjuvants. In a further specific embodiment, compositions of the invention may be administered as vaccine adjuvants to patients suffering from an immune-deficiency. In a further specific embodiment, compositions of the invention may be administered as vaccine adjuvants to patients suffering from HIV.

In a specific embodiment, compositions of the invention may be used to increase or enhance antigen-specific antibody responses to standard and experimental vaccines. In a specific embodiment, compositions of the invention may be used to enhance seroconversion in patients treated with standard and experimental vaccines. In another specific embodiment, compositions of the invention may be used to increase the number of unique epitopes recognized by antibodies elicited by standard and experimental vaccination.

In another specific embodiment, compositions of the invention are used in combination with PNEUMOVAX-23™ to treat, prevent, and/or diagnose infection and/or any disease, disorder, and/or condition associated therewith. In one embodiment, compositions of the invention are used in combination with PNEUMOVAX-23™ to treat, prevent, and/or diagnose any Gram positive bacterial infection and/or any disease, disorder, and/or condition associated therewith. In another embodiment, compositions of the invention are used in combination with PNEUMOVAX-23™ to treat, prevent, and/or diagnose infection and/or any disease, disorder, and/or condition associated with one or more members of the genus Enterococcus and/or the genus Streptococcus. In another embodiment, compositions of the invention are used in any combination with PNEUMOVAX-23™ to treat, prevent, and/or diagnose infection and/or any disease, disorder, and/or condition associated with one or more members of the Group B streptococci. In another embodiment, compositions of the invention are used in combination with PNEUMOVAX-23™ to treat, prevent, and/or diagnose infection and/or any disease, disorder, and/ or condition associated with *Streptococcus pneumoniae*.

The compositions of the invention may be administered alone or in combination with other therapeutic agents. Therapeutic agents that may be administered in combination with the compositions of the invention, include but are not limited to, other members of the TNF family, chemotherapeutic agents, antibiotics, steroidal and non-steroidal anti-inflammatories, conventional immunotherapeutic agents, cytokines, chemokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911), endokine-alpha (International Publication No. WO 98/07880), TR6 (International Publication No. WO 98/30694), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694),TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In a preferred embodiment, the compositions of the invention are administered in combination with TACI (See e.g., U.S. Pat. No. 5,969,102; and von Bulow et al., Science 278:138–141 (1997)), a soluble form of TACI, biologically active fragments, variants, or derivatives of TACI (e.g., TACI-Fc), and/or anti-TACI antibodies (e.g., agonistic or antagonistic antibodies).

In a preferred embodiment, the compositions of the invention are administered in combination with B-cell maturation antigen (BCMA, GenBank accession number NP_001183)), a soluble form of BCMA, biologically active fragments, variants, or derivatives of BCMA (e.g., BCMA-Fc), and/or anti-BCMA antibodies (e.g., agonistic or antagonistic antibodies).

In a preferred embodiment, the compositions of the invention are administered in combination with Neutrokine-alpha (International Publication No. WO 98/18921), a soluble form of Neutrokine alpha, biologically active fragments, variants, or derivatives of Neutrokine-alpha, and/or anti-Neutrokine alpha antibodies (e.g., agonistic or antagonistic antibodies).

In an additional embodiment, the compositions of the invention are administered alone or in combination with an anti-angiogenic agent(s). Anti-angiogenic agents that may be administered with the compositions of the invention include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP- PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4- chloroanthronilic acid disodium or "CCA"; (Takeuchi et al., Agents Actions 36:312–316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkinan *J Pediatr. Surg.* 28:445–51 (1993)); an integrin alpha v beta 3 antagonist (C. Storgard et al., *J Clin. Invest.* 103:47–54 (1999)); carboxynaminolmidazole; Carboxyamidotriazole (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 AstraZeneca (London, UK); APRA (CT2584); Benefin, Byrostatin-1 (SC339555); CGP-41251 (PKC 412); CM101; Dexrazoxane (ICRF187); DMXAA; Endostatin; Flavopridiol; Genestein; GTE; ImmTher; Iressa (ZD1839); Octreotide (Somatostatin); Panretin; Penacillamine; Photopoint; PI-88; Prinomastat (AG-3340) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the compounds of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the compositions of the invention include, but are not limited to, AG-3340 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aetema, St-Foy, Quebec). Examples of anti-angiogenic inhibitors that act by blocking the function of endothelial cell-extracellular matrix adhesion molecules and which may be administered in combination with the compositions of the invention include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with the compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the compositions of the invention include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of compositions of the invention in combination with anti-angiogenic agents is contemplated for the treatment, prevention, and/or amelioration of an autoimmune disease, such as for example, an autoimmune disease described herein.

In a particular embodiment, the use of compositions of the invention in combination with anti-angiogenic agents is contemplated for the treatment, prevention, and/or amelioration of arthritis. In a more particular embodiment, the use of compositions of the invention in combination with anti-angiogenic agents is contemplated for the treatment, prevention, and/or amelioration of rheumatoid arthritis or conditions associated therewith.

In a particular embodiment, the use of compositions of the invention in combination with anti-angiogenic agents is contemplated for the treatment, prevention, and/or amelioration of arthritis. In a more particular embodiment, the use of compositions of the invention in combination with anti-angiogenic agents is contemplated for the treatment, prevention, and/or amelioration of systemic lupus erythematosus or conditions associated therewith.

In another embodiment, compositions of the invention are administered in combination with an anticoagulant. Anticoagulants that may be administered with the compositions of the invention include, but are not limited to, heparin, warfarin, and aspirin. In a specific embodiment, compositions of the invention are administered in combination with heparin and/or warfarin. In another specific embodiment, compositions of the invention are administered in combination with warfarin. In another specific embodiment, compositions of the invention are administered in combination with warfarin and aspirin. In another specific embodiment, compositions of the invention are administered in combination with heparin. In another specific embodiment, compositions of the invention are administered in combination with heparin and aspirin.

In another embodiment, compositions of the invention are administered in combination with an agent that suppresses the production of anticardiolipin antibodies. In specific embodiments, the polynucleotides of the invention are administered in combination with an agent that blocks and/or reduces the ability of anticardiolipin antibodies to bind phospholipid-binding plasma protein beta 2-glycoprotein I (b2GPI).

In another embodiment, therapeutic or pharmaceutical compositions of the invention are administered to an animal to treat, prevent or ameliorate ischemia and arteriosclerosis. Examples of such disorders include, but are not limited to, reperfusion damage (e.g., in the heart and/or brain) and cardiac hypertrophy.

Therapeutic or pharmaceutical compositions of the invention, may also be administered to to modulate blood clotting and to treat or prevent blood clotting disorders, such as, for example, antibody-mediated thrombosis (i.e., antiphospholipid antibody syndrome (APS)). For example, therapeutic or pharmaceutical compositions of the invention, may inhibit the proliferation and differentiation of cells involved in producing anticardiolipin antibodies. These compositions of the invention can be used to treat, prevent, ameliorate, diagnose, and/or prognose thrombotic related events including, but not limited to, stroke (and recurrent stroke), heart attack, deep vein thrombosis, pulmonary embolism, myocardial infarction, coronary artery disease (e.g., antibody-mediated coronary artery disease), thrombosis, graft reocclusion following cardiovascular surgery (e.g., coronary arterial bypass grafts, recurrent fetal loss, and recurrent cardiovascular thromboembolic events.

Conventional nonspecific immunosuppressive agents, that may be administered in combination with the compositions of the invention include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells. Other immunosuppressive agents, that may be administered in combination with the compositions of the invention include, but are not limited to, prednisolone, methotrexate, thalidomide, methoxsalen, rapamycin, leflunomide, mizoribine (BREDININ™), brequinar, deoxyspergualin, and azaspirane (SKF 105685).

In specific embodiments, Therapeutics of the invention are administered in combination with immunosuppressants. Immunosuppressant preparations that may be administered with the Therapeutics of the invention include, but are not limited to, ORTHOCLONE OKT® 3 (muromonab-CD3), SANDIMMUNE™, NEORAL™, SANGDYA™ (cyclosporine), PROGRAF® (FK506, tacrolimus), CELLCEPT® (mycophenolate motefil, of which the active metabolite is mycophenolic acid), IMURAN™ (azathioprine), glucorticosteroids, adrenocortical steroids such as DELTASONE™ (prednisone) and HYDELTRASOL™ (prednisolone), FOLEX™ and MEXATE™ (methotrxate), OXSORALEN-ULTRA™ (methoxsalen) and RAPAMUNE™ (sirolimus). In a specific embodiment, immunosuppressants maybe used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-IRa gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffinan-La Roche), EF-5 (Scotia Pharmaceuticals), BIIL-284 (Boehringer Ingelheim), BIIF-1 149 (Boehringer Ingelheim), LeukoVax (Inflammatics), MK-663 (Merck), ST-1482 (Sigma-Tau), and butixocort propionate (WarnerLambert).

In one embodiment, the compositions of the invention are administered in combination with one or more of the following drugs: infliximab (also known as Remicade™ Centocor, Inc.), Trocade (Roche, RO-32-3555), Leflunomide (also known as Arava™ from Hoechst Marion Roussel), Kineret™ (an IL-I Receptor antagonist also known as Anakinra from Amgen, Inc.), SCIO-469 (p38 kinase inhibitor from Scios, Inc), and/or ASLERA™ (prasterone, dehydroepiandrosterone, GL701) from Genelabs Technologies Inc.

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, LJP 394 (La Jolla Pharmaceutical Company, San Diego, Calif.), and prednisolone.

In a more preferred embodiment, the compositions of the invention are administered in combination with an antimalarial, methotrexate, anti-TNF antibody, ENBREL™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, and suflasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and suflasalazine. In another specific embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBUL™, GAMMAGARD S/D™, and GAMIMUNE™. In a specific embodiment, compositions of the invention are administered in combination with intravenous immune globulin preparations in transplantation therapy (e.g., bone marrow transplant).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

In certain embodiments, compositions of the invention are administered in combination with antiretroviral agents, nucleoside/nucleotide reverse transcriptase inhibitors (NRTIs), non-nucleoside reverse transcriptase inhibitors (NNRTIs), and/or protease inhibitors (PIs). NRTIs that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3- to 10-fold greater activity in vitro; Triangle/Abbott); dOTC (BCH-10652, also structurally related to lamivudine but retains activity against a substantial proportion of lamivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TC-resistant virus); GW420867X (Glaxo Wellcome); ZIAGEN™ (abacavir/159U89; Glaxo Wellcome Inc.); CS-87 (3'azido-2',3'-dideoxyuridine; WO 99/66936); and S-acyl-2-thioethyl (SATE)-bearing prodrug forms of β-L-FD4C and β-L-FddC (WO 98/17281).

Additional NNRTIs include COACTINON™ (Emivirine/MKC-442, potent NNRTI of the HEPT class; Triangle/Abbott); CAPRAVIRE™ (AG- 1549/S-1 153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW-420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myres Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756, 423 (an indinavir analog; Merck); DMP-450 (a cyclic urea compound; Avid & DuPont); AG-1776 (a peptidomimetic with in vitro activity against protease inhibitor-resistant viruses; Agouron); VX-175/GW-433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643–678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX40-4C (a cationic peptide), T22 (an 18 amino acid peptide; Trimeris) and the T22 analogs T134 and T140; CCR5 antagonists such as RANTES (9-68), AOP-RANTES, NNY-RANTES, and TAK-779; and CCR5/CXCR4 antagonists such as NSC 651016 (a distamycin analog). Also included are CCR2B, CCR3, and CCR6 antagonists. Chemokine recpetor agonists such as RANTES, SDF-1, MIP-1α, MIP-1β, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compunds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors sucha as VX-497 (Vertex); and myvopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1α, MIP-1β, SDF-1α, IL-2, PROLEUKIN™ (aldesleukin/L2–7001; Chiron), IL-4, IL-10, IL-12, and IL-13; interferons such as IFN-α2a; antagonists of TNFs, NFκB, GM-CSF, M-CSF, and IL-10; agents that modulate immune activation such as cyclosporin and prednisone; vaccines such as Remune™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targetted to the ER to block surface expression of newly synthesized CCR5 (Yang et al., PNAS 94:11567–72 (1997); Chen et al., Nat. Med. 3:1110–16 (1997)); antibodies such as the anti-CXCR4 antibody 12G5, the anti-CCR5 antibodies 2D7, 5C7, PA8, PA9, PA10, PA11, PA12, and PA1 4, the anti-CD4 antibodies Q4120 and RPA-T4, the anti-CCR3 antibody 7B11, the anti-gp120 antibodies 17b, 48d, 447–52D, 257-D, 268-D and 50.1, anti-Tat antibodies, anti-TNF-α antibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and α-naphthoflavone (WO 98/30213); and antioxidants such as γ-L-glutamyl-L-cysteine ethyl ester (γ-GCE; WO 99/56764).

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPI™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIMSULFAMETHOXAZOLE™, DAPSONE™, PENTAMIDINE™, and/or ATOVAQUONE™ to prophylactically treat, prevent, and/or diagnose an opportunistic *Pneumocystis carini* pneumonia infection. In another specific embodiment, compositions of the invention are used in any combination with ISONLAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCI- COLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPOGEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or combination of one or more of the components of CHOP. In one embodiment, the compositions of the invention are administered in combination with anti-CD20 antibodies, human monoclonal anti-CD20 antibodies. In another embodiment, the compositions of the invention are administered in combination with anti-CD20 antibodies and CHOP, or anti-CD20 antibodies and any combination of one or more of the components of CHOP, particularly cyclophosphamide and/or prednisone. In a specific embodiment, compositions of the invention are administered in combination with Rituximab. In a further embodiment, compositions of the invention are administered with Rituximab and CHOP, or Rituximab and any combination of one or more of the components of CHOP, particularly cyclophosphamide and/or prednisone. In a specific embodiment, compositions of the invention are administered in combination with tositumomab (anti-CD20 antibody from Coulter Pharmaceuticals, San Francisco, Calif.). In a further embodiment, compositions of the invention are administered with tositumomab and CHOP, or tositumomab and any combination of one or more of the components of CHOP, particularly cyclophosphamide and/or prednisone. Tositumomab may optionally be associated with $^{113}$I. The anti-CD20 antibodies may optionally be associated with radioisotopes, toxins or cytotoxic prodrugs.

In another specific embodiment, the compositions of the invention are administered in combination Zevalin™. In a further embodiment, compositions of the invention are administered with Zevalin™ and CHOP, or Zevalin™ and any combination of one or more of the components of CHOP, particularly cyclophosphamide and/or prednisone. Zevalin™ may be associated with one or more radisotopes. Particularly preferred isotopes are $^{90}$Y and $^{111}$In.

In an additional embodiment, the compositions of the invention are administered in combination with cytokines. Cytokines that may be administered with the compositions of the invention include, but are not limited to, IL-2, IL-3, IL-4, IL-5, IL-6, IL-7, IL-10, IL-12, IL-13, IL-15, anti-CD40, CD40L, IFN-gamma and TNF-alpha. In one embodiment, the compositions of the invention are administered in combination with one or more chemokines. In specific embodiments, the compositions of the invention are administered in combination with an alpha(C×C) chemokine selected from the group consisting of gamma-interferon inducible protein-10 (gammaIP-10), interleukin-8 (IL-8), platelet factor-4 (PF4), neutrophil activating protein (NAP-2), GRO-alpha, GRO-beta, GRO-gamma, neutrophil-activating peptide (ENA-78), granulocyte chemoattractant protein-2 (GCP-2), and stromal cell-derived factor-1 (SDF-1, or pre-B cell stimulatory factor (PBSF)); and/or a beta (CC) selected from the group consisting of: RANTES (regulated on activation, normal T expressed and secreted), macrophage inflammatory protein-1 alpha (MP-1 alpha), macrophage inflammatory protein-1 beta (MIP-1beta), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1 gamma), macrophage inflammatory protein-3-alpha (MIP-3-alpha), macrophage inflammatory protein-3-beta (MIP-3-beta), macrophage inflammatory protein-4 (MIP-4/DC-CK-1/PARC), eotaxin, Exodus, and 1–309; and/or the gamma(C) chemokine, lymphotactin.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

The invention also provides a method of screening compounds to identify those which enhance or block the action of TNF delta or TNF epsilon on cells, such as its interaction with TNF delta or TNF epsilon binding molecules such as receptor molecules. An agonist is a compound which increases the natural biological functions of polypeptides of the present invention or which functions in a manner similar to polypeptides of the present invention, while antagonists decrease or eliminate such functions.

For example, a cellular compartment, such as a membrane or a preparation thereof, such as a membrane-preparation, may be prepared from a cell that expresses a molecule that binds TNF delta or TNF epsilon, such as a molecule of a signaling or regulatory pathway modulated by TNF delta or TNF epsilon. The preparation is incubated with labeled TNF delta or TNF epsilon in the absence or the presence of a candidate molecule which may be a TNF delta or TNF epsilon agonist or antagonist. The ability of the candidate molecule to bind the binding molecule is reflected in decreased binding of the labeled ligand. Molecules which bind gratuitously, i.e., without inducing the effects of TNF delta or TNF epsilon on binding the TNF delta or TNF epsilon binding molecule, are most likely to be good antagonists. Molecules that bind well and elicit effects that are the same as or closely related to TNF delta or TNF epsilon are agonists.

TNF delta or TNF epsilon-like effects of potential agonists and antagonists may by measured, for instance, by determining activity of a second messenger system following interaction of the candidate molecule with a cell or appropriate cell preparation, and comparing the effect with that of TNF delta or TNF epsilon or molecules that elicit the same effects as TNF delta or TNF epsilon. Second messenger systems that may be useful in this regard include but are not limited to AMP guanylate cyclase, ion channel or phosphoinositide hydrolysis second messenger systems.

Another example of an assay for TNF delta or TNF epsilon antagonists is a competitive assay that combines TNF delta or TNF epsilon and a potential antagonist with membrane-bound TNF delta or TNF epsilon receptor molecules or recombinant TNF delta or TNF epsilon receptor molecules under appropriate conditions for a competitive inhibition assay. TNF delta or TNF epsilon can be labeled, such as by radioactivity, such that the number of TNF delta or TNF epsilon molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing TNF delta or TNF epsilon-induced activities, thereby preventing the action of a polypeoptide of the present invention by excluding it from binding to its receptor.

Another potential antagonist is a soluble form of the TNF delta or TNF epsilon receptor which binds to TNF delta or TNF epsilon and prevents it from interacting with membrane-bound TNF delta or TNF epsilon receptors. In this way, the receptors are not stimulated by their ligand.

Potential antagonists include a small molecule which binds to and occupies the binding site of the polypeptide thereby preventing binding to cellular binding molecules, such as receptor molecules, such that normal biological activity is prevented. Examples of small molecules include but are not limited to small organic molecules, peptides or non-peptide antagonists.

Other potential antagonists include antisense molecules. Antisense technology can be used to control gene expression through antisense DNA or RNA or through triple-helix formation. Antisense techniques are discussed, for example, in Okano, J. *Neurochem.*, 56:560, 1991; Oligodeoxynucleotides as Antisense Inhibitors of Gene Expression, CRC Press, Boca Raton, Fla. (1988). Triple helix formation is discussed in, for instance Lee et al., *Nucleic Acids Research,* 6:3073 (1979); Cooney et al., *Science,* 241:456 (1988); and Dervan et al., *Science,* 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of TNF delta or TNF epsilon. The antisense RNA oligonucleotide hybridizes to the mRNA in vivo and blocks translation of the mRNA molecule into TNF delta or TNF epsilon polypeptide. The oligonucleotides described above can also be delivered to cells such that the antisense RNA or DNA may be expressed in vivo to inhibit production of a polypeptide of the present invention.

Antisense technology can be used to control gene expression through antisense DNA or RNA or through triple-helix formation. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the extracellular domain of the polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of TNF delta and/or TNF epsilon. The antisense RNA oligonucleotide hybridizes to the mRNA in vivo and blocks translation of the mRNA molecule into TNF delta and/or TNF epsilon polypeptide. The oligonucleotides described above can also be delivered to cells such that the antisense RNA or DNA may be expressed in vivo to inhibit production of TNF delta and/or TNF epsilon.

In one embodiment, the TNF delta and/or TNF epsilon antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TNF delta and/or TNF epsilon antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding TNF delta and/or TNF epsilon, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a TNF delta and/or TNF epsilon gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TNF delta and/or TNF epsilon antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a TNF delta and/or TNF epsilon RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of TNF delta and/or TNF epsilon could be used in an antisense approach to inhibit translation of endogenous TNF delta and/or TNF epsilon mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of TNF delta and/or TNF epsilon mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., Proc. Natl. Acad. Sci. 84:648–652 (1987); PCT Publication No. W088/09810, published December 15, 1988) or the blood-brain barrier (see, e.g., PCT Publication No. WO89/10134, published April 25, 1988), hybridization-triggered cleavage agents. (See, e.g., Krol et al., BioTechniques 6:958–976 (1988)) or intercalating agents. (See, e.g., Zon, Pharm. Res. 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al., Nucl. Acids Res. 15:6625–6641 (1987)). The oligonucleotide is a 2-0-methylribonucleotide (Inoue et al., Nucl. Acids Res. 15:6131–6148 (1987)), or a chimeric RNA-DNA analogue (Inoue et al., FEBS Lett. 215:327–330 (1997)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448–7451 (1988)), etc.

While antisense nucleotides complementary to the TNF delta and/or TNF epsilon coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy TNF delta and/or TNF epsilon mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of TNF delta and/or TNF epsilon. Preferably, the ribozyme is engineered so that the cleavage recognition site is located near the 5' end of the TNF delta and/or TNF epsilon mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express TNF delta and/or TNF epsilon in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TNF delta and/or TNF epsilon messages and inhibit translation. Since ribozymes unlike antisense molecules, are catalytic, a lower intracellular concentration is required for efficiency.

Endogenous gene expression can also be reduced by inactivating or "knocking out" the TNF delta and/or TNF epsilon gene and/or its promoter using targeted homologous recombination. (e.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

Antagonists of the present invention also include antibodies specific for TNF-family receptors or the TNF delta and/or TNF epsilon polypeptides of the invention. Antibodies according to the present invention may be prepared by any of a variety of standard methods using TNF delta and/or TNF epsilon immunogens of the present invention. As indicated, such TNF delta and/or TNF epsilon immunogens include the complete TNF delta and/or TNF epsilon polypeptides and TNF delta and/or TNF epsilon polypeptide fragments comprising, for example, the ligand binding domain, TNF-conserved domain, extracellular domain, transmembrane domain, and/or intracellular domain, or any combination thereof.

Polyclonal and monoclonal antibody agonists or antagonists according to the present invention can be raised according to the methods disclosed in Tartaglia and Goeddel, J. Biol. Chem. 267(7):4304–4307(1992)); Tartaglia et al., Cell 73:213–216 (1993)), and PCT Application WO 94/09137 and are preferably specific to (i.e., bind uniquely to polypeptides of the invention having the amino acid sequence of SEQ ID NO:2. The term "antibody" (Ab) or "monoclonal antibody" (mAb) as used herein is meant to include intact molecules as well as fragments thereof (such as, for example, Fab and F(ab') fragments) which are capable of binding an antigen. Fab, Fab' and F(ab') fragments lack the Fc fragment intact antibody, clear more rapidly from the circulation, and may have less non-specific tissue binding of an intact antibody (Wahl et al., J. Nucl. Med., 24:316–325 (1983)).

In a preferred method, antibodies according to the present invention are mAbs. Such mAbs can be prepared using hybridoma technology (Kohler and Millstein, Nature 256:495–497 (1975) and U.S. Pat. No. 4,376,110; Harlow et al., Antibodies: A Laboratory Manual, Cold Spring Harbor Laboratory Press, Cold Spring Harbor, N.Y., 1988; Monoclonal Antibodies and Hybridomas: A New Dimension in Biological Analyses, Plenum Press, New York, N.Y., 1980; Campbell, "Monoclonal Antibody Technology," In: Laboratory Techniques in Biochemistry and Molecular Biology, Volume 13 (Burdon et al., eds.), Elsevier, Amsterdam (1984)).

Proteins and other compounds which bind the TNF delta and/or TNF epsilon domains are also candidate agonists and antagonists according to the present invention. Such binding compounds can be "captured" using the yeast two-hybrid system (Fields and Song, Nature 340:245–246 (1989)). A modified version of the yeast two- hybrid system has been described by Roger Brent and his colleagues (Gyuris, Cell 75:791–803 (1993); Zervos et al., Cell 72:223–232 (1993)). Preferably, the yeast two-hybrid system is used according to the present invention to capture compounds which bind to the ligand binding domain, extracellular, intracellular, transmembrane, and death domain of the TNF delta and/or TNF epsilon. Such compounds are good candidate agonists and antagonists of the present invention.

For example, using the two-hybrid assay described above, the extracellular or intracellular domain of the TNF delta and/or TNF epsilon receptor, or a portion thereof, may be used to identify cellular proteins which interact with TNF delta and/or TNF epsilon the receptor in vivo. Such an assay may also be used to identify ligands with potential agonistic or antagonistic activity of TNF delta and/or TNF epsilon receptor function. This screening assay has previously been used to identify protein which interact with the cytoplasmic domain of the murine TNF-RII and led to the identification of two receptor associated proteins. Rothe et al., Cell 78:681 (1994). Such proteins and amino acid sequences which bind to the cytoplasmic domain of the TNF delta and/or TNF epsilon receptors are good candidate agonist and antagonist of the present invention.

Other screening techniques include the use of cells which express the polypeptide of the present invention (for example, transfected CHO cells) in a system which measures extracellular pH changes caused by receptor activation, for example, as described in *Science*, 246:181–296 (1989). In another example, potential agonists or antagonists may be contacted with a cell which expresses the polypeptide of the present invention and a second messenger response, e.g., signal transduction may be measured to determine whether the potential antagonist or agonist is effective.

Agonists according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457–1458 (1995)).

Preferred agonists are fragments of TNF delta and/or TNF epsilon polypeptides of the invention which stimulate lymphocyte (e.g., B cell) proliferation, differentiation and/or activation. Further preferred agonists include polyclonal and monoclonal antibodies raised against the TNF delta and/or TNF epsilon polypeptides of the invention, or a fragment thereof. Such agonist antibodies raised against a TNF-family receptor are disclosed in Tartaglia et al., *Proc. Natl. Acad. Sci. USA* 88:9292–9296 (1991); and Tartaglia et al., *J. Biol. Chem.* 267:4304–4307(1992). See, also, PCT Application WO 94/09137.

In an additional embodiment, immunoregulatory molecules such as, for example, IL2, IL3, IL4, IL5, IL6, IL7, IL0, IL12, IL13, IL15, anti-CD40, CD40L, IFN-gamma and TNF-alpha, may be used as agonists of TNF delta and/or TNF epsilon polypeptides of the invention which stimulate lymphocyte (e.g., B cell) proliferation, differentiation and/or activation. In a specific embodiment, IL4 and/or IL10 are used to enhance the TNF delta- and/or TNF epsilon-mediated proliferation of B cells.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

In yet another embodiment of the invention, the activity of TNF delta and/or TNF epsilon polypeptide can be reduced using a "dominant negative." To this end, constructs which encode defective TNF delta and/or TNF epsilon polypeptide, such as, for example, mutants lacking all or a portion of the TNF-conserved domain, can be used in gene therapy approaches to diminish the activity of TNF delta and/or TNF epsilon on appropriate target cells. For example, nucleotide sequences that direct host cell expression of TNF delta and/or TNF epsilon polypeptide in which all or a portion of the TNF-conserved domain is altered or missing can be introduced into monocytic cells or other cells or tissues (either by in vivo or ex vivo gene therapy methods described herein or otherwise known in the art). Alternatively, targeted homologous recombination can be utilized to introduce such deletions or mutations into the subject's endogenous TNF delta and/or TNF epsilon gene in monocytes. The engineered cells will express non-functional TNF delta and/or TNF epsilon polypeptides (i.e., a ligand (e.g., multimer) that may be capable of binding, but which is incapable of inducing signal transduction).

The antagonists may be employed in a composition with a pharmaceutically acceptable carrier, e.g., as hereinafter described.

The antagonists may be employed for instance to treat cachexia which is a lipid clearing defect resulting from a systemic deficiency of lipoprotein lipase, which is suppressed by TNF delta or TNF epsilon. The antagonists may also be employed to treat cerebral malaria in which polypeptides of the present invention appear to play a pathogenic role. The antagonists may also be employed to treat rheumatoid arthritis by inhibiting TNF delta or TNF epsilon induced production of inflammatory cytokines, such as IL1 in the synovial cells. When treating arthritis, the polypeptides of the present invention are preferably injected intra-articularly.

The antagonists may also be employed to prevent graft-host rejection by preventing the stimulation of the immune system in the presence of a graft.

The antagonists may also be employed to inhibit bone resorption and, therefore, to treat and/or prevent osteoporosis.

The antagonists may also be employed as anti-inflammatory agents, and to treat endotoxic shock. This critical condition results from an exaggerated response to bacterial and other types of infection.

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 Fg/kg body weight. In most cases they will be administered in an amount not in excess of about 8 mg/kg body weight per day. Preferably, in most cases, dose is from about 10 Fg/kg to about 1 mg/kg body weight, daily. It will be appreciated that optimum dosage will be determined by standard methods for each treatment modality and indication, taking into account the indication, its severity, route of administration, complicating conditions and the like.

Using the equivalent surface area dosage conversion factors supplied by Freireich, E. J., et al. (*Cancer Chemotherapy Reports* 50(4):219–44 (1966)), one of ordinary skill in the art is able to conveniently convert data obtained from the use of TNF-delta and/or TNF-epsilon in a given experimental system into an accurate estimation of a pharmaceutically effective amount of TNF-delta and/or TNF-epsilon polypeptide to be administered per dose in another experimental system. Experimental data obtained through the administration of TNF-delta and/or TNF-epsilon in mice may be converted through the conversion factors supplied by Freireich, et al., to accurate estimates of pharmaceutically effective doses of TNF-delta and/or TNF-epsilon in rat, monkey, dog, and human. The following conversion table (Table IV) is a summary of the data provided by Freireich, et al. Table IV gives approximate factors for converting doses expressed in terms of mg/kg from one species to an equivalent surface area dose expressed as mg/kg in another species tabulated.

TABLE IV

Equivalent Surface Area Dosage Conversion Factors.

| | TO | | | | |
|---|---|---|---|---|---|
| FROM | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅔ | 1 | ½ |
| Human | 12 | 7 | 3 | 2 | 1 |

Thus, for example, using the conversion factors provided in Table IV, a dose of 50 mg/kg in the mouse converts to an appropriate dose of 12.5 mg/kg in the monkey because (50 mg/kg)×(¼)=12.5 mg/kg. As an additional example, doses of 0.02, 0.08, 0.8, 2, and 8 mg/kg in the mouse equate to effect doses of 1.667 micrograms/kg, 6.67 micrograms/kg, 66.7 micrograms/kg, 166.7 micrograms/kg, and 0.667 mg/kg, respectively, in the human.

The polynucleotides, polypeptides, agonists and antagonists that are polypeptides of this invention may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., *Biotechniques,* 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the 13-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-1 9-17-H2, YCRE, YCRIP, GP+E-86, GP+envAm12, and DAN cell lines as described in Miller, A., *Human Gene Therapy,* 1: 5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., Molecular Cloning: A Laboratory Manual, 2nd Ed.; Cold Spring Harbor Laboratory Press, Cold Spring Harbor, N.Y. (1989), herein referred to as "Sambrook."

All parts or amounts set out in the following examples are by weight, unless otherwise specified. Unless otherwise stated size separation of fragments in the examples below was carried out using standard techniques of agarose and polyacrylamide gel electrophoresis ("PAGE") in Sambrook and numerous other references such as, for instance, by Goeddel et al., *Nucleic Acids Res.,* 8: 4057 (1980). Unless described otherwise, ligations were accomplished using standard buffers, incubation temperatures and times, approximately equimolar amounts of the DNA fragments to be ligated and approximately 10 units of T4 DNA ligase ("ligase") per 0.5 Fg of DNA.

EXAMPLE 1

Expression and Purification of Soluble Form of Human TNF Delta and TNF Epsilon Using Bacteria The DNA sequence encoding human TNF delta or TNF epsilon in the deposited polynucleotide was amplified using PCR oligonucleotide primers specific to the amino acid carboxyl terminal sequence of the human TNF delta or TNF epsilon protein and to vector sequences 3' to the gene. Additional nucleotides containing restriction sites to facilitate cloning were added to the 5' and 3' sequences respectively.

The 5' oligonucleotide primer had the sequence 5' GCG GGA TCC CAG AGC CTC ACC ACA G 3' (SEQ ID NO:7) containing the underlined restriction site, followed by 16 nucleotides of coding sequence set out in the Figures beginning with the 115th base of the ATG codon.

The 3' primer has the sequence 5' CGC AAG CTT ACA ATC ACA GTT TCA CAA AC 3' (SEQ ID NO:8) contains the underlined HindIII restriction site followed by 20 nucleotides complementary to the last 13 nucleotides of the coding sequence set out in FIGS. 1A and 1B and 2A and 2B, including the stop codon.

The restrictions sites were convenient to restriction enzyme sites in the bacterial expression vectors pQE-9, which were used for bacterial expression in these examples. (Qiagen, Inc. Chatsworth, Calif.). pQE-9 encodes ampicillin antibiotic resistance ("Amp$^r$") and contains a bacterial origin of replication ("ori"), an IPTG inducible promoter, a ribosome binding site ("RBS"), a 6-His tag and restriction enzyme sites.

The amplified human TNF delta DNA and the vector pQE-9 both were digested with BamHI and HindIII and the digested DNAs then were ligated together. Insertion of the TNF delta DNA into the pQE-9 restricted vector placed the TNF delta coding region downstream of and operably linked to the vector's IPTG-inducible promoter and in-frame with an initiating AUG appropriately positioned for translation of TNF delta.

The ligation mixture was transformed into competent *E. coli* cells using standard procedures. Such procedures are described in Sambrook et al., Molecular Cloning: A Laboratory Manual, 2nd Ed.; Cold Spring Harbor Laboratory Press, Cold Spring Harbor, N.Y. (1989). *E. coli* strain M1 5/rep4, containing multiple copies of the plasmid pREP4, which expresses lac repressor and confers kanamycin resistance ("Kan$^r$"), was used in carrying out the illustrative example described here. This strain, which is only one of many that are suitable for expressing TNF delta, is available commercially from Qiagen. Transformants were identified by their ability to grow on LB plates in the presence of ampicillin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 micrograms per milliliter) and kanamycin (25 micrograms per milliliter). The O/N culture was used to inoculate a large culture, at a dilution of approximately 1:100 to 1:250. The cells were grown to an optical density at 600 nm ("OD$_{600}$") of between 0.4 and 0.6. Isopropyl-B-D-thiogalactopyranoside ("IPTG") was then added to a final concentration of 1 mM to induce transcription from lac repressor sensitive promoters, by inactivating the lacI repressor. Cells subsequently were incubated further for 3 to 4 hours. Cells then were harvested by centrifugation and disrupted, by standard methods. Inclusion bodies were purified from the disrupted cells using routine collection techniques, and protein was solubilized from the inclusion bodies into 8M urea. The 8M urea solution containing the solubilized protein was passed over a PD-10 column in 2× phosphate buffered saline ("PBS"), thereby removing the urea, exchanging the buffer and refolding the protein. The protein was purified by a further step of chromatography to remove endotoxin. Then, it was sterile filtered. The sterile filtered protein preparation was stored in 2X PBS at a concentration of 95 micrograms per mL.

Analysis of the preparation of TNF delta by standard methods of polyacrylamide gel electrophoresis revealed that the preparation contained about 80% monomer having the expected molecular weight of, approximately, 20.8 kDa.

The protein is purified by chromatography on a nickel-chelate column under conditions that allow for type-binding by proteins containing the 6-HIS tag. The protein is eluted from the column in 6-molar guanidine HCl pH 5.0 and renatured.

EXAMPLE 2

Cloning and Expression of Soluble Human TNF Delta and TNF Epsilon in a Baculovirus Expression System The cDNA sequence encoding the full length human TNF delta or TNF epsilon protein, in the deposited clone is amplified using PCR oligonucleotide primers corresponding to the 5' and 3' sequences of the gene:

The 5' primer has the sequence 5' GCG <u>GGA TCC</u> CCA GAG CCT CAC CAC AG 3' (SEQ ID NO:9) containing the underlined BamHI restriction enzyme site followed by 16 bases of the sequence of TNF delta or TNF epsilon of FIGS. 1A and 1B and 2A and 2B. Inserted into an expression vector, as described below, the 5' end of the amplified fragment encoding human TNF delta or TNF epsilon provides an efficient signal peptide. An efficient signal for initiation of translation in eukaryotic cells, as described by Kozak, M., J. Mol. Biol. 196: 947–950 (1987) is appropriately located in the vector portion of the construct.

The 3' primer has the sequence 5' CGC <u>TCT AGA</u> ACA ATC ACA GTT TCA CAA AC 3' (SEQ ID NO:10) containing the underlined XbaI restriction site followed by nucleotides complementary to the last 13 nucleotides of the TNF delta or TNF epsilon coding sequence set out in FIGS. 1A and 1B and 2A and 2B, including the stop codon.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein F2.

The vector pA2GP is used to express the TNF delta or TNF epsilon protein in the baculovirus expression system, using standard methods, such as those described in Summers et al, A Manual of Methods for Baculovirus Vectors and Insect Cell Culture Procedures, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology,* 170:31–39, among others.

The plasmid is digested with the restriction enzymes BamHI and XbaI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB 101 cells are transformed with ligation mix and spread on culture plates. Bacteria are identified that contain the plasmid with the human TNF delta or TNF epsilon gene by digesting DNA from individual colonies using BamHI and XbaI and then analyzing the digestion product by gel electrophoresis. The sequence of the cloned fragment is confirmed by DNA sequencing. This plasmid is designated herein pBacTNF delta.

Five micrograms of the plasmid pBacTNF delta is co-transfected with 1.0 microgram of a commercially available linearized baculovirus DNA ("BaculoGold™ baculovirus DNA", Pharmingen, San Diego, Calif.), using the lipofection method described by Felgner et al., *Proc. Natl. Acad. Sci. USA,* 84:7413–7417 (1987). 1 microgram of BaculoGold™ virus DNA and 5 micrograms of the plasmid pBacTNF delta are mixed in a sterile well of a microtiter plate containing 50 microliters of serum free Grace's medium (Life Technologies Inc., Gaithersburg, Md.). Afterwards 10 microliters Lipofectin plus 90 microliters Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 microliters of Grace's medium. The agar is removed by a brief centrifugation and the supernatant containing the recombinant baculovirus is used to infect Sf9 cells seeded in 35 mm dishes. Four days later, the supernatants of these culture dishes are harvested and then they are stored at 4° C. A clone containing properly inserted TNF delta or TNF epsilon is identified by DNA or TNF epsilon analysis including restriction mapping and sequencing. This is designated herein as V-TNF delta.

Sf9 cells are grown in Grace's medium supplemented with 10% heat-inactivated FBS. The cells are infected with the recombinant baculovirus V-TNF delta at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 FCi of 35S-methionine and 5 FCi 35S cysteine (available from Amersham) are added. The cells are further incubated for 16 hours and then they are harvested by centrifugation, lysed and the labeled proteins are visualized by SDS-PAGE and autoradiography.

EXAMPLE 3

Tissue Distribution of TNF Delta Expression

Northern blot analysis was carried out to examine the levels of expression of TNF delta in human tissues, using methods described by, among others, Sambrook et al., cited above. Total cellular RNA samples are isolated with RNAzol™ B system (Biotecx Laboratories, Inc. 6023 South Loop East, Houston, Tex. 77033).

About 10 micrograms of Total RNA was isolated from tissue samples. The RNA was size resolved by electrophoresis through a 1% agarose gel under strongly denaturing conditions. RNA was blotted from the gel onto a nylon filter, and the filter then is prepared for hybridization to a detectably labeled polynucleotide probe.

As a probe to detect mRNA that encodes TNF delta, the antisense strand of the coding region of the cDNA insert in the deposited clone was labeled to a high specific activity. The cDNA was labeled by primer extension, using the Prime-It kit, available from Stratagene. The reaction was carried out using 50 nanograms of the cDNA, following the standard reaction protocol as recommended by the supplier. The labeled polynucleotide was purified away from other labeled reaction components by column chromatography using a Select-G-50 column, obtained from 5-Prime - 3-Prime, Inc. of 5603 Arapahoe Road, Boulder, Colo. 80303.

The labeled probe was hybridized to the filter, at a concentration of 1,000,000 cpm/ml, in a small volume of 7% SDS, 0.5 M NaPO$_4$, pH 7.4 at 65° C, overnight.

Thereafter the probe solution was drained and the filter is washed twice at room temperature and twice at 60° C. with 0.5×SSC, 0.1% SDS. The filter then is dried and exposed to film at −70° C. overnight with an intensifying screen.

Autoradiography shows that mRNA for TNF delta was detected in all 16 tissues with highest expression in heart followed by placenta and kidney.

EXAMPLE 4

Gene Therapeutic Expression of Human TNF Delta or TNF Epsilon

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

cDNA capable of expressing active TNF delta or TNF epsilon, is isolated. The ends of the fragment are modified, if necessary, for cloning into the vector. For instance, 5" overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the TNF delta or TNF epsilon fragment are mixed together and joined using T4 DNA ligase. The ligation mixture is used to transform *E. Coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagle's Medium (DMEM) with 10% calf serum (CS), penicillin and streptomycin. The vector containing the TNF delta or TNF epsilon gene is introduced into the packaging cells by standard techniques. Infectious viral particles containing the TNF delta or TNF epsilon gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce TNF delta or TNF epsilon product, and the biological actions of the protein are conveyed to the host.

EXAMPLE 5

Gene Therapy Using Endogenous Human TNF Delta or TNF Epsilon Gene

Another method of gene therapy according to the present invention involves operably associating the endogenous TNF Delta and/or TNF Epsilon sequences with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TNF Delta and/or TNF Epsilon, flanking the promoter. The targeting sequence will be sufficiently near the 5' end of TNF Delta and/or TNF Epsilon so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TNF Delta and/or TNF Epsilon sequence. This results in the expression of TNF Delta and/or TNF Epsilon in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately 3×106 cells/ml. Electroporation should be performed immediately following resuspension.

Plasmid DNA is prepared according to standard techniques. For example, to construct a plasmid for targeting to the TNF Delta and/or TNF Epsilon locus, plasmid pUC18 (MBI Fermentas, Amherst, N.Y.) is digested with Hin dIII.

The CMV promoter is amplified by PCR with an Xba I site on the 5' end and a Bam HI site on the 3'end. Two TNF Delta and/or TNF Epsilon non-coding sequences are amplified via PCR: one TNF Delta and/or TNF Epsilon non-coding sequence (TNF Delta and/or TNF Epsilon fragment 1) is amplified with a Hin dIII site at the 5' end and an Xba site at the 3'end; the other TNF Delta and/or TNF Epsilon non-coding sequence (TNF Delta and/or TNF Epsilon fragment 2) is amplified with a Bam HI site at the 5'end and a Hin dIII site at the 3'end. The CMV promoter and TNF Delta and/or TNF Epsilon fragments are digested with the appropriate enzymes (CMV promoter—Xb aI and BamHI; TNF Delta and/or TNF Epsilon fragment 1—XbaI; TNF Delta and/or TNF Epsilon fragment 2—Bam HI) and ligated together. The resulting ligation product is digested with Hin dIII, and ligated with the Hin dIII-digested pUC18 plasmid.

Plasmid DNA is added to a sterile cuvette with a 0.4 cm electrode gap (Bio-Rad). The final DNA concentration is generally at least 120 microgram/milliliter. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 microF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

EXAMPLE 6

Assays to Detect Stimulation or Inhibition of B Cell Proliferation and Differentiation Background:

Generation of functional humoral immune responses requires both soluble and cognate signaling between B-lineage cells and their microenviromnent. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL-10, IL-13, IL-14 and IL-15. Interestingly, these signals are by themselves weak effectors but can, in combination with various co-stimulatory proteins, induce activation, proliferation, differentiation, homing, tolerance and death among B cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

Experimental Procedures:

In Vitro assay: Purified TNF Delta and/or TNF Epsilon protein, or truncated forms thereof, is assessed for its ability to induce activation, proliferation, differentiation or inhibition and/or death in B-cell populations and their precursors. The activity of TNF Delta and/or TNF Epsilon protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and L-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220). Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with $^3$H-thymidine (6.7 Ci/mM) beginning 72 h post factor addition. The positive and negative controls are IL2 and medium respectively.

In Vivo assay: BALB/c mice are injected (i.p.) twice per day with buffer only, or 2 mg/Kg of TNF Delta and/or TNF Epsilon protein, or truncated forms thereof. Mice receive this treatment for 4 consecutive days, at which time they are sacrificed and various tissues and serum collected for analyses. Comparison of H&E sections from normal and TNF Delta and/or TNF Epsilon protein-treated spleens identify the results of the activity of TNF Delta and/or TNF Epsilon protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from TNF Delta and/or TNF Epsilon protein-treated mice is used to indicate whether TNF Delta and/or TNF Epsilon protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and TNF Delta and/or TNF Epsilon protein-treated mice.

EXAMPLE 7

Protein Fusions of TNF Delta and/or TNF Epsilon

TNF Delta and/or TNF Epsilon polypeptides of the invention are optionally fused to other proteins. These fusion proteins can be used for a variety of applications. For example, fusion of TNF Delta and/or TNF Epsilon polypeptides to His-tag, HA-tag, protein A, IgG domains, and maltose binding protein facilitates purification. (See EP A 394,827; Traunecker, et al., Nature 331:84–86 (1988).) Similarly, fusion to IgG-1, IgG-3, and albumin increases the halflife time in vivo. Nuclear localization signals fused to TNF Delta and/or TNF Epsilon polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule

```
GGGATCCGGAGCCCAAATCTTCTGACAAAACTCACACATGCCCACCGTGCCCAGCACCTGAATTCGAGGGTGCACCGTCAGT  (SEQ ID NO:14)

CTTCCTCTTCCCCCCAAAACCCAAGGACACCCTCATGATCTCCCGGACTCCTGAGGTCACATGCGTGGTGGTGGACGTAAGC

CACGAAGACCCTGAGGTCAAGTTCAACTGGTACGTGGACGGCGTGGAGGTGCATAATGCCAAGACAAAGCCGCGGGAGGAGC

AGTACAACAGCACGTACCGTGTGGTCAGCGTCCTCACCGTCCTGCACCAGGACTGGCTGAATGGCAAGGAGTACAAGTGCAA

GGTCTCCAACAAAGCCCTCCCAACCCCCATCGAGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGACCTGCCTGGTCAAAGGCTTCTATCCAAGCGACA

TCGCCGTGGAGTGGGAGAGCAATGGGCAGCCGGAGAACAACTACAAGACCACGCCTCCCGTGCTGGACTCCGACGGCTCCTT

CTTCCTCTACAGCAAGCTCACCGTGGACAAGAGCAGGTGGCAGCAGGGGAACGTCTTCTCATGCTCCGTGATGCATGAGGCT

CTGCACAACCACTACACGCAGAAGAGCCTCTCCCTGTCTCCGGGTAAATGAGTGCGACGGCCGCGACTCTAGAGGAT.
```

Briefly, the human Fc portion of the IgG molecule can be PCR amplified, using primers that span the 5' and 3' ends of the sequence described below. These primers also preferably contain convenient restriction enzyme sites that will facilitate cloning into an expression vector, preferably a mammalian expression vector.

For example, if the pC4 (ATCC Accession No. 209646) expression vector is used, the human Fc portion can be ligated into the Bam HI cloning site. Note that the 3' Bam HI site should be destroyed. Next, the vector containing the human Fc portion is re-restricted with Bam HI, linearizing the vector, and TNF Delta and/or TNF Epsilon polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

EXAMPLE 8

Isolation of Antibody Fragments Directed Against TNF Delta and/or TNF Epsilon Polypeptides from a Library of scFvs Naturally occuring V-genes isolated from human PBLs are constructed into a large library of antibody fragments which contain reactivities against polypeptides of the present invention to which the donor may or may not have been exposed (see e.g., U.S. Pat. No. 5,885,793 incorporated herein in its entirety by reference).

Rescue of the library

A library of scFvs is constructed from the RNA of human PBLs as described in WO92/01047. To rescue phage displaying antibody fragments, approximately $10^9$ E. coli harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, $2×10^8$ TU of Delta gene 3 helper phage (M13 Delta gene III, see WO92/01047) are added and the culture incubated at 37 C for 45 minutes without shaking and then at 37 C for 45 minutes with shaking. The culture is centrifuged at 4000 r.p.m. for 10 minutes and the pellet resuspended in 2 liters of 2×TY containing 100 ug/ml ampicillin and 50 ug/ml kanamycin and grown overnight. Phage are prepared as described in WO92/01047.

M13 Delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37 C without shaking and then for a further hour at 37 C with shaking. Cells are pelleted (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37 C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37 C and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylarnine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37 C. The E. coli are then plated on TYE plates containing 1% glucose and 100 ug/ml ampicillin. The resulting bacterial library is then rescued with delta gene III helper phage as described above to prepare phage for a subsequent round of selection. This process is then repeated for a total of 4 rounds of affinity purification with tube-washing increased to 20 times with PBS, 0. 1% Tween-20 and 20 times with PBS for rounds 3 and 4.

Characterization of binders

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

EXAMPLE 9

Method of Determining Alterations in the TNF Delta and/or TNF Epsilon Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO: 1. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of TNF Delta and/or TNF Epsilon are also determined and genomic PCR products analyzed to confirm the results. PCR products harboring suspected mutations in TNF Delta and/or TNF Epsilon is then cloned and sequenced to validate the results of the direct sequencing.

PCR products of TNF Delta and/or TNF Epsilon are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in TNF Delta and/or TNF Epsilon not present in unaffected individuals.

Genomic rearrangements are also observed as a method of determining alterations in the TNF Delta and/or TNF Epsilon gene. Genomic clones isolated using techniques known in the art are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-I DNA for specific hybridization to the TNF Delta and/or TNF Epsilon genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of TNF Delta and/or TNF Epsilon (hybridized by the probe) are identified as insertions, deletions, and translocations. These TNF Delta and/or TNF Epsilon alterations are used as a diagnostic marker for an associated disease.

EXAMPLE 10

Method of Detecting Abnormal Levels of TNF Delta and/or TNF Epsilon in a Biological Sample TNF Delta and/or TNF Epsilon polypeptides can be detected in a biological sample, and if an increased or decreased level of TNF Delta and/or TNF Epsilon is detected, this polypeptide is a marker for a particular phenotype. Methods of detection are numerous, and thus, it is understood that one skilled in the art can modify the following assay to fit their particular needs.

For example, antibody-sandwich ELISAs are used to detect TNF Delta and/or TNF Epsilon in a sample, preferably a biological sample. Wells of a microtiter plate are coated with specific antibodies to TNF Delta and/or TNF Epsilon, at a final concentration of 0.2 to 10 ug/ml. The antibodies are either monoclonal or polyclonal and are produced using technique known in the art. The wells are blocked so that non-specific binding of TNF Delta and/or TNF Epsilon to the well is reduced.

The coated wells are then incubated for >2 hours at RT with a sample containing TNF Delta and/or TNF Epsilon. Preferably, serial dilutions of the sample should be used to validate results. The plates are then washed three times with deionized or distilled water to remove unbounded TNF Delta and/or TNF Epsilon.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

75 ul of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is prepared using the experimental results from serial dilutions of a control sample with the sample concentration plotted on the X-axis (log scale) and fluorescence or absorbance on the Y-axis (linear scale). The TNF Delta and/or TNF Epsilon polypeptide concentration in a sample is then interpolated using the standard curve based on the measured flourescence of that sample.

EXAMPLE 11

Method of Treating Decreased Levels of TNF Delta and/or TNF Epsilon

The present invention relates to a method for treating an individual in need of a decreased level of TNF Delta and/or TNF Epsilon biological activity in the body comprising, administering to such an individual a composition comprising a therapeutically effective amount of TNF Delta and/or TNF Epsilon antagonist. Preferred antagonists for use in the present invention are TNF Delta- and/or TNF Epsilon-specific antibodies.

Moreover, it will be appreciated that conditions caused by a decrease in the standard or normal expression level of TNF Delta and/or TNF Epsilon in an individual can be treated by administering TNF Delta and/or TNF Epsilon, preferably in a soluble and/or secreted form. Thus, the invention also provides a method of treatment of an individual in need of an increased level of TNF Delta and/or TNF Epsilon polypeptide comprising administering to such an individual a pharmaceutical composition comprising an amount of TNF Delta and/or TNF Epsilon to increase the biological activity level of TNF Delta and/or TNF Epsilon in such an individual.

For example, a patient with decreased levels of TNF Delta and/or TNF Epsilon polypeptide receives a daily dose 0.1–100 ug/kg of the polypeptide for six consecutive days. Preferably, the polypeptide is in a soluble and/or secreted form.

EXAMPLE 12

Method of Treating Increased Levels of TNF Delta and/or TNF Epsilon

The present invention also relates to a method for treating an individual in need of an increased level of TNF Delta and/or TNF Epsilon biological activity in the body comprising administering to such an individual a composition comprising a therapeutically effective amount of TNF Delta and/or TNF Epsilon or an agonist thereof.

Antisense technology is used to inhibit production of TNF Delta and/or TNF Epsilon. This technology is one example of a method of decreasing levels of TNF Delta and/or TNF Epsilon polypeptide, preferably a soluble and/or secreted form, due to a variety of etiologies, such as cancer.

For example, a patient diagnosed with abnormally increased levels of TNF Delta and/or TNF Epsilon is administered intravenously antisense polynucleotides at 0.5, 1.0, 1.5, 2.0 and 3.0 mg/kg day for 21 days. This treatment is repeated after a 7-day rest period if the is determined to be well tolerated.

EXAMPLE 13

Method of Treatment Using Gene Therapy—Ex Vivo

One method of gene therapy transplants fibroblasts, which are capable of expressing soluble and/or mature TNF Delta and/or TNF Epsilon polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 C for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding TNF Delta and/or TNF Epsilon can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform E. coli HB101, which are then plated onto agar containing kanamycin for the purpose of confirming that the vector contains properly inserted TNF Delta and/or TNF Epsilon.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TNF Delta and/or TNF Epsilon gene is then added to the media and the packaging cells transduced with the vector. The packaging cells now produce infectious viral particles containing the TNF Delta and/or TNF Epsilon gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TNF Delta and/or TNF Epsilon protein is produced. The engineered fibroblasts are then transplanted onto the host, either alone or after having been grown to confluence on cytodex 3 microcarrier beads.

EXAMPLE 14

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) TNF Delta and/or TNF Epsilon sequences into an animal to increase or decrease the expression of the TNF Delta and/or TNF Epsilon polypeptide. The TNF Delta and/or TNF Epsilon polynucleotide may be operatively linked to a promoter or any other genetic elements necessary for the expression of the TNF Delta and/or TNF Epsilon polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al., Cardiovasc. Res. 35:470–479 (1997); Chao J. et al., Pharmacol. Res. 35:517–522 (1997); Wolff J. A. Neuromuscul. Disord. 7:314–318 (1997); Schwartz B. et al., Gene Ther. 3:405–411 (1996); Tsurumi Y. et al., Circulation 94:3281–3290 (1996) (incorporated herein by reference).

The TNF Delta and/or TNF Epsilon polynucleotide constructs may be delivered by any method that delivers injectable materials to the cells of an animal, such as, injection into the interstitial space of tissues (heart, muscle, skin, lung, liver, intestine and the like). The TNF Delta and/or TNF Epsilon polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TNF Delta and/or TNF Epsilon polynucleotides may also be delivered in liposome formulations (such as those taught in Felgner P. L., et al. Ann. NY Acad. Sci. 772:126–139 (1995), and Abdallah B., et al. Biol. Cell 85(1):1–7 (1995)) which can be prepared by methods well known to those skilled in the art.

The TNF Delta and/or TNF Epsilon polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The TNF Delta and/or TNF Epsilon polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TNF Delta and/or TNF Epsilon polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TNF Delta and/or TNF Epsilon polynucleotide constructs can be delivered to arteries during angioplasty by the catheter used in the procedure.

The dose response effects of injected TNF Delta and/or TNF Epsilon polynucleotide in muscle in vivo is determined as follows. Suitable TNF Delta and/or TNF Epsilon template DNA for production of mRNA coding for TNF Delta and/or TNF Epsilon polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for TNF Delta and/or TNF Epsilon protein expression. A time course for TNF Delta and/or TNF Epsilon protein expression may be done in a similar fashion except that quadriceps from different mice are harvested at different times. Persistence of TNF Delta and/or TNF Epsilon DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using TNF Delta and/or TNF Epsilon naked DNA.

EXAMPLE 15

T Cell Proliferation, Costimulation, and Prestimulation Proliferation Assays

Proliferation assay for Resting PBLs.

A CD3-induced proliferation assay is performed on PBMCs and is measured by the uptake of $^3$H-thymidine. The assay is performed as follows. Ninety-six well plates are coated with 100 microliters per well of mAb to CD3 (HIT3a, Pharmingen) or isotype-matched control mAb (B33.1) overnight at 4 C (1 microgram/ml in 0.05M bicarbonate buffer, pH 9.5), then washed three times with PBS. PBMC are isolated by F/H gradient centrifugation from human peripheral blood and added to quadruplicate wells ($5 \times 10^4$/well) of mAb coated plates in RPMI containing 10% FCS and P/S in the presence of varying concentrations of TNF Delta and/or TNF Epsilon protein (total volume 200 microliters). Relevant protein buffer and medium alone are controls. After 48 hr. culture at 37 C, plates are spun for 2 min. at 1000 rpm and 100 microliters of supernatant is removed and stored −20 C for measurement of IL-2 (or other cytokines) if effect on proliferation is observed. Wells are supplemented with 100 microliters of medium containing 0.5 microcuries of $^3$H-thymidine and cultured at 37 C for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of TNF Delta and/or TNF Epsilon proteins.

Alternatively, a proliferation assay on resting PBL (peripheral blood lymphocytes) is measured by the up-take of $^3$H-thymidine. The assay is performed as follows. PBMC are isolated by F/H gradient centrifugation from human peripheral blood, and are cultured overnight in 10% FCS/RPMI. This overnight incubation period allows the adherent cells to attach to the plastic, which results in a lower background in the assay as there are fewer cells that can act as antigen presenting cells or that might be producing growth factors. The following day the non-adherent cells are collected, washed and used in the proliferation assay. The assay is performed in a 96 well plate using 2 x104 cells/well in a final volume of 200 microliters. A supernatant expressing TNF-delta and/or TNF-epsilon is tested at a 30% final dilution, therefore 60 microliters are added to 140 microliters of medium containing the cells. Control supernatants are used at the same final dilution and express the following proteins: vector only (negative control), IL-2, IFNgamma, TNF-alpha, IL-10 and TR2. In addition to the control supernatants recombinant human IL-2 at a final concentration of 100 ng/ml is also used. After 24 hours of culture, each well is pulsed with 1 microcurie of $^3$H-thymidine. Cells are then harvested 20 hours following pulsing and incorporation of $^3$H-thymidine is used as a measure of proliferation. Results are expressed as an average of triplicate samples plus or minus standard error.

Costimulation assay.

A costimulation assay on resting PBL (peripheral blood lymphocytes) is performed in the presence of immobilized antibodies to CD3 and CD28. The use of antibodies specific for the invariant regions of CD3 mimic the induction of T cell activation that would occur through stimulation of the T cell receptor by an antigen. Cross-linking of the TCR (first signal) in the absence of a costimulatory signal (second signal) causes very low induction of proliferation and will eventually result in a state of "anergy", which is characterized by the absence of growth and inability to produce cytokines. The addition of a costimulatory signal such as an antibody to CD28, which mimics the action of the costimulatory molecule B7–1 expressed on activated APCs, results in enhancement of T cell responses including cell survival and production of IL-2. Therefore this type of assay allows to detect both positive and negative effects caused by addition of supernatants expressing the proteins of interest on T cell proliferation.

The assay is performed as follows. Ninety-six well plates are coated with 100 ng/ml anti-CD3 and 5 micrograms per milliliter anti-CD28 in a final volume of 100 microliters and incubated overnight at 4 C. Plates are washed twice with PBS before use. PBMC are isolated by F/H gradient centrifugation from human peripheral blood, and are cultured overnight in 10% FCS/RPMI. This overnight incubation period allows the adherent cells to attach to the plastic, which results in a lower background in the assay as there are fewer cells that can act as antigen presenting cells or that might be producing growth factors. The following day the non-adherent cells are collected, washed and used in the proliferation assay. The assay is performed in a 96 well plate using 2 x104 cells/well in a final volume of 200 microliters.

A supernatant expressing TNF-delta and/or TNF-epsilon is tested at a 30% final dilution, therefore 60 microliters are added to 140 microliters of medium containing the cells. Control supernatants are used at the same final dilution and express the following proteins: vector only (negative control), IL-2, IFN-gamma, TNF-alpha, IL-10 and TR2. In addition to the control supernatants recombinant human IL-2 at a final concentration of 10 ng/ml is also used. After 24 hours of culture, each well is pulsed with 1 microcurie of $^3$H-thymidine. Cells are then harvested 20 hours following pulsing and incorporation of $^3$H-thymidine is used as a measure of proliferation. Results are expressed as an average of triplicate samples plus or minus standard error.

Proliferation assay for preactivated-resting T cells.

A proliferation assay on preactivated-resting T cells is performed on cells that are previously activated with the lectin phytohemagglutinin (PHA). Lectins are polymeric plant proteins that can bind to residues on T cell surface glycoproteins including the TCR and act as polyclonal activators. PBLs treated with PHA and then cultured in the presence of low doses of IL-2 resemble effector T cells. These cells are generally more sensitive to further activation induced by growth factors such as IL-2. This is due to the expression of high affinity IL-2 receptors that allows this population to respond to amounts of IL-2 that are 100 fold lower than what would have an effect on a naive T cell. Therefore the use of this type of cells might enable to detect the effect of very low doses of an unknown growth factor, that would not be sufficient to induce proliferation on resting (naive) T cells.

The assay is performed as follows. PBMC are isolated by F/H gradient centrifugation from human peripheral blood, and are cultured in the presence of 2 micrograms per milliliter PHA for three days. The cells are then washed and cultured in the presence of 5 ng/ml of human recombinant IL-2 for 3 days. The cells are washed and rested in starvation medium (1% FCS/RPMI) for 16 hours prior to the beginning of the proliferation assay. An aliquot of the cells is analyzed by FACS to determine the percentage of T cells (CD3 positive cells), usually it ranges between 93–97% depending on the donor. The assay is performed in a 96 well plate using $2\times10^4$ cells/well in a final volume of 200 microliters. A supernatant expressing TNF-delta and/or TNF-epsilon is tested at a 30% final dilution, therefore 60 microliters are added to 140 microliters of medium containing the cells. Control supernatants are used at the same final dilution and express the following proteins: vector only (negative control), IL-2, IFN-gamma, TNF-alpha, IL-10 and TR2. In addition to the control supernatants recombinant human IL-2 at a final concentration of 10 ng/ml is also used. After 24 hours of culture, each well is pulsed with 1 microcurie of $^3$H-thymidine. Cells are then harvested 20 hours following pulsing and incorporation of $^3$H-thymidine is used as a measure of proliferation. Results are expressed as an average of triplicate samples plus or minus standard error.

Although the studies described in this example test the activity in TNF Delta and/or TNF Epsilon protein, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 16

The Effect of TNF Delta and/or TNF Epsilon on the Growth of Vascular Endothelial Cells On day 1, human umbilical vein endothelial cells (HUVEC) are seeded at $2-5\times10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. TNF Delta and/or TNF Epsilon protein, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that TNF Delta and/or TNF Epsilon may proliferate vascular endothelial cells.

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 17

Stimulatory Effect of TNF Delta and/or TNF Epsilon on the Proliferation of Vascular Endothelial Cells For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 ml serum-supplemented medium and are allowed to attach overnight. After serum-starvation for 12 hours in 0.5% FBS, conditions (bFGF, $VEGF_{165}$ or TNF Delta and/or TNF Epsilon in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. In Vitro Cell. Dev. Biol. 30A:512–518 (1994).

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 18

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2–3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4 ° C. for 2 h after exposing to denaturing solution and then with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6;271(36):21985–21992 (1996).

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 19

Stimulation of Endothelial Migration

This example will be used to explore the possibility that TNF Delta and/or TNF Epsilon may stimulate lymphatic endothelial cell migration. Endothelial cell migration assays are performed using a 48 well microchemotaxis chamber (Neuroprobe Inc., Cabin John, Md.; Falk, W., Goodwin, R. H. J., and Leonard, E. J. "A 48 well micro chemotaxis assembly for rapid and accurate measurement of leukocyte migration." J. Immunological Methods 1980;33 :239–247). Polyvinylpyrrolidone-free polycarbonate filters with a pore size of 8 um (Nucleopore Corp. Cambridge, Mass.) are coated with 0. 1% gelatin for at least 6 hours at room temperature and dried under sterile air. Test substances are diluted to appropriate concentrations in Ml99 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5 \times 10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 20

Stimulation of Nitric Oxide Production by Endothelial Cells

Nitric oxide released by the vascular endothelium is believed to be a mediator of vascular endothelium relaxation. Thus, TNF Delta and/or TNF Epsilon activity can be assayed by determining nitric oxide production by endothelial cells in response to TNF Delta and/or TNF Epsilon.

Nitric oxide is measured in 96-well plates of confluent microvascular endothelial cells after 24 hours starvation and a subsequent 4 hr exposure to various levels of a positive control (such as VEGF-1) and TNF Delta and/or TNF Epsilon. Nitric oxide in the medium is determined by use of the Griess reagent to measure total nitrite after reduction of nitric oxide-derived nitrate by nitrate reductase. The effect of TNF Delta and/or TNF Epsilon on nitric oxide release is examined on HUVEC.

Briefly, NO release from cultured HUVEC monolayer is measured with a NO-specific polarographic electrode connected to a NO meter (Iso-NO, World Precision Instruments Inc.). Calibration of the NO element is performed according to the following equation:

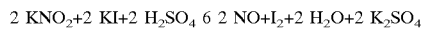

$$2\ KNO_2 + 2\ KI + 2\ H_2SO_4 \rightarrow 2\ NO + I_2 + 2\ H_2O + 2\ K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas. The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) to maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1 \times 10^6$ endothelial cells. All values reported are means of four to six measurements in each group (number of cell culture wells). See, Leak et al. Biochem. and Biophys. Res. Comm. 217:96–105 (1995).

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 21

Effect of TNF Delta and/or TNF Epsilon on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 microliter/well) for 30 min. at 37° C. CADMEC are seeded onto the coated wells at 7,500 cells/well and cultured overnight in Growth Medium. The Growth Medium is then replaced with 300 micrograms Cell Applications° Chord Formation Medium containing control buffer or TNF Delta and/or TNF Epsilon (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. beta-esteradiol (1 ng/ml) is used as a negative control. The appropriate buffer (without protein) is also utilized as a control.

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 22

Angiogenic Effect on Chick Chorioallantoic Membrane

Chick chorioallantoic membrane (CAM) is a well-established system to examine angiogenesis. Blood vessel formation on CAM is easily visible and quantifiable. The ability of TNF Delta and/or TNF Epsilon to stimulate angiogenesis in CAM can be examined.

Fertilized eggs of the White Leghorn chick (Gallus gallus) and the Japanese quail (Coturnix coturnix) are incubated at 37.8° C. and 80% humidity. Differentiated CAM of 16-day-old chick and 13-day-old quail embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors, and the protein to be tested, are dissolved in distilled water and about 3.3 mg/ 5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 23

Angiogenesis Assay Using a Matrigel Implant in Mouse

In order to establish an in vivo model for angiogenesis to test TNF Delta and/or TNF Epsilon protein activities, mice and rats are implanted subcutaneously with methylcellulose disks containing either 20 mg of BSA (negative control), 1 mg of TNF Delta and/or TNF Epsilon or 0.5 mg of VEGF-1 (positive control). The negative control disks should contain little vascularization, while the positive control disks should show signs of vessel formation.

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 24

Rescue of Ischemia in Rabbit Lower Limb Model

To study the in vivo effects of TNF Delta and/or TNF Epsilon on ischemia, a rabbit hindlimb ischemia model is created by surgical removal of one femoral arteries as described previously (Takeshita, S. et al., Am J. Pathol 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al., Am J. Pathol 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked TNF Delta and/or TNF Epsilon expression plasmid by arterial gene transfer technology using a hydrogel-coated balloon catheter as described (Riessen, R. et al., Hum Gene Ther. 4:749–758 (1993); Leclerc, G. et al., J. Clin. Invest. 90: 936–944 (1992)). When TNF Delta and/or TNF Epsilon is used in the treatment, a single bolus of 500 mg TNF Delta and/or TNF Epsilon protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 25

Rat Ischemic Skin Flap Model

The evaluation parameters include skin blood flow, skin temperature, and factor VIII immunohistochemistry or endothelial alkaline phosphatase reaction. TNF Delta and/or TNF Epsilon expression, during the skin ischemia, is studied using in situ hybridization.

The study in this model is divided into three parts as follows:

Ischemic skin

Ischemic skin wounds

Normal wounds

The experimental protocol includes:

Raising a 3×4 cm, single pedicle full-thickness random skin flap (myocutaneous flap over the lower back of the animal).

An excisional wounding (4–6 mm in diameter) in the ischemic skin (skin-flap).

Topical treatment with TNF Delta and/or TNF Epsilon of the excisional wounds (day 0, 1, 2, 3, 4 post-wounding) at the following various dosage ranges: 1 mg to 100 mg.

Harvesting the wound tissues at day 3, 5, 7, 10, 14 and 21 post-wounding for histological, immunohistochemical, and in situ studies.

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 26

Peripheral Arterial Disease Model

Angiogenic therapy using TNF Delta and/or TNF Epsilon is a novel therapeutic strategy to obtain restoration of blood flow around the ischemia in case of peripheral arterial diseases. The experimental protocol includes:

One side of the femoral artery is ligated to create ischemic muscle of the hindlimb, the other side of hindlimb serves as a control.

TNF Delta and/or TNF Epsilon protein, in a dosage range of 20 mg-500 mg, is delivered intravenously and/or intramuscularly 3 times (perhaps more) per week for 2–3 weeks.

The ischemic muscle tissue is collected after ligation of the femoral artery at 1, 2, and 3 weeks for the analysis of TNF Delta and/or TNF Epsilon expression and histology. Biopsy is also performed on the other side of normal muscle of the contralateral hindlimb.

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 27

Ischemic Myocardial Disease Model

TNF Delta and/or TNF Epsilon is evaluated as a potent mitogen capable of stimulating the development of collateral vessels, and restructuring new vessels after coronary artery occlusion. Alteration of TNF Delta and/or TNF Epsilon expression is investigated in situ. The experimental protocol includes:

The heart is exposed through a left-side thoracotomy in the rat. Immediately, the left coronary artery is occluded with a thin suture (6–0) and the thorax is closed.

TNF Delta and/or TNF Epsilon protein, in a dosage range of 20 mg-500 mg, is delivered intravenously and/or intramuscularly 3 times (perhaps more) per week for 2–4 weeks.

Thirty days after the surgery, the heart is removed and cross-sectioned for morphometric and in situ analyzes.

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 28

Rat Corneal Wound Healing Model

This animal model shows the effect of TNF Delta and/or TNF Epsilon on neovascularization. The experimental protocol includes:

Making a 1–1.5 mm long incision from the center of cornea into the stromal layer.

Inserting a spatula below the lip of the incision facing the outer corner of the eye.

Making a pocket (its base is 1–1.5 mm form the edge of the eye).

Positioning a pellet, containing 50 ng-5 ug of TNF Delta and/or TNF Epsilon, within the pocket.

TNF Delta and/or TNF Epsilon treatment can also be applied topically to the corneal wounds in a dosage range of 20 mg-500 mg (daily treatment for five days).

The studies described in this example test the activity in TNF Delta and/or TNF Epsilon protein. However, one skilled in the art could easily modify the exemplified studies to test the activity of TNF Delta and/or TNF Epsilon polynucleotides (e.g., gene therapy), agonists, and/or antagonists of TNF Delta and/or TNF Epsilon.

EXAMPLE 29

Analysis of Binding of TNF Epsilon to TNF Receptor Superfamily Member TACI

The orphan receptor transmembrane activator and CAML-interactor ("TACI") has been previously characterized as a receptor present on B cells and a subset of T cells that is involved in the calcium activation pathway. See, U.S. Pat. No. 5,969,102; International Patent Application Publication No. WO98/39361; and von Bulow, G. U. and Bram, R. J., Science 278:138–41 (1997). An analysis of whether TNF Epsilon binds to TNF Receptor Superfamily (TNFR) member TACI was performed using two independent in vitro methods.

A full-length TACI cDNA clone (SEQ ID NO:21) was generated by PCR using the primers 5'-ATG AGT GGC CTG GGC CGG AGC AGG CGA GGT GGC CGG AGC CGT GTG GAC CAG G-3' (SEQ ID NO:15) and 5'-AAG CTT AGA TCT GCC ACC ATG AGT GGC CTG GGC CGG AGC-3' (SEQ ID NO: 16) at the 5' end together with the 3' primer 5'-GAA TTC TCT AGA CCC CCA TTT ATG CAC CTG G-3' (SEQ ID NO:17). The PCR product was cut with Bgl II and Xba I restriction endonucleases and subcloned into the CMV-based mammalian expression vector pC4.

A full-length TACI-Fc fusion cDNA was generated by a two-step PCR reaction using the following primers to sequentially add on a signal sequence from MPIF. 5' Primer: 5'-CCC TCT CCT GCC TCA TGC TTG TTA CTG CCC TTG GAT CTC AGG CCA TGA GTG GCC TGG GCC GGA GCA GGG AAT TCA GAT CTG CCA CCA TGA AGG TCT CCG TGG CTG CCC TCT CCT GCC TCA TGC TTG TTA CTG CC-3' (SEQ ID NO:18), and 3' Primer: 5'-AAG CTT TCT AGA CTG ATC TGC ACT CAG CTT CAG CCC-3' (SEQ ID NO:19). A truncated form of TACI-Fc with an MPIF signal sequence was generated using the following 5' primer in place of the 5' primer recited supra. 5' Primer: 5'-CTG CCT CAT GCT TGT TAC TGC CCT TGG ATC TCA GGC CAT GAG ATC CTG CCC CGA AGA GCA G-3' (SEQ ID NO:20). The PCR products were cut with Bgl II and Xba I and ligated into the mammalian expression vector pC4-Fc linearized with Bam HI and Xba I.

Full-length TACI-Fc (Met-1 to Gln-159 of SEQ ID NO:22) or truncated TACI-Fc (Met-31 to Gln-159 of SEQ ID NO:22) were purified from transiently transfected culture supernatants by capture on Protein A HyperD resin (Life Technologies, Inc., Rockville, Md.) and eluted with 0.1 M citrate buffer, pH =3.5. To further enrich the dimeric TACI-FC fusion protein, the pool was subject to size-exclusion chromatography on a Superdex S200 column (Amersham- Pharmacia, Piscataway, N.J.). The protein preparation was subsequently purified by capture on cation exchange resin (HS-50 Poros) and the trimeric form of TNF-Epsilon was isolated by size exclusion chromatography. All protein preparations were subject to N-terminal sequence analysis to verify sequence using a model ABI-494 sequencer (Perkin-Elmer Applied Biosystems, Inc., Foster City, Calif.).

The TACI-Fc fusion protein was used to assess the specificity of interaction between TACI and TNF-epsilon. A panel of four conditioned media-containing FLAG-epitope-tagged proteins, i.e., TNF-epsilon, LIGHT (See, Hahne, M., et al., *J. Exp. Med.* 188:1185–90 (1998)), FasL (Suda, T., et al., *Cell* 75:1169–78 (1993)), and Neutrokine-alpha (See, WO98/18921), was used to assess interaction specificity. Immunoprecipitations were carried out using the M2 anti-FLAG peptide antibody available from Sigma, St. Louis, Mo. Immunoprecipitates were detected by Western analysis unsing anti-FLAG antibody. Results of these experiments show that the anti-FLAG antibody immunoprecipitated a TACI-Fc-TNF-epsilon complex that accounted for approximately 20% of the TNF-epsilon present in the conditioned medium.

BIAcore analysis was performed essentially as follows. TACI-Fc protein was immobilized to the BIAcore sensor chip (CM5 chip) via amine groups using N-ethyl-N'-(dimethlaminopropyl)carbodiimide/N-hydroxysuccinimide chemistry. Various dilutions of TNF-epsilon or other TNF ligands were flowed over the receptor-derivatized flow cells at a rate of 15 microliters per minute for a total volume of 50 microliters. The amount of bound protein was determined during washing of the flow cell with HBS buffer (10 mM HEPES, pH 7.4, 150 mM NaCl, 3.4 mM EDTA, 0.005% Surfactant P20). Binding specificity of TNF-epsilon to TACI was determined by competition with soluble competitor. The flow cell surface was regenerated by displacing bound protein by washing with 20 microliters of 10 mM glycine-HCl, pH=2.3.

Results from the BIAcore analysis demonstrate that TNF-epsilon binds to the TACI-Fc BIAcore chip. Furthermore, this interaction was shown to be specific since soluble TACI-Fc inhibited TNF-epsilon from binding to the TACI-Fc chip. These experiments showed that the Kd for the TACI-TNF-epsilon interaction is 6 nM.

It will be clear that the invention may be practiced otherwise than as particularly described in the foregoing description and examples. Numerous modifications

SEQUENCE LISTING

<160> NUMBER OF SEQ ID NOS: 26

<210> SEQ ID NO 1
<211> LENGTH: 1717
<212> TYPE: DNA
<213> ORGANISM: Homo sapiens

<400> SEQUENCE: 1

```
acctctgtcc ttagagggga ctggaaccta attctcctga gcctgaggga gggtggaggg      60
tctcaagaca acgctgtccc cacgacggag tgccaggagc actaacagta cccttagatt     120
gctttcctcc tccctccttt tttattttca agttcctttt tatttctcct tgcgtaacaa     180
ccttcttccc ttctgcacca ctgcccgtac ccttacccgc gccgccacct ccttgctaca     240
ccactcttga aaccacagct gttggcaggg tcccccagct catgccagcc tcatctcctt     300
tcttgctagc ccccaaaggg cctccaggca acatgggggg cccagtcaga gagccggcac     360
tctcagttgc cctctggttg agttgggggg cagctctggg ggccgtggct tgtgccatgg     420
ctctgctgac ccaacaaaca gagctgcaga gcctcaggag agaggtgagc cggctgcaga     480
ggacaggagg cccctcccag aatggggaag ggtatccctg gcagagtctc ccggagcaga     540
gttccgatgc cctggaagcc tgggagaatg gggagagatc ccggaaaagg agagcagtgc     600
tcacccaaaa acagaagaag cagcactctg tcctgcacct ggttcccatt aacgccacct     660
ccaaggatga ctccgatgtg acagaggtga tgtggcaacc agctcttagg cgtgggagag     720
gcctacaggc ccaaggatat ggtgtccgaa tccaggatgc tggagtttat ctgctgtata     780
gccaggtcct gtttcaagac gtgactttca ccatgggtca ggtggtgtct cgagaaggcc     840
aaggaaggca ggagactcta ttccgatgta taagaagtat gccctcccac ccggaccggg     900
cctacaacag ctgctatagc gcaggtgtct tccatttaca ccaaggggat attctgagtg     960
tcataattcc ccgggcaagg gcgaaactta acctctctcc acatggaacc ttcctggggt    1020
ttgtgaaact gtgattgtgt tataaaaagt ggctcccagc ttggaagacc agggtgggta    1080
```

-continued

```
catactggag acagccaaga gctgagtata taaaggagag ggaatgtgca ggaacagagg    1140
cgtcttcctg ggtttggctc cccgttcctc acttttccct tttcattccc accccctaga    1200
ctttgatttt acggatatct tgcttctgtt ccccatggag ctccgaattc ttgcgtgtgt    1260
gtagatgagg ggcggggggac gggcgccagg cattgtccag acctggtcgg ggcccactgg    1320
aagcatccag aacagcacca ccatctagcg gccgctctag aggatccctc gagggggccca    1380 agcttacgcg tgcatgcgac gtcatagctc tctccctata gtgagtcgta ttataagcta    1440
gcttgggatc tttgtgaagg aaccttactt ctgtggtgtg acataattgg acaaactacc    1500
tacagagatt taaagctcta aggtaaatat aaaattttta agtgtataat gtgttaaact    1560
agctgcatat gcttgctgct tgagagtttg gcttactgag tatgattatg aaaatattat    1620
acacaggagc tagtgatcta tgttggtttt agatcaagcc aaggtcattc aggcctcagc    1680
tcaagctgtc atgatcatat cagcatacaa ttgtgag                            1717
```

<210> SEQ ID NO 2
<211> LENGTH: 233
<212> TYPE: PRT
<213> ORGANISM: Homo sapiens

<400> SEQUENCE: 2

```
Met Gly Gly Pro Val Arg Glu Pro Ala Leu Ser Val Ala Leu Trp Leu
  1               5                  10                  15

Ser Trp Gly Ala Ala Leu Gly Ala Val Ala Cys Ala Met Ala Leu Leu
             20                  25                  30

Thr Gln Gln Thr Glu Leu Gln Ser Leu Arg Arg Glu Val Ser Arg Leu
         35                  40                  45

Gln Arg Thr Gly Gly Pro Ser Gln Asn Gly Glu Gly Tyr Pro Trp Gln
     50                  55                  60

Ser Leu Pro Glu Gln Ser Ser Asp Ala Leu Glu Ala Trp Glu Asn Gly
 65                  70                  75                  80

Glu Arg Ser Arg Lys Arg Arg Ala Val Leu Thr Gln Lys Gln Lys Lys
                 85                  90                  95

Gln His Ser Val Leu His Leu Val Pro Ile Asn Ala Thr Ser Lys Asp
            100                 105                 110

Asp Ser Asp Val Thr Glu Val Met Trp Gln Pro Ala Leu Arg Arg Gly
        115                 120                 125

Arg Gly Leu Gln Ala Gln Gly Tyr Gly Val Arg Ile Gln Asp Ala Gly
    130                 135                 140

Val Tyr Leu Leu Tyr Ser Gln Val Leu Phe Gln Asp Val Thr Phe Thr
145                 150                 155                 160

Met Gly Gln Val Val Ser Arg Glu Gly Gln Gly Arg Gln Glu Thr Leu
                165                 170                 175

Phe Arg Cys Ile Arg Ser Met Pro Ser His Pro Asp Arg Ala Tyr Asn
            180                 185                 190

Ser Cys Tyr Ser Ala Gly Val Phe His Leu His Gln Gly Asp Ile Leu
        195                 200                 205

Ser Val Ile Ile Pro Arg Ala Arg Ala Lys Leu Asn Leu Ser Pro His
    210                 215                 220

Gly Thr Phe Leu Gly Phe Val Lys Leu
225                 230
```

<210> SEQ ID NO 3
<211> LENGTH: 1281
<212> TYPE: DNA
<213> ORGANISM: Homo sapiens

<400> SEQUENCE: 3

```
ggggacagga ggcccctccc agaatgggga agggtatccc tggcagagtc tcccggagca      60
gagttccgat gccctggaag cctgggagag tggggagaga tcccgaaaaa ggagagcagt     120
gctcacccaa aaacagaaga atgactccga tgtgacagag gtgatgtggc aaccagctct     180
taggcgtggg agaggcctac aggcccaagg atatggtgtc cgaatccagg atgctggagt     240
ttatctcctg tatagccagg tcctgtttca agacgtgact ttcaccatgg gtcaggtggt     300
gtctcgagaa ggccaaggaa ggcaggagac tctattccga tgtataagaa gtatgccctc     360
ccacccggac cgggcctaca acagctgcta tagcgcaggt gtcttccatt tacaccaagg     420
ggatattctg agtgtcataa ttccccgggc aagggcgaaa cttaacctct ctccacatgg     480
aaccttcctg gggtttgtga actgtgatt gtgttataaa agtggctcc cagcttggaa      540
gaccagggtg gtacatact ggagacagcc aagagctgag tatataaagg agagggaatg      600
tgcaggaaca gaggcgtctt cctgggtttg gctccccgtt cctcactttt ccctttcat     660
tcccacccccc tagactttgg attttacgga tatcttgctt ctgttcccca tggagctccg    720
aattcttgcg tgtgtgtaga tgagggggcgg gggacgggcg ccaggcattg ttcagacctg    780
gtcgggccc actggaagca tccagaacag caccaccatc tagcggcgct cgagggaagc      840
accgcgggtt ggccgaagtc cacgaagccg cctctgctag ggaaaaccct ggttctccat     900
gccacaactc tctccagggt ggcctctgcc tcttcaaccc cacaaagaag ccttaaccta     960
cgtccttctc tccatctatc ggaccccagt ttccatcact atctccagag atgtagctat    1020
tatgcgcccg tctacagggg gtgccccgacg atgacggtgc cttcgcagtc aaattactct    1080
tcgggtccca aggtttggct ttcacgcgct ccattgcccc ggcgtggcag gccattccaa    1140
gcccttccgg gctggaactg tgtcggagg agcctcgggt gtatcgtacg ccctggtgtt    1200
ggtgttgcct cactcctctg agctcttctt tctgatcaag ccctgcttaa agttaaataa    1260
aatagaatga atgataaaaa a                                              1281
```

<210> SEQ ID NO 4
<211> LENGTH: 168
<212> TYPE: PRT
<213> ORGANISM: Homo sapiens

<400> SEQUENCE: 4

Gly Thr Gly Gly Pro Ser Gln Asn Gly Glu Gly Tyr Pro Trp Gln Ser
 1               5                  10                  15

Leu Pro Glu Gln Ser Ser Asp Ala Leu Glu Ala Trp Glu Ser Gly Glu
            20                  25                  30

Arg Ser Arg Lys Arg Arg Ala Val Leu Thr Gln Lys Gln Lys Asn Asp
        35                  40                  45

Ser Asp Val Thr Glu Val Met Trp Gln Pro Ala Leu Arg Arg Gly Arg
    50                  55                  60

Gly Leu Gln Ala Gln Gly Tyr Gly Val Arg Ile Gln Asp Ala Gly Val
65                  70                  75                  80

Tyr Leu Leu Tyr Ser Gln Val Leu Phe Gln Asp Val Thr Phe Thr Met
                85                  90                  95

Gly Gln Val Val Ser Arg Glu Gly Gln Gly Arg Gln Glu Thr Leu Phe
            100                 105                 110

```
Arg Cys Ile Arg Ser Met Pro Ser His Pro Asp Arg Ala Tyr Asn Ser
            115                 120                 125

Cys Tyr Ser Ala Gly Val Phe His Leu His Gln Gly Asp Ile Leu Ser
            130                 135                 140

Val Ile Ile Pro Arg Ala Arg Ala Lys Leu Asn Leu Ser Pro His Gly
145                 150                 155                 160

Thr Phe Leu Gly Phe Val Lys Leu
                165

<210> SEQ ID NO 5
<211> LENGTH: 233
<212> TYPE: PRT
<213> ORGANISM: Homo sapiens

<400> SEQUENCE: 5

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Ser Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 6
<211> LENGTH: 205
<212> TYPE: PRT
<213> ORGANISM: Homo sapiens

<400> SEQUENCE: 6

Met Thr Pro Pro Glu Arg Leu Phe Leu Pro Arg Val Cys Gly Thr Thr
1               5                   10                  15

Leu His Leu Leu Leu Leu Gly Leu Leu Val Leu Leu Pro Gly Ala
            20                  25                  30
```

Gln Gly Leu Pro Gly Val Gly Leu Thr Pro Ser Ala Ala Gln Thr Ala
             35                  40                  45

Arg Gln His Pro Lys Met His Leu Ala His Ser Thr Leu Lys Pro Ala
     50                  55                  60

Ala His Leu Ile Gly Asp Pro Ser Lys Gln Asn Ser Leu Leu Trp Arg
 65                  70                  75                  80

Ala Asn Thr Asp Arg Ala Phe Leu Gln Asp Gly Phe Ser Leu Ser Asn
                 85                  90                  95

Asn Ser Leu Leu Val Pro Thr Ser Gly Ile Tyr Phe Val Tyr Ser Gln
                100                 105                 110

Val Val Phe Ser Gly Lys Ala Tyr Ser Pro Lys Ala Pro Ser Ser Pro
            115                 120                 125

Leu Tyr Leu Ala His Glu Val Gln Leu Phe Ser Ser Gln Tyr Pro Phe
            130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205

<210> SEQ ID NO 7
<211> LENGTH: 25
<212> TYPE: DNA
<213> ORGANISM: Homo sapiens

<400> SEQUENCE: 7
gcgggatccc agagcctcac cacag                                    25

<210> SEQ ID NO 8
<211> LENGTH: 29
<212> TYPE: DNA
<213> ORGANISM: Homo sapiens

<400> SEQUENCE: 8
cgcaagctta caatcacagt ttcacaaac                                29

<210> SEQ ID NO 9
<211> LENGTH: 26
<212> TYPE: DNA
<213> ORGANISM: Homo sapiens

<400> SEQUENCE: 9
gcgggatccc cagagcctca ccacag                                   26

<210> SEQ ID NO 10
<211> LENGTH: 29
<212> TYPE: DNA
<213> ORGANISM: Homo sapiens

<400> SEQUENCE: 10
cgctctagaa caatcacagt ttcacaaac                                29

<210> SEQ ID NO 11
<211> LENGTH: 250
<212> TYPE: PRT
<213> ORGANISM: Homo sapiens

```
<400> SEQUENCE: 11

Met Pro Ala Ser Ser Pro Phe Leu Leu Ala Pro Lys Gly Pro Pro Gly
 1               5                  10                  15

Asn Met Gly Gly Pro Val Arg Glu Pro Ala Leu Ser Val Ala Leu Trp
             20                  25                  30

Leu Ser Trp Gly Ala Ala Leu Gly Ala Val Ala Cys Ala Met Ala Leu
         35                  40                  45

Leu Thr Gln Gln Thr Glu Leu Gln Ser Leu Arg Arg Glu Val Ser Arg
 50                  55                  60

Leu Gln Arg Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 12
<211> LENGTH: 1126
<212> TYPE: DNA
<213> ORGANISM: Homo sapiens

<400> SEQUENCE: 12
cccacccgtc cgcccacgcg tccgccactg cccgtaccct tacccgcccc gccacctact      60
tgctacccca ctcttgaaac cacagctgtt ggcagggtcc ccagctcatg ccagcctcat     120
ctcctttctt gctagccccc aaagggcctc caggcaacat gggggggccca gtcagagagc    180 cggcactctc agttgccctc tggttgagtt gggggggcagc tctgggggcc gtggcttgtg    240
ccatggctct gctgacccaa caaacagagc tgcagagcct caggagagag gtgagccggc    300
tgcagaggac aggaggcccc tcccagaatg gggaagggta tccctggcag agtctcccgg    360
agcagagttc cgatgccctg gaagcctggg agagtgggga gagatcccgg aaaaggagag    420
cagtgctcac ccaaaaacag aagaatgact ccgatgtgac agaggtgatg tggcaaccag    480
ctcttaggcg tgggagaggc ctacaggccc aaggatatgg tgtccgaatc caggatgctg    540
gagtttatct gctgtatagc caggtcctgt ttcaagacgt gactttcacc atgggtcagg    600
tggtgtctcg agaaggccaa ggaaggcagg agactctatt ccgatgtata agaagtatgc    660
```

```
cctcccaccc ggaccgggcc tacaacagct gctatagcgc aggtgtcttc catttacacc      720 aagggggatat tctgagtgtc ataattcccc gggcaagggc gaaacttaac ctctctccac     780
atggaacctt cctggggttt gtgaaactgt gattgtgtta taaaaagtgg ctcccagctt      840
ggaagaccag ggtgggtaca tactggagac agccaagagc tgagtatata aggagaggg      900 aatgtgcagg aacagaggcg tcttcctggg tttggctccc cgttcctcac ttttcccttt     960
tcattcccac cccctagact ttgattttac ggatatcttg cttctgttcc ccatggagct    1020
ccgaattctt gcgtgtgtgt agatgagggg cggggggacg ggcgccaggc attgttcaga    1080
cctggtcggg gcccactgga agcatccaga acagcaccac catcta                   1126
```

<210> SEQ ID NO 13
<211> LENGTH: 234
<212> TYPE: PRT
<213> ORGANISM: Homo sapiens

<400> SEQUENCE: 13

```
Met Pro Ala Ser Ser Pro Phe Leu Leu Ala Pro Lys Gly Pro Pro Gly
 1               5                  10                  15

Asn Met Gly Gly Pro Val Arg Glu Pro Ala Leu Ser Val Ala Leu Trp
             20                  25                  30

Leu Ser Trp Gly Ala Ala Leu Gly Ala Val Ala Cys Ala Met Ala Leu
         35                  40                  45

Leu Thr Gln Gln Thr Glu Leu Gln Ser Leu Arg Arg Glu Val Ser Arg
     50                  55                  60

Leu Gln Arg Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Ser
                 85                  90                  95

Gly Glu Arg Ser Arg Lys Arg Ala Val Leu Thr Gln Lys Gln Lys
            100                 105                 110

Asn Asp Ser Asp Val Thr Glu Val Met Trp Gln Pro Ala Leu Arg Arg
        115                 120                 125

Gly Arg Gly Leu Gln Ala Gln Gly Tyr Gly Val Arg Ile Gln Asp Ala
    130                 135                 140

Gly Val Tyr Leu Leu Tyr Ser Gln Val Leu Phe Gln Asp Val Thr Phe
145                 150                 155                 160

Thr Met Gly Gln Val Val Ser Arg Glu Gly Gln Gly Arg Gln Glu Thr
                165                 170                 175

Leu Phe Arg Cys Ile Arg Ser Met Pro Ser His Pro Asp Arg Ala Tyr
            180                 185                 190

Asn Ser Cys Tyr Ser Ala Gly Val Phe His Leu His Gln Gly Asp Ile
        195                 200                 205

Leu Ser Val Ile Ile Pro Arg Ala Arg Ala Lys Leu Asn Leu Ser Pro
    210                 215                 220

His Gly Thr Phe Leu Gly Phe Val Lys Leu
225                 230
```

<210> SEQ ID NO 14
<211> LENGTH: 733
<212> TYPE: DNA
<213> ORGANISM: Homo sapiens

<400> SEQUENCE: 14

```
gggatccgga gcccaaatct tctgacaaaa ctcacacatg cccaccgtgc ccagcacctg       60
```

```
aattcgaggg tgcaccgtca gtcttcctct tcccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agccctccca accccatcg     360 agaaaaccat ctccaaagcc aaagggcagc ccgagaacc acaggtgtac accctgcccc     420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                       733

<210> SEQ ID NO 15
<211> LENGTH: 52
<212> TYPE: DNA
<213> ORGANISM: Homo sapiens

<400> SEQUENCE: 15
atgagtggcc tgggccggag caggcgaggt ggccggagcc gtgtggacca gg            52

<210> SEQ ID NO 16
<211> LENGTH: 39
<212> TYPE: DNA
<213> ORGANISM: Homo sapiens

<400> SEQUENCE: 16
aagcttagat ctgccaccat gagtggcctg ggccggagc                           39

<210> SEQ ID NO 17
<211> LENGTH: 31
<212> TYPE: DNA
<213> ORGANISM: Homo sapiens

<400> SEQUENCE: 17
gaattctcta gacccccatt tatgcacctg g                                   31

<210> SEQ ID NO 18
<211> LENGTH: 134
<212> TYPE: DNA
<213> ORGANISM: Homo sapiens

<400> SEQUENCE: 18
ccctctcctg cctcatgctt gttactgccc ttggatctca ggccatgagt ggcctgggcc    60
ggagcaggga attcagatct gccaccatga aggtctccgt ggctgccctc tcctgcctca    120
tgcttgttac tgcc                                                      134

<210> SEQ ID NO 19
<211> LENGTH: 36
<212> TYPE: DNA
<213> ORGANISM: Homo sapiens

<400> SEQUENCE: 19
aagctttcta gactgatctg cactcagctt cagccc                              36
```

<210> SEQ ID NO 20
<211> LENGTH: 61
<212> TYPE: DNA
<213> ORGANISM: Homo sapiens

<400> SEQUENCE: 20

```
ctgcctcatg cttgttactg cccttggatc tcaggccatg agatcctgcc ccgaagagca     60
g                                                                    61
```

<210> SEQ ID NO 21
<211> LENGTH: 1377
<212> TYPE: DNA
<213> ORGANISM: Homo sapiens

<400> SEQUENCE: 21

```
agcatcctga gtaatgagtg gcctgggccg gagcaggcga ggtggccgga gccgtgtgga     60
ccaggaggag cgctttccac agggcctgtg gacggggtg gctatgagat cctgccccga    120
agagcagtac tgggatcctc tgctgggtac ctgcatgtcc tgcaaaacca tttgcaacca    180
tcagagccag cgcacctgtg cagccttctg caggtcactc agctgccgca aggagcaagg    240
caagttctat gaccatctcc tgagggactg catcagctgt gcctccatct gtggacagca    300
ccctaagcaa tgtgcatact tctgtgagaa caagctcagg agcccagtga accttccacc    360
agagctcagg agacagcgga gtggagaagt tgaaaacaat tcagacaact cgggaaggta    420
ccaaggattg gagcacagag gctcagaagc aagtccagct ctcccggggc tgaagctgag    480
tgcagatcag gtggccctgg tctacagcac gctggggctc tgcctgtgtg ccgtcctctg    540
ctgcttcctg gtggcggtgg cctgcttcct caagaagagg ggggatccct gctcctgcca    600
gccccgctca aggccccgtc aaagtccggc caagtcttcc caggatcacg cgatggaagc    660
cggcagccct gtgagcacat cccccgagcc agtggagacc tgcagcttct gcttccctga    720
gtgcagggcg cccacgcagg agagcgcagt cacgcctggg accccgaccc cacttgtgc    780
tggaaggtgg gggtgccaca ccaggaccac agtcctgcag ccttgcccac acatcccaga    840
cagtggcctt ggcattgtgt gtgtgcctgc ccaggagggg ggcccaggtg cataaatggg    900
ggtcagggag ggaaaggagg agggagagag atggagagga ggggagagag aaagagaggt    960
ggggagaggg gagagagata tgaggagaga gagacagagg aggcagaaag ggagagaaac   1020
agaggagaca gagagggaga gagagacaga gggagagaga gacagagggg aagagaggca   1080
gagagggaaa gaggcagaga aggaaagaga caggcagaga aggagagagg cagagaggga   1140
gagaggcaga gagggagaga ggcagagaga cagagaggga gagagggaca gagagagata   1200
gagcaggagg tcgggcact ctgagtccca gttcccagtg cagctgtagg tcgtcatcac    1260
ctaaccacac gtgcaataaa gtcctcgtgc ctgctgctca cagcccccga gagcccctcc    1320
tcctggagaa taaaacccttt ggcagctgcc cttcctcaaa aaaaaaaaa aaaaaaa     1377
```

<210> SEQ ID NO 22
<211> LENGTH: 293
<212> TYPE: PRT
<213> ORGANISM: Homo sapiens

<400> SEQUENCE: 22

```
Met Ser Gly Leu Gly Arg Ser Arg Arg Gly Arg Ser Arg Val Asp
  1               5                  10                  15

Gln Glu Glu Arg Phe Pro Gln Gly Leu Trp Thr Gly Val Ala Met Arg
                 20                  25                  30
```

-continued

```
Ser Cys Pro Glu Glu Gln Tyr Trp Asp Pro Leu Leu Gly Thr Cys Met
             35                  40                  45

Ser Cys Lys Thr Ile Cys Asn His Gln Ser Gln Arg Thr Cys Ala Ala
     50                  55                  60

Phe Cys Arg Ser Leu Ser Cys Arg Lys Glu Gln Gly Lys Phe Tyr Asp
 65                  70                  75                  80

His Leu Leu Arg Asp Cys Ile Ser Cys Ala Ser Ile Cys Gly Gln His
                 85                  90                  95

Pro Lys Gln Cys Ala Tyr Phe Cys Glu Asn Lys Leu Arg Ser Pro Val
                100                 105                 110

Asn Leu Pro Pro Glu Leu Arg Arg Gln Arg Ser Gly Glu Val Glu Asn
            115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
                180                 185                 190

Cys Ser Cys Gln Pro Arg Ser Arg Pro Arg Gln Ser Pro Ala Lys Ser
            195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
    275                 280                 285

Gly Gly Pro Gly Ala
    290
```

<210> SEQ ID NO 23
<211> LENGTH: 285
<212> TYPE: PRT
<213> ORGANISM: Homo sapiens

<400> SEQUENCE: 23

```
Met Asp Asp Ser Thr Glu Arg Glu Gln Ser Arg Leu Thr Ser Cys Leu
  1               5                  10                  15

Lys Lys Arg Glu Glu Met Lys Leu Lys Glu Cys Val Ser Ile Leu Pro
                 20                  25                  30

Arg Lys Glu Ser Pro Ser Val Arg Ser Ser Lys Asp Gly Lys Leu Leu
             35                  40                  45

Ala Ala Thr Leu Leu Leu Ala Leu Leu Ser Cys Cys Leu Thr Val Val
     50                  55                  60

Ser Phe Tyr Gln Val Ala Ala Leu Gln Gly Asp Leu Ala Ser Leu Arg
 65                  70                  75                  80

Ala Glu Leu Gln Gly His His Ala Glu Lys Leu Pro Ala Gly Ala Gly
                 85                  90                  95

Ala Pro Lys Ala Gly Leu Glu Glu Ala Pro Ala Val Thr Ala Gly Leu
                100                 105                 110
```

-continued

```
Lys Ile Phe Glu Pro Pro Ala Pro Gly Glu Gly Asn Ser Ser Gln Asn
            115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
            195                 200                 205

Gly His Leu Ile Gln Arg Lys Lys Val His Val Phe Gly Asp Glu Leu
            210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
            275                 280                 285

<210> SEQ ID NO 24
<211> LENGTH: 266
<212> TYPE: PRT
<213> ORGANISM: Homo sapiens

<400> SEQUENCE: 24

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
            85                  90                  95

Ala Pro Lys Ala Gly Leu Glu Glu Ala Pro Ala Val Thr Ala Gly Leu
        100                 105                 110

Lys Ile Phe Glu Pro Pro Ala Pro Gly Glu Gly Asn Ser Ser Gln Asn
    115                 120                 125

Ser Arg Asn Lys Arg Ala Val Gln Gly Pro Glu Glu Thr Gly Ser Tyr
130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
                165                 170                 175

Tyr Gly Gln Val Leu Tyr Thr Asp Lys Thr Tyr Ala Met Gly His Leu
            180                 185                 190

Ile Gln Arg Lys Lys Val His Val Phe Gly Asp Glu Leu Ser Leu Val
        195                 200                 205
```

```
Thr Leu Phe Arg Cys Ile Gln Asn Met Pro Glu Thr Leu Pro Asn Asn
    210                 215                 220

Ser Cys Tyr Ser Ala Gly Ile Ala Lys Leu Glu Glu Gly Asp Glu Leu
225                 230                 235                 240

Gln Leu Ala Ile Pro Arg Glu Asn Ala Gln Ile Ser Leu Asp Gly Asp
                245                 250                 255

Val Thr Phe Gly Ala Leu Lys Leu Leu
            260             265

<210> SEQ ID NO 25
<211> LENGTH: 17
<212> TYPE: PRT
<213> ORGANISM: Homo Sapiens

<400> SEQUENCE: 25

Met Leu Gln Asn Ser Ala Val Leu Leu Leu Val Ile Ser Ala Ser
  1               5                  10                  15

Ala

<210> SEQ ID NO 26
<211> LENGTH: 22
<212> TYPE: PRT
<213> ORGANISM: Artificial Sequence
<220> FEATURE:
<221> NAME/KEY: SIGNAL
<222> LOCATION: (1)..(22)
<223> OTHER INFORMATION: consensus signal sequence

<400> SEQUENCE: 26

Met Pro Thr Trp Ala Trp Trp Leu Phe Leu Val Leu Leu Leu Ala Leu
  1               5                  10                  15

Trp Ala Pro Ala Arg Gly
            20
``` and variations of the present invention are possible in light of the above teachings and, therefore, are within the scope of the appended claims.

What is claimed is:

1. An isolated polypeptide comprising a sequence of amino acid residues selected from the group consisting of:
   (a) amino acid residues 1 to 233 of SEQ ID NO:2; and
   (b) amino acid residues 39 to 233 of SEQ ID NO:2.

2. The isolated polypeptide of claim 1 which comprises amino acid residues 1 to 233 of SEQ ID NO:2.

3. The isolated polypeptide of claim 1 which comprises amino acid residues 39 to 233 of SEQ ID NO:2.

4. The isolated polypeptide of claim 1, wherein said isolated polypeptide is glycosylated.

5. A recombinant protein produced by a method comprising:
   (a) culturing a host cell under conditions suitable to produce the isolated polypeptide of claim 1; and
   (b) recovering the protein from the host cell culture;
   wherein said host cell comprises an exogenously-derived polynucleotide encoding the isolated polypeptide of claim 1 and wherein the recombinant protein is encoded by said polynucleotide.

6. A composition comprising the isolated polypeptide of claim 1 in a carrier.

7. The composition of claim 6, wherein the carrier comprises a liposome.

8. The isolated polypeptide of claim 1 which comprises a heterologous polypeptide.

9. The isolated polypeptide of claim 8, wherein the heterologous polypeptide is an immunoglobulin Fc domain.

10. The isolated polypeptide of claim 8, wherein the heterologous polypeptide is human serum albumin.

11. An isolated polypeptide comprising a fragment of SEQ ID NO:2 wherein said fragment is at least 30 contiguous amino acids in length, and wherein a polypeptide consisting of said fragment is capable of stimulating the activation of a T cell.

12. The isolated polypeptide of claim 11, wherein said isolated polypeptide is glycosylated.

13. A recombinant protein produced by a method comprising;
   (a) culturing a host cell under conditions suitable to produce the isolated polypeptide of claim 11; and
   (b) recovering the protein from the host cell culture;
   wherein said host cell comprises an exogenously-derived polynucleotide encoding the isolated polypeptide of claim 11 and wherein the recombinant protein is encoded by said polynucleotide.

14. A composition comprising the isolated polypeptide of claim 11 in a carrier.

15. The composition of claim 14, wherein the carrier comprises a liposome.

16. The isolated polypeptide of claim 11 which comprises a heterologous polypeptide.

17. The isolated polypeptide of claim 16, wherein the heterologous polypeptide is an immunoglobulin Fc domain.

18. The isolated polypeptide of claim 16, wherein the heterologous polypeptide is human serum albumin.

19. The isolated polypeptide of claim 11 wherein said fragment is at least 50 contiguous amino acids in length.

20. The isolated polypeptide of claim 19, wherein said isolated polypeptide is glycosylated.

21. A recombinant protein produced by a method comprising:
(a) culturing a host cell under conditions suitable to produce the isolated polypeptide of claim 19; and
(b) recovering the protein from the host cell culture;
wherein said host cell comprises an exogenously-derived polynucleotide encoding the isolated polypeptide of claim 19 and wherein the recombinant protein is encoded by said polynucleotide.

22. A composition comprising the isolated polypeptide of claim 19 in a carrier.

23. The composition of claim 22, wherein the carrier comprises a liposome.

24. The isolated polypeptide of claim 19, which comprises a heterologous polypeptide.

25. The isolated polypeptide of claim 24, wherein the heterologous polypeptide is an immunoglobulin Fc domain.

26. The isolated polypeptide of claim 24, wherein the heterologous polypeptide is human serum albumin.

27. An isolated polypeptide encoded by the cDNA contained in ATCC Deposit No. 97377.

28. The isolated polypeptide of claim 27, wherein said isolated polypeptide is glycosylated.

29. A recombinant protein produced by a method comprising:
(a) culturing a host cell under conditions suitable to produce the isolated polypeptide of claim 27; and
(b) recovering the protein from the host cell culture;
wherein said host cell comprises an exogenously-derived polynucleotide encoding the isolated polypeptide of claim 27 and wherein the recombinant protein is encoded by said polynucleotide.

30. A composition comprising the isolated polypeptide of claim 27 in a carrier.

31. The composition of claim 30, wherein the carrier comprises a liposome.

32. The isolated polypeptide of claim 27 which comprises a heterologous polypeptide.

33. The isolated polypeptide of claim 32, wherein the heterologous polypeptide is an immunoglobulin Fc domain.

34. The isolated polypeptide of claim 32, wherein the heterologous polypeptide is human serum albumin.

35. An isolated polypeptide comprising a fragment of the polypeptide encoded by the cDNA contained in ATCC Deposit No. 97377 wherein said fragment is at least 30 contiguous amino acids in length, and wherein a polypeptide consisting of said fragment is capable of stimulating the activation of a T cell.

36. The isolated polypeptide of claim 35, wherein said isolated polypeptide is glycosylated.

37. A recombinant protein produced by a method comprising:
(a) culturing a host cell under conditions suitable to produce the isolated polypeptide of claim 35; and
(b) recovering the protein from the host cell culture;
wherein said host cell comprises an exogenously-derived polynucleotide encoding the isolated polypeptide of claim 35 and wherein the recombinant protein is encoded by said polynucleotide.

38. A composition comprising the isolated polypeptide of claim 35 in a carrier.

39. The composition of claim 38, wherein the carrier comprises a liposome.

40. The isolated polypeptide of claim 35 which comprises a heterologous polypeptide.

41. The isolated polypeptide of claim 40, wherein the heterologous polypeptide is an immunoglobulin Fc domain.

42. The isolated polypeptide of claim 40, wherein the heterologous polypeptide is human serum albumin.

43. The isolated polypeptide of claim 35 wherein said fragment is at least 50 contiguous amino acids in length.

44. A recombinant protein produced by a method comprising:
(a) culturing a host cell under conditions suitable to produce the isolated polypeptide of claim 43; and
(b) recovering the protein from the host cell culture;
wherein said host cell comprises an exogenously-derived polynucleotide encoding the isolated polypeptide of claim 43 and wherein the recombinant protein is encoded by said polynucleotide.

45. The isolated polypeptide of claim 43, wherein said isolated polypeptide is glycosylated.

46. A composition comprising the isolated polypeptide of claim 43 in a carrier.

47. The composition of claim 46, wherein We carrier comprises a liposome.

48. The isolated polypeptide of claim 43 which comprises a heterologous polypeptide.

49. The isolated polypeptide of claim 48, wherein the heterologous polypeptide is an immunoglobulin Fc domain.

50. The isolated polypeptide of claim 48, wherein the heterologous polypeptide is human serum albumin.

* * * * *

UNITED STATES PATENT AND TRADEMARK OFFICE
CERTIFICATE OF CORRECTION

PATENT NO. : 6,541,224 B2
DATED : April 1, 2003
INVENTOR(S) : Yu et al.

It is certified that error appears in the above-identified patent and that said Letters Patent is hereby corrected as shown below:

Please move the three lines immediately preceding the statement, "What Is Claimed Is" to the end of column 214, immediately before the Sequence Listing, so that the following entire paragraph appears before the Sequence Listing:

> "It will be clear that the invention may be practiced otherwise than as particularly described in the foregoing description and examples. Numerous modifications and variations of the present invention are possible in light of the above teachings and, therefore, are within the scope of the appended claims."

Additionally, please insert the following two paragraphs after the foregoing paragraph and before the Sequence Listing in column 214:

-- The entire disclosure of all publications (including patents, patent applications, journal articles, laboratory manuals, books, or other documents) cited herein are hereby incorporated by reference.
Further, the Sequence Listing submitted herewith, and those submitted with copending U.S. Application Serial No. 08/815,783, filed March 12, 1997 and U.S. Provisional Patent Application Serial Nos: 60/293,499, filed May 25, 2001; 60/277,978 filed March 23, 2001; 60/276,248, filed March. 16, 2001; 60/254,375 Filed December 13, 2000; 60/241,952 filed October 23, 2000; and 60/211,537 filed June 15, 2000; and 60/016 ,812, filed on March 14, 1996, in both computer and paper forms, are hereby incorporated by reference in their entireties. --

Column 238,
Line 43, delete "We" and insert -- the --.

Signed and Sealed this

Third Day of August, 2004

JON W. DUDAS
*Acting Director of the United States Patent and Trademark Office*